US009149519B2

(12) United States Patent
Landau et al.

(10) Patent No.: US 9,149,519 B2
(45) Date of Patent: Oct. 6, 2015

(54) CHIMERIC HUMAN IMMUNODEFICIENCY VIRUS TYPE 1 (HIV-1) WITH ENHANCED DENDRITIC CELL AND MACROPHAGE TROPISM COMPRISING THE SIMIAN IMMUNODEFICIENCY VIRUS (SIV) MINIMAL VPX PACKAGING DOMAIN

(71) Applicants: Nathaniel R. Landau, New York, NY (US); Nicole Sunseri, New York, NY (US); Thomas D. Norton, New York, NY (US)

(72) Inventors: Nathaniel R. Landau, New York, NY (US); Nicole Sunseri, New York, NY (US); Thomas D. Norton, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/743,877

(22) Filed: Jan. 17, 2013

(65) Prior Publication Data

US 2013/0183334 A1 Jul. 18, 2013

Related U.S. Application Data

(60) Provisional application No. 61/587,392, filed on Jan. 17, 2012.

(51) Int. Cl.

*A61K 39/21* (2006.01)
*A61K 39/12* (2006.01)
*C12N 7/00* (2006.01)
*C12N 15/86* (2006.01)
*A61K 39/00* (2006.01)

(52) U.S. Cl.

CPC ................. *A61K 39/21* (2013.01); *A61K 39/12* (2013.01); *C12N 7/00* (2013.01); *C12N 15/86* (2013.01); *A61K 2039/5256* (2013.01); *A61K 2039/5258* (2013.01); *C12N 2740/16034* (2013.01); *C12N 2740/16041* (2013.01); *C12N 2740/16045* (2013.01); *C12N 2740/16052* (2013.01); *C12N 2740/16134* (2013.01); *C12N 2740/16234* (2013.01)

(58) Field of Classification Search

CPC ........... C12N 7/00; C12N 2740/16234; C12N 2740/16045

See application file for complete search history.

(56) References Cited

U.S. PATENT DOCUMENTS

2011/0159025 A1 6/2011 Littman et al.

OTHER PUBLICATIONS

Sunseri, N., et al., 2011, Human immunodeficiency virus type 1 modified to package simian immunodeficiency virus Vpx efficiently infects macrophages and dendritic cells, J. Virol. 85(13):6263-6274.*

Xin, K.-Q., et al., 2007, Chimeric adenovirus 5/35 vector containing the Glade C HIV gag gene induces a cross-reactive immune response against HIV, Vaccine 25:3809-3815.*

Someya, K., et al., 2007, Chimeric adenovirus type 5/35 vector encoding SIV gag and HIV env genes affords protective immunity against the simian/human immunodeficiency virus in monkeys, Virol. 367:390-397.*

Accola et al., A conserved dileucine-containing motif in p6gag governs the particle association of Vpx and Vpr of simian immunodeficiency viruses SIVmac and SIVagm, J Virol, 1999, 73, 9992-9999.

Berger et al., "SIVMAC Vpx improves the transduction of dendritic cells with nonintegrative HIV 1-derived vectors", Gene Ther, 2009, 16, 159-163.

Gibbs et al., "Progression to AIDS in the absence of a gene for vpr or vpx", J Virol, 1995, 69, 2378-2383.

Goujon et al., "Characterization of simian immunodeficiency virus SIVSM/human immunodeficiency virus type 2 Vpx function in human myeloid cells", J Virol, 2008, 82, 12335-12345.

Goujon et al., With a little help from a friend: increasing HIV transduction of monocyte-derived dendritic cells with virion-like particles of SIVMAC, Gene Ther, 2006, 13, 991-994.

Goujon et al., "SIVSM/HIV-2 Vpx proteins promote retroviral escape from a proteasome-dependent restriction pathway present in human dendritic cells", Retrovirology, 2007, 4, 2.

Gramberg et al., "Evidence for an activation domain at the amino terminus of simian immunodeficiency virus Vpx", J Virol, 2010, 84, 1387-1396.

Hirsch et al., "Vpx is required for dissemination and pathogenesis of SIVSM PBj: evidence of macrophage-dependent viral amplification", Nat Med, 1998, 4. 1401-1408.

Hrecka et al., "Vpx relieves inhibition of HIV-1 infection of macrophages mediated by the SAMHD1 protein", Nature, 2011, 474, 658-661.

Laguette et al., "SAMHD1 is the dendritic- and myeloid-cell-specific HIV-1 restriction factor counteracted by Vpx", Nature, 2011, 474, 654-657.

Sunseri et al., "Human immunodeficiency virus type 1 modified to package Simian immunodeficiency virus Vpx efficiently infects macrophages and dendritic cells", Journal of Virology, 2011, 85, 6263-6274.

Horton et al., "HIV-2 viral protein X association with the Gag p27 capsid protein", Virology, 1994, 199, 453-457.

(Continued)

*Primary Examiner* — Jeffrey Parkin

(74) *Attorney, Agent, or Firm* — Klauber & Jackson LLC

(57) ABSTRACT

The compositions and methods described herein relate to lentiviral vectors that can be used to generate virions/viruses that exhibit enhanced infectivity with respect to monocyte-derived macrophages (MDM) and dendritic cells (MDDC). Such compositions and methods further relate to production of virions/viruses that can be used as components of vaccines that effectively stimulate innate immune responses. In a particular embodiment, compositions and methods described herein relate to production of virions/viruses that can be used as components of human immunodeficiency-1 (HIV-1) vaccines administered to stimulate innate immune responses to HIV-1.

15 Claims, 46 Drawing Sheets

(56) References Cited

OTHER PUBLICATIONS

Kappes et al., "Human immunodeficiency virus type 2 vpx protein augments viral infectivity", Virology, 1991, 184, 197-209.
Kondo et al., "A conserved LXXLF sequence is the major determinant in p6gag required for the incorporation of human immunodeficiency virus type 1 Vpr", J Virol, 1996, 70, 159-164.
Manel et al., "A cryptic sensor for HIV-1 activates antiviral innate immunity in dendritic cells", Nature, 2010, 467, 214-217.
Sharova et al., "Primate lentiviral Vpx commandeers DDB1 to counteract a macrophage restriction", PLoS Pathog, 2008, 4, e1000057, 1-12.
Wu et al., "Localization of the Vpx packaging signal within the C terminus of the human immunodeficieny virus type 2 Gag precursor protein", J Virol, 1994, 68, 6161-6191.
Yu et al., "The vpx gene of simian immunodeficiency virus facilitates efficient viral replication in fresh lymphocytes and macrophages", J Virol, 1991, 65, 5088-5091.
Zhu et al., "Identification of the 15FRFG domain in HIV-1 Gag p6 essential for Vpr packaging into the virion", Retrovirology, 2004, 1, 26, 1-5.
Ayinde et al., "Limelight on two HIV/SIV accessory proteins in macrophage infection: is Vpx overshading Vpr?", Retrovirology, 2010, 7, 35, 1-12.
Schnell et al., "Development of a self-inactivating, minimal lentivirus vector based on simian immunodeficiency virus", Human Gene Therapy, 2000, 11, 439-447.
Wu et al., "Targeting foreign proteins to human immunodeficiency virus particles via fusion with vpr and vpx", J Virol, 1995, 69, 3389-3398.
Dull et al., "A third-generation lentivirus vector with a conditional packaging system", Journal of Virology, 1998, 72, 8463-8471.

* cited by examiner

FIG. 4
A
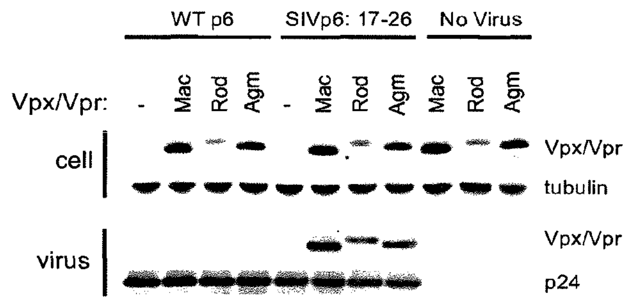
B
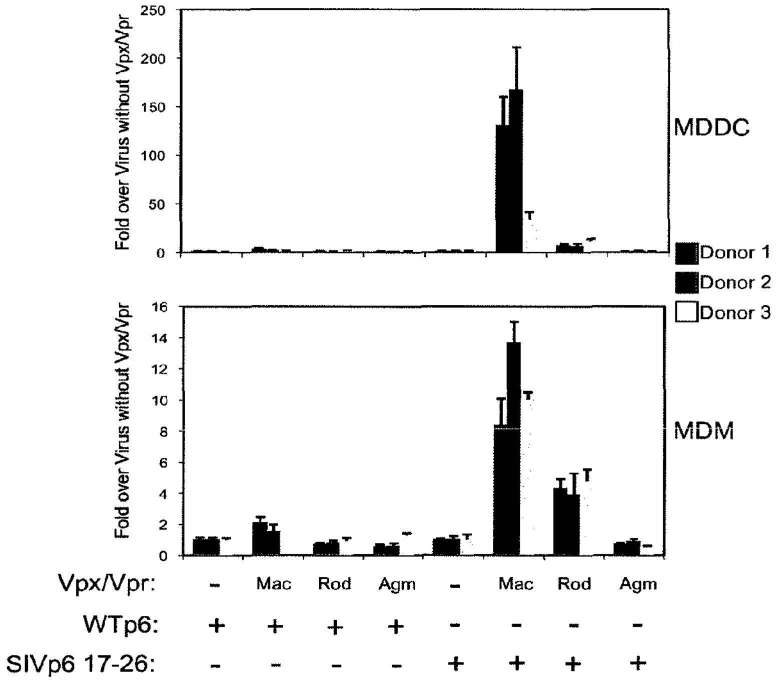

FIG. 8

SIVmac239 Vpx:
ATGAGCGACCCCAGAGAGAGAATCCCCCCCGGCAACAGCGGCGAGGAGACCATCGGCGAGGCCTTCGAGTGGCTGAACA
GAACCGTGGAGGAGATCAACAGAGAGGCCGTGAACCACCTGCCCAGAGAGCTGATCTTCCAGGTGTGGCAGAGAAGCTG
GGAGTACTGGCACGACGAGCAGGGCATGAGCCCCAGCTACGTGAAGTACAGATACCTGTGCCTGATCCAGAAGGCCCTGT
TCATGCACTGCAAGAAGGGCTGCAGATGCCTGGGCGAGGGCCACGGCGCCGGCGGCTGGAGACCCGGCCCTCCTCCTCCT
CCTCCTCCTGGCCTGGCCTGA$^{339}$

HIV-2rod Vpx:
ATGACCGACCCCAGAGAGACCGTGCCCCCCGGCAACAGCGGCGAGGAGACCATCGGCGAGGCCTTCGCCTGGCTGAACA
GAACCGTGGAGGCCATCAACAGAGAGGCCGTGAACCACCTGCCCAGAGAGCTGATCTTCCAGGTGTGGCAGAGAAGCTG
GAGATACTGGCACGACGAGCAGGGCATGAGCGAGAGCTACACCAAGTACAGATACCTGTGCATCATCCAGAAGGCCGTGT
ACATGCACGTGAGAAAGGGCTGCACCTGCCTGGGCAGAGGCCACGGCCCCGGCGGCTGGAGACCCGGCCCTCCTCCTCC
TCCTCCCCCCGGCCTGGTGTGA$^{339}$

SIVagm Vpr:
ATGGCCGAGGGCAGAGACAGCAGAGAGAGAAGACCCGGCTGGCTGGAGATCTGGGACCTGAGCAGAGAGCCCTGGGAC
GAGGGCCTGAGAGACATGGTGGCCGAGCTGAACCAGGAGGCCCAGAGACACTTCGGCAGAGAGCTGCTGTTCCAGGTGT
GGAACTTCTGCCAGGAGGAGGGCGAGAGAAACGGCGCCCCCATGATCGAGAGAGCCTACAGATACTACAGACTGGTGCA
GAAGGCCCTGTTCGTGCACTTCAGATGCGGCTGCAGAAGAAGAACCCCCTTCGAGCCCTACGAGGAGAGAAGAAACGGC
GTGGGCGGCGGCAGAGACGGCAGAGAGCCTCCTCCTGGCCTGGCCTGA$^{363}$

Fig. 11: NL4.3 Sequence – Full Length with Chimeric p6, 17-26

Annotated (primarily HIV-1 where the highlighted region is the SIV p6 region):

```
Sequence: NL4-3 Range: 1 to 9000

     5    10    15    20    25    30    35    40    45    50    55    60    65    70    75
AAA TCT CTA GCA GTG GCG CCC GAA CAG GGA CTT GAA AGC GAA AGT AAA GCC AGA GGA GAT CTC TCG ACG CAG GAC TCG
TTT AGA GAT CGT CAC CGC GGG CTT GTC CCT GAA CTT TCG CTT TCA TTT CGG TCT CCT CTA GAG AGC TGC GTC CTG AGC
   LTR; 5' LT  a >

80     85    90     95    100   105    110    115   120    125    130   135    140    145   150    155
GCT TGC TGA AGC GCG CAC GGC AAG AGG CGA GGG GCG GCG ACT GGT GAG TAC GCC AAA AAT TTT GAC TAG CGG AGG CTA
CGA ACG ACT TCG CGC GTG CCG TTC TCC GCT CCC CGC CGC TGA CCA CTC ATG CGG TTT TTA AAA CTG ATC GCC TCC GAT

          >Gene:_gag
             |
  160   165  |170   175   180    185    190   195    200    205   210    215    220   225    230
GAA GGA GAG AGA TGG GTG CGA GAG CGT CGG TAT TAA GCG GGG GAG AAT TAG ATA AAT GGG AAA AAA TTC GGT TAA GGC
CTT CCT CTC TCT ACC CAC GCT CTC GCA GCC ATA ATT CGC CCC CTC TTA ATC TAT TTA CCC TTT TTT AAG CCA ATT CCG
                 M   G   A   R   A   S   V   L   S   G   G   E   L   D   K   W   E   K   I   R   L   R>
               _b___b___b___b___b___b__GAG POLYPROTEIN PRECURSOR; MATRIX (P17)__b___b___b___b___b___b___>

235   240    245    250   255    260    265   270    275    280   285    290    295   300    305    310
CAG GGC GAA AGA AAC AAT ATA AAC TAA AAC ATA TAG TAT CGG CAA CCA GGG AGC TAG AAC GAT TCG CAG TTA ATC CTG
GTC CCC CTT TCT TTG TTA TAT TTG ATT TTG TAT ATC ATA CCC GTT CGT CCC TCG ATC TTG CTA AGC GTC AAT TAG GAC
P   G   G   K   K   Q   Y   K   L   K   H   I   V   W   A   S   R   E   L   E   R   F   A   V   N   P>
___b___b___b___b___b___b___b___GAG POLYPROTEIN PRECURSOR; MATRIX (P17)_b___b___b___b___b___b___b___b___>

315    320    325   330    335    340   345    350    355   360    365    370   375    380    385   390
GCC TTT TAG AGA CAT CAG AAG GCT GTA GAC AAA TAC TGG GAC AGC TAC AAC CAT CCC TTC AGA CAG GAT CAG AAG AAC
CGG AAA ATC TCT GTA GTC TTC CGA CAT CTG TTT ATG ACC CTG TCG ATG TTG GTA GGG AAG TCT GTC CTA GTC TTC TTG
G   L   L   E   T   S   E   G   C   R   Q   I   L   G   Q   L   Q   P   S   L   Q   T   G   S   E   E>
___b___b___b___b___b___b___b___GAG POLYPROTEIN PRECURSOR; MATRIX (P17)_b___b___b___b___b___b___b___b___>

  395    400    405    410    415   420    425    430   435    440    445   450    455    460   465
TTA GAT CAT TAT ATA ATA CAA TAG CAG TCC TCT ATT GTG TGC ATC AAA GGA TAG ATG TAA AAG ACA CCA AGG AAG CCT
AAT CTA GTA ATA TAT TAT GTT ATC GTC AGG AGA TAA CAC ACG TAG TTT CCT ATC TAC ATT TTC TGT GGT TCC TTC GGA
L   R   S   L   Y   N   T   I   A   V   L   Y   C   V   H   Q   R   I   D   V   K   D   T   K   E   A>
___b___b___b___b___b___b___b___GAG POLYPROTEIN PRECURSOR; MATRIX (P17)_b___b___b___b___b___b___b___b___>

470    475   480    485    490   495    500    505   510    515    520   525    530    535   540    545
TAG ATA AGA TAG AGG AAG AGC AAA ACA AAA GTA AGA AAA AGG CAC AGC AAG CAG CAG CTG ACA CAG GAA ACA ACA GCC
ATC TAT TCT ATC TCC TTC TCG TTT TGT TTT CAT TCT TTT TCC GTG TCG TTC GTC GTC GAC TGT GTC CTT TGT TGT CGG
L   D   K   I   E   E   E   Q   N   K   S   K   K   K   A   Q   Q   A   A   A   D   T   G   N   N   S>
___b___b___b___b___b___b___b___GAG POLYPROTEIN PRECURSOR; MATRIX (P17)_b___b___b___b___b___b___b___b___>

  550   555    560    565   570    575    580   585    590    595   600    605    610   615    620
AGG TCA GCC AAA ATT ACC CTA TAG TGC AGA ACC TCC AGG GGC AAA TGG TAC ATC AGG CCA TAT CAC CTA GAA CTT TAA
TCC AGT CGG TTT TAA TGG GAT ATC ACG TCT TGG AGG TCC CCG TTT ACC ATG TAG TCC GGT ATA GTG GAT CTT GAA ATT
Q   V   S   Q   N   Y   P   I   V   Q   N   L   Q   G   Q   M   V   H   Q   A   I   S   P   R   T   L>
___b___b___b___b___b___b___b___GAG POLYPROTEIN PRECURSOR; MATRIX (P17)_b___b___b___b___b___b___b___b___>

625   630    635    640   645    650    655   660    665    670   675    680    685   690    695    700
ATG CAT GGG TAA AAG TAG TAG AAG AGA AGG CTT TCA GCC CAG AAG TAA TAC CCA TGT TTT CAG CAT TAT CAG AAG GAG
TAC GTA CCC ATT TTC ATC ATC TTC TCT TCC GAA AGT CGG GTC TTC ATT ATG GGT ACA AAA GTC GTA ATA GTC TTC CTC
N   A   W   V   K   V   V   E   E   K   A   F   S   P   E   V   I   P   M   F   S   A   L   S   E   G>
___b___b___b___b___b___b___b___GAG POLYPROTEIN PRECURSOR; MATRIX (P17)_b___b___b___b___b___b___b___b___>

705    710    715   720    725    730   735    740    745   750    755    760   765    770    775   780
CCA CCC CAC AAG ATT TAA ATA CCA TGC TAA ACA CAG TGG GGG GAC ATC AAG CAG CCA TGC AAA TGT TAA AAG AGA CCA
GGT GGG GTG TTC TAA ATT TAT GGT ACG ATT TGT GTC ACC CCC CTG TAG TTC GTC GGT ACG TTT ACA ATT TTC TCT GGT
A   T   P   Q   D   L   N   T   M   L   N   T   V   G   G   H   Q   A   A   M   Q   M   L   K   E   T>
___b___b___b___b___b___b___b___GAG POLYPROTEIN PRECURSOR; MATRIX (P17)_b___b___b___b___b___b___b___b___>

   785    790   795    800    805   810    815    820   825    830    835   840    845    850   855
TCA ATC ACG AAG CTG CAG AAT GGG ATA GAT TGC ATC CAG TGC ATG CAG GGC CTA TTG CAC CAG GCC AGA TGA GAC AAC
AGT TAC TCC TTC GAC GTC TTA CCC TAT CTA ACG TAG GTC ACG TAC GTC CCG GAT AAC GTG GTC CGG TCT ACT CTC TTG
I   N   E   E   A   A   E   W   D   R   L   H   P   V   H   A   G   P   I   A   P   G   Q   M   R   E>
___b___b___b___b___b___b___b___GAG POLYPROTEIN PRECURSOR; MATRIX (P17)_b___b___b___b___b___b___b___b___>

860    865   870    875    880   885    890    895   900    905    910   915    920    925   930    935
CAA GGG GAA GTG ACA TAG CAG GAA CTA CTA GTA CCC TTC AGG AAC AAA TAG GAT GGA TGA CAC ATA ATC CAC CTA TCC
GTT CCC CTT CAC TGT ATC GTC CTT GAT GAT CAT GGG AAG TCC TTG TTT ATC CTA CCT ACT GTG TAT TAG GTG GAT AGG
P   R   G   S   D   I   A   G   T   T   S   T   L   Q   E   Q   I   G   W   M   T   H   N   P   P   I>
___b___b___b___b___b___b___b___GAG POLYPROTEIN PRECURSOR; MATRIX (P17)_b___b___b___b___b___b___b___b___>

  940   945    950    955   960    965    970   975    980    985   990    995   1000  1005   1010
CAG TAG GAG AAA TCT ATA AAA GAT GGA TAA TCC TGG GAT TAA ATA AAA TAG TAA GAA TGT ATA GCC CTA CCA GCA TTC
GTC ATC CTC TTT AGA TAT TTT CTA CCT ATT AGG ACC CTA ATT TAT TTT ATC ATT CTT ACA TAT CGG GAT GGT CGT AAG
P   V   G   E   I   Y   K   R   W   I   I   L   G   L   N   K   I   V   R   M   Y   S   P   T   S   I>
___b___b___b___b___b___b___b___GAG POLYPROTEIN PRECURSOR; MATRIX (P17)_b___b___b___b___b___b___b___b___>
```

Fig. 11: NL4.3 Sequence – Full Length with Chimeric p6, 17-26 (cont)

```
1015  1020   1025   1030  1035   1040   1045  1050   1055   1060  1065   1070   1075  1080   1085   1090
   TGG ACA TAA CAC AAG GAC CAA AGG AAC CCT TTA GAG ACT ATG TAG ACC GAT TCT ATA AAA CTC TAA GAG CCG ACC AAG
   ACC TGT ATT CTG TTC CTG GTT TCC TTG GGA AAT CTC TGA TAC ATC TGG CTA AGA TAT TTT GAG ATT CTC GGC TCG TTC
   L   D   I   R   Q   G   P   K   E   P   F   R   D   Y   V   D   R   F   Y   K   T   L   R   A   E   Q>
      b   b   b   b   b   b   b   GAG POLYPROTEIN PRECURSOR; MATRIX (P17) b   b   b   b   b   b   b   b   >

  1095   1100   1105  1110   1115   1120  1125   1130   1135  1140   1145   1150  1155   1160   1165  1170
   CTT CAC AAG AGG TAA AAA ATT GGA TGA CAG AAA CCT TGT TGG TCC AAA ATG CGA ACC CAG ATT GTA AGA CTA TTT TAA
   GAA GTG TTC TCC ATT TTT TAA CCT ACT GTC TTT GGA ACA ACC AGG TTT TAC GCT TGG GTC TAA CAT TCT GAT AAA ATT
   A   S   Q   E   V   K   N   W   M   T   E   T   L   L   V   Q   N   A   N   P   D   C   K   T   I   L>
   ___b___b___b___b___b___b___b___GAG POLYPROTEIN PRECURSOR; MATRIX (P17)_b___b___b___b___b___b___b___b___>

>conflict;_/replace=t
          |
     1175|  1180  1185   1190   1195  1200   1205   1210  1215   1220   1225  1230   1235   1240  1245
   AAG CAC TGG GAC CAG GAG CGA CAC TAG AAG AAA TGA TGA CAG CAT GTC AGG GAG TGG GGG GAC CCG GCC ATA AAG CAA
   TTC GTG ACC CTG GTC CTC GCT GTG ATC TTC TTT ACT ACT GTC GTA CAG TCC CTC ACC CCC CTG GGC CGG TAT TTC GTT
   K   A   L   G   P   G   A   T   L   E   E   M   M   T   A   C   Q   G   V   G   G   P   G   H   K   A>
   ___b___b___b___b___b___b___b___GAG POLYPROTEIN PRECURSOR; MATRIX (P17)_b___b___b___b___b___b___b___b___>

 1250   1255  1260   1265   1270  1275   1280   1285  1290   1295   1300  1305   1310   1315  1320   1325
   GAG TTT TGG CTG AAG CAA TGA GCC AAG TAA CAA ATC CAG CTA CCA TAA TGA TAC AGA AAG GCA ATT TTA GGA ACC AAA
   CTC AAA ACC GAC TTC GTT ACT CGG TTC ATT GTT TAG GTC GAT GGT ATT ACT ATG TCT TTC CGT TAA AAT CCT TGG TTT
   R   V   L   A   E   A   M   S   Q   V   T   N   P   A   T   I   M   I   Q   K   G   N   F   R   N   Q>
   ___b___b___b___b___b___b___b___GAG POLYPROTEIN PRECURSOR; MATRIX (P17)_b___b___b___b___b___b___b___b___>

    1330  1335   1340   1345  1350   1355   1360  1365   1370   1375  1380   1385   1390  1395   1400
   GAA AGA CTG TTA AGT GTT TCA ATT GTG GCA AAG AAG GGC ACA TAG CCA AAA ATT GCA GGG CCC CTA GGA AAA AGG GCT
   CTT TCT GAC AAT TCA CAA AGT TAA CAC CGT TTC TTC CCG TGT ATC GGT TTT TAA CGT CCC GGG GAT CCT TTT TCC CGA
   R   K   T   V   K   C   F   N   C   G   K   E   G   H   I   A   K   N   C   R   A   P   R   K   K   G>
      b   b   b   b   b   b   b   GAG POLYPROTEIN PRECURSOR; MATRIX (P17) b   b   b   b   b   b   b   b   >

                                                                                 >Gene:_pol
                                                                                      |
1405  1410   1415   1420  1425   1430   1435  1440   1445   1450  1455   1460   1465  1470   1475   1480
   GTT GGA AAT CTG GAA AGG AAG GAC ACC AAA TGA AAG ATT GTA CTG AGA GAC AGC CTA ATT TTT TAG GGA AGA TCT GGC
   CAA CCT TTA CAC CTT TCC TTC CTG TGG TTT ACT TTC TAA CAT GAC TCT CTG TCC GAT TAA AAA ATC CCT TCT AGA CCG
   C   W   K   C   G   K   E   G   H   Q   M   K   D   C   T   E   R   Q   A   N   F   L   G   K   I   W>
      b   b   b   b   b   b   b   GAG POLYPROTEIN PRECURSOR; MATRIX (P17) b   b   b   b   b   b   b   b   >
                                                                                      F   F   R   E   D   L   A>
                                                                                   ___POL POLYPROTEIN PRE____>

  1485   1490   1495  1500   1505   1510  1515   1520   1525  1530   1535   1540  1545   1550   1555  1560
   CTT CCC ACA AGG GAA GGC CAG GGA ATT TTC TTC AGA GCA GAC CAG ACC AAC CAC CCC CAC CAG AAG ACC CAG GTG TGG
   GAA GGG TGT TCC CTT CCG GTC CCT TAA AAG AAG TCT CGT CTG GTC TCG GTT GTC GGG GTG GTC TTC TGG GTC CAC ACC
   P   S   H   K   G   R   P   G   N   F   L   Q   S   R   P   E   P   T   A   P   P   E   D   P   A   V>
   ___b___b___b___b___b___b___b___GAG POLYPROTEIN PRECURSOR; MATRIX (P17)_b___b___b___b___b___b___b___b___>
     F   P   Q   G   K   A   R   E   F   S   S   E   Q   T   R   A   N   S   P   T   R   R   E   L   Q   V>
   ___c___c___c___c___c___c___c___c_POL POLYPROTEIN PRECURSOR; PROTEASE___c___c___c___c___c___c___c___c___>

                                       >conflict;_/replace=a
                                                 |
     1565   1570  1575   1580   1585  1590 | 1595   1600  1605   1610   1615  1620   1625   1630  1635
   ATC TGC TAA AGA ACT ACA TGC AGT CTC AGA GGC AGG AGC CGA TAG ACA AGG AAC TGT ATC CTT TAG CTT CCC TCA GAT
   TAG ACG ATT TCT TGA TGT ACG TCA GAG TCT CCG TCC TCG GCT ATC TGT TCC TTG ACA TAG GAA ATC GAA GGG AGT CTA
   D   L   L   K   N   Y   M   Q   S   Q   R   Q   E   P   I   D   K   E   L   Y   P   L   A   S   L   R>
   ___b___b___b___b___b___b___b___GAG POLYPROTEIN PRECURSOR; MATRIX (P17)_b___b___b___b___b___b___b___b___>
     W   G   R   D   N   N   S   L   S   E   A   G   A   D   R   Q   G   T   V   S   F   S   F   P   Q   I>
   ___c___c___c___c___c___c___c___c_POL POLYPROTEIN PRECURSOR; PROTEASE___c___c___c___c___c___c___c___c___>

 1640   1645  1650   1655   1660  1665   1670   1675  1680   1685   1690  1695   1700   1705  1710   1715
   CAC TCT TTG GCA GCG ACC CCT CGT CAC AAT AAA GAT AGG GGG GCA ATT AAA GGA AGC TCT ATT AGA TAC AGG AGC AGA
   GTG AGA AAC CGT CGC TGG GGA GCA GTG TTA TTT CTA TCC CCC CGT TAA TTT CCT TCG AGA TAA TCT ATG TCC TCG TCT
   S   L   F   G   S   D   P   S   S   Q   *>
   ___GAG POLYPROTEIN PRECURSOR; MATRIX (_b__>
     T   L   W   Q   R   P   L   V   T   I   K   I   G   G   Q   L   K   E   A   L   L   D   T   G   A   D>
   ___c___c___c___c___c___c___c___c_POL POLYPROTEIN PRECURSOR; PROTEASE___c___c___c___c___c___c___c___c___>

    1720  1725   1730   1735  1740   1745   1750  1755   1760   1765  1770   1775   1780  1785   1790
   TGA TAC AGT ATT AGA ACA AAT GAA TTT GCC ACG AAG ATC CAA ACC AAA AAT GAT AGG GGG AAT TGG AGG TTT TAT CAA
   ACT ATG TCA TAA TCT TCT TTA CTT AAA CGG TCC TTC TAC CTT TGG TTT TTA CTA TCC CCC TTA ACC TCC AAA ATA GTT
     D   T   V   L   E   E   M   N   L   P   G   R   W   K   P   K   M   I   G   G   I   G   G   F   I   K>
      c   c   c   c   c   c   c   c POL POLYPROTEIN PRECURSOR; PROTEASE   c   c   c   c   c   c   c   c   >

>conflict;_/replace=g
          |
 1795  1800   1805   1810  1815   1820   1825  1830   1835   1840  1845   1850   1855  1860   1865   1870
   AGT AAG ACA GTA TGA TCA GAT ACT CAT AGA AAT CTG CGG ACA TAA ACC TAT AGG TAC ACT ATT AGT AGG ACC TAC ACC
   TCA TTC TGT CAT ACT AGT CTA TGA GTA TCT TTA GAC GCC TGT ATT TCG ATA TCC ATG TCA TAA TCA TCC TGG ATG TGG
     V   R   Q   Y   D   Q   I   L   I   E   I   C   G   H   K   A   I   G   T   V   L   V   G   P   T   P>
      c   c   c   c   c   c   c   c POL POLYPROTEIN PRECURSOR; PROTEASE   c   c   c   c   c   c   c   c   >
```

Fig. 11: NL4.3 Sequence – Full Length with Chimeric p6, 17-26 (cont)

```
 1875   1880   1885  1890   1895   1900  1905   1910   1915  1920   1925   1930  1935   1940   1945  1950
  TGT CAA CAT AAT TGG AAG AAA TCT GTT GAC TCA GAT TGG CTG CAC TTT AAA TTT TCC CAT TAG TCC TAT TGA GAC TGT
  ACA GTT GTA TTA ACC TTC TTT AGA CAA CTG AGT CTA ACC GAC GTG AAA TTT AAA AGG GTA ATC AGG ATA ACT CTG ACA
    V   N   I   I   G   R   N   L   L   T   Q   I   G   C   T   L   N   F   P   I   S   P   I   E   T   V>
  ___c___c___c___c___c___c___c___c_POL POLYPROTEIN PRECURSOR; PROTEASE___c___c___c___c___c___c___c___c___>

    1955   1960  1965   1970   1975  1980   1985   1990  1995   2000   2005  2010   2015   2020  2025
  ACC AGT AAA ATT AAA GCC AGG AAT GGA TGG CCC AAA AGT TAA ACA ATG GCC ATT GAC AGA AGA AAA AAT AAA AGC ATT
  TGG TCA TTT TAA TTT CGG TCC TTA CCT ACC CGC TTT TCA ATT TGT TAC CGG TAA CTG TCT TCT TTT TTA TTT TCG TAA
    P   V   K   L   K   P   G   M   D   G   P   K   V   K   Q   W   P   L   T   E   E   K   I   K   A   L>
  ___c___c___c___c___c___c___c___c_POL POLYPROTEIN PRECURSOR; PROTEASE___c___c___c___c___c___c___c___c___>

2030   2035  2040   2045   2050  2055   2060   2065  2070   2075   2080  2085   2090   2095  2100   2105
  AGT AGA AAT TTG TAC AGA AAT GGA AAA GGA AGG AAA AAT TTC AAA AAT TGG GCC TGA AAA TCC ATA CAA TAC TCC AGT
  TCA TCT TTA AAC ATG TCT TTA CCT TTT CCT TCC TTT TTA AAG TTT TTA ACC CGG ACT TTT AGG TAT GTT ATG AGG TCA
    V   E   I   C   T   E   M   E   K   E   G   K   I   S   K   I   G   P   E   N   P   Y   N   T   P   V>
  ___c___c___c___c___c___c___c___c_POL POLYPROTEIN PRECURSOR; PROTEASE___c___c___c___c___c___c___c___c___>

   2110  2115   2120   2125  2130   2135   2140  2145   2150   2155  2160   2165   2170  2175   2180
  ATT TCC CAT AAA GAA AAA AGA CAG TAC TAA ATC GAG AAA ATT AGT AGA TTT CAG AGA ACT TAA TAA GAG AAC TCA AGA
  TAA ACG GTA TTT CTT TTT TCT GTC ATG ATT TAC CTC TTT TAA TCA TCT AAA GTC TCT TGA ATT ATT CTC TTG AGT TCT
    F   A   I   K   K   K   D   S   T   K   W   R   K   L   V   D   F   R   E   L   N   K   R   T   Q   D>
  ___c___c___c___c___c___c___c___c_POL POLYPROTEIN PRECURSOR; PROTEASE___c___c___c___c___c___c___c___c___>

2185  2190   2195   2200  2205   2210   2215  2220   2225   2230  2235   2240   2245  2250   2255   2260
  TTT CTC GCA AGT TCA ATT AGG AAT ACC ACA TCC TCC AGG GTT AAA ACA GAA AAA ATC AGT AAC AGT ACT GGA TGT GGG
  AAA GAC CCT TCA AGT TAA TCC TTA TGG TGT AGG ACG TCC CAA TTT TGT CTT TTT TAG TCA TTG TCA TGA CCT ACA CCC
    F   W   E   V   Q   L   G   I   P   H   P   A   G   L   K   Q   K   K   S   V   T   V   L   D   V   G>
  ___c___c___c___c___c___c___c___c_POL POLYPROTEIN PRECURSOR; PROTEASE___c___c___c___c___c___c___c___c___>

 2265   2270   2275  2280   2285   2290  2295   2300   2305  2310   2315   2320  2325   2330   2335  2340
  CGA TCC ATA TTT TTC AGT TCC CTT AGA TAA AGA CTT CAG GAA GTA TAC TGC ATT TAC CAT ACC TAG TAT AAA CAA TGA
  GCT ACG TAT AAA AAG TCA AGG GAA TCT ATT TCT GAA GTC CTT CAT ATG ACG TAA ATG GTA TGG ATC ATA TTT GTT ACT
    D   A   Y   F   S   V   P   L   D   K   D   F   R   K   Y   T   A   F   T   I   P   S   I   N   N   E>
  ___c___c___c___c___c___c___c___c_POL POLYPROTEIN PRECURSOR; PROTEASE___c___c___c___c___c___c___c___c___>

    2345   2350  2355   2360   2365  2370   2375   2380  2385   2390   2395  2400   2405   2410  2415
  GAC ACC AGG GAT TAG ATA TCA GTA CAA TGT GCT TCC ACA GGG ATG GAA AGG ATC ACC AGC AAT ATT CCA GTG TAG CAT
  CTG TGG TCC CTA ATC TAT AGT CAT GTT ACA CGA AGG TGT CCC TAC CTT TCC TAG TGG TCG TTA TAA GGT CAC ATC GTA
    T   P   G   I   R   Y   Q   Y   N   V   L   P   Q   G   W   K   G   S   P   A   I   F   Q   C   S   M>
  ___c___c___c___c___c___c___c___c_POL POLYPROTEIN PRECURSOR; PROTEASE___c___c___c___c___c___c___c___c___>

                                                    >conflict;_/replace=a
                                                                |
2420   2425  2430   2435   2440  2445   2450   2455  2460   2465   2470  2475   2480   2485  2490   2495
  GAC AAA AAT CTT AGA GCC TTT TAG AAA ACA AAA TCC AGA CGT AGT CAT CTA TCA ATA CAT GGA TGA TTT GTA TGT AGG
  CTG TTT TTA GAA TCT CGG AAA ATC TTT TGT TTT AGG TCT GCA TCA GTA GAT AGT TAT GTA CCT ACT AAA CAT ACA TCC
    T   K   I   L   E   P   F   R   K   Q   N   P   D   V   V   I   Y   Q   Y   M   D   D   L   Y   V   G>
  ___c___c___c___c___c___c___c___c_POL POLYPROTEIN PRECURSOR; PROTEASE___c___c___c___c___c___c___c___c___>

   2500  2505   2510   2515  2520   2525   2530  2535   2540   2545  2550   2555   2560  2565   2570
  ATC TGA CTT AGA AAT AGG GCA GCA TAG AAC AAA AAT AGA GGA ACT GAG ACA ACA TCT GTT GAG GTG GGG ATT TAC CAC
  TAG ACT GAA TCT TTA TCC CGT CGT ATC TTG TTT TTA TCT CCT TGA CTC TGT TGT AGA CAA CTC CAC CCC TAA ATG GTG
    S   D   L   E   I   G   Q   H   R   T   K   I   E   E   L   R   Q   H   L   L   R   W   G   F   T   T>
  ___c___c___c___c___c___c___c___c_POL POLYPROTEIN PRECURSOR; PROTEASE___c___c___c___c___c___c___c___c___>

2575  2580   2585   2590  2595   2600   2605  2610   2615   2620  2625   2630   2635  2640   2645   2650
  ACC AGA CAA AAA ACA TCA GAA AGA ACC TCC ATT CCT TTG GAT GGG TTA TGA ACT CCA TCC TGA TAA ATG GAC AGT ACA
  TGG TCT GTT TTT TGT AGT CTT TCT TGG AGG TAA GGA AAC CTA CCC AAT ACT TGA GGT AGG ACT ATT TAC CTG TCA TGT
    P   D   K   K   H   Q   K   E   P   P   F   L   W   M   G   Y   E   L   H   P   D   K   W   T   V   Q>
  ___c___c___c___c___c___c___c___c_POL POLYPROTEIN PRECURSOR; PROTEASE___c___c___c___c___c___c___c___c___>

 2655   2660   2665  2670   2675   2680  2685   2690   2695  2700   2705   2710  2715   2720   2725  2730
  GCC TAT AGT GCT GCC AGA AAA GGA CAG CTG GAC TGT CAA TGA CAT ACA GAA ATT AGT GGG AAA ATT GAA TTG GGC AAG
  CGG ATA TCA CGA CGG TCT TTT CCT GTC GAC CTG ACA GTT ACT GTA TGT CTT TAA TCA CCC TTT TAA CTT AAC CCG TTC
    P   I   V   L   P   E   K   D   S   W   T   V   N   D   I   Q   K   L   V   G   K   L   N   W   A   S>
  ___c___c___c___c___c___c___c___c_POL POLYPROTEIN PRECURSOR; PROTEASE___c___c___c___c___c___c___c___c___>

    2735   2740  2745   2750   2755  2760   2765   2770  2775   2780   2785  2790   2795   2800  2805
  TCA GAT TTA TGC AGG GAT TAA AGT AAG GCA ATT ATG TAA ACT TCT TAG GGG AAC CAA AGC ACT AAC AGA AGT AGT ACC
  AGT CTA AAT ACG TCC CTA ATT TCA TTC CGT TAA TAC ATT TGA AGA ATC CCC TTG GTT TCG TGA TTG TCT TCA TCA TGG
    Q   I   Y   A   G   I   K   V   R   Q   L   C   K   L   L   R   G   T   K   A   L   T   E   V   V   P>
  ___c___c___c___c___c___c___c___c_POL POLYPROTEIN PRECURSOR; PROTEASE___c___c___c___c___c___c___c___c___>

2810   2815  2820   2825   2830  2835   2840   2845  2850   2855   2860  2865   2870   2875  2880   2885
  ACT AAC AGA AGA AGC AGA GCT AGA ACT GGC AGA AAA CAG GGA GAT TCT AAA AGA ACC GGT ACA TGG AGT GTA TTA TGA
  TGA TTG TCT TCT TCG TCT CGA TCT TGA CCG TCT TTT GTC CCT CTA AGA TTT TCT TGG CCA TGT ACC TCA CAT AAT ACT
    L   T   E   E   A   E   L   E   L   A   E   N   R   E   I   L   K   E   P   V   H   G   V   Y   Y   D>
  ___c___c___c___c___c___c___c___c_POL POLYPROTEIN PRECURSOR; PROTEASE___c___c___c___c___c___c___c___c___>
```

Fig. 11: NL4.3 Sequence – Full Length with Chimeric p6, 17-26 (cont)

```
  2890  2895   2900   2905  2910   2915   2920  2925   2930   2935  2940   2945   2950  2955   2960
  CCC ATC AAA AGA CTT AAT AGC AGA AAT ACA GAA CCA GGG GCA AGG CCA ATC GAC ATA TCA AAT TTA TCA AGA GCC ATT
  GGG TAG TTT TCT GAA TTA TCG TCT TTA TGT CTT GGT CCC CGT TCC GGT TAG CTG TAT AGT TTA AAT AGT TCT CGG TAA
    P   S   K   D   L   I   A   E   I   Q   K   Q   G   Q   G   Q   W   T   Y   Q   I   Y   Q   E   P   F>
  ___c___c___c___c___c___c___c___c_POL POLYPROTEIN PRECURSOR; PROTEASE___c___c___c___c___c___c___c___c___>

                       >conflict;_/replace=a
                                 |
2965  2970   2975   2980  2985 | 2990   2995  3000   3005   3010  3015   3020   3025  3030   3035   3040
  TAG AAA TCT GAA AAC AGG AAA GTA TGC AAG AAT GAA GGG TGC CCA CAC TAA TGA TGT GAA ACA ATT AAC AGA GGC AGT
  ATC TTT AGA CTT TTG TCC TTT CAT ACG TTC TTA CTT CCC ACG GGT GTG ATT ACT ACA CTT TGT TAA TTG TCT CCG TCA
    R   N   L   K   T   G   K   Y   A   R   M   K   G   A   H   T   N   D   V   K   Q   L   T   E   A   V>
  ___c___c___c___c___c___c___c___c_POL POLYPROTEIN PRECURSOR; PROTEASE___c___c___c___c___c___c___c___c___>

 3045   3050   3055  3060   3065   3070  3075   3080   3085  3090   3095   3100  3105   3110   3115  3120
  ACA AAA AAT AGC CAC AGA AAG CAT AGT AAT ATG GGG AAA GAC TCC TAA ATT TAA ATT ACC CAT ACA AAA GGA AAC ATG
  TGT TTT TTA TCG GTG TCT TTC GTA TCA TTA TAC CCC TTT CTG AGG ATT TAA ATT TAA TGG GTA TGT TTT CCT TTG TAC
    Q   K   I   A   T   E   S   I   V   I   W   G   K   T   P   K   F   K   L   P   I   Q   K   E   T   W>
  ___c___c___c___c___c___c___c___c_POL POLYPROTEIN PRECURSOR; PROTEASE___c___c___c___c___c___c___c___c___>

   3125   3130  3135   3140   3145  3150   3155   3160  3165   3170   3175  3180   3185   3190  3195
  GGA AGC ATG GTG GAC AGA GTA TTG GCA AGC CAC CTG GAT TCC TGA GTG GGA GTT TGT CAA TAC CCC TCC CTT ACT GAA
  CCT TCG TAC CAC CTG TCT CAT AAC CGT TCC GTG CAC CTA AGG ACT CAC CCT CAA ACA GTT ATG GGG AGG GAA TCA CTT
    E   A   W   W   T   E   Y   W   Q   A   T   W   I   P   E   W   E   F   V   N   T   P   P   L   V   K>
  ___c___c___c___c___c___c___c___c_POL POLYPROTEIN PRECURSOR; PROTEASE___c___c___c___c___c___c___c___c___>

 3200   3205  3210   3215   3220  3225   3230   3235  3240   3245   3250  3255   3260   3265  3270   3275
  GTT ATG GTA CCA GTT AGA GAA AGA ACC CAT AAT AGG AGC AGA AAC TTT CTA TGT AGA TGG GGC AGC CAA TAG GGA AAC
  CAA TAC CAT GGT CAA TCT CTT TCT TGG GTA TTA TCC TCG TCT TTG AAA GAT ACA TCT ACC CCG TCG GTT ATC CCT TTG
    L   W   Y   Q   L   E   K   E   P   I   I   G   A   E   T   F   Y   V   D   G   A   A   N   R   E   T>
  ___c___c___c___c___c___c___c___c_POL POLYPROTEIN PRECURSOR; PROTEASE___c___c___c___c___c___c___c___c___>

  3280  3285   3290   3295  3300   3305   3310  3315   3320   3325  3330   3335   3340  3345   3350
  TAA ATT AGG AAA AGC AGG ATA TGT AAC TGA CAG AGG AAG ACA AAA AGT TGT CCC CCT AAC GGA CAC AAC AAA TCA GAA
  ATT TAA TCC TTT TCG TCC TAT ACA TTG ACT GTC TCC TTC TGT TTT TCA ACA GGG GGA TTG CCT GTG TTG TTT AGT CTT
    K   L   G   K   A   G   Y   V   T   D   R   G   R   Q   K   V   V   P   L   T   D   T   T   N   Q   K>
  ___c___c___c___c___c___c___c___c_POL POLYPROTEIN PRECURSOR; PROTEASE___c___c___c___c___c___c___c___c___>

3355  3360   3365   3370  3375   3380   3385  3390   3395   3400  3405   3410   3415  3420   3425   3430
  GAC TGA GTT ACA AGC AAT TCA TCT AGC TTT GCA GGA TTC GGG ATT AGA AGT AAA CAT AGT GAC AGA CTC ACA ATA TGC
  CTG ACT CAA TGT TCG TTA AGT AGA TCG AAA CGT CCT AAG CCC TAA TCT TCA TTT GTA TCA CTG TCT GAG TGT TAT ACG
    T   E   L   Q   A   I   H   L   A   L   Q   D   S   G   L   E   V   N   I   V   T   D   S   Q   Y   A>
  ___c___c___c___c___c___c___c___c_POL POLYPROTEIN PRECURSOR; PROTEASE___c___c___c___c___c___c___c___c___>

 3435   3440   3445  3450   3455   3460  3465   3470   3475  3480   3485   3490  3495   3500   3505  3510
  ATT GGG AAT CAT TCA AGC ACA ACC AGA TAA GAG TGA ATC AGA GTT AGT CAG TCA AAT AAT AGA GCA GTT AAT AAA AAA
  TAA CCC TTA GTA AGT TCG TGT TGG TCT ATT CTC ACT TAG TCT CAA TCA GTC AGT TTA TTA TCT CGT CAA TTA TTT TTT
    L   G   I   I   Q   A   Q   P   D   K   S   E   S   E   L   V   S   Q   I   I   E   Q   L   I   K   K>
  ___c___c___c___c___c___c___c___c_POL POLYPROTEIN PRECURSOR; PROTEASE___c___c___c___c___c___c___c___c___>

                                                                               >conflict; /replace=g
                                                                                            :
                                                                            >conflict; /replace=g
                                                                                          | :
                                                                          >conflict;_/replace=g
                                                                                         || :
   3515   3520  3525   3530   3535  3540   3545   3550  3555   3560   3565  3570   3575| :3580  3585
  GGA AAA AGT CTA CCT GGC ATG GGT ACC AGC ACA CAA AGG AAT TGG AGG AAA TGA ACA AGT AGA TAA ATT GGT CAG TGC
  CCT TTT TCA GAT GGA CCG TAC CCA TGG TCG TGT GTT TCC TTA ACC TCC TTT ACT TGT TCA TCT ATT TAA CCA GTC ACG
    E   K   V   Y   L   A   W   V   P   A   H   K   G   I   G   G   N   E   Q   V   D   K   L   V   S   A>
  ___c___c___c___c___c___c___c___c_POL POLYPROTEIN PRECURSOR; PROTEASE___c___c___c___c___c___c___c___c___>

 3590   3595  3600   3605   3610  3615   3620   3625  3630   3635   3640  3645   3650   3655  3660   3665
  TGG AAT CAG GAA AGT ACT ATT TTT AGA TGG AAT AGA TAA GGC CCA AGA AGA ACA TGA GAA ATA TCA CAG TAA TTG GAG
  ACC TTA GTC CTT TCA TGA TAA AAA TCT ACC TTA TCT ATT CCG GGT TCT TCT TGT ACT CTT TAT AGT GTC ATT AAC CTC
    G   I   R   K   V   L   F   L   D   G   I   D   K   A   Q   E   E   H   E   K   Y   H   S   N   W   R>
  ___c___c___c___c___c___c___c___c_POL POLYPROTEIN PRECURSOR; PROTEASE___c___c___c___c___c___c___c___c___>

  3670  3675   3680   3685  3690   3695   3700  3705   3710   3715  3720   3725   3730  3735   3740
  AGC AAT GGC TAG TGA TTT TAA CCT ACC ACC TGT AGT AGC AAA AGA AAT AGT AGC CAG CTG TGA TAA ATG TCA GCT AAA
  TCG TTA CCG ATC ACT AAA ATT GGA TGG TGG ACA TCA TCG TTT TCT TTA TCA TCG GTC GAC ACT ATT TAC AGT CGA TTT
    A   M   A   S   D   F   N   L   P   P   V   V   A   K   E   I   V   A   S   C   D   K   C   Q   L   K>
  ___c___c___c___c___c___c___c___c_POL POLYPROTEIN PRECURSOR; PROTEASE___c___c___c___c___c___c___c___c___>

3745  3750   3755   3760  3765   3770   3775  3780   3785   3790  3795   3800   3805  3810   3815   3820
  AGG GGA AGC CAT GCA TGG ACA AGT AGA CTG TAG CCC AGG AAT ATG GCA GCT ACA TTG TAC ACA TTT AGA AGG AAA AGT
  TCC CCT TCG GTA CGT ACC TGT TCA TCT GAC ATC GGG TCC TTA TAC CGT CGA TGT AAC ATG TGT AAA TCT TCC TTT TCA
    G   E   A   M   H   G   Q   V   D   C   S   P   G   I   W   Q   L   D   C   T   H   L   E   G   K   V>
  ___c___c___c___c___c___c___c___c_POL POLYPROTEIN PRECURSOR; PROTEASE___c___c___c___c___c___c___c___c___>

      >conflict;_/replace=a
```

Fig. 11: NL4.3 Sequence – Full Length with Chimeric p6, 17-26 (cont)

```
                |
3825   3830   |3835  3840   3845   3850  3855   3860   3865  3870   3875   3880  3885   3890   3895  3900
 TAT CTT GGT GGC AGT TCA TGT AGC CAG TGG ATA TAT AGA AGC AGA AGT AAT TCC AGC AGA GAC AGG GCA AGA AAC AGC
 ATA GAA CCA CCG TCA AGT ACA TCG GTC ACC TAT ATA TCT TCG TCT TCA TTA AGG TCG TCT CTG TCC CGT TCT TTG TCG
  I   L   V   A   V   H   V   A   S   G   Y   I   E   A   E   V   I   P   A   E   T   G   Q   E   T   A>
 ___c___c___c___c___c___c___c___c_POL POLYPROTEIN PRECURSOR; PROTEASE___c___c___c___c___c___c___c___c___>

  3905   3910  3915   3920   3925  3930   3935   3940  3945   3950   3955  3960   3965   3970  3975
 ATA CTT CCT CTT AAA ATT AGC AGG AAG ATG GCC AGT AAA AAC AGT ACA TAC AGA CAA TGG CAG CAA TTT CAC CAG TAC
 TAT GAA GGA GAA TTT TAA TCG TCC TTC TAC CGG TCA TTT TTG TCA TGT ATG TCT GTT ACC GTC GTT AAA GTG GTC ATG
  Y   F   L   L   K   L   A   G   R   W   P   V   K   T   V   H   T   D   N   G   S   N   F   T   S   T>
 ___c___c___c___c___c___c___c___c_POL POLYPROTEIN PRECURSOR; PROTEASE___c___c___c___c___c___c___c___c___>

                                   >conflict;_/replace=a
                                              |
3980   3985  3990   3995   4000  4005   4010   4015  4020   4025   4030  4035   4040   4045  4050   4055
 TAC AGT TAA GGC CGC CTG TTG GTG GGC GGG AAT CAA GCA GGA ATT TGG CAT TCC CTA CAA TCC CCA AAG TCA AGG AGT
 ATG TCA ATT CCG GCG GAC AAC CAC CCG CCC TTA GTT CGT CCT TAA ACC GTA AGG GAT GTT AGG GGT TTC AGT TCC TCA
  T   V   K   A   A   C   W   W   A   G   I   K   Q   E   F   G   I   P   Y   N   P   Q   S   Q   G   V>
    c   c   c   c   c   c   c   c POL POLYPROTEIN PRECURSOR; PROTEASE   c   c   c   c   c   c   c   c   >

  4060  4065   4070   4075  4080   4085   4090  4095   4100   4105  4110   4115   4120  4125   4130
 AAT AGA ATC TAT GAA TAA AGA ATT AAA GAA AAT TAT AGG ACA GGT AAG AGA TCA GGC TGA ACA TCT TAA CAC AGC AGT
 TTA TCT TAG ATA CTT ATT TCT TAA TTT CTT TTA ATA TCC TGT CCA TTC TCT AGT CCG ACT TGT AGA ATT CTG TCG TCA
  I   E   S   M   N   K   E   L   K   K   I   I   G   Q   V   R   D   Q   A   E   H   L   K   T   A   V>
 ___c___c___c___c___c___c___c___c_POL POLYPROTEIN PRECURSOR; PROTEASE___c___c___c___c___c___c___c___c___>

4135  4140   4145   4150  4155   4160   4165  4170   4175   4180  4185   4190   4195  4200   4205   4210
 ACA AAT GGC AGT ATT CAT CCA CAA TTT TAA AAG AAA AGG GGG GAT TGG GGG GTA CAG TGC AGG GGA AAG AAT AGT AGA
 TGT TTA CCG TCA TAA GTA GGT GTT AAA ATT TTC TTT TCC CCC CTA ACC CCC CAT GTC ACG TCC CCT TTC TTA TCA TCT
  Q   M   A   V   F   I   H   N   F   K   R   K   G   G   I   G   G   Y   S   A   G   E   R   I   V   D>
 ___c___c___c___c___c___c___c___c_POL POLYPROTEIN PRECURSOR; PROTEASE___c___c___c___c___c___c___c___c___>

 4215   4220   4225  4230   4235   4240  4245   4250   4255  4260   4265   4270  4275   4280   4285  4290
 CAT AAT AGC AAC AGA CAT ACA AAC TAA AGA ATT ACA AAA ACA AAT TAC AAA AAT TCA AAA TTT TCG GGT TTA TTA CAG
 GTA TTA TCG TTG TCT GTA TGT TTG ATT TCT TAA TGT TTT TGT TTA ATG TTT TTA AGT TTT AAA AGC CCA AAT AAT GTC
  I   I   A   T   D   I   Q   T   K   E   L   Q   K   Q   I   T   K   I   Q   N   F   R   V   Y   Y   R>
 ___c___c___c___c___c___c___c___c_POL POLYPROTEIN PRECURSOR; PROTEASE___c___c___c___c___c___c___c___c___>

  4295   4300  4305   4310   4315  4320   4325   4330  4335   4340   4345  4350   4355   4360  4365
 GGA CAG CAG AGA TCC AGT TTG GAA AGG ACC AGC AAA GCT CCT CTG GAA AGG TGA AGG GGC AGT AGT AAT ACA AGA TAA
 CCT GTC GTC TCT AGG TCA AAC CTT TCC TGG TCG TTT CGA GGA GAC CTT TCC ACT TCC CCG TCA TCA TTA TGT TCT ATT
  D   S   R   D   P   V   W   K   G   P   A   K   L   L   W   K   G   E   G   A   V   V   I   Q   D   N>
 ___c___c___c___c___c___c___c___c_POL POLYPROTEIN PRECURSOR; PROTEASE___c___c___c___c___c___c___c___c___>

                                                                      >Gene: vif
                                                                           |
4370   4375  4380   4385   4390  4395   4400   4405  4410   4415   4420  4425   4430   4435  4440   4445
 TAC TGA CAT AAA AGT AGT GCC AAG AAG AAA ACC AAA GAT CAT CAG GGA TTA TGG AAA ACA GAT GGC AGG TGA TGA TTG
 ATG ACT GTA TTT TCA TCA CGG TTC TTC TTT TGG TTT CTA GTA GTC CCT AAT ACC TTT TGT CTA CCG TCC ACT ACT AAC
  S   D   I   K   V   V   P   R   R   K   A   K   I   I   R   D   Y   G   K   Q   M   A   G   D   D   C>
 ___c___c___c___c___c___c___c___c_POL POLYPROTEIN PRECURSOR; PROTEASE___c___c___c___c___c___c___c___c___>
                                                                           M   E   N   R   W   Q   V   M   I>
                                                                         _d___d___d__VIF PROTEIN__d___d___d___>

  4450  4455   4460   4465  4470   4475   4480  4485   4490   4495  4500   4505   4510  4515   4520
 TGT GGC AAG TAG ACA GGA TGA GGA TTA ACA CAT GGA AAA GAT TAG TAA AAC ACC ATA TGT ATA TTT CAA GGA AAG CTA
 ACA CCG TTC ATC TGT CCT ACT CCT AAT TGT GTA CCT TTT CTA ATC ATT TTG TGG TAT ACA TAT AAA GTT CCT TTC GAT
  V   A   S   R   Q   D   E   D   *>
   POL POLYPROTEIN PRECURSOR; PRO  c >
 V   W   Q   V   D   R   M   R   I   N   T   W   K   R   L   V   K   H   H   M   Y   I   S   R   K   A>
 ___d___d___d___d___d___d___d___d___d___d___d_VIF PROTEIN___d___d___d___d___d___d___d___d___d___d___d___>

4525  4530   4535   4540  4545   4550   4555  4560   4565   4570  4575   4580   4585  4590   4595   4600
 AGG ACT GGT TTT ATA GAC ATC ACT ATG AAA GTA CTA ATC CAA AAA TAA GTT CAG AAG TAC ACA TCC CAC TAG GGG ATG
 TCC TGA CCA AAA TAT CTG TAG TGA TAC TTT CAT GAT TAG GTT TTT ATT CAA GTC TTC ATG TGT AGG GTG ATC CCC TAC
 K   D   W   F   Y   R   H   H   Y   E   S   T   N   P   K   I   S   S   E   V   H   I   P   L   G   D>
 ___d___d___d___d___d___d___d___d___d___d___d_VIF PROTEIN___d___d___d___d___d___d___d___d___d___d___d___>

 4605   4610   4615  4620   4625   4630  4635   4640   4645  4650   4655   4660  4665   4670   4675  4680
 CTA AAT TAG TAA TAA CAA CAT ATT GGG GTC TGC ATA CAG GAG AAA GAG ACT GGC ATT TGG GTC AGG GAG TCT CCA TAG
 GAT TTA ATC ATT ATT GTT GTA TAA CCC CAG ACG TAT GTC CTC TTT CTC TGA CCG TAA ACC CAG TCC CTC AGA GGT ATC
 A   K   L   V   I   T   T   Y   W   G   L   H   T   G   E   R   D   W   H   L   G   Q   G   V   S   I>
 ___d___d___d___d___d___d___d___d___d___d___d_VIF PROTEIN___d___d___d___d___d___d___d___d___d___d___d___>

  4685   4690  4695   4700   4705  4710   4715   4720  4725   4730   4735  4740   4745   4750  4755
 AAT GGA GGA AAA AGA GAT ATA GCA CAC AAG TAG ACC CTG ACC TAG CAG ACC AAC TAA TTC ATC TGC ACT ATT TTG ATT
 TTA CCT CCT TTT TCT CTA TAT CGT GTG TTC ATC TGG GAC TGG ATC GTC TGG TTG ATT AAG TAG ACG TGA TAA AAC TAA
 E   W   R   K   K   R   Y   S   T   Q   V   D   P   D   L   A   D   Q   L   I   H   L   H   Y   F   D>
 ___d___d___d___d___d___d___d___d___d___d___d_VIF PROTEIN___d___d___d___d___d___d___d___d___d___d___d___>
```

Fig. 11: NL4.3 Sequence – Full Length with Chimeric p6, 17-26 (cont)

```
4760   4765  4770   4775   4780  4785   4790   4795  4800   4805   4810  4815   4820   4825  4830   4835
   GTT TTT CAG AAT CTG CTA TAA GAA ATA CCA TAT TAG GAC GTA TAG TTA GTC CTA GGT GTG AAT ATC AAG CAG GAC ATA
   CAA AAA GTC TTA GAC GAT ATT CTT TAT GGT ATA ATC CTG CAT ATC AAT CAG GAT CCA CAC TTA TAG TTC GTC CTG TAT
   C   F   S   E   S   A   I   R   N   T   I   L   G   R   I   V   S   P   R   C   E   Y   Q   A   G   E>
   ___d___d___d___d___d___d___d___d___d___d___d_VIF PROTEIN___d___d___d___d___d___d___d___d___d___d___d___>

    4840  4845   4850   4855  4860   4865   4870  4875   4880   4885  4890   4895   4900  4905   4910
   ACA AGG TAG GAT CTC TAC AGT ACT TGG CAC TAG CAG CAT TAA TAA AAC CAA AAC AGA TAA AGC CAC CTT TGC CTA GTG
   TGT TCC ATC CTA GAG ATG TCA TGA ACC GTG ATC GTC GTA ATT ATT TTG GTT TTG TCT ATT TCG GTG GAA ACG GAT CAC
   N   K   V   G   S   L   Q   Y   L   A   L   A   A   L   I   K   P   K   Q   I   K   P   P   L   P   S>
   ___d___d___d___d___d___d___d___d___d___d___d_VIF PROTEIN___d___d___d___d___d___d___d___d___d___d___d___>

                              >Gene:_vpr                                              >conflict;_/replace-t
                                 |                                                        |
4915  4920   4925   4930  4935  |4940   4945  4950   4955   4960  4965   4970   4975  4980 | 4985   4990
   TTA GGA AAC TGA CAG AGG ACA GAT GGA ACA AGC CCC AGA AGA CCA AGG GCC ACA GAG GGA GCC ATA CAA CGA ATG GAC
   AAT CCT TTG ACT GTC TCC TGT CTA CCT TGT TCG GGG TCT TCT GGT TCC CGG TGT CTC CCT CGG TAT GTT GCT TAC CTG
   V   R   K   L   T   E   D   R   W   N   K   P   Q   K   T   K   G   F   R   G   S   H   T   T   N   G>
      d   d   d   d   d   d   d   d   d   d   d VIF PROTEIN   d   d   d   d   d   d   d   d   d   d   d   >
                                   M   E   Q   A   P   E   D   Q   G   P   Q   R   E   P   Y   N   E   W   T>
                                  __e___e___e___e___e___e___e____VPR PROTEIN____e___e___e___e___e___e___e___>

>conflict; /replace-a
                                                                                                        |
  4995   5000   5005  5010   5015   5020  5025   5030   5035  5040   5045   5050  5055   5060   5065 |5070
   ACT AGA GCT TTT AGA GGA ACT TAA GAG TGA AGC TGT TAG ACA TTT TCC TAG GAT ATG GCT CCA TAA CTT AGG ACG ACA
   TGA TCT CGA AAA TCT CCT TGA ATT CTC ACT TCG ACA ATC TGT AAA AGG ATC CTA TAC CGA GGT ATT GAA TCC TGC TGT
   H   *>
   ___d__>
     L   F   L   L   E   E   L   K   S   E   A   V   R   H   F   P   R   I   W   L   H   N   L   G   R   H>
      e   e   e   e   e   e   e   e   e   e   e VPR PROTEIN   e   e   e   e   e   e   e   e   e   e   e   >

                                                                                  >conflict;_/replace=c
                                                                                           |
     5075   5080  5085   5090   5095  5100   5105   5110  5115   5120   5125  5130   5135   5140  5145
   TAT CTA TGA AAC TTA CGG GGA TAC TTG GGC AGG AGT GGA AGC CAT AAT AAG AAT TCT GCA ACA ACT GCC GTT TAT CCA
   ATA GAT ACT TTG AAT GCC CCT ATG AAC CCG TCC TCA CCT TCG GTA TTA TTC TTA AGA CGT TGT TGA CGG CAA ATA GGT
     I   Y   E   T   Y   G   D   T   W   A   G   V   E   A   I   I   R   I   L   Q   Q   L   P   F   I   H>
   ___e___e___e___e___e___e___e___e___e___e___e_VPR PROTEIN___e___e___e___e___e___e___e___e___e___e___e___>

                                                                             >Gene: tat
                                                                                |
5150   5155  5160   5165   5170  5175   5180   5185  5190   5195   5200  5205   5210   5215  5220   5225
   TTT CAG AAT TGG GTG TCG ACA TAG CAG AAT AGG CGT TAC TCG ACA GAG GAG AGC AAG AAA TGG AGC CAG TAG ATC CTA
   AAA GTC TTA ACC CAC AGC TGT ATC GTC TTA TCC GCA ATG AGC TGT CTC CTC TCG TTC TTT ACC TCG GTC ATC TAG GAT
     F   R   I   G   C   R   H   S   R   I   G   V   T   R   Q   R   R   A   R   N   G   A   S   R   S   *>
   ___e___e___e___e___e___e___e___e___e___e___e_VPR PROTEIN___e___e___e___e___e___e___e___e___e___e___e___>
                                                                                  M   E   P   V   D   P>
                                                                                 _f_TAT PROTEIN; /FUNC____>

    5230  5235   5240   5245  5250   5255   5260  5265   5270   5275  5280   5285   5290  5295   5300
   GAC TAC AGC CCT GGA AGC ATC CAG GAA GTC AGC CTA AAA CTG CTT GTA CCA ATT CCT ATT GTA AAA AGT GTT GCT TTC
   CTG ATC TCG GGA CCT TCG TAG GTC CTT CAG TCG GAT TTT GAC GAA CAT GGT TAA CGA TAA CAT TTT TCA CAA CGA AAG
   _>
   R   L   E   P   W   K   H   P   G   S   Q   P   K   T   A   C   T   N   C   Y   C   K   K   C   C   F>
      f   f   f   f   f   f   f    TAT PROTEIN; /FUNCTION-TRANSACTIVATOR  f   f   f   f   f   f   f   f   >

                                                       >Gene:_rev
                                                          |
5305  5310   5315   5320  5325   5330   5335  5340   5345  |5350  5355   5360   5365  5370   5375   5380
   ATT GCC AAG TTT GTT TCA TGA CAA AAG CCT TAG GCA TCT CCT ATG GCA GGA AGA AGC GGA GAC AGC GAC GAA GAG CTC
   TAA CCC TTC AAA CAA AGT ACT GTT TTC GCA ATC CGT AGA GGA TAC CGT CCT TCT TCG CCT CTG TCG CTG CTT CTC GAC
   H   C   Q   V   C   F   M   T   K   A   L   G   I   S   Y   G   R   K   K   R   R   Q   R   R   R   A>
   ___f___f___f___f___f___f___f____TAT PROTEIN; /FUNCTION=TRANSACTIVATOR__f___f___f___f___f___f___f___f___>
                                                           M   A   G   R   S   G   D   S   D   E   E   L>
                                                             REV PROTEIN; /FUNCTION-REGULATOR OF VIRA    >

                                                                          >Gene:_vpu
                                                                              |
  5385   5390   5395  5400   5405   5410  5415   5420   5425  5430   5435   5440  5445   5450   5455  5460
   ATC AGA ACA GTC AGA CTC ATC AAG CTT CTC TAT CAA AGC AGT AAG TAG TAC ATG TAA TGC AAC CTA TAA TAG TAG CAA
   TAG TCT TGT CAG TCT GAG TAG TTC GAA GAC ATA GTT TCG TCA TTC ATC ATG TAC ATT ACG TTG GAT ATT ATC ATC GTT
   H   Q   N   S   Q   T   H   Q   A   S   L   S   K   Q>
   ___f___TAT PROTEIN; /FUNCTION=TRANSACTIVATOR___f___f_>
    T   R   T   V   R   L   I   K   L   L   Y   Q   S   N>
      REV PROTEIN; /FUNCTION-REGULATOR OF VIRAL EXPR  g >
                                                                             M   Q   P   I   I   V   A>
                                                                            _h___h__VPU PROTEIN__h___h___>

     5465   5470  5475   5480   5485  5490   5495   5500  5505   5510   5515  5520   5525   5530  5535
```

Fig. 11: NL4.3 Sequence – Full Length with Chimeric p6, 17-26 (cont)

```
    TAC TAG CAT TAG TAG TAC CAA TAA TAA TAG CAA TAG TTG TGT GGT CCA TAC TAA TCA TAG AAT ATA GGA AAA TAT TAA
    ATC ATC GTA ATC ATC ATC GTT ATT ATT ATC GTT ATC AAC ACA CCA CCT ATC ATT ACT ATC TTA TAT CCT TTT ATA ATT
    I   V   A   L   V   V   A   I   I   I   A   I   V   V   W   S   I   V   I   I   E   Y   R   K   I   L>
    ___h___h___h___h___h___h___h___h___h___h___h_VPU PROTEIN___h___h___h___h___h___h___h___h___h___h___h___>

                                                                                   >Gene:_env
                                                                                       |
5540   5545  5550   5555   5560  5565   5570   5575  5580   5585   5590  5595   5600   5605  5610   5615
    GAC AAA GAA AAA TAG ACA GGT TAA TTG ATA GAC TAA TAG AAA GAG CAG AAG ACA GTG GCA ATG AGA GTG AAG GAG AAG
    CTG TTT CTT TTT ATC TGT CCA ATT AAC TAT CTG ATT ATC TTT CTC GTC TTC TGT CAC CGT TAC TCT CAC TTC CTC TTC
    R   Q   R   K   I   D   R   L   I   D   R   L   I   E   R   A   E   D   S   G   N   E   S   E   G   E>
    ___h___h___h___h___h___h___h___h___h___h___h_VPU PROTEIN___h___h___h___h___h___h___h___h___h___h___h___>
                                                                                    M   R   V   K   E   K>
                                                                                   ___ENV POLYPROTEIN ____>

     5620  5625   5630   5635  5640   5645   5650  5655   5660   5665  5670   5675   5680  5685   5690
    TAT CAG CAC TTG TGG AGA TGG GGG TGG AAA TGG GGC ACC ATG CTC CTT GGG ATA TTG ATG ATC TGT AGT GCT ACA GAA
    ATA GTC GTG AAC ACC TCT ACC CCC ACC TTT ACC CCG TGG TAC GAG GAA CCC TAT AAC TAC TAG ACA TCA CGA TGT CTT
    V   S   A   L   V   E   M   G   V   E   M   G   H   H   A   P   W   D   I   D   D   L   *>
       h   h   h   h   h   h   h   h   h   VPU PROTEIN h   h   h   h   h   h   h   h   h   h  >
      Y   Q   H   L   W   R   W   G   W   K   W   G   T   M   L   L   G   I   L   M   I   C   S   A   T   E>
    ___i___i___i___i___i___i___i___i___ENV POLYPROTEIN PRECURSOR; GP120____i___i___i___i___i___i___i___i___>

5695  5700   5705   5710  5715   5720   5725  5730   5735   5740  5745   5750   5755  5760   5765   5770
    AAA TTG TGG GTC ACA GTC TAT TAT GGG GTA CCT GTG TGG AAG GAA GCA ACC ACC ACT CTA TTT TGT GCA TCA GAT GCT
    TTT AAC ACC CAG TGT CAG ATA ATA CCC CAT GGA CAC ACC TTC CTT CGT TGG TGG TGA GAT AAA ACA CGT AGT CTA CGA
      K   L   W   V   T   V   Y   Y   G   V   P   V   W   K   E   A   T   T   T   L   F   C   A   S   D   A>
    ___i___i___i___i___i___i___i___i___ENV POLYPROTEIN PRECURSOR; GP120____i___i___i___i___i___i___i___i___>

  5775   5780   5785  5790   5795   5800  5805   5810   5815  5820   5825   5830  5835   5840   5845  5850
    AAA GCA TAT GAT ACA GAG GTA CAT AAT GTT TGG GCC ACA CAT GCC TGT GTA CCC ACA GAC CCC AAC CCA CAA GAA GTA
    TTT CGT ATA CTA TGT CTC CAT GTA TTA CAA ACC CGG TGT GTA CGG ACA CAT GGG TGT CTG GGG TTG GGT GTT CTT CAT
      K   A   Y   D   T   E   V   H   N   V   W   A   T   H   A   C   V   P   T   D   P   N   P   Q   E   V>
    ___i___i___i___i___i___i___i___i___ENV POLYPROTEIN PRECURSOR; GP120____i___i___i___i___i___i___i___i___>

                                                  >conflict;_/replace=g
                                                          |
     5855   5860  5865   5870   5875  5880   5885   5890  5895   5900   5905  5910   5915   5920  5925
    GTA TTG GTA AAT GTG ACA GAA AAT TTT AAC ATG TGG AAA GAT GAC ATG GTA GAA CAG ATG CAT GAG GAT ATA ATC AGT
    CAT AAC CAT TTA CAC TGT CTT TTA AAA TTG TAC ACC TTT CTA CTG TAC CAT CTT GTC TAC GTA CTC CTA TAT TAG TCA
      V   L   V   N   V   T   E   N   F   N   M   W   K   D   D   M   V   E   Q   M   H   E   D   I   I   S>
    ___i___i___i___i___i___i___i___i___ENV POLYPROTEIN PRECURSOR; GP120____i___i___i___i___i___i___i___i___>

5930   5935  5940   5945   5950  5955   5960   5965  5970   5975   5980  5985   5990   5995  6000   6005
    TTA TGG GAT CAA AGC CTA AAG CCA TGT GTA AAA TTA ACC CCA CTC TGT GTT AGT TTA AAG TGC ACT GAT TTG AAG AAT
    AAT ACC CTA GTT TCG GAT TTC GGT ACA CAT TTT AAT TGG GGT GAG ACA CAA TCA AAT TTC ACG TGA CTA AAC TTC TTA
      L   W   D   Q   S   L   K   P   C   V   K   L   T   P   L   C   V   S   L   K   C   T   D   L   K   N>
        i   i   i   i   i   i   i   i   ENV POLYPROTEIN PRECURSOR; GP120    i   i   i   i   i   i   i   i   >

     6010  6015   6020   6025  6030   6035   6040  6045   6050   6055  6060   6065   6070  6075   6080
    GAT ACT AAT ACC AAT AGT AGT AGC GGG AGA ATG ATA ATG GAG AAA GGA GAG ATA AAA AAC TGC TCT TTC AAT ATC AGC
    CTA TGA TTA TGG TTA TCA TCA TCG CCC TCT TAC TAT TAC CTC TTT CCT CTC TAT TTT TTG ACG AGA AAG TTA TAG TCG
      D   T   N   T   N   S   S   S   G   R   M   I   M   E   K   G   E   I   K   N   C   S   F   N   I   S>
    ___i___i___i___i___i___i___i___i___ENV POLYPROTEIN PRECURSOR; GP120____i___i___i___i___i___i___i___i___>

6085  6090   6095   6100  6105   6110   6115  6120   6125   6130  6135   6140   6145  6150   6155   6160
    ACA AGC ATA AGA CAT AAC GTG CAG AAA GAA TAT GCA TTC TTT TAT AAA CTT GAT ATA GTA CCA ATA GAT AAT ACC AGC
    TGT TCG TAT TCT GTA TTG CAC GTC TTT CTT ATA CGT AAG AAA ATA TTT GAA CTA TAT CAT GGT TAT CTA TTA TGG TCG
      T   S   I   R   D   K   V   Q   K   E   Y   A   F   F   Y   K   L   D   I   V   P   I   D   N   T   S>
    ___i___i___i___i___i___i___i___i___ENV POLYPROTEIN PRECURSOR; GP120____i___i___i___i___i___i___i___i___>

>conflict;_/replace=t
                                                                                                      |
  6165   6170   6175  6180   6185   6190  6195   6200   6205  6210   6215   6220  6225   6230   6235  6240
    TAT AGG TTG ATA AGT TGT AAC ACC TCA GTC ATT ACA CAG GCC TGT CCA AAG GTA TCC TTT GAG CCA ATC CCC ATA CAT
    ATA TCC AAC TAT TCA ACA TTG TGG AGT CAG TAA TGT GTC CGG ACA GGT TTC CAT AGG AAA CTC GGT TAG GGG TAT GTA
      Y   R   L   I   S   C   N   T   S   V   I   T   Q   A   C   P   K   V   S   F   E   P   I   P   I   H>
    ___i___i___i___i___i___i___i___i___ENV POLYPROTEIN PRECURSOR; GP120____i___i___i___i___i___i___i___i___>

     6245   6250  6255   6260   6265  6270   6275   6280  6285   6290   6295  6300   6305   6310  6315
    TAT TGT GCC CCG GCT GGT TTT GCG ATT CTA AAA TGT AAT AAT AAG ACG TTC AAT GGA ACA GGA CCA TGT ACA AAT GTC
    ATA ACA CGG GGC CGA CCA AAA CGC TAA GAT TTT ACA TTA TTA TTC TGC AAG TTA CCT TGT CCT GGT ACA TGT TTA CAG
      Y   C   A   P   A   G   F   A   I   L   K   C   N   N   K   T   F   N   G   T   G   P   C   T   N   V>
        i   i   i   i   i   i   i   i   ENV POLYPROTEIN PRECURSOR; GP120    i   i   i   i   i   i   i   i   >

6320   6325  6330   6335   6340  6345   6350   6355  6360   6365   6370  6375   6380   6385  6390   6395
    AGC ACA GTA CAA TGT ACA CAT GGA ATC AGG CCA GTA GTA TCA ACT CAA CTG CTG TTA AAT GGC AGT CTA GCA GAA GAA
    TCG TGT CAT GTT ACA TGT GTA CCT TAG TCC GGT CAT CAT AGT TGA GTT GAC GAC AAT TTA CCG TCA GAT CGT CTT CTT
      S   T   V   Q   C   T   H   G   I   R   P   V   V   S   T   Q   L   L   L   N   G   S   L   A   E   E>
        i   i   i   i   i   i   i   i   ENV POLYPROTEIN PRECURSOR; GP120    i   i   i   i   i   i   i   i   >
```

Fig. 11: NL4.3 Sequence – Full Length with Chimeric p6, 17-26 (cont)

```
  6400  6405   6410   6415  6420   6425   6430  6435   6440   6445  6450   6455   6460  6465   6470
 GAT GTA GTA ATT AGA TCT GCC AAT TTC ACA GAC AAT GCT AAA ACC ATA ATA GTA CAG CTG AAC ACA TCT GTA GAA ATT
 CTA CAT CAT TAA TCT AGA CGG TTA AAG TGT CTG TTA CGA TTT TGG TAT TAT CAT GTC GAC TTG TGT AGA CAT CTT TAA
  D   V   V   I   R   S   A   N   F   T   D   N   A   K   T   I   I   V   Q   L   N   T   S   V   E   I>
 ___i___i___i___i___i___i___i___i___ENV POLYPROTEIN PRECURSOR; GP120____i___i___i___i___i___i___i___i___>

6475  6480   6485   6490  6495   6500   6505  6510   6515   6520  6525   6530   6535  6540   6545   6550
 AAT TGT ACA AGA CCC AAC AAC AAT ACA AGA AAA AGT ATC CGT ATC CAG AGG GGA CCA GGG AGA GCA TTT GTT ACA ATA
 TTA ACA TGT TCT GGG TTG TTG TTA TGT TCT TTT TCA TAC CCA TAG GTC TCC CCT GGT CCC TCT CGT AAA CAA TGT TAT
  N   C   T   R   P   N   N   N   T   R   K   S   I   R   I   Q   R   G   P   G   R   A   F   V   T   I>
 ___i___i___i___i___i___i___i___i___ENV POLYPROTEIN PRECURSOR; GP120____i___i___i___i___i___i___i___i___>

  6555   6560   6565  6570   6575   6580  6585   6590   6595  6600   6605   6610  6615   6620   6625  6630
 GGA AAA ATA GGA AAT ATG AGA CAA GCA CAT TGT AAC ATT ACT AGA GCA AAA TGG AAT GCC ACT TTA AAA CAG ATA GCT
 CCT TTT TAT CCT TTA TAC TCT GTT CGT GTA ACA TTG TAA TCA TCT CGT TTT ACC TTA CGG TGA AAT TTT GTC TAT CGA
  G   K   I   G   N   M   R   Q   A   H   C   N   I   S   R   A   K   W   N   A   T   L   K   Q   I   A>
    i   i   i   i   i   i   i   i   ENV POLYPROTEIN PRECURSOR; GP120    i   i   i   i   i   i   i   i   >

   6635   6640  6645   6650   6655  6660   6665   6670  6675   6680   6685  6690   6695   6700  6705
 AGC AAA TTA AGA GAA CAA TTT GGA AAT AAT AAA ACA ATA ATC TTT AAG CAA TCC TCA GGA GGG GAC CCA GAA ATT GTA
 TCG TTT AAT TCT CTT GTT AAA CCT TTA TTA TTT TGT TAT TAG AAA TTC GTT AGG AGT CCT CCC CTG GGT CTT TAA CAT
  S   K   L   R   E   Q   F   G   N   N   K   T   I   I   F   K   Q   S   S   G   G   D   P   E   I   V>
 ___i___i___i___i___i___i___i___i___ENV POLYPROTEIN PRECURSOR; GP120____i___i___i___i___i___i___i___i___>

 6710   6715  6720   6725   6730  6735   6740   6745  6750   6755   6760  6765   6770   6775  6780   6785
 ACG CAC AGT TTT AAT TGT GGA GGG GAA TTT TTC TAC TGT AAT TCA ACA CAA CTG TTT AAT AGT ACT TGG TTT AAT AGT
 TGC GTG TCA AAA TTA ACA CCT CCC CTT AAA AAG ATG ACA TTA AGT TGT GTT GAC AAA TTA TCA TGA ACC AAA TTA TCA
  T   H   S   F   N   C   G   G   E   F   F   Y   C   N   S   T   Q   L   F   N   S   T   W   F   N   S>
 ___i___i___i___i___i___i___i___i___ENV POLYPROTEIN PRECURSOR; GP120____i___i___i___i___i___i___i___i___>

  6790  6795   6800   6805  6810   6815   6820  6825   6830   6835  6840   6845   6850  6855   6860
 ACT TGG AGT ACT GAA GGG TCA AAT AAC ACT GAA GGA AGT GAC ACA ATC ACA CTC CCA TGC AGA ATA AAA CAA TTT ATA
 TCA ACC TCA TGA CTT CCC AGT TTA TTG TGA CTT CCT TCA CTG TGT TAG TGT GAG GGT ACG TCT TAT TTT GTT AAA TAT
  T   W   S   T   E   G   S   N   N   T   E   G   S   D   T   I   T   L   P   C   R   I   K   Q   F   I>
 ___i___i___i___i___i___i___i___i___ENV POLYPROTEIN PRECURSOR; GP120____i___i___i___i___i___i___i___i___>

6865  6870   6875   6880  6885   6890   6895  6900   6905   6910  6915   6920   6925  6930   6935   6940
 AAC ATG TGG CAG GAA GTA GGA AAA GCA ATG TAT GCC CCT CCC ATC AGT GGA CAA ATT AGA TGT TCA TCA AAT ATT ACT
 TTG TAC ACC GTC CTT CAT CCT TTT CGT TAC ATA CGG GGA GGG TAG TCA CCT GTT TAA TCT ACA AGT AGT TTA TAA TGA
  N   M   W   Q   E   V   G   K   A   M   Y   A   P   P   I   S   G   Q   I   R   C   S   S   N   I   T>
 ___i___i___i___i___i___i___i___i___ENV POLYPROTEIN PRECURSOR; GP120____i___i___i___i___i___i___i___i___>

  6945   6950   6955  6960   6965   6970  6975   6980   6985  6990   6995   7000  7005   7010   7015  7020
 GGG CTG CTA TTA ACA AGA GAT GGT GGT AAT AAC AAC AAT GGG TCC GAG ATC TTC AGA CCT GGA GGA GGC GAT ATG AGG
 CCC GAC GAT AAT TGT TCT CTA CCA CCA TTA TTG TTG TTA CCC AGG CTC TAG AAG TCT GGA CCT CCT CCG CTA TAC TCC
  G   L   L   L   T   R   D   G   G   N   N   N   N   G   S   E   I   F   R   P   G   G   G   D   M   R>
 ___i___i___i___i___i___i___i___i___ENV POLYPROTEIN PRECURSOR; GP120____i___i___i___i___i___i___i___i___>

   7025   7030  7035   7040   7045  7050   7055   7060  7065   7070   7075  7080   7085   7090  7095
 GAC AAT TGG AGA AGT GAA TTA TAT AAA TAT AAA GTA GTA AAA ATT GAA CCA TTA GGA GTA GCA CCC ACC AAG GCA AAG
 CTG TTA ACC TCT TCA CTT AAT ATA TTT ATA TTT CAT CAT TTT TAA CTT GGT AAT CCT CAT CGT GGG TGG TTC CGT TTC
  D   N   W   R   S   E   L   Y   K   Y   K   V   V   K   I   E   P   L   G   V   A   P   T   K   A   K>
 ___i___i___i___i___i___i___i___i___ENV POLYPROTEIN PRECURSOR; GP120____i___i___i___i___i___i___i___i___>

 7100   7105  7110   7115   7120  7125   7130   7135  7140   7145   7150  7155   7160   7165  7170   7175
 AGA AGA GTG GTG CAG AGA GAA AAA AGA GCA GTG GGA ATA GGA GCT TTG TTC CTT GGG TTC TTG GGA GCA GCA GGA AGC
 TCT TCT CAC CAC GTC TCT CTT TTT TCT CGT CAC CCT TAT CCT CGA AAC AAG GAA CCC AAG AAC CCT CGT CGT CCT TCG
  R   R   V   V   Q   R   E   K   R   A   V   G   I   G   A   L   F   L   G   F   L   G   A   A   G   S>
    i   i   i   i   i   i   i   i   ENV POLYPROTEIN PRECURSOR; GP120    i   i   i   i   i   i   i   i   >

>conflict;_This_base_is_deleted_in_the_original_1986_NL4-
3_sequence,_however_there_is_a_T_insertion_3_bases_upstream_whi
                                      |
>conflict;_This_base_is_deleted_in_the_sequence_reported_in_this_entry,_but_an_insertion_3_base_downstream_restores_
the_
                                |     |
  7180  7185 | 7190   7195  7200   7205   7210  7215   7220   7225  7230   7235   7240  7245   7250
 ACT ATG GGC GCA GCG TCA ATG ACG CTG ACG GTA CAG GCC AGA CAA TTA TTG TCT GAT ATA GTG CAG CAG CAG AAC AAT
 TGA TAC CCG CGT CGC AGT TAC TGC GAC TGC CAT GTC CGG TCT GTT AAT AAC AGA CTA TAT CAC GTC GTC GTC TTG TTA
  T   M   G   A   A   S   M   T   L   T   V   Q   A   R   Q   L   L   S   D   I   V   Q   Q   Q   N   N>
 ___i___i___i___i___i___i___i___i___ENV POLYPROTEIN PRECURSOR; GP120____i___i___i___i___i___i___i___i___>

7255  7260   7265   7270  7275   7280   7285  7290   7295   7300  7305   7310   7315  7320   7325   7330
 TTG CTG AGG GCT ATT GAG GCG CAA CAG CAT CTG TTG CAA CTC ACA GTC TGG GGC ATC AAA CAG CTC CAG GCA AGA ATC
 AAC GAC TCC CGA TAA CTC CGC GTT GTC GTA GAC AAC GTT GAG TGT CAG ACC CCG TAG TTT GTC GAG GTC CGT TCT TAG
  L   L   R   A   I   E   A   Q   Q   H   L   L   Q   L   T   V   W   G   I   K   Q   L   Q   A   R   I>
    i   i   i   i   i   i   i   i   ENV POLYPROTEIN PRECURSOR; GP120    i   i   i   i   i   i   i   i   >

  7335   7340   7345  7350   7355   7360  7365   7370   7375  7380   7385   7390  7395   7400   7405  7410
 CTG GCT GTG GAA AGA TAC CTA AAG GAT CAA CAG CTC CTG GGG ATT TGG GGT TGC TCT GGA AAA CTC ATT TGC ACC ACT
```

Fig. 11: NL4.3 Sequence – Full Length with Chimeric p6, 17-26 (cont)

```
 GAC CGA CAC CTT TCT ATG GAT TTC CTA GTT GTC GAG GAC CCC TAA ACC CCA ACG AGA CCT TTT GAG TAA ACG TGG TGA
  L   A   V   E   R   Y   L   K   D   Q   Q   L   L   C   T   W   G   C   S   G   K   L   I   C   T   T>
 ___i___i___i___i___i___i___i___i___ENV POLYPROTEIN PRECURSOR; GP120____i___i___i___i___i___i___i___i___>

   7415   7420  7425   7430   7435  7440   7445   7450  7455   7460   7465  7470   7475   7480  7485
 GCT GTG CCT TGG AAT GCT AGT TGG AGT AAT AAA TCT CTG GAA CAG ATT TGG AAT AAC ATG ACC TGG ATG GAG TGG GAC
 CGA CAC GGA ACC TTA CGA TCA ACC TCA TTA TTT AGA GAC CTT GTC TAA ACC TTA TTG TAC TGG ACC TAC CTC ACC CTG
  A   V   P   W   N   A   S   W   S   N   K   S   L   E   Q   I   W   N   N   M   T   W   M   E   W   D>
    i   i   i   i   i   i   i   i   ENV POLYPROTEIN PRECURSOR; GP120    i   i   i   i   i   i   i   i   >

7490   7495  7500   7505   7510  7515   7520   7525  7530   7535   7540  7545   7550   7555  7560   7565
 AGA GAA ATT AAC AAT TAC ACA AGC TTA ATA CAC TCC TTA ATT GAA GAA TCG CAA AAC CAG CAA GAA AAG AAT GAA CAA
 TCT CTT TAA TTG TTA ATG TGT TCG AAT TAT GTG AGG AAT TAA CTT CTT AGC GTT TTG GTC GTT CTT TTC TTA CTT GTT
  R   E   I   N   N   Y   T   S   L   I   H   S   L   I   E   E   S   Q   N   Q   Q   E   K   N   E   Q>
 ___i___i___i___i___i___i___i___i___ENV POLYPROTEIN PRECURSOR; GP120____i___i___i___i___i___i___i___i___>

   7570  7575   7580   7585  7590   7595   7600  7605   7610   7615  7620   7625   7630  7635   7640
 GAA TTA TTG GAA TTA GAT AAA TGG GCA AGT TTG TGG AAT TGG TTT AAC ATA ACA AAT TGG CTG TGG TAT ATA AAA TTA
 CTT AAT AAC CTT AAT CTA TTT ACC CGT TCA AAC ACC TTA ACC AAA TTG TAT TGT TTA ACC GAC ACC ATA TAT TTT AAT
  E   L   L   E   L   D   K   W   A   S   L   W   N   W   F   N   I   T   N   W   L   W   Y   I   K   L>
    i   i   i   i   i   i   i   i   ENV POLYPROTEIN PRECURSOR; GP120    i   i   i   i   i   i   i   i   >

7645  7650   7655   7660  7665   7670   7675  7680   7685   7690  7695   7700   7705  7710   7715   7720
 TTC ATA ATG ATA GTA GGA GGC TTG GTA GGT TTA AGA ATA GTT TTT GCT GTA CTT TCT ATA GTG AAT AGA GTT AGG CAG
 AAG TAT TAC TAT CAT CCT CCG AAC CAT CCA AAT TCT TAT CAA AAA CGA CAT GAA AGA TAT CAC TTA TCT CAA TCC GTC
  F   I   M   I   V   G   G   L   V   G   L   R   I   V   F   A   V   L   S   I   V   N   R   V   R   Q>
 ___i___i___i___i___i___i___i___i___ENV POLYPROTEIN PRECURSOR; GP120____i___i___i___i___i___i___i___i___>

  7725   7730   7735  7740   7745   7750  7755   7760   7765  7770   7775   7780  7785   7790   7795  7800
 GGA TAT TCA CCA TTA TCG TTT CAG ACC CAC CTC CCA ATC CCG AGG GGA CCC GAC AGG CCC GAA GGA ATA GAA GAA GAA
 CCT ATA AGT GGT AAT AGC AAA GTC TGG GTG GAG GGT TAG GGC TCC CCT GGG CTG TCC GGG CTT CCT TAT CTT CTT CTT
                                      P   T   S   Q   S   R   G   D   P   T   G   P   K   E   *>
                                   __f___f____TAT PROTEIN; /FUNCTION=TRANSACTIVATOR__f___f___f_>
                                        P   P   P   N   P   E   G   T   R   Q   A   R   R   N   R   R   R>
                                     _g___g__REV PROTEIN; /FUNCTION-REGULATOR OF VIRAL EXPRESSION_g___g___>
  G   Y   S   P   L   S   F   Q   T   H   L   P   I   P   R   G   P   D   R   P   E   G   I   E   E   E>
 ___i___i___i___i___i___i___i___i___ENV POLYPROTEIN PRECURSOR; GP120____i___i___i___i___i___i___i___i___>

        >conflict;_/replace=a
                   |
   7805   7810  7815   7820   7825  7830   7835   7840  7845   7850   7855  7860   7865   7870  7875
 GGT GGA GAG AGA GGC AGA GAC AGA TCC ATT CGA TTA GTG AAC GGA TCC TTA GCA CTT ATC TGG GAC GAT CTG CGG AGC
 CCA CCT CTC TCT CCG TCT CTG TCT AGG TAA GCT AAT CAC TTG CCT AGG AAT CGT GAA TAG ACC CTG CTA GAC GCC TCG
 R   W   R   E   R   Q   R   Q   I   H   S   I   S   E   R   I   L   S   T   Y   L   G   R   S   A   E>
 ___g___g___g___g___g___g_REV PROTEIN; /FUNCTION=REGULATOR OF VIRAL EXPRESSION__g___g___g___g___g___g___>
  G   G   E   R   G   R   D   R   S   I   R   L   V   N   G   S   L   A   L   I   W   D   D   L   R   S>
    i   i   i   i   i   i   i   i   ENV POLYPROTEIN PRECURSOR; GP120    i   i   i   i   i   i   i   i   >

7880   7885  7890   7895   7900  7905   7910   7915  7920   7925   7930  7935   7940   7945  7950   7955
 CTG TGC CTC TTC AGC TAC CAC CGC TTG AGA GAC TTA CTC TTG ATT GTA ACG AGG ATT GTG GAA CTT CTG GGA CGC AGG
 GAC ACG GAG AAG TCG ATG GTG GCG AAC TCT CTG AAT GAG AAC TAA CAT TGC TCC TAA CAC CTT GAA GAC CCT GCG TCC
 P   V   P   L   Q   L   P   P   L   E   R   L   T   L   D   C   N   E   D   C   G   T   S   G   T   Q>
 ___g___g___g___g___g___g_REV PROTEIN; /FUNCTION-REGULATOR OF VIRAL EXPRESSION__g___g___g___g___g___g___>
  L   C   L   F   S   Y   H   R   L   R   D   L   L   L   I   V   T   R   I   V   E   L   L   G   R   R>
 ___i___i___i___i___i___i___i___i___ENV POLYPROTEIN PRECURSOR; GP120____i___i___i___i___i___i___i___i___>

   7960  7965   7970   7975  7980   7985   7990  7995   8000   8005  8010   8015   8020  8025   8030
 GGG TGG GAA GCC CTC AAA TAT TGG TGG AAT CTC CTA CAG TAT TGG AGT CAG GAA CTA AAG AAT AGT GCT GTT AAC TTG
 CCC ACC CTT CGG GAG TTT ATA ACC ACC TTA GAG GAT GTC ATA ACC TCA GTC CTT GAT TTC TTA TCA CGA CAA TTG AAC
 G   V   G   S   P   Q   I   L   V   E   S   P   T   V   L   E   S   G   T   K   E   *>
 ___g___g___g____REV PROTEIN; /FUNCTION-REGULATOR OF VIRAL EXPRESSION___g___g___g___g__>
  G   W   E   A   L   K   Y   W   W   N   L   L   Q   Y   W   S   Q   E   L   K   N   S   A   V   N   L>
 ___i___i___i___i___i___i___i___i___ENV POLYPROTEIN PRECURSOR; GP120____i___i___i___i___i___i___i___i___>

8035  8040   8045   8050  8055   8060   8065  8070   8075   8080  8085   8090   8095  8100   8105   8110
 CTC AAT GCC ACA GCC ATA GCA GTA GCT GAC GCG ACA GAT ACG GTT ATA GAA GTA TTA CAA GCA GCT TAT AGA GCT ATT
 GAG TTA CGG TGT CGG TAT CGT CAT CGA CTC CCC TGT CTA TCC CAA TAT CTT CAT AAT GTT CGT CGA ATA TCT CGA TAA
  L   N   A   T   A   I   A   V   A   E   G   T   D   R   V   I   E   V   L   Q   A   A   Y   R   A   I>
 ___i___i___i___i___i___i___i___i___ENV POLYPROTEIN PRECURSOR; GP120____i___i___i___i___i___i___i___i___>

                                                                         >Gene:_nef
                                                                              |
  8115   8120   8125  8130   8135   8140  8145   8150   8155  8160   8165   8170  8175   8180   8185  8190
 CGC CAC ATA CCT AGA AGA ATA AGA CAG GGC TTG GAA AGG ATT TTG CTA TAA GAT GGG TGG CAA GTG GTC AAA AAG TAG
 GCG GTG TAT GGA TCT TCT TAT TCT GTC CCG AAC CTT TCC TAA AAC GAT ATT CTA CCC ACC GTT CAC CAG TTT TTC ATC
  R   H   I   P   R   R   I   R   Q   G   L   E   R   I   L   L   *>
 ___i___i___i___i_ENV POLYPROTEIN PRECURSOR; GP120__i___i___i___i___>
                                                                          M   G   G   K   W   S   K   S   S>
                                                                        __j___j____NEF PROTEIN____j___j___>

    8195   8200  8205   8210   8215  8220   8225   8230  8235   8240   8245  8250   8255   8260  8265
```

Fig. 11: NL4.3 Sequence – Full Length with Chimeric p6, 17-26 (cont)

```
     TGT GAT TGG ATG GCC TGC TGT AAG GGA AAG AAT GAG ACG AGC TGA GCC AGC AGC AGA TGG GGT GGG AGC AGT ATC TCG
     ACA CTA ACC TAC CGG ACG ACA TTC CCT TTC TTA CTC TGC TCG ACT CGG TCG TCG TCT ACC CCA CCC TCG TCA TAG AGC
      V   I   G   W   P   A   V   R   E   R   M   R   R   A   E   P   A   A   D   G   V   G   A   V   S   R>
     ___j___j___j___j___j___j___j___j___j___j___j_NEF PROTEIN___j___j___j___j___j___j___j___j___j___j___j___>

   8270    8275  8280    8285    8290  8295    8300    8305  8310    8315    8320  8325    8330    8335  8340    8345
     AGA CCT AGA AAA ACA TGG AGC AAT CAC AAG TAG CAA TAC AGC AGC TAA CAA TGC TGC TTG TGC CTG GCT AGA AGC ACA
     TCT GGA TCT TTT TGT ACC TCG TTA GTG TTC ATC GTT ATG TCG TCG ATT GTT ACG ACG AAC ACG GAC CGA TCT TCG TGT
      D   L   E   K   H   G   A   I   T   S   S   N   T   A   A   N   N   A   A   C   A   W   L   E   A   Q>
     ___j___j___j___j___j___j___j___j___j___j___j_NEF PROTEIN___j___j___j___j___j___j___j___j___j___j___j___>

     8350  8355    8360    8365  8370    8375    8380  8385    8390    8395  8400    8405    8410  8415    8420
     AGA GGA GGA AGA GGT GGG TTT TCC AGT CAC ACC TCA GGT ACC TTT AAG ACC AAT GAC TTA CAA GGC AGC TGT AGA TCT
     TCT CCT CCT TCT CCA CCC AAA AGG TCA GTG TGG AGT CCA TGG AAA TTC TGG TTA CTG AAT GTT CCG TCG ACA TCT AGA
      E   E   E   E   V   G   F   P   V   T   P   Q   V   P   L   R   P   M   T   Y   K   A   A   V   D   L>
       j   j   j   j   j   j   j   j   j   j   j NEF PROTEIN   j   j   j   j   j   j   j   j   j   j   j   >

 8425  8430    8435    8440  8445    8450    8455  8460    8465    8470  8475    8480    8485  8490    8495    8500
     TAC CCA CTT TTT AAA AGA AAA GGG CCG ACT CCA AGG CCT AAT TCA CTC CCA AAC AAG ACA AGA TAT CCT TCA TCT CTG
     ATG GGT GAA AAA TTT TCT TTT CCC CCC TGA CCT TCC GGA TTA AGT GAG GGT TTC TTC TGT TCT ATA GGA AGT AGA GAC
      S   H   F   L   K   E   K   G   G   L   E   G   L   I   H   S   Q   R   R   Q   D   I   L   D   L   W>
     ___j___j___j___j___j___j___j___j___j___j___j_NEF PROTEIN___j___j___j___j___j___j___j___j___j___j___j___>
                                                 _k___k___k___LTR; /FUNCTION=5' LTR U3 AND R REGIONS__k___k___k___>

   8505    8510    8515  8520    8525    8530  8535    8540    8545  8550    8555    8560  8565    8570    8575  8580
     GAT CTA CCA CAC ACA AGG CTA CTT CCC TGA TTG GCA GAA CTA CAC ACC AGG GCC AGG GGT CAG ATA TCC ACT GAC CTT
     CTA GAT GGT GTG TGT TCC GAT GAA GGG ACT AAC CGT CTT GAT GTG TGG TCC CGG TCC CCA GTC TAT AGG TGA CTG GAA
      I   Y   H   T   Q   G   Y   F   P   D   W   Q   N   Y   T   P   G   P   G   V   R   Y   P   L   T   F>
       j   j   j   j   j   j   j   j   j   j   j NEF PROTEIN   j   j   j   j   j   j   j   j   j   j   j   >
     ___k___k___k___k___k___k___k____LTR; /FUNCTION=5' LTR U3 AND R REGIONS_k___k___k___k___k___k___k___k___>

     8585    8590  8595    8600    8605  8610    8615    8620  8625    8630    8635  8640    8645    8650  8655
     TGG ATG GTC CTA CAA GCT AGT ACC AGT TGA GCC AGA TAA GGT AGA AGA GGC CAA TAA AGG AGA GAA CAC CAG CTT GTT
     ACC TAC CAC GAT GTT CGA TCA TGG TCA ACT CGG TCT ATT CCA TCT TCT CCG GTT ATT TCC TCT CTT GTG GTC GAA CAA
      G   W   C   Y   K   L   V   P   V   E   P   D   K   V   E   E   A   N   K   G   E   N   T   S   L   L>
     ___j___j___j___j___j___j___j___j___j___j___j_NEF PROTEIN___j___j___j___j___j___j___j___j___j___j___j___>
     ___k___k___k___k___k___k___k____LTR; /FUNCTION=5' LTR U3 AND R REGIONS_k___k___k___k___k___k___k___k___>

   8660    8665  8670    8675    8680  8685    8690    8695  8700    8705    8710  8715    8720    8725  8730    8735
     ACA CCC TGT GAG CCT GCA TGG AAT GGA TGA CCC TGA GAG AGA AGT GTT AGA GTG GAG GTT TGA CAG CCG CCT AGC ATT
     TGT GGG ACA CTC GGA CGT ACC TTA CCT ACT GGG ACT CTC TCT TCA CAA TCT CAC CTC CAA ACT GTC GGC GGA TCG TAA
      H   P   V   S   L   H   G   M   D   D   P   E   R   E   V   L   E   W   R   F   D   S   R   L   A   F>
     ___j___j___j___j___j___j___j___j___j___j___j_NEF PROTEIN___j___j___j___j___j___j___j___j___j___j___j___>
     ___k___k___k___k___k___k___k____LTR; /FUNCTION=5' LTR U3 AND R REGIONS_k___k___k___k___k___k___k___k___>

     8740  8745    8750    8755  8760    8765    8770  8775    8780    8785  8790    8795    8800  8805    8810
     TCA TCA CGT GGC CCG AGA GCT GCA TCC GGA GTA CTT CAA GAA CTG CTG ACA TCG AGC TTG CTA CAA GGG ACT TTC CGC
     AGT AGT GCA CCG GGC TCT CGA CGT AGG CCT CAT GAA GTT CTT GAC GAC TGT AGC TCG AAC GAT GTT CCC TGA AAG GCG
      H   H   V   A   R   E   L   H   P   E   Y   F   K   N   C   *>
       j   j   j   j   j   j  NEF PROTEIN j   j   j   j   j   j   j >
       k   k   k   k   k   k   k    LTR; /FUNCTION=5' LTR U3 AND R REGIONS k   k   k   k   k   k   k   k   >

 8815  8820    8825    8830  8835    8840    8845  8850    8855    8860  8865    8870    8875  8880    8885    8890
     TGG GGA CTT TCC AGG GAG GCG TGG CCT GGG CGG GAC TGG GGA GTG GCG AGC CCT CAG ATG CTG CAT ATA AGC AGC TGC
     ACC CCT GAA AGG TCC CTC CGC ACC GGA CCC GCC CTG ACC CCT CAC CGC TCG GGA GTC TAC GAC GTA TAT TCG TCG ACG
     ___k___k___k___k___k___k___k____LTR; /FUNCTION=5' LTR U3 AND R REGIONS_k___k___k___k___k___k___k___k___>

   8895    8900    8905  8910    8915    8920  8925    8930    8935  8940    8945    8950  8955    8960    8965  8970
     TTT TTG CCT GTA CTG GGT CTC TCT GGT TAG ACC AGA TCT GAG CCT GGG AGC TCT CTG GCT AAC TAG GGA ACC CAC TGC
     AAA AAC GGA CAT GAC CCA GAG AGA CCA ATC TGG TCT AGA CTC GGA CCC TCG AGA GAC CGA TTG ATC CCT TGG GTG ACG
     ___k___k___k___k___k___k___k____LTR; /FUNCTION=5' LTR U3 AND R REGIONS_k___k___k___k___k___k___k___k___>

                               >conflict;_/replace=t
                                         |
       8975    8980  8985    8990    8995  9000
     TTA AGC CTC AAT AAA GCT TGC CTT GAG GGC
     AAT TCG GAG TTA TTT CGA ACG GAA CTC CCG
     ___LTR; /FUNCTION=5' LTR U3 AND R R____>
```

Unannotated (sense strand only, primarily HIV-1 where the highlighted region is SIV p6):

AAATCTCTAGCAGTGGCGCCCGAACAGGGACTTGAAAGCGAAAGTAAAGCCAGAGGAGATCTCTCGACGCAGGACTCGGCTTGCTGAAGCGCGCACGGCAA
GAGGCGAGGGGCGGCGACTGGTGAGTACGCCAAAAATTTTGACTAGCGGAGGCTAGAAGGAGAGAGATGGGTGCGAGAGCGTCGGTATTAAGCGGGGGAGA
ATTAGATAAATGGGAAAAAATTCGGTTAAGGCCAGGGGGAAAGAAACAATATAAACTAAAACATATAGTATGGGCAAGCAGGGAGCTAGAACGATTCGCAG
TTAATCCTGGCCTTTTAGAGACATCAGAAGGCTGTAGACAAATACTGGGACAGCTACAACCATCCCTTCAGACAGGATCAGAAGAACTTAGATCATTATAT
AATACAATAGCAGTCCTCTATTGTGTGCATCAAAGGATAGATGTAAAAGACACCAAGGAAGCCTTAGATAAGATAGAGGAAGAGCAAAACAAAAGTAAGAA

Fig. 11: NL4.3 Sequence – Full Length with Chimeric p6, 17-26 (cont)

```
AAAGGCACAGCAAGCAGCAGCTGACACAGGAAACAACAGCCAGGTCAGCCAAAATTACCCTATAGTGCAGAACCTCCAGGGGCAAATGGTACATCAGGCCA
TATCACCTAGAACTTTAAATGCATGGGTAAAAGTAGTAGAAGAGAAGGCTTTCAGCCCAGAAGTAATACCCATGTTTTCAGCATTATCAGAAGGAGCCACC
CCACAAGATTTAAATACCATGCTAAACACAGTGGGGGGACATCAAGCAGCCATGCAAATGTTAAAAGAGACCATCAATGAGGAAGCTGCAGAATGGGATAG
ATTGCATCCAGTGCATGCAGGGCCTATTGCACCAGGCCAGATGAGAGAACCAAGGGGAAGTGACATAGCAGGAACTACTAGTACCCTTCAGGAACAAATAG
GATGGATGACACATAATCCACCTATCCCAGTAGGAGAAATCTATAAAAGATGGATAATCCTGGGATTAAATAAAATAGTAAGAATGTATAGCCCTACCAGC
ATTCTGGACATAAGACAAGGACCAAAGGAACCCTTTAGAGACTATGTAGACCGGTTCTATAAAACTCTAAGAGCCGAGCAAGCTTCACAAGAGGTAAAAAA
TTGGATGACAGAAACCTTGTTGGTCCAAAATGCGAACCCAGATTGTAAGACTATTTTAAAAGCACTGGGACCAGGAGCGACACTAGAAGAAATGATGACAG
CATGTCAGGGAGTGGGGGGACCCGGCCATAAAGCAAGAGTTTTGGCTGAAGCAATGAGCCAAGTAACAAATCCAGCTACCATAATGATACAGAAAGGCAAT
TTTAGGAACCAAAGAAAGACTGTTAAGTGTTTCAATTGTGGCAAAGAAGGGCACATAGCCAAAAATTGCAGGGCCCCTAGGAAAAAGGGCTGTTGGAAATG
TGGAAAGGAAGGACACCAAATGAAAGATTGTACTGAGAGACAGGCTAATTTTTTAGGGAAGATCTGGCCTTCCCACAAGGGAAGGCCAGGGAATTTTCTTC
ACACCACACCACACCCAACAGCCCCACCAGAA**GACCCAGCTGTGGATCTGCTAAAGAACTAC**ACTCCCTCTCAGAGCCAGCAGCCCATAGACAAGCAACTC
TATCCTTTAGCTTCCCTCAGATCACTCTTTGGCAGCGACCCCTCGTCACAATAAAGATAGGGGGGCAATTAAAGGAAGCTCTATTAGATACAGGAGCAGAT
GATACAGTATTAGAAGAAATGAATTTGCCAGGAAGATGGAAACCAAAAATGATAGGGGGAATTGGAGGTTTTATCAAAGTAAGACAGTATGATCAGATACT
CATAGAAATCTGCGGACATAAAGCTATAGGTACAGTATTAGTAGGACCTACACCTGTCAACATAATTGGAAGAAATCTGTTGACTCAGATTGGCTGCACTT
TAAATTTTCCCATTAGTCCTATTGAGACTGTACCAGTAAAATTAAAGCCAGGAATGGATGGCCCAAAAGTTAAACAATGGCCATTGACAGAAGAAAAAATA
AAAGCATTAGTAGAAATTTGTACAGAAATGGAAAAGGAAGGAAAAATTTCAAAAATTGGGCCTGAAAATCCATACAATACTCCAGTATTTGCCATAAAGAA
AAAAGACAGTACTAAATGGAGAAAATTAGTAGATTTCAGAGAACTTAATAAGAGAACTCAAGATTTCTGGGAAGTTCAATTAGGAATACCACATCCTGCAG
GGTTAAAACAGAAAAAATCAGTAACAGTACTGGATGTGGGCGATGCATATTTTTCAGTTCCCTTAGATAAAGACTTCAGGAAGTATACTGCATTTACCATA
CCTAGTATAAACAATGAGACACCAGGGATTAGATATCAGTACAATGTGCTTCCACAGGGATGGAAAGGATCACCAGCAATATTCCAGTGTAGCATGACAAA
AATCTTAGAGCCTTTTAGAAAACAAAATCCAGACGTAGTCATCTATCAATACATGGATGATTTGTATGTAGGATCTGACTTAGAAATAGGGCAGCATAGAA
CAAAAATAGAGGAACTGAGACAACATCTGTTGAGGTGGGGATTTACCACACCAGACAAAAAACATCAGAAAGAACCTCCATTCCTTTGGATGGGTTATGAA
CTCCATCCTGATAAATGGACAGTACAGCCTATAGTGCTGCCAGAAAAGGACAGCTGGACTGTCAATGACATACAGAAATTAGTGGGAAAATTGAATTGGGC
AAGTCAGATTTATCCAGCCATTAAAGTAAGGCAATTATGTAAACTTCTTAGGGGAACCAAAGCACTAACAGAAGTAGTACCACTAACAGAAGAAGCAGAGC
TAGAACTGGCACAAAACAGGGAGATTCTAAAAGAACCGGTACATGGAGTGTATTATGACCCATCAAAAGACTTAATAGCAGAAATACAGAAGCAGGGCAA
GCCCAATCGACATATCAAATTTATCAAGAGCCATTTAGAAATCTGAAAACAGGAAAGTATGCAAGAATGAAGGGTGCCCACACTAATCATGTCAAACAATT
AACAGAGGCAGTACAAAAAATAGCCACAGAAAGCATAGTAATATGGGGAAAGACTCCTAAATTTAAATTACCCATACAAAAGGAAACATGGGAAGCATGGT
GGACAGAGTATTGGCAAGCCACCTGGATTCCTGAGTGGGAGTTTGTCAATACCCCTCCCTTAGTGAAGTTATGGTACCAGTTAGAGAAAGAACCCATAATA
GGAGCAGAAACTTTCTATGTAGATGGGGCAGCCAATAGGGAAACTAAATTAGGAAAAGCAGGATATGTAACTGACAGAGGAAGACAAAAAGTTGTCCCCCT
AACGGACACAACAAATCAGAAGACTGAGTTACAAGCAATTCATCTAGCTTTGCAGGATTCGGGATTAGAAGTAAACATAGTGACAGACTCACAATATGCAT
TGGGAATCATTCAAGCACAACCAGATAAGAGTGAATCAGAGTTAGTCAGTCAAATAATAGAGCAGTTAATAAAAAAGGAAAAAGTCTACCTGGCATGGGTA
CCAGCACACAAAGGAATTGGAGGAAATGAACAAGTAGATAAATTGGTCAGTGCTGGAATCAGGAAAGTACTATTTTTAGATGGAATAGATAAGGCCCAAGA
AGAACATGAGAAATATCACAGTAATTGGAGAGCAATGGCTAGTGATTTTAACCTACCACCTGTAGTAGCAAAAGAAATAGTAGCCAGCTGTGATAAATGTC
AGCTAAAAGGGGAAGCCATGCATGGACAAGTAGACTGTAGCCCAGGAATATGGCAGCTAGATTGTACACATTTAGAAGGAAAAGTTATCTTGGTGGCAGTT
CATGTAGCCAGTGGATATATAGAAGCAGAAGTAATTCCAGCAGAGACAGGGCAAGAAACAGCATACTTCCTCTTAAAATTAGCAGGAAGATGGCCAGTAAA
AACAGTACATACACACAATGGCAGCAATTTCACCAGTACTACAGTTAAGGCCGCCTGTTGGTGGGCGGGAATCAAGCAGGAATTTGGCATTCCCTACAATC
CCCAAAGTCAAGGAGTAATAGAATCTATGAATAAAGAATTAAAGAAAATTATAGGACAGGTAAGAGATCAGGCTGAACATCTTAAGACAGCAGTACAAATG
GCAGTATTCATCCACAATTTTAAAAGAAAAGGGGGGATTGGGGGGTACAGTGCAGGGGAAAGAATAGTAGACATAATAGCAACAGACATACAAACTAAAGA
ATTACAAAAACAAATTACAAAAATTCAAAATTTTCGGGTTTATTACAGGGACAGCAGAGATCCAGTTTGGAAAGGACCAGCAAAGCTCCTCTGGAAAGGTG
AAGGGGCAGTAGTAATACAAGATAATAGTGACATAAAAGTAGTGCCAAGAAGAAAAGCAAAGATCATCAGGGATTATGGAAAACAGATGGCAGGTGATGAT
TGTGTGGCAAGTAGACAGGATGAGGATTAACACATGGAAAAGATTAGTAAAACACCATATGTATATTTCAAGGAAAGCTAAGGACTGGTTTTATAGACATC
ACTATGAAAGTACTAATCCAAAAATAAGTTCAGAAGTACACATCCCACTAGGGGATGCTAAATTAGTAATAACAACATATTGGGGTCTGCATACAGGAGAA
AGAGACTGGCATTTGGGTCAGGGAGTCTCCATAGAATGGAGGAAAAAGAGATATAGCACACAAGTAGACCCTGACCTAGCAGACCAACTAATTCATCTGCA
CTATTTTGATTGTTTTTCAGAATCTGCTATAAGAAATACCATATTAGGACGTATAGTTAGTCCTAGGTGTGAATATCAAGCAGGACATAACAAGGTAGGAT
CTCTACAGTACTTGGCACTAGCAGCATTAATAAAACCAAAACAGATAAAGCCACCTTTGCCTAGTGTTAGGAAACTGACAGAGGACAGATGGAACAAGCCC
CAGAAGACCAAGGGCCACAGAGGGAGCCATACAATGAATGGACACTAGAGCTTTTAGAGGAACTTAAGAGTGAAGCTGTTAGACATTTTCCTAGGATATGG
CTCCATAACTTAGGACGACATATCTATGAAACTTACGGGGATACTTGGGCAGGAGTGGAAGCCATAATAAGAATTCTGCAACAACTGCCGTTTATCCATTT
CAGAATTGGGTGTCGACATAGCAGAATAGGCGTTACTCGACAGAGGAGAGCAAGAAATGGAGCCAGTAGATCCTAGACTAGAGCCCTGGAAGCATCCAGGA
ACTCACCCTAAAACTGCTTGTACCAATTGCTATTGTAAAAAGTGTTGCTTTCATTGCCAAGTTTGTTTCATGACAAAAGCCTTAGGCATCTCCTATGGCAG
```

Fig. 11: NL4.3 Sequence – Full Length with Chimeric p6, 17-26 (cont)

GAAGAAGCGGAGACAGCGACGAAGAGCTCATCAGAACAGTCAGACTCATCAAGCTTCTCTATCAAAGCAGTAAGTAGTACATGTAATGCAACCTATAATAG
TAGCAATAGTAGCATTAGTAGTAGCAATAATAATAGCAATAGTTGTGTGGTCCATAGTAATCATAGAATATAGGAAAATATTAAGACAAAGAAAAATAGAC
AGGTTAATTGATAGACTAATAGAAAGAGCAGAAGACAGTGGCAATGAGAGTGAAGGAGAAGTATCAGCACTTGTGGAGATGGGGGTGGAAATGGGGCACCA
TGCTCCTTGGGATATTGATGATCTGTAGTGCTACAGAAAAATTGTGGGTCACAGTCTATTATGGGGTACCTGTGTGGAAGGAAGCAACCACCACTCTATTT
TGTGCATCAGATGCTAAAGCATATGATACAGAGGTACATAATGTTTGGGCCACACATGCCTGTGTACCCACAGACCCCAACCCACAAGAAGTAGTATTGGT
AAATGTGACAGAAAATTTTAACATGTGGAAAGATGACATGGTAGAACAGATGCATGAGGATATAATCAGTTTATGGGATCAAAGCCTAAAGCCATGTGTAA
AATTAACCCCACTCTGTGTTAGTTTAAAGTGCACTGATTTGAAGAATGATACTAATACCAATAGTAGTAGCGGGAGAATGATAATGGAGAAAGGAGAGATA
AAAAACTGCTCTTTCAATATCAGCACAAGCATAAGAGATAAGGTGCAGAAAGAATATGCATTCTTTTATAAACTTGATATAGTACCAATAGATAATACCAG
CTATAGGTTGATAAGTTGTAACACCTCAGTCATTACACAGGCCTGTCCAAAGGTATCCTTTGAGCCAATCCCCATACATTATTGTGCCCCGGCTGGTTTTG
CGATTCTAAAATGTAATAATAAGACGTTCAATGGAACAGGACCATGTACAAATGTCAGCACAGTACAATGTACACATGGAATCAGGCCAGTAGTATCAACT
CAACTGCTGTTAAATGGCAGTCTAGCAGAAGAAGATGTAGTAATTAGATCTGCCAATTTCACAGACAATGCTAAAACCATAATAGTACAGCTGAACACATC
TGTAGAAATTAATTGTACAAGACCCAACAACAATACAAGAAAAAGTATCCGTATCCAGAGGGGACCAGGGAGAGCATTTGTTACAATAGGAAAAATAGGAA
ATATGAGACAAGCACATTGTAACATTAGTAGAGCAAAATGGAATGCCACTTTAAAACAGATAGCTAGCAAATTAAGAGAACAATTTGGAAATAATAAAACA
ATAATCTTTAAGCAATCCTCAGGAGGGGACCCAGAAATTGTAACGCACAGTTTTAATTGTGGAGGGGAATTTTTCTACTGTAATTCAACACAACTGTTTAA
TAGTACTTGGTTTAATAGTACTTGGAGTACTGAAGGGTCAAATAACACTGAAGGAAGTGACACAATCACACTCCCATGCAGAATAAAACAATTTATAAACA
TGTGGCAGGAAGTAGGAAAAGCAATGTATGCCCCTCCCATCAGTGGACAAATTAGATGTTCATCAAATATTACTGGGCTGCTATTAACAAGAGATGGTGGT
AATAACAACAATGGGTCCGAGATCTTCAGACCTGGAGGAGGCGATATGAGGGACAATTGGAGAAGTGAATTATATAAATATAAAGTAGTAAAAATTGAACC
ATTAGGAGTAGCACCCACCAAGGCAAAGAGAAGAGTGGTGCAGAGAGAAAAAAGAGCAGTGGGAATAGGAGCTTTGTTCCTTGGGTTCTTGGGAGCAGCAG
GAAGCACTATGGGCGCAGCGTCAATGACGCTGACGGTACAGGCCAGACAATTATTGTCTGATATAGTGCAGCAGCAGAACAATTTGCTGAGGGCTATTGAG
GCGCAACAGCATCTGTTGCAACTCACAGTCTGGGGCATCAAACAGCTCCAGGCAAGAATCCTGGCTGTGGAAAGATACCTAAAGGATCAACAGCTCCTGGG
GATTTGGGGTTGCTCTGGAAAACTCATTTGCACCACTGCTGTGCCTTGGAATGCTAGTTGGAGTAATAAATCTCTGGAACAGATTTGGAATAACATGACCT
GGATGGAGTGGGACAGAGAAATTAACAATTACACAAGCTTAATACACTCCTTAATTGAAGAATCGCAAAACCAGCAAGAAAAGAATGAACAAGAATTATTG
GAATTAGATAAATGGGCAAGTTTGTGGAATTGGTTTAACATAACAAATTGGCTGTGGTATATAAAATTATTCATAATGATAGTAGGAGGCTTGGTAGGTTT
AAGAATAGTTTTTGCTGTACTTTCTATAGTGAATAGAGTTAGGCAGGGATATTCACCATTATCGTTTCAGACCCACCTCCCAATCCCGAGGGGACCCGACA
GGCCCGAACGAATAGAACAAGAAGGTCGAGAGAGACGCAGAGACAGATCCATTCGATTAGTGAACGGATCCTTAGCACTTATCTGGCACCATCTGCCGAGC
CTGTGCCTCTTCAGCTACCACCGCTTGAGAGACTTACTCTTGATTGTAACGAGGATTGTGGAACTTCTGGGACGCAGGGGGTGGGAAGCCCTCAAATATTG
GTGGAATCTCCTACAGTATTGGAGTCAGGAACTAAAGAATAGTGCTGTTAACTTGCTCAATGCCACAGCCATAGCAGTAGCTGAGGGGACAGATAGGGTTA
TAGAAGTATTACAAGCAGCTTATAGAGCTATTCGCCACATACCTAGAAGAATAAGACAGGGCTTGGAAAGGATTTTGCTATAAGATGGGTGGCAAGTGGTC
AAAAAGTAGTGTGATTGGATGGCCTGCTGTAAGGGAAAGAATGAGACGAGCTGAGCCAGCAGCAGATGGGGTGGGAGCAGTATCTCGAGACCTAGAAAAAC
ATGGAGCAATCACAAGTAGCAATACAGCAGCTAACAATGCTGCTTGTGCCTGGCTAGAAGCACAAGAGGAGGAAGAGGTGGGTTTTCCAGTCACACCTCAG
GTACCTTTAAGACCAATGACTTACAAGGCAGCTGTAGATCTTAGCCACTTTTTAAAAGAAAAGGGGGGACTGGAAGGGCTAATTCACTCCCAAAGAAGACA
AGATATCCTTGATCTGTGGATCTACCACACACAAGGCTACTTCCCTGATTGGCAGAACTACACACCAGGGCCAGGGGTCAGATATCCACTGACCTTTGGAT
GGTGCTACAAGCTAGTACCAGTTGAGCCAGATAAGCTAGAAGAGCCCAATAAACGAGAGAACACCAGCTTGTTACACCCTCTGAGCCTGCATGGAATGCAT
GACCCTGAGAGAGAAGTGTTAGAGTGGAGGTTTGACAGCCGCCTAGCATTTCATCACGTGGCCCGAGAGCTGCATCCGGAGTACTTCAAGAACTGCTGACA
TCGAGCTTGCTACAAGGGACTTTCCGCTGGGGACTTTCCAGGGAGGCGTGGCCTGGGCGGGACTGGGGAGTGGCGAGCCCTCAGATGCTGCATATAAGCAG
CTGCTTTTTGCCTGTACTGGGTCTCTCTGGTTAGACCAGATCTGAGCCTGGGAGCTCTCTGGCTAACTAGGGAACCCACTGCTTAAGCCTCAATAAAGCTT
GCCTTGAGGGC

Fig. 12: NL4.3 Sequence – Full Length, Wild Type

Annotated:

```
Sequence: NL4-3 Range: 1 to 9000

     5      10    15     20     25     30     35     40     45     50     55    60     65     70    75
AAA TCT CTA GCA GTG GCG CCC GAA CAG GGA CTT GAA AGC GAA AGT AAA GCC AGA GGA GAT CTC TCC ACG CAG GAC TCG
TTT AGA GAT CGT CAC CGC GGG CTT GTC CCT GAA CTT TCG CTT TCA TTT CGG TCT CCT CTA GAG AGC TGC GTC CTG AGC
___LTR; 5' LT__a_>

80      85    90      95    100    105     110    115    120     125    130    135     140    145   150    155
GCT TGC TGA AGC GCG CAC GGC AAG AGG CGA GGG GCG GCG ACT GGT GAG TAC GCC AAA AAT TTT GAC TAG CGG AGG CTA
CGA ACG ACT TCG CGC GTG CCG TTC TCC GCT CCC CGC CGC TGA CCA CTC ATG CGG TTT TTA AAA CTG ATC GCC TCC GAT

            >Gene:_gag
                :
  160   165    :170    175   180    185    190   195    200    205   210    215    220   225    230
GAA GGA GAG AGA TGG GTG CGA GAG CGT CGG TAT TAA GCG GGG GAG AAT TAG ATA AAT GGG AAA AAA TTC GGT TAA GGC
CTT CCT CTC TCT ACC CAC GCT CTC GCA GCC ATA ATT CGC CCC CTC TTA ATC TAT TTA CCC TTT TTT AAG CCA ATT CCG
                 M   G   A   R   A   S   V   L   S   G   G   E   L   D   K   W   E   K   I   R   L   R>
                b   b   b   b   b   b  GAG POLYPROTEIN PRECURSOR; MATRIX (P17)  b   b   b   b   b   b   >

235   240    245    250   255    260    265   270    275    280   285    290    295   300    305    310
CAG GGG GAA AGA AAC AAT ATA AAC TAA AAC ATA TAG TAT GGG CAA GCA GGG AGC TAG AAC GAT TCG CAG TTA ATC CTG
GTC CCC CTT TCT TTG TTA TAT TTG ATT TTG TAT ATC ATA CCC GTT CGT CCC TCG ATC TTG CTA AGC GTC AAT TAG GAC
P   G   G   K   K   Q   Y   K   L   K   H   I   V   W   A   S   R   E   L   E   R   F   A   V   N   P>
___b___b___b___b___b___b___b___GAG POLYPROTEIN PRECURSOR; MATRIX (P17)_b___b___b___b___b___b___b___b___>

315    320    325   330    335    340   345    350    355   360    365    370   375    380    385   390
GCC TTT TAG AGA CAT CAG AAG GCT GTA CAC AAA TAC TGG GAC AGC TAC AAC CAT CCC TTC AGA CAG GAT CAG AAG AAC
CGG AAA ATC TCT GTA GTC TTC CGA CAT CTG TTT ATG ACC CTG TCG ATG TTG GTA GGG AAG TCT GTC CTA GTC TTC TTG
G   L   L   E   T   S   E   G   C   R   Q   I   L   G   Q   L   Q   P   S   L   Q   T   G   S   E   E>
   b   b   b   b   b   b   b   GAG POLYPROTEIN PRECURSOR; MATRIX (P17) b   b   b   b   b   b   b   b   >

   395    400   405    410    415   420    425    430   435    440    445   450    455    460   465
TTA GAT CAT TAT ATA ATA CAA TAG CAG TCC TCT ATT GTG TGC ATC AAA GGA TAG ATG TAA AAG ACA CCA AGG AAG CCT
AAT CTA GTA ATA TAT TAT GTT ATC GTC AGG AGA TAA CAC ACG TAG TTT CCT ATC TAC ATT TTC TGT GGT TCC TTC GGA
L   R   S   L   Y   N   T   I   A   V   L   Y   C   V   H   Q   R   I   D   V   K   D   T   K   E   A>
___b___b___b___b___b___b___b___GAG POLYPROTEIN PRECURSOR; MATRIX (P17)_b___b___b___b___b___b___b___b___>

 470    475   480    485    490   495    500    505   510    515    520   525    530    535   540    545
TAG ATA AGA TAG AGG AAG AGC AAA ACA AAA GTA AGA AAA AGG CAC AGC AAG CAG CAG CTG ACA CAG GAA ACA ACA GCC
ATC TAT TCT ATC TCC TTC TCG TTT TGT TTT CAT TCT TTT TCC GTG TCG TTC GTC GTC GAC TGT GTC CTT TGT TGT CGG
L   D   K   I   E   E   E   Q   N   K   S   K   K   K   A   Q   Q   A   A   A   D   T   G   N   N   S>
___b___b___b___b___b___b___b___GAG POLYPROTEIN PRECURSOR; MATRIX (P17)_b___b___b___b___b___b___b___b___>

  550   555    560    565   570    575    580   585    590    595   600    605    610   615    620
AGG TCA GCC AAA ATT ACC CTA TAG TGC AGA ACC TCC AGG GGC AAA TGG TAC ATC AGG CCA TAT CAC CTA GAA CTT TAA
TCC AGT CGG TTT TAA TGG GAT ATC ACG TCT TGG AGG TCC CCG TTT ACC ATG TAG TCC GGT ATA GTG GAT CTT GAA ATT
Q   V   S   Q   N   Y   P   I   V   Q   N   L   Q   G   Q   M   V   H   Q   A   I   S   P   R   T   L>
   b   b   b   b   b   b   b   GAG POLYPROTEIN PRECURSOR; MATRIX (P17) b   b   b   b   b   b   b   b   >

625   630    635    640   645    650    655   660    665    670   675    680    685   690    695    700
ATG CAT GGG TAA AAG TAG TAG AAG AGA AGG CTT TCA GCC CAG AAG TAA TAC CCA TGT TTT CAG CAT TAT CAG AAG GAG
TAC GTA CCC ATT TTC ATC ATC TTC TCT TCC GAA AGT CGG GTC TTC ATT ATG GGT ACA AAA GTC GTA ATA GTC TTC CTC
N   A   W   V   K   V   V   E   E   K   A   F   S   P   E   V   I   P   M   F   S   A   L   S   E   G>
___b___b___b___b___b___b___b___GAG POLYPROTEIN PRECURSOR; MATRIX (P17)_b___b___b___b___b___b___b___b___>

705    710    715   720    725    730   735    740    745   750    755    760   765    770    775   780
CCA CCC CAC AAG ATT TAA ATA CCA TGC TAA ACA CAG TGG GGG GAC ATC AAG CAG CCA TGC AAA TGT TAA AAG AGA CCA
GGT GGG GTG TTC TAA ATT TAT GGT ACG ATT TGT GTC ACC CCC CTG TAG TTC GTC GGT ACG TTT ACA ATT TTC TCT GGT
A   T   P   Q   D   L   N   T   M   L   N   T   V   G   G   H   Q   A   A   M   Q   M   L   K   E   T>
   b   b   b   b   b   b   b   GAG POLYPROTEIN PRECURSOR; MATRIX (P17) b   b   b   b   b   b   b   b   >

   785    790   795    800    805   810    815    820   825    830    835   840    845    850   855
TCA ATG AGG AAG CTG CAG AAT GGG ATA GAT TGC ATC CAG TGC ATG CAG GGC CTA TTG CAC CAG GCC AGA TGA GAG AAC
AGT TAC TCC TTC GAC GTC TTA CCC TAT CTA ACG TAG GTC ACG TAC GTC CCG GAT AAC GTG GTC CGG TCT ACT CTC TTG
I   N   E   E   A   A   E   W   D   R   L   H   P   V   H   A   G   P   I   A   P   G   Q   M   R   E>
___b___b___b___b___b___b___b___GAG POLYPROTEIN PRECURSOR; MATRIX (P17)_b___b___b___b___b___b___b___b___>

 860    865   870    875    880   885    890    895   900    905    910   915    920    925   930    935
CAA GGG GAA GTG ACA TAG CAG GAA CTA CTA GTA CCC TTC AGG AAC AAA TAG GAT GGA TGA CAC ATA ATC CAC CTA TCC
GTT CCC CTT CAC TGT ATC GTC CTT GAT GAT CAT GGG AAG TCC TTG TTT ATC CTA CCT ACT GTG TAT TAG GTG GAT AGG
P   R   G   S   D   I   A   G   T   T   S   T   L   Q   E   Q   I   G   W   M   T   H   N   P   P   I>
___b___b___b___b___b___b___b___GAG POLYPROTEIN PRECURSOR; MATRIX (P17)_b___b___b___b___b___b___b___b___>

  940   945    950    955   960    965    970   975    980    985   990    995   1000  1005   1010
CAG TAG GAG AAA TCT ATA AAA GAT GGA TAA TCC TGG GAT TAA ATA AAA TAG TAA GAA TGT ATA GCC CTA CCA GCA TTC
GTC ATC CTC TTT AGA TAT TTT CTA CCT ATT AGG ACC CTA ATT TAT TTT ATC ATT CTT ACA TAT CGG GAT GGT CGT AAG
P   V   G   E   I   Y   K   R   W   I   I   L   G   L   N   K   I   V   R   M   Y   S   P   T   S   I>
   b   b   b   b   b   b   b   GAG POLYPROTEIN PRECURSOR; MATRIX (P17) b   b   b   b   b   b   b   b   >
```

Fig. 12: NL4.3 Sequence – Full Length, Wild Type (cont)

```
1015 1020   1025   1030  1035   1040   1045  1050   1055   1060  1065   1070   1075  1080   1085   1090
   TGG ACA TAA GAC AAG GAC CAA AGG AAC CCT TTA GAG ACT ATG TAG ACC GAT TCT ATA AAA CTC TAA GAG CCG AGC AAG
   ACC TGT ATT CTG TTC CTG GTT TCC TTG GGA AAT CTC TGA TAC ATC TGG CTA AGA TAT TTT GAG ATT CTC GGC TCG TTC
   L   D   I   R   Q   G   P   K   E   P   F   R   D   Y   V   D   R   F   Y   K   T   L   R   A   E   Q>
   ___b___b___b___b___b___b___b___GAG POLYPROTEIN PRECURSOR; MATRIX (P17)_b___b___b___b___b___b___b___b___>

 1095   1100   1105  1110   1115   1120  1125   1130   1135  1140   1145   1150  1155   1160   1165  1170
   CTT CAC AAG AGG TAA AAA ATT GGA TGA CAG AAA CCT TGT TGG TCC AAA ATG CGA ACC CAG ATT GTA AGA CTA TTT TAA
   GAA GTG TTC TCC ATT TTT TAA CCT ACT GTC TTT GGA ACA ACC AGG TTT TAC GCT TGC GTC TAA CAT TCT GAT AAA ATT
   A   S   Q   E   V   K   N   W   M   T   E   T   L   L   V   Q   N   A   N   P   D   C   K   T   I   L>
   ___b___b___b___b___b___b___b___GAG POLYPROTEIN PRECURSOR; MATRIX (P17)_b___b___b___b___b___b___b___b___>

>conflict;_/replace=t
           |
   1175|  1180  1185   1190   1195  1200   1205   1210  1215   1220   1225  1230   1235   1240  1245
   AAG CAC TGG GAC CAG GAG CGA CAC TAG AAG AAA TGA TGA CAG CAT GTC AGG GAG TGG GGG GAC CCG GCC ATA AAG CAA
   TTC GTG ACC CTG GTC CTC GCT GTG ATC TTC TTT ACT ACT GTC GTA CAG TCC CTC ACC CCC CTG GGC CGG TAT TTC GTT
   K   A   L   G   P   G   A   T   L   E   E   M   M   T   A   C   Q   G   V   G   G   P   G   H   K   A>
   ___b___b___b___b___b___b___b___GAG POLYPROTEIN PRECURSOR; MATRIX (P17)_b___b___b___b___b___b___b___b___>

 1250   1255  1260   1265   1270  1275   1280   1285  1290   1295   1300  1305   1310   1315  1320   1325
   GAG TTT TGG CTG AAG CAA TGA GCC AAG TAA CAA ATC CAG CTA CCA TAA TGA TAC AGA AAG GCA ATT TTA GGA ACC AAA
   CTC AAA ACC GAC TTC GTT ACT CGG TTC ATT GTT TAG GTC GAT GGT ATT ACT ATG TCT TTC CGT TAA AAT CCT TGG TTT
   R   V   L   A   E   A   M   S   Q   V   T   N   P   A   T   I   M   I   Q   K   G   N   F   R   N   Q>
   ___b___b___b___b___b___b___b___GAG POLYPROTEIN PRECURSOR; MATRIX (P17)_b___b___b___b___b___b___b___b___>

  1330  1335   1340   1345  1350   1355   1360  1365   1370   1375  1380   1385   1390  1395   1400
   GAA AGA CTG TTA AGT GTT TCA ATT GTG GCA AAG AAG GGC ACA TAG CCA AAA ATT GCA GGG CCC CTA GGA AAA AGG GCT
   CTT TCT GAC AAT TCA CAA AGT TAA CAC CGT TTC TTC CCG TGT ATC GGT TTT TAA CGT CCC GGG GAT CCT TTT TCC CGA
   R   K   T   V   K   C   F   N   C   G   K   E   G   H   I   A   K   N   C   R   A   P   R   K   K   G>
   ___b___b___b___b___b___b___b___GAG POLYPROTEIN PRECURSOR; MATRIX (P17)_b___b___b___b___b___b___b___b___>

                                                                                      >Gene:_pol
                                                                                          |
1405  1410   1415   1420  1425   1430   1435  1440   1445   1450  1455   1460   1465  1470   1475   1480
   GTT GGA AAT GTG GAA AGG AAG GAC ACC AAA TGA AAG ATT GTA CTG AGA GAC AGG CTA ATT TTT TAG GGA AGA TCT GGC
   CAA CCT TTA CAC CTT TCC TTC CTG TGG TTT ACT TTC TAA CAT GAC TCT CTG TCC GAT TAA AAA ATC CCT TCT AGA CCG
   C   W   K   C   G   K   E   G   H   Q   M   K   D   C   T   E   R   Q   A   N   F   L   G   K   I   W>
   ___b___b___b___b___b___b___b___GAG POLYPROTEIN PRECURSOR; MATRIX (P17)_b___b___b___b___b___b___b___b___>
                                                                                  F   F   R   E   D   L   A>
                                                                                  ___POL POLYPROTEIN PRE____>

 1485   1490   1495  1500   1505   1510  1515   1520   1525  1530   1535   1540  1545   1550   1555  1560
   CTT CCC ACA AGG GAA GGC CAG GGA ATT TTC TTC AGA GCA GAC CAG AGC CAA CAG CCC CAC CAG AAG AGA GCT TCA GGT
   GAA GGG TGT TCC CTT CCG GTC CCT TAA AAG AAG TCT CGT CTG GTC TCG GTT GTC GGG GTG GTC TTC TCT CGA AGT CCA
   P   S   H   K   G   R   P   G   N   F   L   Q   S   R   P   E   P   T   A   P   P   E   E   S   F   R>
   ___b___b___b___b___b___b___b___GAG POLYPROTEIN PRECURSOR; MATRIX (P17)_b___b___b___b___b___b___b___b___>
     F   P   Q   G   K   A   R   E   F   S   S   E   Q   T   R   A   N   S   P   T   R   R   E   L   Q   V>
   ___c___c___c___c___c___c___c___c_POL POLYPROTEIN PRECURSOR; PROTEASE___c___c___c___c___c___c___c___c___>

                                   >conflict;_/replace=a
                                             |
   1565   1570  1575   1580   1585  1590 | 1595   1600  1605   1610   1615  1620   1625   1630  1635
   TTG GGG AAG AGA CAA CAA CTC CCT CTC AGA GGC AGG AGC CGA TAG ACA AGG AAC TGT ATC CTT TAG CTT CCC TCA GAT
   AAC CCC TTC TCT GTT GTT GAG GGA GAG TCT CCG TCC TCG GCT ATC TGT TCC TTG ACA TAG GAA ATC GAA GGG AGT CTA
   F   G   E   E   T   T   T   P   S   Q   R   Q   E   P   I   D   K   E   L   Y   P   L   A   S   L   R>
   ___b___b___b___b___b___b___b___GAG POLYPROTEIN PRECURSOR; MATRIX (P17)_b___b___b___b___b___b___b___b___>
     W   G   R   D   N   N   S   L   S   E   A   G   A   D   R   Q   G   T   V   S   F   S   F   P   Q   I>
   ___c___c___c___c___c___c___c___c_POL POLYPROTEIN PRECURSOR; PROTEASE___c___c___c___c___c___c___c___c___>

 1640   1645  1650   1655   1660  1665   1670   1675  1680   1685   1690  1695   1700   1705  1710   1715
   CAC TCT TTG GCA GCG ACC CCT CGT CAC AAT AAA GAT AGG GGG GCA ATT AAA GGA AGC TCT ATT AGA TAC AGG AGC AGA
   GTG AGA AAC CGT CGC TGG GGA GCA GTG TTA TTT CTA TCC CCC CGT TAA TTT CCT TCG AGA TAA TCT ATG TCC TCG TCT
   S   L   F   G   S   D   P   S   S   Q   *>
   ___GAG POLYPROTEIN PRECURSOR; MATRIX (_b__>
     T   L   W   Q   R   P   L   V   T   I   K   I   G   G   Q   L   K   E   A   L   L   D   T   G   A   D>
   ___c___c___c___c___c___c___c___c_POL POLYPROTEIN PRECURSOR; PROTEASE___c___c___c___c___c___c___c___c___>

  1720  1725   1730   1735  1740   1745   1750  1755   1760   1765  1770   1775   1780  1785   1790
   TGA TAC AGT ATT AGA AGA AAT GAA TTT GCC AGG AAG ATG GAA ACC AAA AAT GAT AGG GGG AAT TGG AGG TTT TAT CAA
   ACT ATG TCA TAA TCT TCT TTA CTT AAA CGG TCC TTC TAC CTT TGG TTT TTA CTA TCC CCC TTA ACC TCC AAA ATA GTT
     D   T   V   L   E   E   M   N   L   P   G   R   W   K   P   K   M   I   G   G   I   G   G   F   I   K>
   ___c___c___c___c___c___c___c___c_POL POLYPROTEIN PRECURSOR; PROTEASE___c___c___c___c___c___c___c___c___>

>conflict;_/replace=g
           |
1795  1800   1805   1810  1815   1820   1825  1830   1835   1840  1845   1850   1855  1860   1865   1870
   AGT AAG ACA GTA TGA TCA GAT ACT CAT AGA AAT CTG CGG ACA TAA AGC TAT AGG TAC AGT ATT AGT AGG ACC TAC ACC
   TCA TTC TGT CAT ACT AGT CTA TGA GTA TCT TTA GAC GCC TGT ATT TCG ATA TCC ATG TCA TAA TCA TCC TGG ATG TGG
     V   R   Q   Y   D   Q   I   L   I   E   I   C   G   H   K   A   I   G   T   V   L   V   G   P   T   P>
   ___c___c___c___c___c___c___c___c_POL POLYPROTEIN PRECURSOR; PROTEASE___c___c___c___c___c___c___c___c___>
```

Fig. 12: NL4.3 Sequence – Full Length, Wild Type (cont)

```
 1875    1880    1885  1890    1895    1900  1905    1910    1915  1920    1925    1930  1935    1940    1945  1950
  TGT CAA CAT AAT TGG AAG AAA TCT GTT GAC TCA GAT TGG CTG CAC TTT AAA TTT TCC CAT TAG TCC TAT TGA GAC TGT
  ACA GTT GTA TTA ACC TTC TTT AGA CAA CTG AGT CTA ACC GAC GTG AAA TTT AAA AGG GTA ATC AGG ATA ACT CTG ACA
    V   N   I   I   G   R   N   L   L   T   Q   I   G   C   T   L   N   F   P   I   S   P   I   E   T   V>
  ___c___c___c___c___c___c___c___c_POL POLYPROTEIN PRECURSOR; PROTEASE___c___c___c___c___c___c___c___c___>

   1955    1960  1965    1970    1975  1980    1985    1990  1995    2000    2005  2010    2015    2020  2025
  ACC AGT AAA ATT AAA GCC AGG AAT GGA TGG CCC AAA AGT TAA ACA ATG GCC ATT GAC AGA AGA AAA AAT AAA AGC ATT
  TGG TCA TTT TAA TTT CGG TCC TTA CCT ACC GGG TTT TCA ATT TGT TAC CGG TAA CTG TCT TCT TTT TTA TTT TCG TAA
    P   V   K   L   K   P   G   M   D   G   P   K   V   K   Q   W   P   L   T   E   E   K   I   K   A   L>
  ___c___c___c___c___c___c___c___c_POL POLYPROTEIN PRECURSOR; PROTEASE___c___c___c___c___c___c___c___c___>

2030    2035  2040    2045    2050  2055    2060    2065  2070    2075    2080  2085    2090    2095  2100    2105
  AGT AGA AAT TTG TAC AGA AAT GGA AAA GGA AGG AAA AAT TTC AAA AAT TGG GCC TGA AAA TCC ATA CAA TAC TCC AGT
  TCA TCT TTA AAC ATG TCT TTA CCT TTT CCT TCC TTT TTA AAG TTT TTA ACC CGG ACT TTT AGG TAT GTT ATG AGG TCA
    V   E   I   C   T   E   M   E   K   E   G   K   I   S   K   I   G   P   E   N   P   Y   N   T   P   V>
     c   c   c   c   c   c   c   c POL POLYPROTEIN PRECURSOR; PROTEASE   c   c   c   c   c   c   c   c   >

  2110  2115    2120    2125  2130    2135    2140  2145    2150    2155  2160    2165    2170  2175    2180
  ATT TGC CAT AAA GAA AAA AGA CAG TAC TAA ATG GAG AAA ATT AGT ACA TTT CAG AGA ACT TAA TAA CAG AAC TCA ACA
  TAA ACG GTA TTT CTT TTT TCT GTC ATG ATT TAC CTC TTT TAA TCA TCT AAA GTC TCT TGA ATT ATT CTC TTG AGT TCT
    F   A   I   K   K   K   D   S   T   K   W   R   K   L   V   D   F   R   E   L   N   K   R   T   Q   D>
  ___c___c___c___c___c___c___c___c_POL POLYPROTEIN PRECURSOR; PROTEASE___c___c___c___c___c___c___c___c___>

2185  2190    2195    2200  2205    2210    2215  2220    2225    2230  2235    2240    2245  2250    2255    2260
  TTT CTG GGA AGT TCA ATT AGG AAT ACC ACA TCC TGC AGG GTT AAA ACA GAA AAA ATC AGT AAC AGT ACT GGA TGT GGG
  AAA GAC CCT TCA ACT TAA TCC TTA TGG TGT AGG ACG TCC CAA TTT TCT CTT TTT TAG TCA TTG TCA TGA CCT ACA CCC
    F   W   E   V   Q   L   G   I   P   H   P   A   G   L   K   Q   K   K   S   V   T   V   L   D   V   G>
  ___c___c___c___c___c___c___c___c_POL POLYPROTEIN PRECURSOR; PROTEASE___c___c___c___c___c___c___c___c___>

 2265    2270    2275  2280    2285    2290  2295    2300    2305  2310    2315    2320  2325    2330    2335  2340
  CGA TGC ATA TTT TTC AGT TCC CTT AGA TAA AGA CTT CAG GAA GTA TAC TGC ATT TAC CAT ACC TAG TAT AAA CAA TGA
  GCT ACG TAT AAA AAG TCA AGG GAA TCT ATT TCT GAA GTC CTT CAT ATG ACG TAA ATG CTA TGG ATC ATA TTT GTT ACT
    D   A   Y   F   S   V   P   L   D   K   D   F   R   K   Y   T   A   F   T   I   P   S   I   N   N   E>
  ___c___c___c___c___c___c___c___c_POL POLYPROTEIN PRECURSOR; PROTEASE___c___c___c___c___c___c___c___c___>

   2345    2350  2355    2360    2365  2370    2375    2380  2385    2390    2395  2400    2405    2410  2415
  GAC ACC AGG GAT TAG ATA TCA GTA CAA TGT GCT TCC ACA GGG ATG GAA AGG ATC ACC AGC AAT ATT CCA GTG TAG CAT
  CTG TGG TCC CTA ATC TAT AGT CAT GTT ACA CGA AGG TGT CCC TAC CTT TCC TAG TGG TCG TTA TAA GGT CAC ATC GTA
    T   P   G   I   R   Y   Q   Y   N   V   L   P   Q   G   W   K   G   S   P   A   I   F   Q   C   S   M>
  ___c___c___c___c___c___c___c___c_POL POLYPROTEIN PRECURSOR; PROTEASE___c___c___c___c___c___c___c___c___>

                                                >conflict;_/replace=a
                                                       |
2420    2425  2430    2435    2440  2445    2450    2455  2460    2465    2470  2475    2480    2485  2490    2495
  GAC AAA AAT CTT AGA GCC TTT TAG AAA ACA AAA TCC AGA CGT AGT CAT CTA TCA ATA CAT GGA TGA TTT GTA TGT AGG
  CTG TTT TTA GAA TCT CGG AAA ATC TTT TGT TTT AGG TCT GCA TCA GTA GAT AGT TAT GTA CCT ACT AAA CAT ACA TCC
    T   K   I   L   E   P   F   R   K   Q   N   P   D   V   V   I   Y   Q   Y   M   D   D   L   Y   V   G>
  ___c___c___c___c___c___c___c___c_POL POLYPROTEIN PRECURSOR; PROTEASE___c___c___c___c___c___c___c___c___>

  2500  2505    2510    2515  2520    2525    2530  2535    2540    2545  2550    2555    2560  2565    2570
  ATC TGA CTT AGA AAT AGG GCA GCA TAG AAC AAA AAT AGA GGA ACT GAG ACA ACA TCT GTT GAG GTG GGG ATT TAC CAC
  TAG ACT GAA TCT TTA TCC CGT CGT ATC TTG TTT TTA TCT CCT TGA CTC TGT TGT AGA CAA CTC CAC CCC TAA ATG GTG
    S   D   L   E   I   G   Q   H   R   T   K   I   E   E   L   R   Q   H   L   L   R   W   G   F   T   T>
  ___c___c___c___c___c___c___c___c_POL POLYPROTEIN PRECURSOR; PROTEASE___c___c___c___c___c___c___c___c___>

2575  2580    2585    2590  2595    2600    2605  2610    2615    2620  2625    2630    2635  2640    2645    2650
  ACC AGA CAA AAA ACA TCA GAA AGA ACC TCC ATT CCT TTG GAT GGG TTA TGA ACT CCA TCC TGA TAA ATG GAC AGT ACA
  TGG TCT GTT TTT TGT AGT CTT TCT TGG AGG TAA GGA AAC CTA CCC AAT ACT TGA GGT AGG ACT ATT TAC CTG TCA TGT
    P   D   K   K   H   Q   K   E   P   P   F   L   W   M   G   Y   E   L   H   P   D   K   W   T   V   Q>
  ___c___c___c___c___c___c___c___c_POL POLYPROTEIN PRECURSOR; PROTEASE___c___c___c___c___c___c___c___c___>

 2655    2660    2665  2670    2675    2680  2685    2690    2695  2700    2705    2710  2715    2720    2725  2730
  GCC TAT AGT GCT GCC AGA AAA GGA CAG CTG GAC TGT CAA TGA CAT ACA GAA ATT AGT GGG AAA ATT GAA TTG GGC AAG
  CGG ATA TCA CGA CGG TCT TTT CCT GTC GAC CTG ACA GTT ACT GTA TGT CTT TAA TCA CCC TTT TAA CTT AAC CCG TTC
    P   I   V   L   P   E   K   D   S   W   T   V   N   D   I   Q   K   L   V   G   K   L   N   W   A   S>
  ___c___c___c___c___c___c___c___c_POL POLYPROTEIN PRECURSOR; PROTEASE___c___c___c___c___c___c___c___c___>

   2735    2740  2745    2750    2755  2760    2765    2770  2775    2780    2785  2790    2795    2800  2805
  TCA GAT TTA TGC AGG GAT TAA AGT AAG GCA ATT ATG TAA ACT TCT TAG GGG AAC CAA AGC ACT AAC AGA AGT AGT ACC
  AGT CTA AAT ACG TCC CTA ATT TCA TTC CGT TAA TAC ATT TGA AGA ATC CCC TTG GTT TCG TGA TTG TCT TCA TCA TGG
    Q   I   Y   A   G   I   K   V   R   Q   L   C   K   L   L   R   G   T   K   A   L   T   E   V   V   P>
     c   c   c   c   c   c   c   c POL POLYPROTEIN PRECURSOR; PROTEASE   c   c   c   c   c   c   c   c   >

2810    2815  2820    2825    2830  2835    2840    2845  2850    2855    2860  2865    2870    2875  2880    2885
  ACT AAC AGA AGA AGC AGA GCT AGA ACT GGC AGA AAA CAG GGA GAT TCT AAA AGA ACC GGT ACA TGG AGT GTA TTA TGA
  TGA TTG TCT TCT TCG TCT CGA TCT TGA CCG TCT TTT GTC CCT CTA AGA TTT TCT TGG CCA TGT ACC TCA CAT AAT ACT
    L   T   E   E   A   E   L   E   L   A   E   N   R   E   I   L   K   E   P   V   H   G   V   Y   Y   D>
     c   c   c   c   c   c   c   c POL POLYPROTEIN PRECURSOR; PROTEASE   c   c   c   c   c   c   c   c   >
```

Fig. 12: NL4.3 Sequence – Full Length, Wild Type (cont)

```
  2890  2895   2900   2905  2910   2915   2920  2925   2930   2935  2940   2945   2950  2955   2960
 CCC ATC AAA AGA CTT AAT AGC AGA AAT ACA GAA GCA GGG GCA AGG CCA ATG GAC ATA TCA AAT TTA TCA AGA GCC ATT
 GGG TAG TTT TCT GAA TTA TCG TCT TTA TGT CTT CGT CCC CGT TCC GGT TAC CTG TAT AGT TTA AAT AGT TCT CGG TAA
  P   S   K   D   L   I   A   E   I   Q   K   Q   G   Q   G   Q   W   T   Y   Q   I   Y   Q   E   P   F>
 ___c___c___c___c___c___c___c___c_POL POLYPROTEIN PRECURSOR; PROTEASE___c___c___c___c___c___c___c___c___>

                 >conflict;_/replace=a
                           |
2965  2970   2975   2980  2985 | 2990   2995  3000   3005   3010  3015   3020   3025  3030   3035   3040
 TAG AAA TCT GAA AAC AGG AAA GTA TGC AAG AAT GAA GGG TGC CCA CAC TAA TGA TGT GAA ACA ATT AAC AGA GGC AGT
 ATC TTT AGA CTT TTG TCC TTT CAT ACG TTC TTA CTT CCC ACG GGT GTG ATT ACT ACA CTT TGT TAA TTG TCT CCG TCA
  R   N   L   K   T   G   K   Y   A   R   M   K   G   A   H   T   N   D   V   K   Q   L   T   E   A   V>
 ___c___c___c___c___c___c___c___c_POL POLYPROTEIN PRECURSOR; PROTEASE___c___c___c___c___c___c___c___c___>

 3045   3050   3055  3060   3065   3070  3075   3080   3085  3090   3095   3100  3105   3110   3115  3120
 ACA AAA AAT AGC CAC AGA AAG CAT AGT AAT ATG GGG AAA GAC TCC TAA ATT TAA ATT ACC CAT ACA AAA GGA AAC ATG
 TGT TTT TTA TCG GTG TCT TTC GTA TCA TTA TAC CCC TTT CTG AGG ATT TAA ATT TAA TGG GTA TGT TTT CCT TTG TAC
  Q   K   I   A   T   E   S   I   V   I   W   G   K   T   P   K   F   K   L   P   I   Q   K   E   T   W>
 ___c___c___c___c___c___c___c___c_POL POLYPROTEIN PRECURSOR; PROTEASE___c___c___c___c___c___c___c___c___>

   3125   3130  3135   3140   3145  3150   3155   3160  3165   3170   3175  3180   3185   3190  3195
 GGA AGC ATG GTG GAC AGA GTA TTG GCA AGC CAC CTG GAT TCC TGA GTG GGA GTT TGT CAA TAC CCC TCC CTT AGT GAA
 CCT TCG TAC CAC CTG TCT CAT AAC CGT TCG GTG GAC CTA AGG ACT CAC CCT CAA ACA GTT ATG GGG AGG GAA TCA CTT
  E   A   W   W   T   E   Y   W   Q   A   T   W   I   P   E   W   E   F   V   N   T   P   P   L   V   K>
 ___c___c___c___c___c___c___c___c_POL POLYPROTEIN PRECURSOR; PROTEASE___c___c___c___c___c___c___c___c___>

3200   3205  3210   3215   3220  3225   3230   3235  3240   3245   3250  3255   3260   3265  3270   3275
 GTT ATG GTA CCA GTT AGA GAA AGA ACC CAT AAT AGG AGC AGA AAC TTT CTA TGT AGA TGG GGC AGC CAA TAG GGA AAC
 CAA TAC CAT GGT CAA TCT CTT TCT TGG GTA TTA TCC TCG TCT TTG AAA GAT ACA TCT ACC CCG TCG GTT ATC CCT TTG
  L   W   Y   Q   L   E   K   E   P   I   I   G   A   E   T   F   Y   V   D   C   A   A   N   R   E   T>
 ___c___c___c___c___c___c___c___c_POL POLYPROTEIN PRECURSOR; PROTEASE___c___c___c___c___c___c___c___c___>

  3280  3285   3290   3295  3300   3305   3310  3315   3320   3325  3330   3335   3340  3345   3350
 TAA ATT AGG AAA AGC AGG ATA TGT AAC TGA CAG AGG AAG ACA AAA AGT TGT CCC CCT AAC GGA CAC AAC AAA TCA GAA
 ATT TAA TCC TTT TCG TCC TAT ACA TTG ACT GTC TCC TTC TGT TTT TCA ACA GGG GGA TTG CCT GTG TTG TTT AGT CTT
  K   L   G   K   A   G   Y   V   T   D   R   G   R   Q   K   V   V   P   L   T   D   T   T   N   Q   K>
 ___c___c___c___c___c___c___c___c_POL POLYPROTEIN PRECURSOR; PROTEASE___c___c___c___c___c___c___c___c___>

3355  3360   3365   3370  3375   3380   3385  3390   3395   3400  3405   3410   3415  3420   3425   3430
 GAC TGA GTT ACA AGC AAT TCA TCT AGC TTT GCA GGA TTC GGG ATT AGA AGT AAA CAT AGT GAC AGA CTC ACA ATA TGC
 CTG ACT CAA TGT TCG TTA AGT AGA TCG AAA CGT CCT AAG CCC TAA TCT TCA TTT GTA TCA CTG TCT GAG TGT TAT ACG
  T   E   L   Q   A   I   H   L   A   L   Q   D   S   G   L   E   V   N   I   V   T   D   S   Q   Y   A>
 ___c___c___c___c___c___c___c___c_POL POLYPROTEIN PRECURSOR; PROTEASE___c___c___c___c___c___c___c___c___>

 3435   3440   3445  3450   3455   3460  3465   3470   3475  3480   3485   3490  3495   3500   3505  3510
 ATT GGG AAT CAT TCA AGC ACA ACC AGA TAA GAG TGA ATC AGA GTT AGT CAG TCA AAT AAT AGA GCA GTT AAT AAA AAA
 TAA CCC TTA GTA AGT TCG TGT TGG TCT ATT CTC ACT TAG TCT CAA TCA GTC AGT TTA TTA TCT CGT CAA TTA TTT TTT
  L   G   I   I   Q   A   Q   P   D   K   S   E   S   E   L   V   S   Q   I   I   E   Q   L   I   K   K>
 ___c___c___c___c___c___c___c___c_POL POLYPROTEIN PRECURSOR; PROTEASE___c___c___c___c___c___c___c___c___>

                                                                        >conflict; /replace-g
                                                                                  |
                                                                      >conflict;_/replace=g
                                                                                |  |
                                                                     >conflict;_/replace=g
                                                                               || |
   3515   3520  3525   3530   3535  3540   3545   3550  3555   3560   3565  3570   3575| |3580  3585
 GGA AAA AGT CTA CCT GGC ATG GGT ACC AGC ACA CAA AGG AAT TGG AGG AAA TGA ACA AGT AGA TAA ATT GGT CAG TGC
 CCT TTT TCA GAT GGA CCG TAC CCA TGG TCG TGT GTT TCC TTA ACC TCC TTT ACT TGT TCA TCT ATT TAA CCA GTC ACG
  E   K   V   Y   L   A   W   V   P   A   H   K   G   I   G   G   N   E   Q   V   D   K   L   V   S   A>
 ___c___c___c___c___c___c___c___c_POL POLYPROTEIN PRECURSOR; PROTEASE___c___c___c___c___c___c___c___c___>

3590   3595  3600   3605   3610  3615   3620   3625  3630   3635   3640  3645   3650   3655  3660   3665
 TGG AAT CAG GAA AGT ACT ATT TTT AGA TGG AAT AGA TAA GGC CCA AGA AGA ACA TGA GAA ATA TCA CAG TAA TTG GAG
 ACC TTA GTC CTT TCA TGA TAA AAA TCT ACC TTA TCT ATT CCG GGT TCT TCT TGT ACT CTT TAT AGT GTC ATT AAC CTC
  G   I   R   K   V   L   F   L   D   G   I   D   K   A   Q   E   E   H   E   K   Y   H   S   N   W   R>
 ___c___c___c___c___c___c___c___c_POL POLYPROTEIN PRECURSOR; PROTEASE___c___c___c___c___c___c___c___c___>

  3670  3675   3680   3685  3690   3695   3700  3705   3710   3715  3720   3725   3730  3735   3740
 AGC AAT GGC TAG TGA TTT TAA CCT ACC ACC TGT AGT AGC AAA AGA AAT AGT AGC CAG CTG TGA TAA ATG TCA GCT AAA
 TCG TTA CCG ATC ACT AAA ATT GGA TGG TGG ACA TCA TCG TTT TCT TTA TCA TCG GTC GAC ACT ATT TAC AGT CGA TTT
  A   M   A   S   D   F   N   L   P   P   V   V   A   K   E   I   V   A   S   C   D   K   C   Q   L   K>
 ___c___c___c___c___c___c___c___c_POL POLYPROTEIN PRECURSOR; PROTEASE___c___c___c___c___c___c___c___c___>

3745  3750   3755   3760  3765   3770   3775  3780   3785   3790  3795   3800   3805  3810   3815   3820
 AGG CCA ACC CAT GCA TGG ACA AGT AGA CTG TAC CCC AGG AAT ATG GCA GCT AGA TTG TAC ACA TTT AGA AGG AAA AGT
 TCC CCT TCG GTA CGT ACC TGT TCA TCT GAC ATC GGG TCC TTA TAC CGT CGA TCT AAC ATG TGT AAA TCT TCC TTT TCA
  G   E   A   M   H   G   Q   V   D   C   S   P   G   I   W   Q   L   D   C   T   H   L   E   G   K   V>
 ___c___c___c___c___c___c___c___c_POL POLYPROTEIN PRECURSOR; PROTEASE___c___c___c___c___c___c___c___c___>

   >conflict; /replace=a
```

Fig. 12: NL4.3 Sequence – Full Length, Wild Type (cont)

```
              |
3825   3830  |3835  3840   3845   3850  3855   3860   3865  3870   3875   3880  3885   3890   3895  3900
 TAT CTT GGT GCC AGT TCA TGT ACC CAC TGG ATA TAT AGA AGC AGA ACT AAT TCC AGC ACA GAC AGG GCA ACA AAC AGC
 ATA GAA CCA CCG TCA AGT ACA TGG GTC ACC TAT ATA TCT TCG TCT TCA TTA AGG TCG TCT CTG TCC CGT TCT TTG TCG
   I   L   V   A   V   H   V   A   S   G   Y   I   E   A   E   V   I   P   A   E   T   G   Q   E   T   A>
 ___c___c___c___c___c___c___c___c_POL POLYPROTEIN PRECURSOR; PROTEASE___c___c___c___c___c___c___c___c___>

  3905   3910  3915   3920   3925  3930   3935   3940  3945   3950   3955  3960   3965   3970  3975
 ATA CTT CCT CTT AAA ATT AGC AGG AAG ATG GCC AGT AAA AAC AGT ACA TAC AGA CAA TGG CAG CAA TTT CAC CAG TAC
 TAT GAA GGA GAA TTT TAA TCG TCC TTC TAC CGG TCA TTT TTG TCA TGT ATG TCT GTT ACC GTC GTT AAA GTG GTC ATG
   Y   F   L   L   K   L   A   G   R   W   P   V   K   T   V   H   T   D   N   G   S   N   F   T   S   T>
 ___c___c___c___c___c___c___c___c_POL POLYPROTEIN PRECURSOR; PROTEASE___c___c___c___c___c___c___c___c___>

                                >conflict;_/replace=a
                                          |
3980   3985  3990   3995   4000  4005   4010   4015  4020   4025   4030  4035   4040   4045  4050   4055
 TAC AGT TAA GGC CGC CTG TTG GTG GGC GGG AAT CAA GCA GGA ATT TGG CAT TCC CTA CAA TCC CCA AAG TCA AGG AGT
 ATG TCA ATT CCG GCG GAC AAC CAC CCG CCC TTA GTT CGT CCT TAA ACC GTA AGG GAT GTT AGG GGT TTC AGT TCC TCA
   T   V   K   A   A   C   W   W   A   G   I   K   Q   E   F   G   I   P   Y   N   P   Q   S   Q   G   V>
 ___c___c___c___c___c___c___c___c_POL POLYPROTEIN PRECURSOR; PROTEASE___c___c___c___c___c___c___c___c___>

  4060  4065   4070   4075  4080   4085   4090  4095   4100   4105  4110   4115   4120  4125   4130
 AAT AGA ATC TAT GAA TAA AGA ATT AAA GAA AAT TAT AGG ACA GGT AAG AGA TCA GGC TGA ACA TCT TAA GAC AGC AGT
 TTA TCT TAG ATA CTT ATT TCT TAA TTT CTT TTA ATA TCC TGT CCA TTC TCT AGT CCG ACT TGT AGA ATT CTG TCG TCA
   I   E   S   M   N   K   E   L   K   K   I   I   G   Q   V   R   D   Q   A   E   H   L   K   T   A   V>
 ___c___c___c___c___c___c___c___c_POL POLYPROTEIN PRECURSOR; PROTEASE___c___c___c___c___c___c___c___c___>

4135  4140   4145   4150  4155   4160   4165  4170   4175   4180  4185   4190   4195  4200   4205   4210
 ACA AAT GGC AGT ATT CAT CCA CAA TTT TAA AAG AAA AGG GGG GAT TGG GGG GTA CAG TGC AGG GGA AAG AAT AGT AGA
 TGT TTA CCG TCA TAA GTA GGT GTT AAA ATT TTC TTT TCC CCC CTA ACC CCC CAT GTC ACG TCC CCT TTC TTA TCA TCT
   Q   M   A   V   F   I   H   N   F   K   R   K   G   G   I   G   G   Y   S   A   G   E   R   I   V   D>
 ___c___c___c___c___c___c___c___c_POL POLYPROTEIN PRECURSOR; PROTEASE___c___c___c___c___c___c___c___c___>

 4215   4220   4225  4230   4235   4240  4245   4250   4255  4260   4265   4270  4275   4280   4285  4290
 CAT AAT AGC AAC AGA CAT ACA AAC TAA AGA ATT ACA AAA ACA AAT TAC AAA AAT TCA AAA TTT TCG GGT TTA TTA CAG
 GTA TTA TCG TTG TCT GTA TGT TTG ATT TCT TAA TGT TTT TGT TTA ATG TTT TTA AGT TTT AAA AGC CCA AAT AAT GTC
   I   I   A   T   D   I   Q   T   K   E   L   Q   K   Q   I   T   K   I   Q   N   F   R   V   Y   Y   R>
 ___c___c___c___c___c___c___c___c_POL POLYPROTEIN PRECURSOR; PROTEASE___c___c___c___c___c___c___c___c___>

  4295   4300  4305   4310   4315  4320   4325   4330  4335   4340   4345  4350   4355   4360  4365
 GGA CAG CAG ACA TCC AGT TTG GAA AGC ACC AGC AAA GCT CCT CTG GAA AGC TGA AGG GCC AGT AGT AAT ACA AGA TAA
 CCT GTC GTC TGT AGG TCA AAC CTT TCG TGG TCG TTT CGA GGA GAC CTT TCG ACT TCC CGG TCA TCA TTA TGT TCT ATT
   D   S   R   D   P   V   W   K   G   P   A   K   L   L   W   K   G   E   G   A   V   V   I   Q   D   N>
 ___c___c___c___c___c___c___c___c_POL POLYPROTEIN PRECURSOR; PROTEASE___c___c___c___c___c___c___c___c___>

                                                               >Gene:_vif
                                                                    |
4370   4375  4380   4385   4390  4395   4400   4405  4410   4415   4420  4425   4430   4435  4440   4445
 TAG TGA CAT AAA AGT AGT GCC AAG AAG AAA AGC AAA GAT CAT CAG GGA TTA TGG AAA ACA GAT GGC AGG TGA TGA TTG
 ATC ACT GTA TTT TCA TCA CGG TTC TTC TTT TCG TTT CTA GTA GTC CCT AAT ACC TTT TGT CTA CCG TCC ACT ACT AAC
   S   D   I   K   V   V   P   R   R   K   A   K   I   I   R   D   Y   G   K   Q   M   A   G   D   D   C>
 ___c___c___c___c___c___c___c___c_POL POLYPROTEIN PRECURSOR; PROTEASE___c___c___c___c___c___c___c___c___>
                                                                     M   E   N   R   W   Q   V   M   I>
                                                                   _d___d___d__VIF PROTEIN__d___d___d___>

  4450  4455   4460   4465  4470   4475   4480  4485   4490   4495  4500   4505   4510  4515   4520
 TGT GGC AAG TAG ACA GGA TGA GCA TTA ACA CAT GCA AAA GAT TAG TAA AAC ACC ATA TCT ATA TTT CAA GCA AAC CTA
 ACA CCG TTC ATC TGT CCT ACT CGT AAT TGT GTA CGT TTT CTA ATC ATT TTG TGG TAT AGA TAT AAA GTT CGT TTG GAT
   V   A   S   R   Q   D   E   D   *>
 ___POL POLYPROTEIN PRECURSOR; PRO__c_>
 V   W   Q   V   D   R   M   R   I   N   T   W   K   R   L   V   K   H   H   M   Y   I   S   R   K   A>
 ___d___d___d___d___d___d___d___d___d___d___d_VIF PROTEIN___d___d___d___d___d___d___d___d___d___d___d___>

4525  4530   4535   4540  4545   4550   4555  4560   4565   4570  4575   4580   4585  4590   4595   4600
 AGC ACT GGT TTT ATA GAC ATC ACT ATC AAA GTA CTA ATC CAA AAA TAA GTT CAG AAG TAC ACA TCC CAC TAG GGC ATG
 TCG TGA CCA AAA TAT CTG TAG TGA TAG TTT CAT GAT TAG GTT TTT ATT CAA GTC TTC ATG TGT AGG GTG ATC CCG TAC
 K   D   W   F   Y   R   H   H   Y   E   S   T   N   P   K   I   S   S   E   V   H   I   P   L   G   D>
 ___d___d___d___d___d___d___d___d___d___d___d_VIF PROTEIN___d___d___d___d___d___d___d___d___d___d___d___>

 4605   4610   4615  4620   4625   4630  4635   4640   4645  4650   4655   4660  4665   4670   4675  4680
 CTA AAT TAG TAA TAA CAA CAT ATT GGG GTC TGC ATA CAG GAG AAA GAG ACT GGC ATT TGG GTC AGG GAG TCT CCA TAG
 GAT TTA ATC ATT ATT GTT GTA TAA CCC CAG ACG TAT GTC CTC TTT CTC TGA CCG TAA ACC CAG TCC CTC AGA GGT ATC
 A   K   L   V   I   T   T   Y   W   G   L   H   T   G   E   R   D   W   H   L   G   Q   G   V   S   I>
 ___d___d___d___d___d___d___d___d___d___d___d_VIF PROTEIN___d___d___d___d___d___d___d___d___d___d___d___>

  4685   4690  4695   4700   4705  4710   4715   4720  4725   4730   4735  4740   4745   4750  4755
 AAT GGA GGA AAA AGA GAT ATA GCA CAC AAG TAG ACC CTG ACC TAG CAG ACC AAC TAA TTC ATC TGC ACT ATT TTG ATT
 TTA CCT CCT TTT TCT CTA TAT CGT GTG TTC ATC TGG GAC TGG ATC GTC TGG TTG ATT AAG TAG ACG TGA TAA AAC TAA
 E   W   R   K   K   R   Y   S   T   Q   V   D   P   D   L   A   D   Q   L   I   H   L   H   Y   F   D>
 ___d___d___d___d___d___d___d___d___d___d___d_VIF PROTEIN___d___d___d___d___d___d___d___d___d___d___d___>
```

Fig. 12: NL4.3 Sequence – Full Length, Wild Type (cont)

```
4760   4765  4770   4775   4780  4785   4790   4795  4800   4805   4810  4815   4820   4825  4830   4835
  CTT TTT CAG AAT CTG CTA TAA GAA ATA CCA TAT TAG GAC CTA TAG TTA GTC CTA GGT GTG AAT ATC AAG CAG GAC ATA
  CAA AAA GTC TTA GAC GAT ATT CTT TAT GGT ATA ATC CTG CAT ATC AAT CAG GAT CCA CAC TTA TAG TTC GTC CTG TAT
  C   F   S   E   S   A   I   R   N   T   I   L   G   R   I   V   S   P   R   C   E   Y   Q   A   G   E>
     d   d   d   d   d   d   d   d   d   d   d VIF PROTEIN  d   d   d   d   d   d   d   d   d   d   d   >

  4840  4845   4850   4855  4860   4865   4870  4875   4880   4885  4890   4895   4900  4905   4910
  ACA AGG TAG GAT CTC TAC AGT ACT TGG CAC TAG CAG CAT TAA TAA AAC CAA AAC AGA TAA AGC CAC CTT TGC CTA GTG
  TGT TCC ATC CTA GAG ATG TCA TGA ACC GTG ATC GTC GTA ATT ATT TTG GTT TTG TCT ATT TCG GTG GAA ACG GAT CAC
  N   K   V   G   S   L   Q   Y   L   A   L   A   A   L   I   K   P   K   Q   I   K   P   P   L   P   S>
  ___d___d___d___d___d___d___d___d___d___d___d_VIF PROTEIN___d___d___d___d___d___d___d___d___d___d___d___>

                            >Gene:_vpr                                          >conflict;_/replace-t
                                 |                                                      |
4915  4920   4925   4930  4935  |4940   4945  4950   4955   4960  4965   4970   4975  4980 | 4985   4990
  TTA GGA AAC TGA CAG AGG ACA GAT GGA ACA AGC CCC AGA AGA CCA AGG GCC ACA GAG GGA GCC ATA CAA CGA ATG GAC
  AAT CCT TTG ACT GTC TCC TGT CTA CCT TGT TCG GGG TCT TCT GGT TCC CGG TGT CTC CCT CGG TAT GTT GCT TAC CTG
  V   R   K   L   T   E   D   R   W   N   K   P   Q   K   T   K   G   H   R   G   S   H   T   T   N   G>
  ___d___d___d___d___d___d___d___d___d___d___d_VIF PROTEIN___d___d___d___d___d___d___d___d___d___d___d___>
                                 M   E   Q   A   P   E   D   Q   G   P   Q   R   E   P   Y   N   E   W   T>
                                __c___c___c___c___c___c___c____VPR PROTEIN____c___c___c___c___c___c___c___>

>conflict;_/replace=a
                                                                                                     |
 4995   5000   5005  5010   5015   5020  5025   5030   5035  5040   5045   5050  5055   5060   5065 |5070
  ACT AGA GCT TTT AGA GGA ACT TAA GAG TGA AGC TGT TAG ACA TTT TCC TAG GAT ATG GCT CCA TAA CTT AGG ACG ACA
  TGA TCT CGA AAA TCT CCT TGA ATT CTC ACT TCG ACA ATC TGT AAA AGG ATC CTA TAC CGA GGT ATT GAA TCC TGC TGT
  H   *>
  ___d__>
   L   E   L   L   E   E   L   K   S   E   A   V   R   H   F   P   R   I   W   L   H   N   L   G   R   H>
  ___e___e___e___e___e___e___e___e___e___e___e_VPR PROTEIN___e___e___e___e___e___e___e___e___e___e___e___>

                                                                                 >conflict;_/replace=c
                                                                                          |
   5075   5080  5085   5090   5095  5100   5105   5110  5115   5120   5125  5130   5135   5140  5145
  TAT CTA TGA AAC TTA CGG GGA TAC TTG GGC AGG AGT GGA AGC CAT AAT AAG AAT TCT GCA ACA ACT GCC GTT TAT CCA
  ATA GAT ACT TTG AAT GCC CCT ATG AAC CCG TCC TCA CCT TCG GTA TTA TTC TTA AGA CGT TGT TGA CGG CAA ATA GGT
   I   Y   E   T   Y   G   D   T   W   A   G   V   E   A   I   I   R   I   L   Q   Q   L   P   F   I   H>
  ___c___c___c___c___c___c___c___c___c___c___c_VPR PROTEIN___c___c___c___c___c___c___c___c___c___c___c___>

                                                                             >Gene: tat
                                                                                  |
5150   5155  5160   5165   5170  5175   5180   5185  5190   5195   5200  5205   5210   5215  5220   5225
  TTT CAG AAT TGG GTG TCG ACA TAG CAG AAT AGG CGT TAC TCG ACA GAG GAG AGC AAG AAA TGG AGC CAG TAG ATC CTA
  AAA GTC TTA ACC CAC AGC TGT ATC GTC TTA TCC GCA ATG AGC TGT CTC CTC TCG TTC TTT ACC TCG GTC ATC TAG GAT
   F   R   I   G   C   R   H   S   R   I   G   V   T   R   Q   R   R   A   R   N   G   A   S   R   S   *>
  ___e___e___e___e___e___e___e___e___e___e___e_VPR PROTEIN___e___e___e___e___e___e___e___e___e___e___e___>
                                                                                  M   E   P   V   D   P>
                                                                                 _f_TAT PROTEIN; /FUNC____>

  5230  5235   5240   5245  5250   5255   5260  5265   5270   5275  5280   5285   5290  5295   5300
  GAC TAG AGC CCT GGA AGC ATC CAG GAA GTC AGC CTA AAA CTG CTT GTA CCA ATT GCT ATT GTA AAA AGT GTT GCT TTC
  CTG ATC TCG GGA CCT TCG TAG GTC CTT CAG TCG GAT TTT GAC GAA CAT GGT TAA CGA TAA CAT TTT TCA CAA CGA AAG
  _>
  R   L   E   P   W   K   H   P   G   S   Q   P   K   T   A   C   T   N   C   Y   C   K   K   C   C   F>
  ___f___f___f___f___f___f___f____TAT PROTEIN; /FUNCTION=TRANSACTIVATOR__f___f___f___f___f___f___f___f___>

                                                         >Gene:_rev
                                                              |
5305  5310   5315   5320  5325   5330   5335  5340   5345  |5350  5355   5360   5365  5370   5375   5380
  ATT CCC AAG TTT GTT TCA TGA CAA AAC CCT TAG GCA TCT CCT ATG GCA GGA ACA AGC GGA GAC AGC GAC GAA GAC CTC
  TAA CGG TTC AAA CAA AGT ACT GTT TTC GGA ATC CGT AGA GGA TAC CGT CCT TCT TCG CCT CTG TCG CTG CTT CTG GAG
  H   C   Q   V   C   F   M   T   K   A   L   G   I   S   Y   G   R   K   K   R   R   Q   R   R   R   A>
     f   f   f   f   f   f   f    TAT PROTEIN; /FUNCTION=TRANSACTIVATOR  f   f   f   f   f   f   f   f   >
                                                              M   A   G   R   S   G   D   S   D   E   E   L>
                                                             ___REV PROTEIN; /FUNCTION=REGULATOR OF VIRA____>

                                                                              >Gene:_vpu
                                                                                   |
 5385   5390   5395  5400   5405   5410  5415   5420   5425  5430   5435   5440  5445   5450   5455  5460
  ATC AGA ACA GTC AGA CTC ATC AAG CTT CTC TAT CAA AGC AGT AAG TAG TAC ATG TAA TGC AAC CTA TAA TAG TAG CAA
  TAG TCT TGT CAG TCT GAG TAG TTC GAA GAG ATA GTT TCG TCA TTC ATC ATG TAC ATT ACG TTG GAT ATT ATC ATC GTT
  H   Q   N   S   Q   T   H   Q   A   S   L   S   K   Q>
  ___f___TAT PROTEIN; /FUNCTION=TRANSACTIVATOR___f___f_>
   I   R   T   V   R   L   I   K   L   L   Y   Q   S   N>
  ___REV PROTEIN; /FUNCTION=REGULATOR OF VIRAL EXPR__g_>
                                                                                   M   Q   P   I   I   V   A>
                                                                                  h   h  VPU PROTEIN  h   h   >

   5465   5470  5475   5480   5485  5490   5495   5500  5505   5510   5515  5520   5525   5530  5535
```

Fig. 12: NL4.3 Sequence – Full Length, Wild Type (cont)

```
 TAG TAG CAT TAG TAG TAG CAA TAA TAA TAG CAA TAG TTG TGT GGT CCA TAG TAA TCA TAG AAT ATA GGA AAA TAT TAA
 ATC ATC GTA ATC ATC ATC GTT ATT ATT ATC GTT ATC AAC ACA CCA GGT ATC ATT AGT ATC TTA TAT CCT TTT ATA ATT
 I   V   A   L   V   V   A   I   I   I   A   I   V   V   W   S   I   V   I   I   E   Y   R   K   I   L>
 ___h___h___h___h___h___h___h___h___h___h___h_VPU PROTEIN___h___h___h___h___h___h___h___h___h___h___h___>

                                                                                     >Gene:_env
                                                                                         |
5540   5545  5550   5555   5560  5565   5570   5575  5580   5585   5590  5595   5600   5605  5610   5615
 GAC AAA GAA AAA TAG ACA GGT TAA TTG ATA GAC TAA TAG AAA GAG CAG AAG ACA GTG GCA ATG AGA GTG AAG GAG AAG
 CTG TTT CTT TTT ATC TGT CCA ATT AAC TAT CTG ATT ATC TTT CTC GTC TTC TGT CAC CGT TAC TCT CAC TTC CTC TTC
 R   Q   R   K   I   D   R   L   I   D   R   L   I   E   R   A   E   D   S   G   N   E   S   E   G   E>
 ___h___h___h___h___h___h___h___h___h___h___h_VPU PROTEIN___h___h___h___h___h___h___h___h___h___h___h___>
                                                                                 M   R   V   K   E   K>
                                                                                ___ENV POLYPROTEIN ____>

 5620  5625   5630   5635  5640   5645   5650  5655   5660   5665  5670   5675   5680  5685   5690
 TAT CAG CAC TTG TGG AGA TGG GGG TGG AAA TGG GGC ACC ATG CTC CTT GGG ATA TTG ATG ATC TGT AGT GCT ACA GAA
 ATA GTC GTG AAC ACC TCT ACC CCC ACC TTT ACC CCG TGG TAC GAG GAA CCC TAT AAC TAC TAG ACA TCA CGA TGT CTT
 V   S   A   L   V   E   M   G   V   E   M   G   H   H   A   P   W   D   T   D   D   L   *>
 ___h___h___h___h___h___h___h___h___h___VPU PROTEIN_h___h___h___h___h___h___h___h___h___h__>
  Y   Q   H   L   W   R   W   G   W   K   W   G   T   M   L   L   G   I   L   M   I   C   S   A   T   E>
    i   i   i   i   i   i   i   i   ENV POLYPROTEIN PRECURSOR; GP120    i   i   i   i   i   i   i   i   >

5695  5700   5705   5710  5715   5720   5725  5730   5735   5740  5745   5750   5755  5760   5765   5770
 AAA TTG TGG GTC ACA GTC TAT TAT GGG GTA CCT GTG TGG AAG GAA GCA ACC ACC ACT CTA TTT TGT GCA TCA GAT GCT
 TTT AAC ACC CAG TGT CAG ATA ATA CCC CAT GGA CAC ACC TTC CTT CGT TGG TGG TGA GAT AAA ACA CGT AGT CTA CGA
  K   L   W   V   T   V   Y   Y   G   V   P   V   W   K   E   A   T   T   T   L   F   C   A   S   D   A>
 ___i___i___i___i___i___i___i___i___ENV POLYPROTEIN PRECURSOR; GP120____i___i___i___i___i___i___i___i___>

 5775   5780   5785  5790   5795   5800  5805   5810   5815  5820   5825   5830  5835   5840   5845  5850
 AAA GCA TAT GAT ACA GAG GTA CAT AAT GTT TGG GCC ACA CAT GCC TGT GTA CCC ACA GAC CCC AAC CCA CAA GAA GTA
 TTT CGT ATA CTA TGT CTC CAT GTA TTA CAA ACC CGG TGT GTA CGG ACA CAT GGG TGT CTG GGG TTG GGT GTT CTT CAT
  K   A   Y   D   T   E   V   H   N   V   W   A   T   H   A   C   V   P   T   D   P   N   P   Q   E   V>
 ___i___i___i___i___i___i___i___i___ENV POLYPROTEIN PRECURSOR; GP120____i___i___i___i___i___i___i___i___>

                                            >conflict;_/replace=g
                                                       :
  5855   5860  5865   5870   5875  5880   5885   5890  5895   5900   5905  5910   5915   5920  5925
 CTA TTG GTA AAT GTG ACA GAA AAT TTT AAC ATG TGG AAA CAT GAC ATG GTA CAA CAG ATG CAT GAG GAT ATA ATC AGT
 CAT AAC CAT TTA CAC TGT CTT TTA AAA TTG TAC ACC TTT CTA CTG TAC CAT CTT GTC TAC GTA CTC CTA TAT TAG TCA
  V   L   V   N   V   T   E   N   F   N   M   W   K   D   D   M   V   E   Q   M   H   E   D   I   I   S>
 ___i___i___i___i___i___i___i___i___ENV POLYPROTEIN PRECURSOR; GP120____i___i___i___i___i___i___i___i___>

5930   5935  5940   5945   5950  5955   5960   5965  5970   5975   5980  5985   5990   5995  6000   6005
 TTA TGG GAT CAA AGC CTA AAG CCA TGT GTA AAA TTA ACC CCA CTC TGT GTT AGT TTA AAG TGC ACT GAT TTG AAG AAT
 AAT ACC CTA GTT TCG GAT TTC GGT ACA CAT TTT AAT TGG GGT GAG ACA CAA TCA AAT TTC ACG TGA CTA AAC TTC TTA
  L   W   D   Q   S   L   K   P   C   V   K   L   T   P   L   C   V   S   L   K   C   T   D   L   K   N>
 ___i___i___i___i___i___i___i___i___ENV POLYPROTEIN PRECURSOR; GP120____i___i___i___i___i___i___i___i___>

 6010  6015   6020   6025  6030   6035   6040  6045   6050   6055  6060   6065   6070  6075   6080
 GAT ACT AAT ACC AAT AGT AGT AGC GGG AGA ATG ATA ATG GAG AAA GGA GAG ATA AAA AAC TGC TCT TTC AAT ATC AGC
 CTA TGA TTA TGG TTA TCA TCA TCG CCC TCT TAC TAT TAC CTC TTT CCT CTC TAT TTT TTG ACG AGA AAG TTA TAG TCG
  D   T   N   T   N   S   S   S   G   R   M   I   M   E   K   G   E   I   K   N   C   S   F   N   I   S>
 ___i___i___i___i___i___i___i___i___ENV POLYPROTEIN PRECURSOR; GP120____i___i___i___i___i___i___i___i___>

6085  6090   6095   6100  6105   6110   6115  6120   6125   6130  6135   6140   6145  6150   6155   6160
 ACA AGC ATA AGA GAT AAG GTG CAG AAA GAA TAT GCA TTC TTT TAT AAA CTT GAT ATA GTA CCA ATA GAT AAT ACC AGC
 TGT TCG TAT TCT CTA TTC CAC GTC TTT CTT ATA CGT AAG AAA ATA TTT GAA CTA TAT CAT GGT TAT CTA TTA TGG TCG
  T   S   I   R   D   K   V   Q   K   E   Y   A   F   F   Y   K   L   D   I   V   P   I   D   N   T   S>
 ___i___i___i___i___i___i___i___i___ENV POLYPROTEIN PRECURSOR; GP120____i___i___i___i___i___i___i___i___>


>conflict;_/replace=t
                                                                                                     :
 6165   6170   6175  6180   6185   6190  6195   6200   6205  6210   6215   6220  6225   6230   6235  6240
 TAT AGG TTG ATA AGT TGT AAC ACC TCA GTC ATT ACA CAG GCC TGT CCA AAG GTA TCC TTT GAG CCA ATC CCC ATA CAT
 ATA TCC AAC TAT TCA ACA TTG TGG AGT CAG TAA TGT GTC CGG ACA GGT TTC CAT AGG AAA CTC GGT TAG GGG TAT GTA
  Y   R   L   I   S   C   N   T   S   V   I   T   Q   A   C   P   K   V   S   F   E   P   I   P   I   E>
    i   i   i   i   i   i   i   i   ENV POLYPROTEIN PRECURSOR; GP120    i   i   i   i   i   i   i   i   >

  6245   6250  6255   6260   6265  6270   6275   6280  6285   6290   6295  6300   6305   6310  6315
 TAT TGT GCC CCG GCT GGT TTT GCG ATT CTA AAA TGT AAT AAT AAG ACG TTC AAT GGA ACA GGA CCA TGT ACA AAT GTC
 ATA ACA CGG GGC CGA CCA AAA CGC TAA GAT TTT ACA TTA TTA TTC TGC AAG TTA CCT TGT CCT GGT ACA TGT TTA CAG
  Y   C   A   P   A   G   F   A   I   L   K   C   N   N   K   T   F   N   G   T   G   P   C   T   N   V>
 ___i___i___i___i___i___i___i___i___ENV POLYPROTEIN PRECURSOR; GP120____i___i___i___i___i___i___i___i___>

6320   6325  6330   6335   6340  6345   6350   6355  6360   6365   6370  6375   6380   6385  6390   6395
 AGC ACA GTA CAA TGT ACA CAT GGA ATC AGG CCA GTA GTA TCA ACT CAA CTG CTG TTA AAT GGC AGT CTA GCA GAA GAA
 TCG TGT CAT GTT ACA TGT GTA CCT TAG TCC GGT CAT CAT AGT TGA GTT GAC GAC AAT TTA CCG TCA GAT CGT CTT CTT
  S   T   V   Q   C   T   H   G   I   R   P   V   V   S   T   Q   L   L   L   N   G   S   L   A   E   E>
 ___i___i___i___i___i___i___i___i___ENV POLYPROTEIN PRECURSOR; GP120____i___i___i___i___i___i___i___i___>
```

Fig. 12: NL4.3 Sequence – Full Length, Wild Type (cont)

```
  6400  6405   6410   6415  6420   6425   6430  6435   6440   6445  6450   6455   6460  6465   6470
 GAT GTA GTA ATT AGA TCT GCC AAT TTC ACA GAC AAT GCT AAA ACC ATA ATA GTA CAG CTG AAC ACA TCT GTA GAA ATT
 CTA CAT CAT TAA TCT AGA CGG TTA AAG TGT CTG TTA CGA TTT TGG TAT TAT CAT GTC GAC TTG TGT AGA CAT CTT TAA
  D   V   V   I   R   S   A   N   F   T   D   N   A   K   T   I   I   V   Q   L   N   T   S   V   E   I>
 ___i___i___i___i___i___i___i___i___ENV POLYPROTEIN PRECURSOR; GP120____i___i___i___i___i___i___i___i___>

6475  6480   6485   6490  6495   6500   6505  6510   6515   6520  6525   6530   6535  6540   6545   6550
 AAT TGT ACA AGA CCC AAC AAC AAT ACA AGA AAA AGT ATC CGT ATC CAG AGG GGA CCA GGG AGA GCA TTT GTT ACA ATA
 TTA ACA TGT TCT GGG TTG TTG TTA TGT TCT TTT TCA TAG GCA TAG GTC TCC CCT GGT CCC TCT CGT AAA CAA TGT TAT
  N   C   T   R   P   N   N   N   T   R   K   S   I   R   I   Q   R   G   P   G   R   A   F   V   T   I>
 ___i___i___i___i___i___i___i___i___ENV POLYPROTEIN PRECURSOR; GP120____i___i___i___i___i___i___i___i___>

 6555   6560   6565  6570   6575   6580  6585   6590   6595  6600   6605   6610  6615   6620   6625  6630
 GGA AAA ATA GGA AAT ATG AGA CAA GCA CAT TGT AAC ATT AGT AGA GCA AAA TGG AAT GCC ACT TTA AAA CAG ATA GCT
 CCT TTT TAT CCT TTA TAC TCT GTT CGT GTA ACA TTG TAA TCA TCT CGT TTT ACC TTA CGG TGA AAT TTT GTC TAT CGA
  G   K   I   G   N   M   R   Q   A   H   C   N   I   S   R   A   K   W   N   A   T   L   K   Q   I   A>
 ___i___i___i___i___i___i___i___i___ENV POLYPROTEIN PRECURSOR; GP120____i___i___i___i___i___i___i___i___>

   6635   6640  6645   6650   6655  6660   6665   6670  6675   6680   6685  6690   6695   6700  6705
 AGC AAA TTA AGA GAA CAA TTT GGA AAT AAT AAA ACA ATA ATC TTT AAG CAA TCC TCA GGA GGG GAC CCA GAA ATT GTA
 TCG TTT AAT TCT CTT GTT AAA CCT TTA TTA TTT TGT TAT TAG AAA TTC GTT AGG AGT CCT CCC CTG GGT CTT TAA CAT
  S   K   L   R   E   Q   F   G   N   N   K   T   I   I   F   K   Q   S   S   G   G   D   P   E   I   V>
 ___i___i___i___i___i___i___i___i___ENV POLYPROTEIN PRECURSOR; GP120____i___i___i___i___i___i___i___i___>

 6710   6715  6720   6725   6730  6735   6740   6745  6750   6755   6760  6765   6770   6775  6780   6785
 ACG CAC AGT TTT AAT TGT GGA GGG GAA TTT TTC TAC TGT AAT TCA ACA CAA CTG TTT AAT AGT ACT TGG TTT AAT AGT
 TGC GTG TCA AAA TTA ACA CCT CCC CTT AAA AAG ATG ACA TTA AGT TGT GTT GAC AAA TTA TCA TGA ACC AAA TTA TCA
  T   H   S   F   N   C   G   G   E   F   F   Y   C   N   S   T   Q   L   F   N   S   T   W   F   N   S>
 ___i___i___i___i___i___i___i___i___ENV POLYPROTEIN PRECURSOR; GP120____i___i___i___i___i___i___i___i___>

  6790  6795   6800   6805  6810   6815   6820  6825   6830   6835  6840   6845   6850  6855   6860
 ACT TGG AGT ACT GAA GGG TCA AAT AAC ACT GAA GGA AGT GAC ACA ATC ACA CTC CCA TGC AGA ATA AAA CAA TTT ATA
 TGA ACC TCA TGA CTT CCC AGT TTA TTG TGA CTT CCT TCA CTG TGT TAG TGT GAG GGT ACG TCT TAT TTT GTT AAA TAT
  T   W   S   T   E   G   S   N   N   T   E   G   S   D   T   I   T   L   P   C   R   I   K   Q   F   I>
    i   i   i   i   i   i   i   i   ENV POLYPROTEIN PRECURSOR; GP120    i   i   i   i   i   i   i   i   >

6865  6870   6875   6880  6885   6890   6895  6900   6905   6910  6915   6920   6925  6930   6935   6940
 AAC ATG TGG CAG GAA GTA GGA AAA GCA ATG TAT GCC CCT CCC ATC AGT GGA CAA ATT AGA TGT TCA TCA AAT ATT ACT
 TTG TAC ACC GTC CTT CAT CCT TTT CGT TAC ATA CGG GGA GGG TAG TCA CCT GTT TAA TCT ACA AGT AGT TTA TAA TGA
  N   M   W   Q   E   V   G   K   A   M   Y   A   P   P   I   S   G   Q   I   R   C   S   S   N   I   T>
 ___i___i___i___i___i___i___i___i___ENV POLYPROTEIN PRECURSOR; GP120____i___i___i___i___i___i___i___i___>

 6945   6950   6955  6960   6965   6970  6975   6980   6985  6990   6995   7000  7005   7010   7015  7020
 GGG CTG CTA TTA ACA AGA GAT GGT GGT AAT AAC AAC AAT GGG TCC GAG ATC TTC AGA CCT GGA GGA GGC GAT ATG AGG
 CCC GAC GAT AAT TGT TCT CTA CCA CCA TTA TTG TTG TTA CCC AGG CTC TAG AAG TCT GGA CCT CCT CCG CTA TAC TCC
  G   L   L   L   T   R   D   G   G   N   N   N   N   G   S   E   I   F   R   P   G   G   G   D   M   R>
 ___i___i___i___i___i___i___i___i___ENV POLYPROTEIN PRECURSOR; GP120____i___i___i___i___i___i___i___i___>

   7025   7030  7035   7040   7045  7050   7055   7060  7065   7070   7075  7080   7085   7090  7095
 GAC AAT TGG AGA AGT GAA TTA TAT AAA TAT AAA GTA GTA AAA ATT GAA CCA TTA GGA GTA GCA CCC ACC AAG GCA AAG
 CTG TTA ACC TCT TCA CTT AAT ATA TTT ATA TTT CAT CAT TTT TAA CTT GGT AAT CCT CAT CGT GGG TGG TTC CGT TTC
  D   N   W   R   S   E   L   Y   K   Y   K   V   V   K   I   E   P   L   G   V   A   P   T   K   A   K>
 ___i___i___i___i___i___i___i___i___ENV POLYPROTEIN PRECURSOR; GP120____i___i___i___i___i___i___i___i___>

 7100   7105  7110   7115   7120  7125   7130   7135  7140   7145   7150  7155   7160   7165  7170   7175
 AGA AGA GTG GTG CAG AGA GAA AAA AGA GCA GTG GGA ATA GGA GCT TTG TTC CTT GGG TTC TTG GGA GCA GCA GGA AGC
 TCT TCT CAC CAC GTC TCT CTT TTT TCT CGT CAC CCT TAT CCT CGA AAC AAG GAA CCC AAG AAC CCT CGT CGT CCT TCG
  R   R   V   V   Q   R   E   K   R   A   V   G   I   G   A   L   F   L   G   F   L   G   A   A   G   S>
 ___i___i___i___i___i___i___i___i___ENV POLYPROTEIN PRECURSOR; GP120____i___i___i___i___i___i___i___i___>

>conflict;_This_base_is_deleted_in_the_original_1986_NL4-
3_sequence,_however_there_is_a_T_insertion_3_bases_upstream_whi
                                  |
>conflict;_This_base_is_deleted_in_the_sequence_reported_in_this_entry,_but_an_insertion_3_base_downstream_restores_
the
                                  |
  7180  7185   7190   7195  7200   7205   7210  7215   7220   7225  7230   7235   7240  7245   7250
 ACT ATG GGC GCA GCG TCA ATG ACG CTG ACG GTA CAG GCC AGA CAA TTA TTG TCT GAT ATA GTG CAG CAG CAG AAC AAT
 TGA TAC CCG CGT CGC AGT TAC TGC GAC TGC CAT GTC CGG TCT GTT AAT AAC AGA CTA TAT CAC GTC GTC GTC TTG TTA
  T   M   G   A   A   S   M   T   L   T   V   Q   A   R   Q   L   L   S   D   I   V   Q   Q   Q   N   N>
 ___i___i___i___i___i___i___i___i___ENV POLYPROTEIN PRECURSOR; GP120____i___i___i___i___i___i___i___i___>

7255  7260   7265   7270  7275   7280   7285  7290   7295   7300  7305   7310   7315  7320   7325   7330
 TTG CTG AGG GCT ATT GAG GCG CAA CAG CAT CTG TTG CAA CTC ACA GTC TGG GGC ATC AAA CAG CTC CAG GCA AGA ATC
 AAC GAC TCC CGA TAA CTC CGC GTT GTC GTA GAC AAC GTT GAG TGT CAG ACC CCG TAG TTT GTC GAG GTC CGT TCT TAG
  L   L   R   A   I   E   A   Q   Q   H   L   L   Q   L   T   V   W   G   I   K   Q   L   Q   A   R   I>
 ___i___i___i___i___i___i___i___i___ENV POLYPROTEIN PRECURSOR; GP120____i___i___i___i___i___i___i___i___>

 7335   7340   7345  7350   7355   7360  7365   7370   7375  7380   7385   7390  7395   7400   7405  7410
 CTG GCT GTG GAA AGA TAC CTA AAG GAT CAA CAG CTC CTG GGG ATT TGG GGT TGC TCT GGA AAA CTC ATT TGC ACC ACT
```

Fig. 12: NL4.3 Sequence – Full Length. Wild Type (cont)

```
GAC CCA CAC CTT TCT ATG GAT TTC CTA GTT GTC GAG GAC CCC TAA ACC CCA ACG AGA CCT TTT GAG TAA ACG TGG TGA
 L   A   V   E   R   Y   L   K   D   Q   Q   L   L   G   I   W   G   C   S   G   K   L   I   C   T   T>
___i___i___i___i___i___i___i___i___ENV POLYPROTEIN PRECURSOR; GP120____i___i___i___i___i___i___i___i___>

  7415   7420  7425   7430   7435  7440   7445   7450  7455   7460   7465  7470   7475   7480  7485
GCT GTG CCT TGG AAT GCT AGT TGG AGT AAT AAA TCT CTG GAA CAG ATT TGG AAT AAC ATG ACC TGG ATG GAG TGG GAC
CGA CAC GGA ACC TTA CGA TCA ACC TCA TTA TTT AGA GAC CTT GTC TAA ACC TTA TTG TAC TGG ACC TAC CTC ACC CTG
 A   V   P   W   N   A   S   W   S   N   K   S   L   E   Q   I   W   N   N   M   T   W   M   E   W   D>
___i___i___i___i___i___i___i___i___ENV POLYPROTEIN PRECURSOR; GP120____i___i___i___i___i___i___i___i___>

7490   7495  7500   7505   7510  7515   7520   7525  7530   7535   7540  7545   7550   7555  7560   7565
AGA GAA ATT AAC AAT TAC ACA AGC TTA ATA CAC TCC TTA ATT GAA GAA TCG CAA AAC CAG CAA GAA AAG AAT GAA CAA
TCT CTT TAA TTG TTA ATG TGT TCG AAT TAT GTG AGG AAT TAA CTT CTT AGC GTT TTG GTC GTT CTT TTC TTA CTT GTT
 R   E   I   N   N   Y   T   S   L   I   H   S   L   I   E   E   S   Q   N   Q   Q   E   K   N   E   Q>
___i___i___i___i___i___i___i___i___ENV POLYPROTEIN PRECURSOR; GP120____i___i___i___i___i___i___i___i___>

 7570  7575   7580   7585  7590   7595   7600  7605   7610   7615  7620   7625   7630  7635   7640
GAA TTA TTG GAA TTA GAT AAA TGG GCA AGT TTG TGG AAT TGG TTT AAC ATA ACA AAT TGG CTG TGG TAT ATA AAA TTA
CTT AAT AAC CTT AAT CTA TTT ACC CGT TCA AAC ACC TTA ACC AAA TTG TAT TGT TTA ACC GAC ACC ATA TAT TTT AAT
 E   L   L   E   L   D   K   W   A   S   L   W   N   W   F   N   I   T   N   W   L   W   Y   I   K   L>
___i___i___i___i___i___i___i___i___ENV POLYPROTEIN PRECURSOR; GP120____i___i___i___i___i___i___i___i___>

7645  7650   7655   7660  7665   7670   7675  7680   7685   7690  7695   7700   7705  7710   7715   7720
TTC ATA ATG ATA GTA GGA GGC TTG GTA GGT TTA AGA ATA GTT TTT GCT GTA CTT TCT ATA GTG AAT AGA GTT AGG CAG
AAG TAT TAC TAT CAT CCT CCG AAC CAT CCA AAT TCT TAT CAA AAA CGA CAT GAA AGA TAT CAC TTA TCT CAA TCC GTC
 F   I   M   I   V   G   G   L   V   G   L   R   I   V   F   A   V   L   S   I   V   N   R   V   R   Q>
___i___i___i___i___i___i___i___i___ENV POLYPROTEIN PRECURSOR; GP120____i___i___i___i___i___i___i___i___>

 7725   7730   7735  7740   7745   7750  7755   7760   7765  7770   7775   7780  7785   7790   7795  7800
GGA TAT TCA CCA TTA TCG TTT CAG ACC CAC CTC CCA ATC CCG AGG GGA CCC GAC AGG CCC GAA GGA ATA GAA GAA GAA
CCT ATA AGT GGT AAT AGC AAA GTC TGG GTG GAG GGT TAG GGC TCC CCT GGG CTG TCC GGG CTT CCT TAT CTT CTT CTT
                                         F   T   S   Q   S   R   G   D   P   T   G   P   K   E   *>
                                       __f___f____TAT PROTEIN; /FUNCTION=TRANSACTIVATOR__f___f___f_>
                                           P   P   P   N   P   E   G   T   R   Q   A   R   R   N   R   R   R>
                                        _g___g__REV PROTEIN; /FUNCTION-REGULATOR OF VIRAL EXPRESSION_g___g___>
 G   Y   S   P   L   S   F   Q   T   H   L   P   I   P   R   G   P   D   R   P   E   G   I   E   E   E>
___i___i___i___i___i___i___i___i___ENV POLYPROTEIN PRECURSOR; GP120____i___i___i___i___i___i___i___i___>

       >conflict; /replace=a
                  |
  7805   7810  7815   7820   7825  7830   7835   7840  7845   7850   7855  7860   7865   7870  7875
GGT GGA GAG AGA GGC AGA GAC AGA TCC ATT CGA TTA GTG AAC GGA TCC TTA GCA CTT ATC TGG GAC GAT CTG CGG AGC
CCA CCT CTC TCT CCG TCT CTG TCT AGG TAA GCT AAT CAC TTG CCT AGG AAT CGT GAA TAG ACC CTG CTA GAC GCC TCG
 R   W   R   E   R   Q   R   Q   I   H   S   T   S   E   R   T   L   S   T   Y   L   G   R   S   A   E>
___g___g___g___g___g___g_REV PROTEIN; /FUNCTION=REGULATOR OF VIRAL EXPRESSION__g___g___g___g___g___g___>
 G   C   E   R   G   R   D   R   S   I   R   L   V   N   G   S   L   A   L   I   W   D   D   L   R   S>
___i___i___i___i___i___i___i___i___ENV POLYPROTEIN PRECURSOR; GP120____i___i___i___i___i___i___i___i___>

7880   7885  7890   7895   7900  7905   7910   7915  7920   7925   7930  7935   7940   7945  7950   7955
CTG TGC CTC TTC AGC TAC CAC CGC TTG AGA GAC TTA CTC TTG ATT GTA ACG AGG ATT GTG GAA CTT CTG GGA CGC AGG
GAC ACG GAG AAG TCG ATG GTG GCG AAC TCT CTG AAT GAG AAC TAA CAT TGC TCC TAA CAC CTT GAA GAC CCT GCG TCC
P   V   P   L   Q   L   P   P   L   E   R   L   T   L   D   C   N   E   D   C   G   T   S   G   T   Q>
___g___g___g___g___g___g_REV PROTEIN; /FUNCTION-REGULATOR OF VIRAL EXPRESSION__g___g___g___g___g___g___>
 L   C   L   F   S   Y   H   R   L   R   D   L   L   L   I   V   T   R   I   V   E   L   L   G   R   R>
___i___i___i___i___i___i___i___i___ENV POLYPROTEIN PRECURSOR; GP120____i___i___i___i___i___i___i___i___>

 7960  7965   7970   7975  7980   7985   7990  7995   8000   8005  8010   8015   8020  8025   8030
GGG TGG GAA GCC CTC AAA TAT TGG TGG AAT CTC CTA CAG TAT TGG AGT CAG GAA CTA AAG AAT AGT GCT GTT AAC TTG
CCC ACC CTT CGG GAG TTT ATA ACC ACC TTA GAG GAT GTC ATA ACC TCA GTC CTT GAT TTC TTA TCA CGA CAA TTG AAC
G   V   G   S   P   Q   I   L   V   E   S   P   T   V   L   E   S   G   T   K   E   *>
___g___g___g____REV PROTEIN; /FUNCTION-REGULATOR OF VIRAL EXPRESSION___g___g___g___g__>
 G   W   E   A   L   K   Y   W   W   N   L   L   Q   Y   W   S   Q   E   L   K   N   S   A   V   N   L>
___i___i___i___i___i___i___i___i___ENV POLYPROTEIN PRECURSOR; GP120____i___i___i___i___i___i___i___i___>

8035  8040   8045   8050  8055   8060   8065  8070   8075   8080  8085   8090   8095  8100   8105   8110
CTC AAT GCC ACA GCC ATA GCA GTA GCT GAG GGG ACA GAT AGG GTT ATA GAA GTA TTA CAA GCA GCT TAT AGA GCT ATT
GAG TTA CGG TGT CGG TAT CGT CAT CGA CTC CCC TGT CTA TCC CAA TAT CTT CAT AAT GTT CGT CGA ATA TCT CGA TAA
 L   N   A   T   A   I   A   V   A   E   G   T   D   R   V   I   E   V   L   Q   A   A   Y   R   A   I>
___i___i___i___i___i___i___i___i___ENV POLYPROTEIN PRECURSOR; GP120____i___i___i___i___i___i___i___i___>

                                                                    >Gene:_nef
                                                                         |
 8115   8120   8125  8130   8135   8140  8145   8150   8155  8160   8165   8170  8175   8180   8185  8190
CGC CAC ATA CCT AGA AGA ATA AGA CAG GGC TTG GAA AGG ATT TTG CTA TAA GAT GGG TGG CAA GTG GTC AAA AAG TAG
GCG GTG TAT GGA TCT TCT TAT TCT GTC CCG AAC CTT TCC TAA AAC GAT ATT CTA CCC ACC GTT CAC CAG TTT TTC ATC
 R   H   I   P   R   R   I   R   Q   G   L   E   R   I   L   L   *>
   i   i   i   i ENV POLYPROTEIN PRECURSOR; GP120  i   i   i   i   >
                                                                     M   G   G   K   W   S   K   S   S>
                                                                      j   j    NEF PROTEIN    j   j   >

  8195   8200  8205   8210   8215  8220   8225   8230  8235   8240   8245  8250   8255   8260  8265
```

Fig. 12: NL4.3 Sequence – Full Length, Wild Type (cont)

```
 TGT GAT TGG ATG GCC TGC TGT AAG GGA AAG AAT GAG ACG AGC TGA GCC AGC AGC AGA TGG GGT GGG AGC AGT ATC TCG
 ACA CTA ACC TAC CGG ACG ACA TTC CCT TTC TTA CTC TGC TCG ACT CGG TCG TCG TCT ACC CCA CCC TCG TCA TAG AGC
   V   I   G   W   P   A   V   R   E   R   M   R   R   A   E   P   A   A   D   G   V   G   A   V   S   R>
 ___j___j___j___j___j___j___j___j___j___j___j_NEF PROTEIN___j___j___j___j___j___j___j___j___j___j___j___>

8270  8275  8280  8285  8290  8295  8300  8305  8310  8315  8320  8325  8330  8335  8340  8345
 AGA CCT AGA AAA ACA TGG AGC AAT CAC AAG TAG CAA TAC AGC AGC TAA CAA TGC TGC TTG TGC CTG GCT AGA AGC ACA
 TCT GGA TCT TTT TGT ACC TCG TTA GTG TTC ATC GTT ATG TCG TCG ATT GTT ACG ACG AAC ACG GAC CGA TCT TCG TGT
   D   L   E   K   H   G   A   I   T   S   S   N   T   A   A   N   N   A   A   C   A   W   L   E   A   Q>
 ___j___j___j___j___j___j___j___j___j___j___j_NEF PROTEIN___j___j___j___j___j___j___j___j___j___j___j___>

 8350  8355  8360  8365  8370  8375  8380  8385  8390  8395  8400  8405  8410  8415  8420
 AGA GGA GGA AGA GGT GGG TTT TCC AGT CAC ACC TCA GGT ACC TTT AAG ACC AAT GAC TTA CAA GGC AGC TGT AGA TCT
 TCT CCT CCT TCT CCA CCC AAA AGG TCA GTG TGG AGT CCA TGG AAA TTC TGG TTA CTG AAT GTT CCG TCG ACA TCT AGA
   E   E   E   E   V   G   F   P   V   T   P   Q   V   P   L   R   P   M   T   Y   K   A   A   V   D   L>
 ___j___j___j___j___j___j___j___j___j___j___j_NEF PROTEIN___j___j___j___j___j___j___j___j___j___j___j___>

8425  8430  8435  8440  8445  8450  8455  8460  8465  8470  8475  8480  8485  8490  8495  8500
 TAG CCA CTT TTT AAA AGA AAA GGG GGG ACT GGA AGG GCT AAT TCA CTC CCA AAG AAG ACA AGA TAT CCT TGA TCT GTG
 ATC GGT GAA AAA TTT TCT TTT CCC CCC TGA CCT TCC CGA TTA AGT GAG GGT TTC TTC TGT TCT ATA GGA ACT AGA CAC
   S   H   F   L   K   E   K   G   G   L   E   G   L   I   H   S   Q   R   R   Q   D   I   L   D   L   W>
 ___j___j___j___j___j___j___j___j___j___j___j_NEF PROTEIN___j___j___j___j___j___j___j___j___j___j___j___>
                                             _k___k___k___LTR; /FUNCTION=5' LTR U3 AND R REGIONS__k___k___k___>

 8505  8510  8515  8520  8525  8530  8535  8540  8545  8550  8555  8560  8565  8570  8575  8580
 GAT CTA CCA CAC ACA AGG CTA CTT CCC TGA TTG GCA GAA CTA CAC ACC AGG GCC AGG GGT CAG ATA TCC ACT GAC CTT
 CTA GAT GGT GTG TGT TCC GAT GAA GGG ACT AAC CGT CTT GAT GTG TGG TCC CGG TCC CCA GTC TAT AGG TGA CTG GAA
   I   Y   H   T   Q   G   Y   F   P   D   W   Q   N   Y   T   P   G   P   G   V   R   Y   P   L   T   F>
 ___j___j___j___j___j___j___j___j___j___j___j_NEF PROTEIN___j___j___j___j___j___j___j___j___j___j___j___>
 ___k___k___k___k___k___k___k____LTR; /FUNCTION=5' LTR U3 AND R REGIONS_k___k___k___k___k___k___k___k___>

 8585  8590  8595  8600  8605  8610  8615  8620  8625  8630  8635  8640  8645  8650  8655
 TGG ATG GTG CTA CAA GCT AGT ACC AGT TGA GCC AGA TAA GGT AGA AGA GGC CAA TAA AGG AGA GAA CAC CAG CTT GTT
 ACC TAC CAC GAT GTT CGA TCA TGG TCA ACT CGG TCT ATT CCA TCT TCT CCG GTT ATT TCC TCT CTT GTG GTC GAA CAA
   G   W   C   Y   K   L   V   P   V   E   P   D   K   V   E   E   A   N   K   G   E   N   T   S   L   L>
 ___j___j___j___j___j___j___j___j___j___j___j_NEF PROTEIN___j___j___j___j___j___j___j___j___j___j___j___>
 ___k___k___k___k___k___k___k____LTR; /FUNCTION=5' LTR U3 AND R REGIONS_k___k___k___k___k___k___k___k___>

8660  8665  8670  8675  8680  8685  8690  8695  8700  8705  8710  8715  8720  8725  8730  8735
 ACA CCC TGT GAG CCT GCA TGG AAT GGA TGA CCC TGA GAG AGA AGT GTT AGA GTG GAG GTT TGA CAG CCG CCT AGC ATT
 TGT GGG ACA CTC GGA CGT ACC TTA CCT ACT GGG ACT CTC TCT TCA CAA TCT CAC CTC CAA ACT GTC GGC GGA TCG TAA
   H   P   V   S   L   H   G   M   D   D   P   E   R   E   V   L   E   W   R   F   D   S   R   L   A   F>
 ___j___j___j___j___j___j___j___j___j___j___j_NEF PROTEIN___j___j___j___j___j___j___j___j___j___j___j___>
 ___k___k___k___k___k___k___k____LTR; /FUNCTION=5' LTR U3 AND R REGIONS_k___k___k___k___k___k___k___k___>

 8740  8745  8750  8755  8760  8765  8770  8775  8780  8785  8790  8795  8800  8805  8810
 TCA TCA CGT GGC CCG AGA GCT GCA TCC GGA GTA CTT CAA GAA CTG CTG ACA TCG AGC TTG CTA CAA GGG ACT TTC CGC
 AGT AGT GCA CCG GGC TCT CGA CGT AGG CCT CAT GAA GTT CTT GAC GAC TGT AGC TCG AAC GAT GTT CCC TGA AAG GCG
   H   H   V   A   R   E   L   H   P   E   Y   F   K   N   C   *>
 ___j___j___j___j___j___j__NEF PROTEIN__j___j___j___j___j___j___j_>
 ___k___k___k___k___k___k___k____LTR; /FUNCTION=5' LTR U3 AND R REGIONS_k___k___k___k___k___k___k___k___>

8815  8820  8825  8830  8835  8840  8845  8850  8855  8860  8865  8870  8875  8880  8885  8890
 TGC GGA CTT TCC AGG GAG GCG TGG CCT GGG CGG GAC TGG GGA GTG GCG AGC CCT CAG ATG CTG CAT ATA AGC AGC TGC
 ACG CCT GAA AGG TCC CTC CGC ACC GGA CCC GCC CTG ACC CCT CAC CGC TCG GGA GTC TAC GAC GTA TAT TCG TCG ACG
 ___k___k___k___k___k___k___k____LTR; /FUNCTION=5' LTR U3 AND R REGIONS_k___k___k___k___k___k___k___k___>

 8895  8900  8905  8910  8915  8920  8925  8930  8935  8940  8945  8950  8955  8960  8965  8970
 TTT TTG CCT GTA CTG GGT CTC TCT GGT TAG ACC AGA TCT GAG CCT GGG AGC TCT CTG GCT AAC TAG GGA ACC CAC TGC
 AAA AAC GGA CAT GAC CCA GAG AGA CCA ATC TGG TCT AGA CTC GGA CCC TCG AGA GAC CGA TTG ATC CCT TGG GTG ACG
 ___k___k___k___k___k___k___k____LTR; /FUNCTION=5' LTR U3 AND R REGIONS_k___k___k___k___k___k___k___k___>

                                 >conflict;_/replace-t
                                                     :
  8975  8980  8985  8990  8995  9000
 TTA AGC CTC AAT AAA GCT TGC CTT GAG TGC
 AAT TCG GAG TTA TTT CGA ACG GAA CTC ACG
 ___LTR; /FUNCTION=5' LTR U3 AND R R____>
```

Unannotated (sense strand only, p6 region where chimera will be inserted is highlighted):

AAATCTCTAGCAGTGGCGCCCGAACAGGGACTTGAAAGCGAAAGTAAAGCCAGAGGAGATCTCTCGACGCAGGACTCGGCTTGCTGAAGCGCGCACGGCAA
GAGGCGAGGGGCGGCGACTGGTGAGTACGCCAAAAATTTTGACTAGCGGAGGCTAGAAGGAGAGAGATGGGTGCGAGAGCGTCGGTATTAAGCGGGGGAGA
ATTAGATAAATGGGAAAAAATTCGGTTAAGGCCAGGGGGAAAGAAACAATATAAACTAAAACATATAGTATGGGCAAGCAGGGAGCTAGAACGATTCGCAG
TTAATCCTGGCCTTTTAGAGACATCAGAAGGCTGTAGACAAATACTGGGACAGCTACAACCATCCCTTCAGACAGGATCAGAAGAACTTAGATCATTATAT
AATACAATAGCAGTCCTCTATTGTGTGCATCAAAGGATAGATGTAAAAGACACCAAGGAAGCCTTAGATAAGATAGAGGAAGAGCAAAACAAAAGTAAGAA
AAAGGCACAGCAAGCAGCAGCTGACACAGGAAACAACAGCCAGGTCAGCCAAAATTACCCTATAGTGCAGAACCTCCAGGGGCAAATGGTACATCAGGCCA

Fig. 12: NL4.3 Sequence – Full Length, Wild Type (cont)

TATCACCTACAACTTTAAATGCATGGCTAAAACTACTAGAAGACAACCGCTTTCAGCCCAGAAGTAATACCCATGTTTTCAGCATTATCAGAAGCACCCACC
CCACAAGATTTAAATACCATGCTAAACACAGTGGGGGCACATCAAGCAGCCATGCAAATGTTAAAACAGACCATCAATGAGGAACCTGCAGAATGCGATAG
ATTGCATCCACTGCATGCAGGGCCTATTGCACCAGGCCAGATGAGAGAACCAAGGGGAAGTGACATAGCAGGAACTACTAGTACCCTTCAGGAACAAATAG
GATGGATGACACATAATCCACCTATCCCAGTAGGAGAAATCTATAAAAGATGGATAATCCTGGGATTAAATAAAATAGTAAGAATGTATAGCCCTACCAGC
ATTCTGGACATAAGACAAGGACCAAAGGAACCCTTTAGAGACTATGTAGACCGATTCTATAAAACTCTAAGAGCCGAGCAAGCTTCACAAGAGGTAAAAAA
TTGGATGACAGAAACCTTGTTGGTCCAAAATGCGAACCCAGATTGTAAGACTATTTTAAAAGCACTGGGACCAGGAGCGACACTAGAAGAAATGATGACAG
CATGTCAGGGAGTGGGGGGACCCGGCCATAAAGCAAGAGTTTTGGCTGAAGCAATGAGCCAAGTAACAAATCCAGCTACCATAATGATACAGAAAGGCAAT
TTTAGGAACCAAAGAAAGACTGTTAAGTGTTTCAATTGTGGCAAAGAAGGGCACATAGCCAAAAATTGCAGGGCCCCTAGGAAAAAGGGCTGTTGGAAATG
TGGAAAGGAAGGACACCAAATGAAAGATTGTACTGAGAGACAGGCTAATTTTTTAGGGAAGATCTGGCCTTCCCACAAGGGAAGGCCAGGGAATTTTCTTC
AGAGCAGACCAGAGCCAACAGCCCCACCAGAAGAGAGCTTCAGGTTTGGGGAAGAGACAACAACTCCCTCTCAGAGGCAGGAGCCGATAGACAAGGAACTG
TATCCTTTAGCTTCCCTCAGATCACTCTTTGGCAGCGACCCCTCGTCACAATAAAGATAGGGGGGCAATTAAAGGAAGCTCTATTAGATACAGGAGCAGAT
GATACAGTATTAGAAGAAATGAATTTGCCAGGAAGATGGAAACCAAAAATGATAGGGGGAATTGGAGGTTTTATCAAAGTAAGACAGTATGATCAGATACT
CATAGAAATCTGCGGACATAAAGCTATAGGTACAGTATTAGTAGGACCTACACCTGTCAACATAATTGGAAGAAATCTGTTGACTCAGATTGGCTGCACTT
TAAATTTTCCCATTAGTCCTATTGAGACTGTACCAGTAAAATTAAAGCCAGGAATGGATGGCCCAAAAGTTAAACAATGGCCATTGACAGAAGAAAAAATA
AAAGCATTAGTAGAAATTTGTACAGAAATGGAAAAGGAAGGAAAAATTTCAAAAATTGGGCCTGAAAATCCATACAATACTCCAGTATTTGCCATAAAGAA
AAAAGACAGTACTAAATGGAGAAAATTAGTAGATTTCAGAGAACTTAATAAGAGAACTCAAGATTTCTGGGAAGTTCAATTAGGAATACCACATCCTGCAG
GGTTAAAACAGAAAAAATCAGTAACAGTACTGGATGTGGGCGATGCATATTTTTCAGTTCCCTTAGATAAAGACTTCAGGAAGTATACTGCATTTACCATA
CCTAGTATAAACAATGAGACACCAGGCATTAGATATCAGTACAATGTGCTTCCACAGGGATGGAAAGGATCACCAGCAATATTCCAGTGTAGCATGACAAA
AATCTTAGAGCCTTTTAGAAAACAAAATCCAGACGTAGTCATCTATCAATACATGGATGATTTGTATGTAGGATCTGACTTAGAAATAGGGCAGCATAGAA
CAAAAATAGAGGAACTGAGACAACATCTGTTGAGGTGGGGATTTACCACACCAGACAAAAAACATCAGAAAGAACCTCCATTCCTTTGGATGGGTTATGAA
CTCCATCCTGATAAATGGACAGTACAGCCTATAGTGCTGCCAGAAAAGGACAGCTGGACTGTCAATGACATACAGAAATTAGTGGGAAAATTGAATTGGGC
AAGTCAGATTTATGCAGGGATTAAAGTAAGGCAATTATGTAAACTTCTTAGGGGAACCAAAGCACTAACAGAAGTAGTACCACTAACAGAAGAAGCAGAGC
TAGAACTGGCAGAAAACAGGGAGATTCTAAAAGAACCGGTACATGGAGTGTATTATGACCCATCAAAAGACTTAATAGCAGAAATACAGAAGCAGGGGCAA
GGCCAATGGACATATCAAATTTATCAAGAGCCATTTAGAAATCTGAAAACAGGAAAGTATGCAAGAATGAAGGGTGCCCACACTAATGATGTGAAACAATT
AACAGAGGCAGTACAAAAAATAGCCACAGAAAGCATAGTAATATGGGGAAAGACTCCTAAATTTAAATTACCCATACAAAAGGAAACATGGGAAGCATGGT
GGACAGAGTATTGGCAAGCCACCTGGATTCCTGAGTGGGAGTTTGTCAATACCCCTCCCTTAGTGAAGTTATGGTACCAGTTAGAGAAAGAACCCATAATA
GGAGCAGAAACTTTCTATGTAGATGGGGCAGCCAATAGGGAAACTAAATTAGGAAAAGCAGGATATGTAACTGACAGAGGAAGACAAAAAGTTGTCCCCCT
AACGGACACAACAAATCAGAAGACTGAGTTACAAGCAATTCATCTAGCTTTGCAGGATTCGGGATTAGAAGTAAACATAGTGACAGACTCACAATATGCAT
TGGGAATCATTCAAGCACAACCAGATAAGAGTGAATCAGAGTTAGTCAGTCAAATAATAGAGCAGTTAATAAAAAAGGAAAAAGTCTACCTGGCATGGGTA
CCAGCACACAAAGGAATTGGAGGAAATGAACAAGTAGATAAATTGGTCAGTGCTGGAATCAGGAAAGTACTATTTTTAGATGGAATAGATAAGGCCCAAGA
AGAACATGAGAAATATCACAGTAATTGGAGAGCAATGGCTAGTGATTTTAACCTACCACCTGTAGTAGCAAAAGAAATAGTAGCCAGCTGTGATAAATGTC
AGCTAAAAGGGGAAGCCATGCATGGACAAGTAGACTGTAGCCCAGGAATATGGCAGCTAGATTGTACACATTTAGAAGGAAAAGTTATCTTGGTGGCAGTT
CATGTAGCCAGTGGATATATAGAAGCAGAAGTAATTCCAGCAGAGACAGGGCAAGAAACAGCATACTTCCTCTTAAAATTAGCAGGAAGATGGCCAGTAAA
AACAGTACATACAGACAATGGCAGCAATTTCACCAGTACTACAGTTAAGGCCGCCTGTTGGTGGGCGGGAATCAAGCAGGAATTTGGCATTCCCTACAATC
CCCAAAGTCAAGGAGTAATAGAATCTATGAATAAAGAATTAAAGAAAATTATAGGACAGGTAAGAGATCAGGCTGAACATCTTAAGACAGCAGTACAAATG
GCAGTATTCATCCACAATTTTAAAAGAAAAGGGGGGATTGGGGGGTACAGTGCAGGGGAAAGAATAGTAGACATAATAGCAACAGACATACAAACTAAAGA
ATTACAAAAACAAATTACAAAAATTCAAAATTTTCGGGTTTATTACAGGGACAGCAGAGATCCAGTTTGGAAAGGACCAGCAAAGCTCCTCTGGAAAGGTG
AAGGGGCAGTAGTAATACAAGATAATAGTGACATAAAAGTAGTGCCAAGAAGAAAAGCAAAGATCATCAGGGATTATGGAAAACAGATGGCAGGTGATGAT
TGTGTGGCAAGTAGACAGGATGAGGATTAACACATGGAAAAGATTAGTAAAACACCATATGTATATTTCAAGGAAAGCTAAGGACTGGTTTTATAGACATC
ACTATGAAAGTACTAATCCAAAAATAAGTTCAGAAGTACACATCCCACTAGGGGATGCTAAATTAGTAATAACAACATATTGGGGTCTGCATACAGGAGAA
AGAGACTGGCATTTGGGTCAGGGAGTCTCCATAGAATGGAGGAAAAAGAGATATAGCACACAAGTAGACCCTGACCTAGCAGACCAACTAATTCATCTGCA
CTATTTTGATTGTTTTTCAGAATCTGCTATAAGAAATACCATATTAGGACGTATAGTTAGTCCTAGGTGTGAATATCAAGCAGGACATAACAAGGTAGGAT
CTCTACAGTACTTGGCACTAGCAGCATTAATAAAACCAAAACAGATAAAGCCACCTTTGCCTAGTGTTAGGAAACTGACAGAGGACAGATGGAACAAGCCC
CAGAAGACCAAGGGCCACAGAGGGAGCCATACAACGAATGGACACTAGAGCTTTTAGAGGAACTTAAGAGTGAAGCTGTTAGACATTTTCCTAGGATATGG
CTCCATAACTTAGGACGACATATCTATGAAACTTACGGGGATACTTGGGCAGGAGTGGAAGCCATAATAAGAATTCTGCAACAACTGCCGTTTATCCATTT
CAGAATTGGGTGTCGACATAGCAGAATAGGCGTTACTCGACAGAGGAGAGCAAGAAATGGAGCCAGTAGATCCTAGACTAGAGCCCTGGAAGCATCCAGGA
AGTCAGCCTAAAACTGCTTGTACCAATTGCTATTGTAAAAAGTGTTGCTTTCATTGCCAAGTTTGTTTCATGACAAAAGCCTTAGGCATCTCCTATGGCAG
GAAGAAGCGGAGACAGCGACGAAGAGCTCATCAGAACAGTCAGACTCATCAAGCTTCTCTATCAAAGCAGTAAGTAGTACATGTAATGCAACCTATAATAG

Fig. 12: NL4.3 Sequence – Full Length, Wild Type (cont)

TAGCAATAGTAGCATTAGTAGTAGCAATAATAATAGCAATAGTTGTGTGGTCCATAGTAATCATAGAATATAGGAAAATATTAAGACAAAGAAAAATAGAC
AGGTTAATTGATAGACTAATAGAAAGAGCAGAAGACAGTGGCAATGAGAGTGAAGGAGAAGTATCAGCACTTGTGGAGATGGGGGTGGAAATGGGGCACCA
TCCTCCTTGGGATATTGATGATCTGTAGTGCTACAGAAAAATTGTGGGTCACAGTCTATTATGGGGTACCTGTGTGGAAGGAAGCAACCACCACTCTATTT
TGTGCATCAGATGCTAAAGCATATGATACAGAGGTACATAATGTTTGGGCCACACATGCCTGTGTACCCACAGACCCCAACCCACAAGAAGTAGTATTGGT
AAATGTGACAGAAAATTTTAACATGTGGAAAGATGACATGGTAGAACAGATGCATGAGGATATAATCAGTTTATGGGATCAAAGCCTAAAGCCATGTGTAA
AATTAACCCCACTCTGTGTTAGTTTAAAGTGCACTGATTTGAAGAATGATACTAATACCAATAGTAGTAGCGGGAGAATGATAATGGAGAAAGGAGAGATA
AAAAACTGCTCTTTCAATATCAGCACAAGCATAAGAGATAAGGTGCAGAAAGAATATGCATTCTTTTATAAACTTGATATAGTACCAATAGATAATACCAG
CTATAGGTTGATAAGTTGTAACACCTCAGTCATTACACAGGCCTGTCCAAAGGTATCCTTTGAGCCAATTCCCATACATTATTGTGCCCCGGCTGGTTTTG
CGATTCTAAAATGTAATAATAAGACGTTCAATGGAACAGGACCATGTACAAATGTCAGCACAGTACAATGTACACATGGAATCAGGCCAGTAGTATCAACT
CAACTGCTGTTAAATGGCAGTCTAGCAGAAGAAGATGTAGTAATTAGATCTGCCAATTTCACAGACAATGCTAAAACCATAATAGTACAGCTGAACACATC
TGTAGAAATTAATTGTACAAGACCCAACAACAATACAAGAAAAAGTATCCGTATCCAGAGGGGACCAGGGAGAGCATTTGTTACAATAGGAAAAATAGGAA
ATATGAGACAAGCACATTGTAACATTAGTAGAGCAAAATGGAATGCCACTTTAAAACAGATAGCTAGCAAATTAAGAGAACAATTTGGAAATAATAAAACA
ATAATCTTTAAGCAATCCTCAGGAGGGGACCCAGAAATTGTAACGCACAGTTTTAATTGTGGAGGGGAATTTTTCTACTGTAATTCAACACAACTGTTTAA
TAGTACTTGGTTTAATAGTACTTGGAGTACTGAAGGGTCAAATAACACTGAAGGAAGTGACACAATCACACTCCCATGCAGAATAAAACAATTTATAAACA
TGTGGCAGGAAGTAGGAAAAGCAATGTATGCCCCTCCCATCAGTGGACAAATTAGATGTTCATCAAATATTACTGGGCTGCTATTAACAAGAGATGGTGGT
AATAACAACAATGGGTCCGAGATCTTCAGACCTGGAGGAGGCGATATGAGGGACAATTGGAGAAGTGAATTATATAAATATAAAGTAGTAAAAATTGAACC
ATTAGGAGTAGCACCCACCAAGGCAAAGAGAAGAGTGGTGCAGAGAGAAAAAAGAGCAGTGGGAATAGGAGCTTTGTTCCTTGGGTTCTTGGGAGCAGCAG
GAAGCACTATGGGCGCAGCGTCAATGACGCTGACGGTACAGGCCAGACAATTATTGTCTGATATAGTGCAGCAGCAGAACAATTTGCTGAGGGCTATTGAG
GCGCAACAGCATCTGTTGCAACTCACAGTCTGGGGCATCAAACAGCTCCAGGCAAGAATCCTGGCTGTGGAAAGATACCTAAAGGATCAACAGCTCCTGGG
GATTTGGGGTTGCTCTGGAAAACTCATTTGCACCACTGCTGTGCCTTGGAATGCTAGTTGGAGTAATAAATCTCTGGAACAGATTTGGAATAACATGACCT
GGATGGAGTGGGACAGAGAAATTAACAATTACACAAGCTTAATACACTCCTTAATTGAAGAATCGCAAAACCAGCAAGAAAAGAATGAACAAGAATTATTG
GAATTAGATAAATGGGCAAGTTTGTGGAATTGGTTTAACATAACAAATTGGCTGTGGTATATAAAATTATTCATAATGATAGTAGGAGGCTTGGTAGGTTT
AAGAATAGTTTTTGCTGTACTTTCTATAGTGAATAGAGTTAGGCAGGGATATTCACCATTATCGTTTCAGACCCACCTCCCAATCCCGAGGGGACCCGACA
GGCCCGAAGGAATAGAAGAAGAAGGTGGAGAGAGAGACAGAGACAGATCCATTCGATTAGTGAACGGATCCTTAGCACTTATCTGGGACGATCTGCGGAGC
CTGTGCCTCTTCAGCTACCACCGCTTGAGAGACTTACTCTTGATTGTAACGAGGATTGTGGAACTTCTGGGACGCAGGGGGTGGGAAGCCCTCAAATATTG
GTGGAATCTCCTACAGTATTGGAGTCAGGAACTAAAGAATAGTGCTGTTAACTTGCTCAATGCCACAGCCATAGCAGTAGCTGAGGGGACAGATAGGGTTA
TAGAAGTATTACAAGCAGCTTATAGAGCTATTCGCCACATACCTAGAAGAATAAGACAGGGCTTGGAAAGGATTTTGCTATAAGATGGGTGGCAAGTGGTC
AAAAAGTAGTGTGATTGGATGGCCTGCTGTAAGGGAAAGAATGAGACGAGCTGAGCCAGCAGCAGATGGGGTGGGAGCAGTATCTCGAGACCTAGAAAAAC
ATGGAGCAATCACAAGTAGCAATACAGCAGCTAACAATGCTGCTTGTGCCTGGCTAGAAGCACAAGAGGAGGAAGAGGTGGGTTTTCCAGTCACACCTCAG
GTACCTTTAAGACCAATGACTTACAAGGCAGCTGTAGATCTTAGCCACTTTTTAAAAGAAAAGGGGGGACTGGAAGGGCTAATTCACTCCCAAAGAAGACA
AGATATCCTTGATCTGTGGATCTACCACACACAAGGCTACTTCCCTGATTGGCAGAACTACACACCAGGGCCAGGGGTCAGATATCCACTGACCTTTGGAT
GGTGCTACAAGCTAGTACCAGTTGAGCCAGATAAGGTAGAAGAGGCCAATAAAGGAGAGAACACCAGCTTGTTACACCCTGTGAGCCTGCATGGAATGGAT
GACCCTGAGAGAGAAGTGTTAGAGTGGAGGTTTGACAGCCGCCTAGCATTTCATCACGTGGCCCGAGAGCTGCATCCGGAGTACTTCAAGAACTGCTGACA
TCGAGCTTGCTACAAGGGACTTTCCGCTGGGGACTTTCCAGGGAGGCGTGGCCTGGGCGGGACTGGGGAGTGGCGAGCCCTCAGATGCTGCATATAAGCAG
CTGCTTTTTGCCTGTACTGGGTCTCTCTGGTTAGACCAGATCTGAGCCTGGGAGCTCTCTGGCTAACTAGGGAACCCACTGCTTAAGCCTCAATAAAGCTT
GCCTTGAGTGC

Fig.13:SIVmac239 Vpx wild-type and codon-optimized sequences

Amino acid sequence

MSDPRERIPPGNSGEETIGEAFEWLNRTVEEINREAVNHLPRELIFQVWQRSWEYWHDEQGMSPSYVKYRYLCLIQKALFMHCKKGCRCLGEGHG
AGGWRPGPPPPPPPGLA

Alignment of Vpx coding sequence (top row, lower case) and codon optimized (bottom row, upper case). Changed codons are indicated in bold atg tca gat ccc agg gag aga atc cca cct gga aac agt gga gaa gag aca ata gga gag gcc ttc gaa tgg
ATG AGC GAC CCC AGA GAG AGA ATC CCC CCC GGC AAC AGC GGC GAG GAG ACC ATC GGC GAG GCC TTC GAG TGG cta aac aga aca gta gag gag ata aac aga gag gcg gta aac cac cta cca agg gag cta att ttc cag gtt
CTG AAC AGA ACC GTG GAG GAG ATC AAC AGA GAG GCC GTG AAC CAC CTG CCC AGA GAG CTG ATC TTC CAG GTG tgg caa agg tct tgg gaa tac tgg cat gat gaa caa ggg atg tca cca agc tat gta aaa tac aga tac ttg
TGG CAG AGA AGC TGG GAG TAC TGG CAC GAC GAG CAG GGC ATG AGC CCC AGC TAC GTG AAG TAC AGA TAC CTG tgt tta ata caa aag gct tta ttt atg cat tgc aag aaa ggc tgt aga tgt cta ggg gaa gga cat ggg gca
TGC CTG ATC CAG AAG GCC CTG TTC ATG CAC TGC AAG AAG GGC TGC AGA TGC CTG GGC GAG GGC CAC GGC GCC ggg gga tgg aga cca gga cct cct cct cct ccc cct cca gga cta gca taa
GGC GGC TGG AGA CCC GGC CCC CCC CCC CCC CCC CCC CCC GGC CTG GCC TGA

SEQUENCE LISTING

```
<160> NUMBER OF SEQ ID NOS: 87

<210> SEQ ID NO 1
<211> LENGTH: 10
<212> TYPE: PRT
<213> ORGANISM: Simian immunodeficiency virus

<400> SEQUENCE: 1

Asp Pro Ala Val Asp Leu Leu Lys Asn Tyr
 1              5                   10


<210> SEQ ID NO 2
<211> LENGTH: 11
<212> TYPE: PRT
<213> ORGANISM: Simian immunodeficiency virus

<400> SEQUENCE: 2

Asp Pro Ala Val Asp Leu Leu Lys Asn Tyr Met
 1              5                   10


<210> SEQ ID NO 3
<211> LENGTH: 12
<212> TYPE: PRT
<213> ORGANISM: Simian immunodeficiency virus

<400> SEQUENCE: 3

Asp Pro Ala Val Asp Leu Leu Lys Asn Tyr Met Gly
 1              5                   10


<210> SEQ ID NO 4
```

-continued

<211> LENGTH: 13
<212> TYPE: PRT
<213> ORGANISM: Simian immunodeficiency virus

<400> SEQUENCE: 4

Asp Pro Ala Val Asp Leu Leu Lys Asn Tyr Met Gln Leu
1 5 10

<210> SEQ ID NO 5
<211> LENGTH: 14
<212> TYPE: PRT
<213> ORGANISM: Simian immunodeficiency virus

<400> SEQUENCE: 5

Asp Pro Ala Val Asp Leu Leu Lys Asn Tyr Met Gln Leu Gly
1 5 10

<210> SEQ ID NO 6
<211> LENGTH: 15
<212> TYPE: PRT
<213> ORGANISM: Simian immunodeficiency virus

<400> SEQUENCE: 6

Asp Pro Ala Val Asp Leu Leu Lys Asn Tyr Met Gln Leu Gly Lys
1 5 10 15

<210> SEQ ID NO 7
<211> LENGTH: 16
<212> TYPE: PRT
<213> ORGANISM: Simian immunodeficiency virus

<400> SEQUENCE: 7

Asp Pro Ala Val Asp Leu Leu Lys Asn Tyr Met Gln Leu Gly Lys Gln
1 5 10 15

<210> SEQ ID NO 8
<211> LENGTH: 17
<212> TYPE: PRT
<213> ORGANISM: Simian immunodeficiency virus

<400> SEQUENCE: 8

Asp Pro Ala Val Asp Leu Leu Lys Asn Tyr Met Gln Leu Gly Lys Gln
1 5 10 15

Gln

<210> SEQ ID NO 9
<211> LENGTH: 19
<212> TYPE: PRT
<213> ORGANISM: Simian immunodeficiency virus

<400> SEQUENCE: 9

Asp Pro Ala Val Asp Leu Leu Lys Asn Tyr Met Gln Leu Gly Lys Gln
1 5 10 15

Gln Arg Glu

<210> SEQ ID NO 10
<211> LENGTH: 20
<212> TYPE: PRT
<213> ORGANISM: Simian immunodeficiency virus

<400> SEQUENCE: 10

Asp Pro Ala Val Asp Leu Leu Lys Asn Tyr Met Gln Leu Gly Lys Gln
1 5 10 15

Gln Arg Glu Lys
20

<210> SEQ ID NO 11
<211> LENGTH: 21
<212> TYPE: PRT
<213> ORGANISM: Simian immunodeficiency virus

<400> SEQUENCE: 11

Asp Pro Ala Val Asp Leu Leu Lys Asn Tyr Met Gln Leu Gly Lys Gln
1 5 10 15

Gln Arg Glu Lys Gln
20

<210> SEQ ID NO 12
<211> LENGTH: 21
<212> TYPE: PRT
<213> ORGANISM: Simian immunodeficiency virus

<400> SEQUENCE: 12

Asp Pro Ala Val Asp Leu Leu Lys Asn Tyr Met Gln Leu Gly Lys Gln
1 5 10 15

Gln Arg Glu Lys Gln
20

<210> SEQ ID NO 13
<211> LENGTH: 22
<212> TYPE: PRT
<213> ORGANISM: Simian immunodeficiency virus

<400> SEQUENCE: 13

Asp Pro Ala Val Asp Leu Leu Lys Asn Tyr Met Gln Leu Gly Lys Gln
1 5 10 15

Gln Arg Glu Lys Gln Arg
20

<210> SEQ ID NO 14
<211> LENGTH: 23
<212> TYPE: PRT
<213> ORGANISM: Simian immunodeficiency virus

<400> SEQUENCE: 14

Asp Pro Ala Val Asp Leu Leu Lys Asn Tyr Met Gln Leu Gly Lys Gln
1 5 10 15

Gln Arg Glu Lys Gln Arg Glu
20

<210> SEQ ID NO 15
<211> LENGTH: 24
<212> TYPE: PRT
<213> ORGANISM: Simian immunodeficiency virus

<400> SEQUENCE: 15

Asp Pro Ala Val Asp Leu Leu Lys Asn Tyr Met Gln Leu Gly Lys Gln
1 5 10 15

Gln Arg Glu Lys Gln Arg Glu Ser
20

<210> SEQ ID NO 16
<211> LENGTH: 25
<212> TYPE: PRT
<213> ORGANISM: Simian immunodeficiency virus -continued

<400> SEQUENCE: 16

Asp Pro Ala Val Asp Leu Leu Lys Asn Tyr Met Gln Leu Gly Lys Gln
1 5 10 15

Gln Arg Glu Lys Gln Arg Glu Ser Arg
20 25

<210> SEQ ID NO 17
<211> LENGTH: 26
<212> TYPE: PRT
<213> ORGANISM: Simian immunodeficiency virus

<400> SEQUENCE: 17

Asp Pro Ala Val Asp Leu Leu Lys Asn Tyr Met Gln Leu Gly Lys Gln
1 5 10 15

Gln Arg Glu Lys Gln Arg Glu Ser Arg Glu
20 25

<210> SEQ ID NO 18
<211> LENGTH: 27
<212> TYPE: PRT
<213> ORGANISM: Simian immunodeficiency virus

<400> SEQUENCE: 18

Asp Pro Ala Val Asp Leu Leu Lys Asn Tyr Met Gln Leu Gly Lys Gln
1 5 10 15

Gln Arg Glu Lys Gln Arg Glu Ser Arg Glu Lys
20 25

<210> SEQ ID NO 19
<211> LENGTH: 28
<212> TYPE: PRT
<213> ORGANISM: Simian immunodeficiency virus

<400> SEQUENCE: 19

Asp Pro Ala Val Asp Leu Leu Lys Asn Tyr Met Gln Leu Gly Lys Gln
1 5 10 15

Gln Arg Glu Lys Gln Arg Glu Ser Arg Glu Lys Pro
20 25

<210> SEQ ID NO 20
<211> LENGTH: 29
<212> TYPE: PRT
<213> ORGANISM: Simian immunodeficiency virus

<400> SEQUENCE: 20

Asp Pro Ala Val Asp Leu Leu Lys Asn Tyr Met Gln Leu Gly Lys Gln
1 5 10 15

Gln Arg Glu Lys Gln Arg Glu Ser Arg Glu Lys Pro Tyr
20 25

<210> SEQ ID NO 21
<211> LENGTH: 30
<212> TYPE: PRT
<213> ORGANISM: Simian immunodeficiency virus

<400> SEQUENCE: 21

Asp Pro Ala Val Asp Leu Leu Lys Asn Tyr Met Gln Leu Gly Lys Gln
1 5 10 15

Gln Arg Glu Lys Gln Arg Glu Ser Arg Glu Lys Pro Tyr Lys
20 25 30

-continued

<210> SEQ ID NO 22
<211> LENGTH: 31
<212> TYPE: PRT
<213> ORGANISM: Simian immunodeficiency virus

<400> SEQUENCE: 22

Asp Pro Ala Val Asp Leu Leu Lys Asn Tyr Met Gln Leu Gly Lys Gln
1 5 10 15

Gln Arg Glu Lys Gln Arg Glu Ser Arg Glu Lys Pro Tyr Lys Glu
20 25 30

<210> SEQ ID NO 23
<211> LENGTH: 32
<212> TYPE: PRT
<213> ORGANISM: Simian immunodeficiency virus

<400> SEQUENCE: 23

Asp Pro Ala Val Asp Leu Leu Lys Asn Tyr Met Gln Leu Gly Lys Gln
1 5 10 15

Gln Arg Glu Lys Gln Arg Glu Ser Arg Glu Lys Pro Tyr Lys Glu Val
20 25 30

<210> SEQ ID NO 24
<211> LENGTH: 1513
<212> TYPE: DNA
<213> ORGANISM: Human immunodeficiency virus

<400> SEQUENCE: 24
atgggtgcga gagcgtcggt attaagcggg ggagaattag ataaatggga aaaaattcgg 60
ttaaggccag ggggaaagaa acaatataaa ctaaaacata tagtatgggc aagcagggag 120
ctagaacgat tcgcagttaa tcctggcctt ttagagacat cagaaggctg tagacaaata 180
ctgggacagc tacaaccatc ccttcagaca ggatcagaag aacttagatc attatataat 240
acaatagcag tcctctattg tgtgcatcaa aggatagatg taaaagacac caaggaagcc 300
ttagataaga tagaggaaga gcaaaacaaa agtaagaaaa aggcacagca agcagcagct 360
gacacaggaa acaacagcca ggtcagccaa aattacccta tagtgcagaa cctccagggg 420
caaatggtac atcaggccat atcacctaga actttaaatg catgggtaaa agtagtagaa 480
gagaaggctt tcagcccaga agtaataccc atgttttcag cattatcaga aggagccacc 540
ccacaagatt taaataccat gctaaacaca gtgggggggac atcaagcagc catgcaaatg 600
ttaaaagaga ccatcaatga ggaagctgca gaatgggata gattgcatcc agtgcatgca 660
gggcctattg caccaggcca gatgagagaa ccaaggggaa gtgacatagc aggaactact 720
agtacccttc aggaacaaat aggatggatg acacataatc cacctatccc agtaggagaa 780
atctataaaa gatggataat cctgggatta aataaaatag taagaatgta tagccctacc 840
agcattctgg acataagaca aggaccaaag gaacccttta gagactatgt agaccgattc 900
tataaaactc taagagccga gcaagcttca caagaggtaa aaaattggat gacagaaacc 960
ttgttggtcc aaaatgcgaa cccagattgt aagactattt taaaagcact gggaccagga 1020
gcgacactag aagaaatgat gacagcatgt cagggagtgg ggggacccgg ccataaagca 1080
agagttttgg ctgaagcaat gagccaagta acaaatccag ctaccataat gatacagaaa 1140
ggcaatttta ggaaccaaag aaagactgtt aagtgtttca attgtggcaa agaagggcac 1200
atagccaaaa attgcagggc ccctaggaaa aagggctgtt ggaaatgtgg aaaggaagga 1260
caccaaatga aagattgtac tgagagacag gctaattttt tagggaagat ctggccttcc 1320

-continued

```
cacaagggaa ggccagggaa ttttcttcag agcagaccag agccaacagc cccaccagaa   1380

gagagcttca ggtttgggga agagacaaca actccctctc agaggcagga gccgatagac   1440

aaggaactgt atcctttagc ttccctcaga tcactctttg gcagcgaccc ctcgtcacaa   1500

taaagatagg ggg                                                      1513
```

<210> SEQ ID NO 25
<211> LENGTH: 500
<212> TYPE: PRT
<213> ORGANISM: Human immunodeficiency virus

<400> SEQUENCE: 25

```
Met Gly Ala Arg Ala Ser Val Leu Ser Gly Gly Glu Leu Asp Lys Trp
 1               5                  10                  15

Glu Lys Ile Arg Leu Arg Pro Gly Gly Lys Lys Gln Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Ile Ala Val Leu Tyr Cys Val His Gln Arg Ile Asp Val Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Asn Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335
```

-continued

```
Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Phe Gly Glu Glu Thr Thr Thr Pro Ser Gln Arg Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500


<210> SEQ ID NO 26
<211> LENGTH: 3012
<212> TYPE: DNA
<213> ORGANISM: Human immunodeficiency virus

<400> SEQUENCE: 26

tttttaggg aagatctggc cttcccacaa gggaaggcca gggaatttc ttcagagcag      60

accagagcca acagccccac cagaagagag cttcaggttt ggggaagaga caacaactcc    120

ctctcagagg caggagccga tagacaagga actgtatcct ttagcttccc tcagatcact    180

ctttggcagc gacccctcgt cacaataaag ataggggggc aattaaagga agctctatta    240

gatacaggag cagatgatac agtattagaa gaaatgaatt tgccaggaag atggaaacca    300

aaaatgatag ggggaattgg aggttttatc aaagtaagac agtatgatca gatactcata    360

gaaatctgcg gacataaagc tataggtaca gtattagtag gacctacacc tgtcaacata    420

attggaagaa atctgttgac tcagattggc tgcactttaa attttcccat tagtcctatt    480

gagactgtac cagtaaaatt aaagccagga atggatggcc caaaagttaa acaatggcca    540

ttgacagaag aaaaaataaa agcattagta gaaatttgta cagaaatgga aaaggaagga    600

aaaatttcaa aaattgggcc tgaaaatcca tacaatactc cagtatttgc cataaagaaa    660

aaagacagta ctaaatggag aaaattagta gatttcagag aacttaataa gagaactcaa    720

gatttctggg aagttcaatt aggaatacca catcctgcag ggttaaaaca gaaaaaatca    780

gtaacagtac tggatgtggg cgatgcatat ttttcagttc ccttagataa agacttcagg    840

aagtatactg catttaccat acctagtata aacaatgaga caccagggat tagatatcag    900

tacaatgtgc ttccacaggg atggaaagga tcaccagcaa tattccagtg tagcatgaca    960

aaaatcttag agccttttag aaaacaaaat ccagacgtag tcatctatca atacatggat   1020

gatttgtatg taggatctga cttagaaata gggcagcata gaacaaaaat agaggaactg   1080

agacaacatc tgttgaggtg gggatttacc acaccagaca aaaaacatca gaaagaacct   1140
```

```
ccattccttt ggatgggtta tgaactccat cctgataaat ggacagtaca gcctatagtg   1200

ctgccagaaa aggacagctg gactgtcaat gacatacaga aattagtggg aaaattgaat   1260

tgggcaagtc agatttatgc agggattaaa gtaaggcaat tatgtaaact tcttagggga   1320

accaaagcac taacagaagt agtaccacta acagaagaag cagagctaga actggcagaa   1380

aacagggaga ttctaaaaga accggtacat ggagtgtatt atgacccatc aaaagactta   1440

atagcagaaa tacagaagca ggggcaaggc caatggacat atcaaattta tcaagagcca   1500

tttagaaatc tgaaaacagg aaagtatgca agaatgaagg gtgcccacac taatgatgtg   1560

aaacaattaa cagaggcagt acaaaaaata gccacagaaa gcatagtaat atggggaaag   1620

actcctaaat ttaaattacc catacaaaag gaaacatggg aagcatggtg gacagagtat   1680

tggcaagcca cctggattcc tgagtgggag tttgtcaata cccctccctt agtgaagtta   1740

tggtaccagt tagagaaaga acccataata ggagcagaaa ctttctatgt agatggggca   1800

gccaataggg aaactaaatt aggaaaagca ggatatgtaa ctgacagagg aagacaaaaa   1860

gttgtccccc taacggacac aacaaatcag aagactgagt tacaagcaat tcatctagct   1920

ttgcaggatt cgggattaga agtaaacata gtgacagact cacaatatgc attgggaatc   1980

attcaagcac aaccagataa gagtgaatca gagttagtca gtcaaataat agagcagtta   2040

ataaaaaagg aaaaagtcta cctggcatgg gtaccagcac acaaaggaat tggaggaaat   2100

gaacaagtag ataaattggt cagtgctgga atcaggaaag tactattttt agatggaata   2160

gataaggccc aagaagaaca tgagaaatat cacagtaatt ggagagcaat ggctagtgat   2220

tttaacctac cacctgtagt agcaaaagaa atagtagcca gctgtgataa atgtcagcta   2280

aaaggggaag ccatgcatgg acaagtagac tgtagcccag gaatatggca gctagattgt   2340

acacatttag aaggaaaagt tatcttggtg gcagttcatg tagccagtgg atatatagaa   2400

gcagaagtaa ttccagcaga gacagggcaa gaaacagcat acttcctctt aaaattagca   2460

ggaagatggc cagtaaaaac agtacataca gacaatggca gcaatttcac cagtactaca   2520

gttaaggccg cctgttggtg ggcgggaatc aagcaggaat ttggcattcc ctacaatccc   2580

caaagtcaag gagtaataga atctatgaat aaagaattaa agaaaattat aggacaggta   2640

agagatcagg ctgaacatct taagacagca gtacaaatgg cagtattcat ccacaatttt   2700

aaaagaaaag gggggattgg ggggtacagt gcaggggaaa gaatagtaga cataatagca   2760

acagacatac aaactaaaga attacaaaaa caaattacaa aaattcaaaa ttttcgggtt   2820

tattacaggg acagcagaga tccagtttgg aaaggaccag caaagctcct ctggaaaggt   2880

gaaggggcag tagtaataca agataatagt gacataaaag tagtgccaag aagaaaagca   2940

aagatcatca gggattatgg aaaacagatg gcaggtgatg attgtgtggc aagtagacag   3000

gatgaggatt aa                                                        3012
```

<210> SEQ ID NO 27
<211> LENGTH: 1003
<212> TYPE: PRT
<213> ORGANISM: Human immunodeficiency virus

<400> SEQUENCE: 27

```
Phe Phe Arg Glu Asp Leu Ala Phe Pro Gln Gly Lys Ala Arg Glu Phe
 1               5                  10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
```

```
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Gln Lys Lys Ser Val Thr Val Leu Asp Val Gly Asp Ala Tyr Phe Ser
            260                 265                 270

Val Pro Leu Asp Lys Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Cys Ser Met Thr
305                 310                 315                 320

Lys Ile Leu Glu Pro Phe Arg Lys Gln Asn Pro Asp Val Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Phe Thr Thr Pro Asp Lys Lys His Gln Lys Glu Pro Pro Phe Leu Trp
    370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Ala Gly Ile Lys Val Arg
            420                 425                 430

Gln Leu Cys Lys Leu Leu Arg Gly Thr Lys Ala Leu Thr Glu Val Val
        435                 440                 445

Pro Leu Thr Glu Glu Ala Glu Leu Glu Leu Ala Glu Asn Arg Glu Ile
    450                 455                 460
```

-continued

```
Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Arg Asn Leu Lys Thr Gly Lys Tyr Ala Arg Met
            500                 505                 510

Lys Gly Ala His Thr Asn Asp Val Lys Gln Leu Thr Glu Ala Val Gln
        515                 520                 525

Lys Ile Ala Thr Glu Ser Ile Val Ile Trp Gly Lys Thr Pro Lys Phe
    530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Ile Gly Ala
            580                 585                 590

Glu Thr Phe Tyr Val Asp Gly Ala Ala Asn Arg Glu Thr Lys Leu Gly
        595                 600                 605

Lys Ala Gly Tyr Val Thr Asp Arg Gly Arg Gln Lys Val Val Pro Leu
    610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
    690                 695                 700

Lys Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Asp Phe Asn Leu Pro Pro Val Val Ala Lys Glu Ile Val
            740                 745                 750

Ala Ser Cys Asp Lys Cys Gln Leu Lys Gly Glu Ala Met His Gly Gln
        755                 760                 765

Val Asp Cys Ser Pro Gly Ile Trp Gln Leu Asp Cys Thr His Leu Glu
    770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Val His Thr Asp Asn
            820                 825                 830

Gly Ser Asn Phe Thr Ser Thr Thr Val Lys Ala Ala Cys Trp Trp Ala
        835                 840                 845

Gly Ile Lys Gln Glu Phe Gly Ile Pro Tyr Asn Pro Gln Ser Gln Gly
    850                 855                 860

Val Ile Glu Ser Met Asn Lys Glu Leu Lys Lys Ile Ile Gly Gln Val
865                 870                 875                 880
```

-continued

```
Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
        915                 920                 925

Gln Lys Gln Ile Thr Lys Ile Gln Asn Phe Arg Val Tyr Tyr Arg Asp
    930                 935                 940

Ser Arg Asp Pro Val Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln Asp Glu Asp
        995                 1000


<210> SEQ ID NO 28
<211> LENGTH: 579
<212> TYPE: DNA
<213> ORGANISM: Human immunodeficiency virus

<400> SEQUENCE: 28

atggaaaaca gatggcaggt gatgattgtg tggcaagtag acaggatgag gattaacaca      60

tggaaaagat tagtaaaaca ccatatgtat atttcaagga aagctaagga ctggttttat     120

agacatcact atgaaagtac taatccaaaa ataagttcag aagtacacat cccactaggg     180

gatgctaaat tagtaataac aacatattgg ggtctgcata caggagaaag agactggcat     240

ttgggtcagg gagtctccat agaatggagg aaaaagagat atagcacaca agtagaccct     300

gacctagcag accaactaat tcatctgcac tattttgatt gtttttcaga atctgctata     360

agaaatacca tattaggacg tatagttagt cctaggtgtg aatatcaagc aggacataac     420

aaggtaggat ctctacagta cttggcacta gcagcattaa taaaaccaaa acagataaag     480

ccacctttgc ctagtgttag gaaactgaca gaggacagat ggaacaagcc ccagaagacc     540

aagggccaca gagggagcca tacaacgaat ggacactag                            579


<210> SEQ ID NO 29
<211> LENGTH: 192
<212> TYPE: PRT
<213> ORGANISM: Human immunodeficiency virus

<400> SEQUENCE: 29

Met Glu Asn Arg Trp Gln Val Met Ile Val Trp Gln Val Asp Arg Met
 1               5                  10                  15

Arg Ile Asn Thr Trp Lys Arg Leu Val Lys His His Met Tyr Ile Ser
            20                  25                  30

Arg Lys Ala Lys Asp Trp Phe Tyr Arg His His Tyr Glu Ser Thr Asn
        35                  40                  45

Pro Lys Ile Ser Ser Glu Val His Ile Pro Leu Gly Asp Ala Lys Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
```

-continued

```
            100                 105                 110

Asp Cys Phe Ser Glu Ser Ala Ile Arg Asn Thr Ile Leu Gly Arg Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Lys Pro Lys Gln Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Thr Asn Gly His
            180                 185                 190


<210> SEQ ID NO 30
<211> LENGTH: 291
<212> TYPE: DNA
<213> ORGANISM: Human immunodeficiency virus

<400> SEQUENCE: 30

atggaacaag ccccagaaga ccaagggcca cagagggagc catacaacga atggacacta     60

gagcttttag aggaacttaa gagtgaagct gttagacatt ttcctaggat atggctccat    120

aacttaggac gacatatcta tgaaacttac ggggatactt gggcaggagt ggaagccata    180

ataagaattc tgcaacaact gccgtttatc catttcagaa ttgggtgtcg acatagcaga    240

ataggcgtta ctcgacagag gagagcaaga aatggagcca gtagatccta g             291


<210> SEQ ID NO 31
<211> LENGTH: 86
<212> TYPE: PRT
<213> ORGANISM: Human immunodeficiency virus

<400> SEQUENCE: 31

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Met Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Ser Arg Gly Asp
65                  70                  75                  80

Pro Thr Gly Pro Lys Glu
                85


<210> SEQ ID NO 32
<211> LENGTH: 2585
<212> TYPE: DNA
<213> ORGANISM: Human immunodeficiency virus

<400> SEQUENCE: 32

atggagccag tagatcctag actagagccc tggaagcatc caggaagtca gcctaaaact     60

gcttgtacca attgctattg taaaaagtgt tgctttcatt gccaagtttg tttcatgaca    120

aaagccttag gcatctccta tggcaggaag aagcggagac agcgacgaag agctcatcag    180

aacagtcaga ctcatcaagc ttctctatca aagcagtaag tagtacatgt aatgcaacct    240

ataatagtag caatagtagc attagtagta gcaataataa tagcaatagt tgtgtggtcc    300
```

-continued

```
atagtaatca tagaatatag gaaaatatta agacaaagaa aaatagacag gttaattgat    360
agactaatag aaagagcaga agacagtggc aatgagagtg aaggagaagt atcagcactt    420
gtggagatgg gggtggaaat ggggcaccat gctccttggg atattgatga tctgtagtgc    480
tacagaaaaa ttgtgggtca cagtctatta tggggtacct gtgtggaagg aagcaaccac    540
cactctattt tgtgcatcag atgctaaagc atatgataca gaggtacata atgtttgggc    600
cacacatgcc tgtgtaccca cagaccccaa cccacaagaa gtagtattgg taaatgtgac    660
agaaaatttt aacatgtgga aagatgacat ggtagaacag atgcatgagg atataatcag    720
tttatgggat caaagcctaa agccatgtgt aaaattaacc ccactctgtg ttagtttaaa    780
gtgcactgat ttgaagaatg atactaatac caatagtagt agcgggagaa tgataatgga    840
gaaaggagag ataaaaaact gctctttcaa tatcagcaca agcataagag ataaggtgca    900
gaaagaatat gcattctttt ataaacttga tatagtacca atagataata ccagctatag    960
gttgataagt tgtaacacct cagtcattac acaggcctgt ccaaaggtat cctttgagcc   1020
aatccccata cattattgtg ccccggctgg ttttgcgatt ctaaaatgta ataataagac   1080
gttcaatgga acaggaccat gtacaaatgt cagcacagta caatgtacac atggaatcag   1140
gccagtagta tcaactcaac tgctgttaaa tggcagtcta gcagaagaag atgtagtaat   1200
tagatctgcc aatttcacag acaatgctaa aaccataata gtacagctga acacatctgt   1260
agaaattaat tgtacaagac ccaacaacaa tacaagaaaa agtatccgta tccagagggg   1320
accagggaga gcatttgtta caataggaaa aataggaaat atgagacaag cacattgtaa   1380
cattagtaga gcaaaatgga atgccacttt aaaacagata gctagcaaat taagagaaca   1440
atttggaaat aataaaacaa taatctttaa gcaatcctca ggaggggacc cagaaattgt   1500
aacgcacagt tttaattgtg gaggggaatt tttctactgt aattcaacac aactgtttaa   1560
tagtacttgg tttaatagta cttggagtac tgaagggtca aataacactg aaggaagtga   1620
cacaatcaca ctcccatgca gaataaaaca atttataaac atgtggcagg aagtaggaaa   1680
agcaatgtat gcccctccca tcagtggaca aattagatgt tcatcaaata ttactgggct   1740
gctattaaca agagatggtg gtaataacaa caatgggtcc gagatcttca gacctggagg   1800
aggcgatatg agggacaatt ggagaagtga attatataaa tataaagtag taaaaattga   1860
accattagga gtagcaccca ccaaggcaaa gagaagagtg gtgcagagag aaaaaagagc   1920
agtgggaata ggagctttgt tccttgggtt cttgggagca gcaggaagca ctatgggcgc   1980
agcgtcaatg acgctgacgg tacaggccag acaattattg tctgatatag tgcagcagca   2040
gaacaatttg ctgagggcta ttgaggcgca acagcatctg ttgcaactca cagtctgggg   2100
catcaaacag ctccaggcaa gaatcctggc tgtggaaaga tacctaaagg atcaacagct   2160
cctggggatt tggggttgct ctggaaaact catttgcacc actgctgtgc cttggaatgc   2220
tagttggagt aataaatctc tggaacagat ttggaataac atgacctgga tggagtggga   2280
cagagaaatt aacaattaca caagcttaat acactcctta attgaagaat cgcaaaacca   2340
gcaagaaaag aatgaacaag aattattgga attagataaa tgggcaagtt tgtggaattg   2400
gtttaacata acaaattggc tgtggtatat aaaattattc ataatgatag taggaggctt   2460
ggtaggttta agaatagttt ttgctgtact ttctatagtg aatagagtta ggcagggata   2520
ttcaccatta tcgtttcaga cccacctccc aatcccgagg ggacccgaca ggcccgaagg   2580
aatag                                                               2585
```

-continued

<210> SEQ ID NO 33
<211> LENGTH: 86
<212> TYPE: PRT
<213> ORGANISM: Human immunodeficiency virus

<400> SEQUENCE: 33

```
Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Met Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Ser Arg Gly Asp
65                  70                  75                  80

Pro Thr Gly Pro Lys Glu
                85
```

<210> SEQ ID NO 34
<211> LENGTH: 2675
<212> TYPE: DNA
<213> ORGANISM: Human immunodeficiency virus

<400> SEQUENCE: 34

```
atggcaggaa gaagcggaga cagcgacgaa gagctcatca gaacagtcag actcatcaag      60

cttctctatc aaagcagtaa gtagtacatg taatgcaacc tataatagta gcaatagtag     120

cattagtagt agcaataata atagcaatag ttgtgtggtc catagtaatc atagaatata     180

ggaaaatatt aagacaaaga aaaatagaca ggttaattga tagactaata gaaagagcag     240

aagacagtgg caatgagagt gaaggagaag tatcagcact tgtggagatg gggtggaaa     300

tggggcacca tgctccttgg gatattgatg atctgtagtg ctacagaaaa attgtgggtc     360

acagtctatt atggggtacc tgtgtggaag gaagcaacca ccactctatt ttgtgcatca     420

gatgctaaag catatgatac agaggtacat aatgtttggg ccacacatgc ctgtgtaccc     480

acagacccca acccacaaga agtagtattg gtaaatgtga cagaaaattt taacatgtgg     540

aaagatgaca tggtagaaca gatgcatgag gatataatca gtttatggga tcaaagccta     600

aagccatgtg taaaattaac cccactctgt gttagtttaa agtgcactga tttgaagaat     660

gatactaata ccaatagtag tagcgggaga atgataatgg agaaaggaga gataaaaaac     720

tgctctttca atatcagcac aagcataaga gataaggtgc agaaagaata tgcattcttt     780

tataaacttg atatagtacc aatagataat accagctata ggttgataag ttgtaacacc     840

tcagtcatta cacaggcctg tccaaaggta tcctttgagc caatccccat acattattgt     900

gccccggctg gttttgcgat tctaaaatgt aataataaga cgttcaatgg aacaggacca     960

tgtacaaatg tcagcacagt acaatgtaca catggaatca ggccagtagt atcaactcaa    1020

ctgctgttaa atggcagtct agcagaagaa gatgtagtaa ttagatctgc caatttcaca    1080

gacaatgcta aaaccataat agtacagctg aacacatctg tagaaattaa ttgtacaaga    1140

cccaacaaca atacaagaaa aagtatccgt atccagaggg gaccagggag agcatttgtt    1200

acaataggaa aaataggaaa tatgagacaa gcacattgta acattagtag agcaaaatgg    1260

aatgccactt taaaacagat agctagcaaa ttaagagaac aatttggaaa taataaaaca    1320

ataatcttta agcaatcctc aggaggggac ccagaaattg taacgcacag ttttaattgt    1380
```

-continued

```
ggaggggaat ttttctactg taattcaaca caactgttta atagtacttg gtttaatagt   1440

acttggagta ctgaagggtc aaataacact gaaggaagtg acacaatcac actcccatgc   1500

agaataaaac aatttataaa catgtggcag gaagtaggaa aagcaatgta tgcccctccc   1560

atcagtggac aaattagatg ttcatcaaat attactgggc tgctattaac aagagatggt   1620

ggtaataaca acaatgggtc cgagatcttc agacctggag gaggcgatat gagggacaat   1680

tggagaagtg aattatataa atataaagta gtaaaaattg aaccattagg agtagcaccc   1740

accaaggcaa agagaagagt ggtgcagaga gaaaaaagag cagtgggaat aggagctttg   1800

ttccttgggt tcttgggagc agcaggaagc actatgggcg cagcgtcaat gacgctgacg   1860

gtacaggcca gacaattatt gtctgatata gtgcagcagc agaacaattt gctgagggct   1920

attgaggcgc aacagcatct gttgcaactc acagtctggg gcatcaaaca gctccaggca   1980

agaatcctgg ctgtggaaag atacctaaag gatcaacagc tcctggggat ttggggttgc   2040

tctggaaaac tcatttgcac cactgctgtg ccttggaatg ctagttggag taataaatct   2100

ctggaacaga tttggaataa catgacctgg atggagtggg acagagaaat taacaattac   2160

acaagcttaa tacactcctt aattgaagaa tcgcaaaacc agcaagaaaa gaatgaacaa   2220

gaattattgg aattagataa atgggcaagt ttgtggaatt ggtttaacat aacaaattgg   2280

ctgtggtata taaaattatt cataatgata gtaggaggct tggtaggttt aagaatagtt   2340

tttgctgtac tttctatagt gaatagagtt aggcagggat attcaccatt atcgtttcag   2400

acccacctcc caatcccgag gggacccgac aggcccgaag gaatagaaga agaaggtgga   2460

gagagaggca gagacagatc cattcgatta gtgaacggat ccttagcact tatctgggac   2520

gatctgcgga gcctgtgcct cttcagctac caccgcttga gagacttact cttgattgta   2580

acgaggattg tggaacttct gggacgcagg gggtgggaag ccctcaaata ttggtggaat   2640

ctcctacagt attggagtca ggaactaaag aatag                              2675
```

<210> SEQ ID NO 35
<211> LENGTH: 116
<212> TYPE: PRT
<213> ORGANISM: Human immunodeficiency virus

<400> SEQUENCE: 35

```
Met Ala Gly Arg Ser Gly Asp Ser Asp Glu Glu Leu Ile Arg Thr Val
1               5                   10                  15

Arg Leu Ile Lys Leu Leu Tyr Gln Ser Asn Pro Pro Pro Asn Pro Glu
            20                  25                  30

Gly Thr Arg Gln Ala Arg Arg Asn Arg Arg Arg Arg Trp Arg Glu Arg
        35                  40                  45

Gln Arg Gln Ile His Ser Ile Ser Glu Arg Ile Leu Ser Thr Tyr Leu
    50                  55                  60

Gly Arg Ser Ala Glu Pro Val Pro Leu Gln Leu Pro Pro Leu Glu Arg
65                  70                  75                  80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Val Leu Glu Ser
            100                 105                 110

Gly Thr Lys Glu
        115
```

<210> SEQ ID NO 36
<211> LENGTH: 246

<212> TYPE: DNA
<213> ORGANISM: Human immunodeficiency virus

<400> SEQUENCE: 36
atgcaaccta taatagtagc aatagtagca ttagtagtag caataataat agcaatagtt 60
gtgtggtcca tagtaatcat agaatatagg aaaatattaa gacaaagaaa aatagacagg 120
ttaattgata gactaataga aagagcagaa gacagtggca atgagagtga aggagaagta 180
tcagcacttg tggagatggg ggtggaaatg gggcaccatg ctccttggga tattgatgat 240
ctgtag 246

<210> SEQ ID NO 37
<211> LENGTH: 81
<212> TYPE: PRT
<213> ORGANISM: Human immunodeficiency virus

<400> SEQUENCE: 37

Met Gln Pro Ile Ile Val Ala Ile Val Ala Leu Val Val Ala Ile Ile
1 5 10 15

Ile Ala Ile Val Val Trp Ser Ile Val Ile Ile Glu Tyr Arg Lys Ile
20 25 30

Leu Arg Gln Arg Lys Ile Asp Arg Leu Ile Asp Arg Leu Ile Glu Arg
35 40 45

Ala Glu Asp Ser Gly Asn Glu Ser Glu Gly Glu Val Ser Ala Leu Val
50 55 60

Glu Met Gly Val Glu Met Gly His His Ala Pro Trp Asp Ile Asp Asp
65 70 75 80

Leu

<210> SEQ ID NO 38
<211> LENGTH: 2565
<212> TYPE: DNA
<213> ORGANISM: Human immunodeficiency virus

<400> SEQUENCE: 38
atgagagtga aggagaagta tcagcacttg tggagatggg ggtggaaatg gggcaccatg 60
ctccttggga tattgatgat ctgtagtgct acagaaaaat tgtgggtcac agtctattat 120
ggggtacctg tgtggaagga agcaaccacc actctatttt gtgcatcaga tgctaaagca 180
tatgatacag aggtacataa tgtttgggcc acacatgcct gtgtacccac agaccccaac 240
ccacaagaag tagtattggt aaatgtgaca gaaaatttta acatgtggaa agatgacatg 300
gtagaacaga tgcatgagga tataatcagt ttatgggatc aaagcctaaa gccatgtgta 360
aaattaaccc cactctgtgt tagtttaaag tgcactgatt tgaagaatga tactaatacc 420
aatagtagta gcgggagaat gataatggag aaaggagaga taaaaaactg ctctttcaat 480
atcagcacaa gcataagaga taaggtgcag aaagaatatg cattctttta taaacttgat 540
atagtaccaa tagataatac cagctatagg ttgataagtt gtaacacctc agtcattaca 600
caggcctgtc caaaggtatc ctttgagcca atccccatac attattgtgc cccggctggt 660
tttgcgattc taaaatgtaa taataagacg ttcaatggaa caggaccatg tacaaatgtc 720
agcacagtac aatgtacaca tggaatcagg ccagtagtat caactcaact gctgttaaat 780
ggcagtctag cagaagaaga tgtagtaatt agatctgcca atttcacaga caatgctaaa 840
accataatag tacagctgaa cacatctgta gaaattaatt gtacaagacc caacaacaat 900
acaagaaaaa gtatccgtat ccagagggga ccagggagag catttgttac aataggaaaa 960

```
ataggaaata tgagacaagc acattgtaac attagtagag caaaatggaa tgccacttta   1020

aaacagatag ctagcaaatt aagagaacaa tttggaaata ataaaacaat aatctttaag   1080

caatcctcag gaggggaccc agaaattgta acgcacagtt ttaattgtgg aggggaattt   1140

ttctactgta attcaacaca actgtttaat agtacttggt ttaatagtac ttggagtact   1200

gaagggtcaa ataacactga aggaagtgac acaatcacac tcccatgcag aataaaacaa   1260

tttataaaca tgtggcagga agtaggaaaa gcaatgtatg cccctcccat cagtggacaa   1320

attagatgtt catcaaatat tactgggctg ctattaacaa gagatggtgg taataacaac   1380

aatgggtccg agatcttcag acctggagga ggcgatatga gggacaattg gagaagtgaa   1440

ttatataaat ataaagtagt aaaaattgaa ccattaggag tagcacccac caaggcaaag   1500

agaagagtgg tgcagagaga aaaaagagca gtgggaatag gagctttgtt ccttgggttc   1560

ttgggagcag caggaagcac tatgggcgca gcgtcaatga cgctgacggt acaggccaga   1620

caattattgt ctgatatagt gcagcagcag aacaatttgc tgagggctat tgaggcgcaa   1680

cagcatctgt tgcaactcac agtctggggc atcaaacagc tccaggcaag aatcctggct   1740

gtggaaagat acctaaagga tcaacagctc ctggggattt ggggttgctc tggaaaactc   1800

atttgcacca ctgctgtgcc ttggaatgct agttggagta ataaatctct ggaacagatt   1860

tggaataaca tgacctggat ggagtgggac agagaaatta acaattacac aagcttaata   1920

cactccttaa ttgaagaatc gcaaaaccag caagaaaaga atgaacaaga attattggaa   1980

ttagataaat gggcaagttt gtggaattgg tttaacataa caaattggct gtggtatata   2040

aaattattca taatgatagt aggaggcttg gtaggtttaa gaatagtttt tgctgtactt   2100

tctatagtga atagagttag gcagggatat tcaccattat cgtttcagac ccacctccca   2160

atcccgaggg gacccgacag gcccgaagga atagaagaag aaggtggaga gagaggcaga   2220

gacagatcca ttcgattagt gaacggatcc ttagcactta tctgggacga tctgcggagc   2280

ctgtgcctct tcagctacca ccgcttgaga gacttactct tgattgtaac gaggattgtg   2340

gaacttctgg gacgcagggg gtgggaagcc ctcaaatatt ggtggaatct cctacagtat   2400

tggagtcagg aactaaagaa tagtgctgtt aacttgctca atgccacagc catagcagta   2460

gctgagggga cagatagggt tatagaagta ttacaagcag cttatagagc tattcgccac   2520

atacctagaa gaataagaca gggcttggaa aggattttgc tataa                   2565
```

<210> SEQ ID NO 39
<211> LENGTH: 854
<212> TYPE: PRT
<213> ORGANISM: Human immunodeficiency virus

<400> SEQUENCE: 39

```
Met Arg Val Lys Glu Lys Tyr Gln His Leu Trp Arg Trp Gly Trp Lys
 1               5                  10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
```

-continued

```
                85                  90                  95

Lys Asp Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Asp Lys Val Gln Lys Glu Tyr Ala Phe Phe
                165                 170                 175

Tyr Lys Leu Asp Ile Val Pro Ile Asp Asn Thr Ser Tyr Arg Leu Ile
            180                 185                 190

Ser Cys Asn Thr Ser Val Ile Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220

Lys Cys Asn Asn Lys Thr Phe Asn Gly Thr Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Asp Val Val Ile Arg Ser
            260                 265                 270

Ala Asn Phe Thr Asp Asn Ala Lys Thr Ile Ile Val Gln Leu Asn Thr
        275                 280                 285

Ser Val Glu Ile Asn Cys Thr Arg Pro Asn Asn Asn Thr Arg Lys Ser
    290                 295                 300

Ile Arg Ile Gln Arg Gly Pro Gly Arg Ala Phe Val Thr Ile Gly Lys
305                 310                 315                 320

Ile Gly Asn Met Arg Gln Ala His Cys Asn Ile Ser Arg Ala Lys Trp
                325                 330                 335

Asn Ala Thr Leu Lys Gln Ile Ala Ser Lys Leu Arg Glu Gln Phe Gly
            340                 345                 350

Asn Asn Lys Thr Ile Ile Phe Lys Gln Ser Ser Gly Gly Asp Pro Glu
        355                 360                 365

Ile Val Thr His Ser Phe Asn Cys Gly Gly Glu Phe Phe Tyr Cys Asn
    370                 375                 380

Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys
                405                 410                 415

Arg Ile Lys Gln Phe Ile Asn Met Trp Gln Glu Val Gly Lys Ala Met
            420                 425                 430

Tyr Ala Pro Pro Ile Ser Gly Gln Ile Arg Cys Ser Ser Asn Ile Thr
        435                 440                 445

Gly Leu Leu Leu Thr Arg Asp Gly Gly Asn Asn Asn Asn Gly Ser Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Arg Ala Val Gly
            500                 505                 510
```

-continued

```
Ile Gly Ala Leu Phe Leu Gly Phe Leu Gly Ala Ala Gly Ser Thr Met
        515                 520                 525

Gly Ala Ala Ser Met Thr Leu Thr Val Gln Ala Arg Gln Leu Leu Ser
    530                 535                 540

Asp Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Ile Leu Ala Val Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ala Ser Trp Ser Asn Lys Ser Leu Glu Gln Ile Trp Asn Asn Met
    610                 615                 620

Thr Trp Met Glu Trp Asp Arg Glu Ile Asn Asn Tyr Thr Ser Leu Ile
625                 630                 635                 640

His Ser Leu Ile Glu Glu Ser Gln Asn Gln Gln Glu Lys Asn Glu Gln
                645                 650                 655

Glu Leu Leu Glu Leu Asp Lys Trp Ala Ser Leu Trp Asn Trp Phe Asn
            660                 665                 670

Ile Thr Asn Trp Leu Trp Tyr Ile Lys Leu Phe Ile Met Ile Val Gly
        675                 680                 685

Gly Leu Val Gly Leu Arg Ile Val Phe Ala Val Leu Ser Ile Val Asn
    690                 695                 700

Arg Val Arg Gln Gly Tyr Ser Pro Leu Ser Phe Gln Thr His Leu Pro
705                 710                 715                 720

Ile Pro Arg Gly Pro Asp Arg Pro Glu Gly Ile Glu Glu Glu Gly Gly
                725                 730                 735

Glu Arg Gly Arg Asp Arg Ser Ile Arg Leu Val Asn Gly Ser Leu Ala
            740                 745                 750

Leu Ile Trp Asp Asp Leu Arg Ser Leu Cys Leu Phe Ser Tyr His Arg
        755                 760                 765

Leu Arg Asp Leu Leu Leu Ile Val Thr Arg Ile Val Glu Leu Leu Gly
    770                 775                 780

Arg Arg Gly Trp Glu Ala Leu Lys Tyr Trp Trp Asn Leu Leu Gln Tyr
785                 790                 795                 800

Trp Ser Gln Glu Leu Lys Asn Ser Ala Val Asn Leu Leu Asn Ala Thr
                805                 810                 815

Ala Ile Ala Val Ala Glu Gly Thr Asp Arg Val Ile Glu Val Leu Gln
            820                 825                 830

Ala Ala Tyr Arg Ala Ile Arg His Ile Pro Arg Arg Ile Arg Gln Gly
        835                 840                 845

Leu Glu Arg Ile Leu Leu
    850
```

<210> SEQ ID NO 40
<211> LENGTH: 621
<212> TYPE: DNA
<213> ORGANISM: Human immunodeficiency virus

<400> SEQUENCE: 40

```
atgggtggca agtggtcaaa aagtagtgtg attggatggc ctgctgtaag ggaaagaatg      60

agacgagctg agccagcagc agatggggtg ggagcagtat ctcgagacct agaaaaacat     120
```

ggagcaatca caagtagcaa tacagcagct aacaatgctg cttgtgcctg gctagaagca 180
caagaggagg aagaggtggg ttttccagtc acacctcagg tacctttaag accaatgact 240
tacaaggcag ctgtagatct tagccacttt ttaaaagaaa aggggggact ggaagggcta 300
attcactccc aaagaagaca agatatcctt gatctgtgga tctaccacac acaaggctac 360
ttccctgatt ggcagaacta cacaccaggg ccaggggtca gatatccact gacctttgga 420
tggtgctaca agctagtacc agttgagcca gataaggtag aagaggccaa taaaggagag 480
aacaccagct tgttacaccc tgtgagcctg catggaatgg atgaccctga gagagaagtg 540
ttagagtgga ggtttgacag ccgcctagca tttcatcacg tggcccgaga gctgcatccg 600
gagtacttca agaactgctg a 621

<210> SEQ ID NO 41
<211> LENGTH: 206
<212> TYPE: PRT
<213> ORGANISM: Human immunodeficiency virus

<400> SEQUENCE: 41

```
Met Gly Gly Lys Trp Ser Lys Ser Ser Val Ile Gly Trp Pro Ala Val
 1               5                  10                  15

Arg Glu Arg Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Asn Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205
```

<210> SEQ ID NO 42
<211> LENGTH: 2635
<212> TYPE: DNA
<213> ORGANISM: Human immunodeficiency virus

<400> SEQUENCE: 42
ccaacatagc agaataggta ttattcaaca gaggagagca agaaatggag ccagtagatc 60
ctaaactaga gccctggaag catccaggaa gtcagcctaa gactgcttgt accacttgct 120
attgtaaaaa gtgttgcttt cattgccaag tttgcttcat aacaaaaggc ttaggcatct 180

-continued

```
cctatggcag gaggaagcgg agacagcgac gaagagctcc tcaagacagt cagactcatc    240
aagtttctct atcaaagcag taagtagtac atgtaatgca agctttacaa atatcagcaa    300
tagtaggatt agtagtagca gcaataatag caatagttgt gtggaccata gtattcatag    360
aatataggaa aatattaagg caaagaaaaa tagacaggtt aattgataga ataacagaaa    420
gagcagaaga cagtggcaat gagagtgatg gagatcagga ggaattatca gcactggtgg    480
agatggggca tcatgctcct tgggatgtta atgatctgta atgctgaaga aaaattgtgg    540
gtcacagtct attatggggt acctgtgtgg aaagaagcaa ccaccactct attttgtgca    600
tcagatgcta aagcatatga tacagaggta cataatgttt gggccacaca tgcctgtgta    660
cccacagacc ccgacccaca agaagtaaaa ttggaaaatg tgacagaaaa ttttaacatg    720
tggaaaaata aaatggtaga acagatgcat gaggatataa tcagtttatg ggatcaaagc    780
ctaaagccat gtgtaaaatt aactccactc tgtgttactt taaattgcac tgtaagcggg    840
ggaatgatgg ggggaggaga aatgaaaaat tgctctttca atatcaccac aaacataaga    900
ggtaaggtgc agaaagaata tgcacttttt tatgaacttg atatagtacc aatagataat    960
aaaaatgata gctataggtt gataagttgt aacacctcag tcattacaca ggcctgtcca   1020
aaggtatcct ttgagccaat tcccatacat tattgtgccc cggctggttt tgcgattcta   1080
aagtgtaaag ataataagtt caatggaaaa ggaccatgta caaatgtcag cacagtacaa   1140
tgtacacatg gaattaggcc agtagtatca actcaactgc tgttaaatgg cagtctagca   1200
gaagaagagg tagtaattag atccgaaaat ttcacgaaca atgctaaaac cataatagta   1260
cagctgaatg aatctgtagt aattaattgt acaagaccca acaacaatac aagaaaaagt   1320
ataaatatag gaccaggcag agcattttat acaacaggag aaataatagg agatataaga   1380
caagcacatt gtaaccttag tagagcaaaa tggaatgaca ctttaaataa gatagttata   1440
aaattaagag aacaatttgg gaataaaaca atagtcttta agcactcctc aggaggagac   1500
ccagaaattg tgacgcacag ttttaattgt ggaggggaat tttctactg taattcaaca   1560
caactgttta atagtacttg gaatgttact gaagagtcaa ataacactgt agaaaataac   1620
acaatcacac tcccatgcag aataaaacaa attataaaca tgtggcagga agtaggaaga   1680
gcaatgtatg cccctcccat cagaggacaa attagatgtt catcaaatat tacagggctg   1740
ctattaacaa gagatggtgg tcctgaggac aacaagaccg aggtcttcag acctggagga   1800
ggagatatga gggataattg gagaagtgaa ttatataaat ataaagtagt aaaaattgaa   1860
ccattaggag tagcacccac caaggcaaag agaagagtgg tgcagagaga aaaaagagca   1920
gtgggaatag gagctgtgtt ccttgggttc ttgggagcag caggaagcac tatgggcgca   1980
gcgtcaatga cgctgacggt acaggccaga ctattattgt ctggtatagt gcaacagcag   2040
aacaatctgc tgagagctat tgaggcgcaa cagcatctgt tgcaactcac agtctggggc   2100
atcaagcagc tccaggcaag agtcctggct gtggaaagat acctaaggga tcaacagctc   2160
ctggggattt ggggttgctc tggaaaactc atctgcacca ctgctgtgcc ttggaatgct   2220
agttggagta ataaatctct gaataagatt tgggataaca tgacctggat ggagtgggac   2280
agagaaatta acaattacac aagcataata tacagcttaa ttgaagaatc gcagaaccaa   2340
caagaaaaga atgaacaaga attattagaa ttagataaat gggcaagttt gtggaattgg   2400
tttgacataa caaaatggct gtggtatata aaaatattca taatgatagt aggaggcttg   2460
ataggtttaa gaatagtttt ttctgtactt tctatagtga atagagttag gcagggatac   2520
tcaccattat cgtttcagac ccacctccca gcctcgaggg gacccgacag gcccggagga   2580
```

atcgaagaag aaggtggaga gagagacaga gacagatccg gttcattagt gaacg 2635

<210> SEQ ID NO 43
<211> LENGTH: 786
<212> TYPE: DNA
<213> ORGANISM: Homo sapiens

<400> SEQUENCE: 43
atgatcgaaa catacaacca aacttctccc cgatctgcgg ccactggact gcccatcagc 60
atgaaaattt ttatgtattt acttactgtt tttcttatca cccagatgat tgggtcagca 120
ctttttgctg tgtatcttca tagaaggttg gacaagatag aagatgaaag gaatcttcat 180
gaagattttg tattcatgaa aacgatacag agatgcaaca caggagaaag atccttatcc 240
ttactgaact gtgaggagat taaaagccag tttgaaggct ttgtgaagga tataatgtta 300
aacaaagagg agacgaagaa agaaaacagc tttgaaatgc aaaaaggtga tcagaatcct 360
caaattgcgg cacatgtcat aagtgaggcc agcagtaaaa caacatctgt gttacagtgg 420
gctgaaaaag gatactacac catgagcaac aacttggtaa ccctggaaaa tgggaaacag 480
ctgaccgtta aaagacaagg actctattat atctatgccc aagtcacctt ctgttccaat 540
cgggaagctt cgagtcaagc tccatttata gccagcctct gcctaaagtc ccccggtaga 600
ttcgagagaa tcttactcag agctgcaaat acccacagtt ccgccaaacc ttgcgggcaa 660
caatccattc acttgggagg agtatttgaa ttgcaaccag gtgcttcggt gtttgtcaat 720
gtgactgatc caagccaagt gagccatggc actggcttca cgtcctttgg cttactcaaa 780
ctctga 786

<210> SEQ ID NO 44
<211> LENGTH: 261
<212> TYPE: PRT
<213> ORGANISM: Homo sapiens

<400> SEQUENCE: 44

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175
```

```
Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260


<210> SEQ ID NO 45
<211> LENGTH: 9
<212> TYPE: PRT
<213> ORGANISM: Human immunodeficiency virus

<400> SEQUENCE: 45

Ala Leu Val Glu Ile Cys Thr Glu Met
 1               5


<210> SEQ ID NO 46
<211> LENGTH: 9
<212> TYPE: PRT
<213> ORGANISM: Human immunodeficiency virus

<400> SEQUENCE: 46

Tyr Leu Lys Glu Pro Val His Gly Val
 1               5


<210> SEQ ID NO 47
<211> LENGTH: 9
<212> TYPE: PRT
<213> ORGANISM: Human immunodeficiency virus

<400> SEQUENCE: 47

Tyr Leu Thr Pro Leu Cys Val Ser Leu
 1               5


<210> SEQ ID NO 48
<211> LENGTH: 9
<212> TYPE: PRT
<213> ORGANISM: Human immunodeficiency virus

<400> SEQUENCE: 48

Tyr Leu Asn Ala Trp Val Lys Val Val
 1               5


<210> SEQ ID NO 49
<211> LENGTH: 9
<212> TYPE: PRT
<213> ORGANISM: Human immunodeficiency virus

<400> SEQUENCE: 49

Tyr Ile Tyr Gln Tyr Met Asp Asp Leu
 1               5


<210> SEQ ID NO 50
<211> LENGTH: 10
<212> TYPE: PRT
<213> ORGANISM: Human immunodeficiency virus
```

<400> SEQUENCE: 50

Tyr Leu Thr Phe Gly Trp Cys Phe Lys Leu
1 5 10

<210> SEQ ID NO 51
<211> LENGTH: 11
<212> TYPE: PRT
<213> ORGANISM: Human immunodeficiency virus

<400> SEQUENCE: 51

Val Leu Asp Val Gly Asp Ala Tyr Phe Ser Val
1 5 10

<210> SEQ ID NO 52
<211> LENGTH: 9
<212> TYPE: PRT
<213> ORGANISM: Human immunodeficiency virus

<400> SEQUENCE: 52

Tyr Leu Val Lys Leu Trp Tyr Gln Leu
1 5

<210> SEQ ID NO 53
<211> LENGTH: 9
<212> TYPE: PRT
<213> ORGANISM: Human immunodeficiency virus

<400> SEQUENCE: 53

Ser Leu Tyr Asn Thr Val Ala Thr Leu
1 5

<210> SEQ ID NO 54
<211> LENGTH: 9
<212> TYPE: PRT
<213> ORGANISM: Human immunodeficiency virus

<400> SEQUENCE: 54

Tyr Met Met Thr Ala Cys Gln Gly Val
1 5

<210> SEQ ID NO 55
<211> LENGTH: 10
<212> TYPE: PRT
<213> ORGANISM: Human immunodeficiency virus

<400> SEQUENCE: 55

Leu Leu Asp Thr Gly Ala Asp Asp Thr Val
1 5 10

<210> SEQ ID NO 56
<211> LENGTH: 9
<212> TYPE: PRT
<213> ORGANISM: Human immunodeficiency virus

<400> SEQUENCE: 56

Leu Leu Trp Lys Gly Glu Gly Ala Val
1 5

<210> SEQ ID NO 57
<211> LENGTH: 9
<212> TYPE: PRT
<213> ORGANISM: Human immunodeficiency virus

<400> SEQUENCE: 57

Tyr Leu Thr Pro Leu Cys Val Thr Leu
1 5

<210> SEQ ID NO 58
<211> LENGTH: 5
<212> TYPE: PRT
<213> ORGANISM: Human immunodeficiency virus
<220> FEATURE:
<221> NAME/KEY: misc_feature
<222> LOCATION: (2)...(3)
<223> OTHER INFORMATION: Xaa is any amino acid

<400> SEQUENCE: 58

Leu Xaa Xaa Leu Phe
1 5

<210> SEQ ID NO 59
<211> LENGTH: 4
<212> TYPE: PRT
<213> ORGANISM: Human immunodeficiency virus

<400> SEQUENCE: 59

Phe Arg Phe Gly
1

<210> SEQ ID NO 60
<211> LENGTH: 7
<212> TYPE: PRT
<213> ORGANISM: Simian immunodeficiency virus
<220> FEATURE:
<221> NAME/KEY: misc_feature
<222> LOCATION: (2)...(2)
<223> OTHER INFORMATION: Xaa is any amino acid
<220> FEATURE:
<221> NAME/KEY: misc_feature
<222> LOCATION: (4)...(5)
<223> OTHER INFORMATION: Xaa is any amino acid

<400> SEQUENCE: 60

Asp Xaa Ala Xaa Xaa Leu Leu
1 5

<210> SEQ ID NO 61
<211> LENGTH: 5
<212> TYPE: PRT
<213> ORGANISM: Simian immunodeficiency virus

<400> SEQUENCE: 61

Pro Thr Ala Pro Pro
1 5

<210> SEQ ID NO 62
<211> LENGTH: 9
<212> TYPE: PRT
<213> ORGANISM: Influenza virus

<400> SEQUENCE: 62

Gly Ile Leu Gly Phe Val Phe Thr Leu
1 5

<210> SEQ ID NO 63
<211> LENGTH: 18
<212> TYPE: PRT
<213> ORGANISM: Adenovirus

<400> SEQUENCE: 63

```
Met Arg Tyr Met Ile Leu Gly Leu Leu Ala Leu Ala Ala Val Cys Ser
 1               5                  10                  15

Ala Ala


<210> SEQ ID NO 64
<211> LENGTH: 22
<212> TYPE: PRT
<213> ORGANISM: Picornavirus 2A

<400> SEQUENCE: 64

Gly Ser Gly Ala Thr Asn Phe Ser Leu Leu Lys Gln Ala Gly Asp Val
 1               5                  10                  15

Glu Glu Asn Pro Gly Pro
            20


<210> SEQ ID NO 65
<211> LENGTH: 52
<212> TYPE: PRT
<213> ORGANISM: Human immunodeficiency virus

<400> SEQUENCE: 65

Leu Gln Ser Arg Pro Glu Pro Thr Ala Pro Pro Glu Glu Ser Phe Arg
 1               5                  10                  15

Phe Gly Val Glu Thr Thr Thr Pro Pro Gln Lys Gln Glu Pro Ile Asp
            20                  25                  30

Lys Glu Leu Tyr Pro Leu Thr Ser Leu Arg Ser Leu Phe Gly Asn Asp
        35                  40                  45

Pro Ser Ser Gln
    50


<210> SEQ ID NO 66
<211> LENGTH: 61
<212> TYPE: PRT
<213> ORGANISM: Simian immunodeficiency virus

<400> SEQUENCE: 66

Ala Gln Val His Gln Gly Leu Met Pro Thr Ala Pro Pro Glu Asp Pro
 1               5                  10                  15

Ala Val Asp Leu Leu Lys Asn Tyr Met Gln Leu Gly Lys Gln Gln Arg
            20                  25                  30

Glu Lys Gln Arg Glu Ser Arg Glu Lys Pro Tyr Lys Glu Val Thr Glu
        35                  40                  45

Asp Leu Leu His Leu Asn Ser Leu Phe Gly Gly Asp Gln
    50                  55                  60


<210> SEQ ID NO 67
<211> LENGTH: 7
<212> TYPE: PRT
<213> ORGANISM: Artificial Sequence
<220> FEATURE:
<223> OTHER INFORMATION: Synthetic peptide

<400> SEQUENCE: 67

Asp Thr Ala Pro Gln Leu Leu
 1               5


<210> SEQ ID NO 68
<211> LENGTH: 339
<212> TYPE: DNA
<213> ORGANISM: Simian immunodeficiency virus

<400> SEQUENCE: 68
```

```
atgagcgacc ccagagagag aatccccccc ggcaacagcg gcgaggagac catcggcgag     60

gccttcgagt ggctgaacag aaccgtggag gagatcaaca gagaggccgt gaaccacctg    120

cccagagagc tgatcttcca ggtgtggcag agaagctggg agtactggca cgacgagcag    180

ggcatgagcc ccagctacgt gaagtacaga tacctgtgcc tgatccagaa ggccctgttc    240

atgcactgca agaagggctg cagatgcctg ggcgagggcc acggcgccgg cggctggaga    300

cccggccctc ctcctcctcc tcctcctggc ctggcctga                           339
```

<210> SEQ ID NO 69
<211> LENGTH: 339
<212> TYPE: DNA
<213> ORGANISM: Human immunodeficiency virus

<400> SEQUENCE: 69

```
atgaccgacc ccagagagac cgtgcccccc ggcaacagcg gcgaggagac catcggcgag     60

gccttcgcct ggctgaacag aaccgtggag gccatcaaca gagaggccgt gaaccacctg    120

cccagagagc tgatcttcca ggtgtggcag agaagctgga gatactggca cgacgagcag    180

ggcatgagcg agagctacac caagtacaga tacctgtgca tcatccagaa ggccgtgtac    240

atgcacgtga gaaagggctg cacctgcctg ggcagaggcc acggccccgg cggctggaga    300

cccggccctc ctcctcctcc tccccccggc ctggtgtga                           339
```

<210> SEQ ID NO 70
<211> LENGTH: 363
<212> TYPE: DNA
<213> ORGANISM: Simian immunodeficiency virus

<400> SEQUENCE: 70

```
atggccgagg gcagagacag cagagagaga agacccggct ggctggagat ctgggacctg     60

agcagagagc cctgggacga gggcctgaga gacatggtgg ccgagctgaa ccaggaggcc    120

cagagacact tcggcagaga gctgctgttc caggtgtgga acttctgcca ggaggagggc    180

gagagaaacg gcgcccccat gatcgagaga gcctacagat actacagact ggtgcagaag    240

gccctgttcg tgcacttcag atgcggctgc agaagaagaa ccccccttcga gccctacgag    300

gagagaagaa acggcgtggg cggcggcaga gacggcagag agcctcctcc tggcctggcc    360

tga                                                                  363
```

<210> SEQ ID NO 71
<211> LENGTH: 9000
<212> TYPE: DNA
<213> ORGANISM: Artificial Sequence
<220> FEATURE:
<223> OTHER INFORMATION: Synthetic human immunodeficiency/simian
      immunodeficiency virus with chimeric p6

<400> SEQUENCE: 71

```
aaatctctag cagtggcgcc cgaacaggga cttgaaagcg aaagtaaagc cagaggagat     60

ctctcgacgc aggactcggc ttgctgaagc gcgcacggca agaggcgagg ggcggcgact    120

ggtgagtacg ccaaaaattt tgactagcgg aggctagaag gagagagatg ggtgcgagag    180

cgtcggtatt aagcggggga gaattagata aatgggaaaa aattcggtta aggccagggg    240

gaaagaaaca atataaacta aaacatatag tatgggcaag cagggagcta gaacgattcg    300

cagttaatcc tggcctttta gagacatcag aaggctgtag acaaatactg ggacagctac    360

aaccatccct tcagacagga tcagaagaac ttagatcatt atataataca atagcagtcc    420
```

```
tctattgtgt gcatcaaagg atagatgtaa aagacaccaa ggaagcctta gataagatag    480
aggaagagca aaacaaaagt aagaaaaagg cacagcaagc agcagctgac acaggaaaca    540
acagccaggt cagccaaaat taccctatag tgcagaacct ccaggggcaa atggtacatc    600
aggccatatc acctagaact ttaaatgcat gggtaaaagt agtagaagag aaggctttca    660
gcccagaagt aatacccatg ttttcagcat tatcagaagg agccacccca caagatttaa    720
ataccatgct aaacacagtg gggggacatc aagcagccat gcaaatgtta aaagagacca    780
tcaatgagga agctgcagaa tgggatagat tgcatccagt gcatgcaggg cctattgcac    840
caggccagat gagagaacca aggggaagtg acatagcagg aactactagt acccttcagg    900
aacaaatagg atggatgaca cataatccac ctatcccagt aggagaaatc tataaaagat    960
ggataatcct gggattaaat aaaatagtaa gaatgtatag ccctaccagc attctggaca   1020
taagacaagg accaaaggaa ccctttagag actatgtaga ccgattctat aaaactctaa   1080
gagccgagca agcttcacaa gaggtaaaaa attggatgac agaaaccttg ttggtccaaa   1140
atgcgaaccc agattgtaag actattttaa aagcactggg accaggagcg acactagaag   1200
aaatgatgac agcatgtcag ggagtggggg gacccggcca taaagcaaga gttttggctg   1260
aagcaatgag ccaagtaaca aatccagcta ccataatgat acagaaaggc aattttagga   1320
accaaagaaa gactgttaag tgtttcaatt gtggcaaaga agggcacata gccaaaaatt   1380
gcagggcccc taggaaaaag ggctgttgga aatgtggaaa ggaaggacac caaatgaaag   1440
attgtactga gagacaggct aattttttag ggaagatctg gccttcccac aagggaaggc   1500
cagggaattt tcttcagagc agaccagagc caacagcccc accagaagac ccagctgtgg   1560
atctgctaaa gaactacact ccctctcaga ggcaggagcc gatagacaag gaactgtatc   1620
ctttagcttc cctcagatca ctctttggca gcgacccctc gtcacaataa agataggggg   1680
gcaattaaag gaagctctat tagatacagg agcagatgat acagtattag aagaaatgaa   1740
tttgccagga agatggaaac caaaaatgat agggggaatt ggaggtttta tcaaagtaag   1800
acagtatgat cagatactca tagaaatctg cggacataaa gctataggta cagtattagt   1860
aggacctaca cctgtcaaca taattggaag aaatctgttg actcagattg gctgcacttt   1920
aaattttccc attagtccta ttgagactgt accagtaaaa ttaaagccag gaatggatgg   1980
cccaaaagtt aaacaatggc cattgacaga agaaaaaata aaagcattag tagaaatttg   2040
tacagaaatg gaaaaggaag gaaaaatttc aaaaattggg cctgaaaatc catacaatac   2100
tccagtattt gccataaaga aaaaagacag tactaaatgg agaaaattag tagatttcag   2160
agaacttaat aagagaactc aagatttctg ggaagttcaa ttaggaatac cacatcctgc   2220
agggttaaaa cagaaaaaat cagtaacagt actggatgtg ggcgatgcat atttttcagt   2280
tcccttagat aaagacttca ggaagtatac tgcatttacc atacctagta taaacaatga   2340
gacaccaggg attagatatc agtacaatgt gcttccacag ggatggaaag gatcaccagc   2400
aatattccag tgtagcatga caaaaatctt agagcctttt agaaaacaaa atccagacgt   2460
agtcatctat caatacatgg atgatttgta tgtaggatct gacttagaaa tagggcagca   2520
tagaacaaaa atagaggaac tgagacaaca tctgttgagg tggggattta ccacaccaga   2580
caaaaaacat cagaaagaac ctccattcct ttggatgggt tatgaactcc atcctgataa   2640
atggacagta cagcctatag tgctgccaga aaaggacagc tggactgtca atgacataca   2700
gaaattagtg ggaaaattga attgggcaag tcagatttat gcagggatta aagtaaggca   2760
```

-continued

```
attatgtaaa cttcttaggg gaaccaaagc actaacagaa gtagtaccac taacagaaga   2820
agcagagcta gaactggcag aaaacaggga gattctaaaa gaaccggtac atggagtgta   2880
ttatgaccca tcaaaagact taatagcaga aatacagaag caggggcaag gccaatggac   2940
atatcaaatt tatcaagagc catttagaaa tctgaaaaca ggaaagtatg caagaatgaa   3000
gggtgcccac actaatgatg tgaaacaatt aacagaggca gtacaaaaaa tagccacaga   3060
aagcatagta atatggggaa agactcctaa atttaaatta cccatacaaa aggaaacatg   3120
ggaagcatgg tggacagagt attggcaagc cacctggatt cctgagtggg agtttgtcaa   3180
tacccctccc ttagtgaagt tatggtacca gttagagaaa gaacccataa taggagcaga   3240
aactttctat gtagatgggg cagccaatag ggaaactaaa ttaggaaaag caggatatgt   3300
aactgacaga ggaagacaaa aagttgtccc cctaacggac acaacaaatc agaagactga   3360
gttacaagca attcatctag ctttgcagga ttcgggatta gaagtaaaca tagtgacaga   3420
ctcacaatat gcattgggaa tcattcaagc acaaccagat aagagtgaat cagagttagt   3480
cagtcaaata atagagcagt taataaaaaa ggaaaaagtc tacctggcat gggtaccagc   3540
acacaaagga attggaggaa atgaacaagt agataaattg gtcagtgctg gaatcaggaa   3600
agtactattt ttagatggaa tagataaggc ccaagaagaa catgagaaat atcacagtaa   3660
ttggagagca atggctagtg attttaacct accacctgta gtagcaaaag aaatagtagc   3720
cagctgtgat aaatgtcagc taaaagggga agccatgcat ggacaagtag actgtagccc   3780
aggaatatgg cagctagatt gtacacattt agaaggaaaa gttatcttgg tggcagttca   3840
tgtagccagt ggatatatag aagcagaagt aattccagca gagacagggc aagaaacagc   3900
atacttcctc ttaaaattag caggaagatg gccagtaaaa acagtacata cagacaatgg   3960
cagcaatttc accagtacta cagttaaggc cgcctgttgg tgggcgggaa tcaagcagga   4020
atttggcatt ccctacaatc cccaaagtca aggagtaata gaatctatga ataaagaatt   4080
aaagaaaatt ataggacagg taagagatca ggctgaacat cttaagacag cagtacaaat   4140
ggcagtattc atccacaatt ttaaaagaaa aggggggatt ggggggtaca gtgcagggga   4200
aagaatagta gacataatag caacagacat acaaactaaa gaattacaaa aacaaattac   4260
aaaaattcaa aattttcggg tttattacag ggacagcaga gatccagttt ggaaaggacc   4320
agcaaagctc ctctggaaag gtgaaggggc agtagtaata caagataata gtgacataaa   4380
agtagtgcca agaagaaaag caaagatcat cagggattat ggaaaacaga tggcaggtga   4440
tgattgtgtg gcaagtagac aggatgagga ttaacacatg gaaaagatta gtaaaacacc   4500
atatgtatat ttcaaggaaa gctaaggact ggttttatag acatcactat gaaagtacta   4560
atccaaaaat aagttcagaa gtacacatcc cactagggga tgctaaatta gtaataacaa   4620
catattgggg tctgcataca ggagaaagag actggcattt gggtcaggga gtctccatag   4680
aatggaggaa aaagagatat agcacacaag tagaccctga cctagcagac caactaattc   4740
atctgcacta ttttgattgt ttttcagaat ctgctataag aaataccata ttaggacgta   4800
tagttagtcc taggtgtgaa tatcaagcag gacataacaa ggtaggatct ctacagtact   4860
tggcactagc agcattaata aaaccaaaac agataaagcc acctttgcct agtgttagga   4920
aactgacaga ggacagatgg aacaagcccc agaagaccaa gggccacaga gggagccata   4980
caacgaatgg acactagagc ttttagagga acttaagagt gaagctgtta gacattttcc   5040
taggatatgg ctccataact taggacgaca tatctatgaa acttacgggg atacttgggc   5100
aggagtggaa gccataataa gaattctgca acaactgccg tttatccatt tcagaattgg   5160
```

```
gtgtcgacat agcagaatag gcgttactcg acagaggaga gcaagaaatg gagccagtag   5220
atcctagact agagccctgg aagcatccag gaagtcagcc taaaactgct tgtaccaatt   5280
gctattgtaa aaagtgttgc tttcattgcc aagtttgttt catgacaaaa gccttaggca   5340
tctcctatgg caggaagaag cggagacagc gacgaagagc tcatcagaac agtcagactc   5400
atcaagcttc tctatcaaag cagtaagtag tacatgtaat gcaacctata atagtagcaa   5460
tagtagcatt agtagtagca ataataatag caatagttgt gtggtccata gtaatcatag   5520
aatataggaa aatattaaga caaagaaaaa tagacaggtt aattgataga ctaatagaaa   5580
gagcagaaga cagtggcaat gagagtgaag gagaagtatc agcacttgtg gagatggggg   5640
tggaaatggg gcaccatgct ccttgggata ttgatgatct gtagtgctac agaaaaattg   5700
tgggtcacag tctattatgg ggtacctgtg tggaaggaag caaccaccac tctattttgt   5760
gcatcagatg ctaaagcata tgatacagag gtacataatg tttgggccac acatgcctgt   5820
gtacccacag accccaaccc acaagaagta gtattggtaa atgtgacaga aaattttaac   5880
atgtggaaag atgacatggt agaacagatg catgaggata taatcagttt atgggatcaa   5940
agcctaaagc catgtgtaaa attaacccca ctctgtgtta gtttaaagtg cactgatttg   6000
aagaatgata ctaataccaa tagtagtagc gggagaatga taatggagaa aggagagata   6060
aaaaactgct ctttcaatat cagcacaagc ataagagata aggtgcagaa agaatatgca   6120
ttcttttata aacttgatat agtaccaata gataatacca gctataggtt gataagttgt   6180
aacacctcag tcattacaca ggcctgtcca aaggtatcct ttgagccaat ccccatacat   6240
tattgtgccc cggctggttt tgcgattcta aaatgtaata ataagacgtt caatggaaca   6300
ggaccatgta caaatgtcag cacagtacaa tgtacacatg gaatcaggcc agtagtatca   6360
actcaactgc tgttaaatgg cagtctagca gaagaagatg tagtaattag atctgccaat   6420
ttcacagaca atgctaaaac cataatagta cagctgaaca catctgtaga aattaattgt   6480
acaagaccca acaacaatac aagaaaaagt atccgtatcc agaggggacc agggagagca   6540
tttgttacaa taggaaaaat aggaaatatg agacaagcac attgtaacat tagtagagca   6600
aaatggaatg ccactttaaa acagatagct agcaaattaa gagaacaatt tggaaataat   6660
aaaacaataa tctttaagca atcctcagga ggggacccag aaattgtaac gcacagtttt   6720
aattgtggag gggaattttt ctactgtaat tcaacacaac tgtttaatag tacttggttt   6780
aatagtactt ggagtactga agggtcaaat aacactgaag gaagtgacac aatcacactc   6840
ccatgcagaa taaaacaatt tataaacatg tggcaggaag taggaaaagc aatgtatgcc   6900
cctcccatca gtggacaaat tagatgttca tcaaatatta ctgggctgct attaacaaga   6960
gatggtggta ataacaacaa tgggtccgag atcttcagac ctggaggagg cgatatgagg   7020
gacaattgga gaagtgaatt atataaatat aaagtagtaa aaattgaacc attaggagta   7080
gcacccacca aggcaaagag aagagtggtg cagagagaaa aaagagcagt gggaatagga   7140
gctttgttcc ttgggttctt gggagcagca ggaagcacta tgggcgcagc gtcaatgacg   7200
ctgacggtac aggccagaca attattgtct gatatagtgc agcagcagaa caatttgctg   7260
agggctattg aggcgcaaca gcatctgttg caactcacag tctggggcat caaacagctc   7320
caggcaagaa tcctggctgt ggaaagatac ctaaaggatc aacagctcct ggggatttgg   7380
ggttgctctg gaaaactcat ttgcaccact gctgtgcctt ggaatgctag ttggagtaat   7440
aaatctctgg aacagatttg gaataacatg acctggatgg agtgggacag agaaattaac   7500
```

```
aattacacaa gcttaataca ctccttaatt gaagaatcgc aaaaccagca agaaaagaat   7560

gaacaagaat tattggaatt agataaatgg gcaagtttgt ggaattggtt taacataaca   7620

aattggctgt ggtatataaa attattcata atgatagtag gaggcttggt aggtttaaga   7680

atagtttttg ctgtactttc tatagtgaat agagttaggc agggatattc accattatcg   7740

tttcagaccc acctcccaat cccgagggga cccgacaggc ccgaaggaat agaagaagaa   7800

ggtggagaga gaggcagaga cagatccatt cgattagtga acggatcctt agcacttatc   7860

tgggacgatc tgcggagcct gtgcctcttc agctaccacc gcttgagaga cttactcttg   7920

attgtaacga ggattgtgga acttctggga cgcagggggt gggaagccct caaatattgg   7980

tggaatctcc tacagtattg gagtcaggaa ctaaagaata gtgctgttaa cttgctcaat   8040

gccacagcca tagcagtagc tgaggggaca gatagggtta tagaagtatt acaagcagct   8100

tatagagcta ttcgccacat acctagaaga ataagacagg gcttggaaag gattttgcta   8160

taagatgggt ggcaagtggt caaaaagtag tgtgattgga tggcctgctg taagggaaag   8220

aatgagacga gctgagccag cagcagatgg ggtgggagca gtatctcgag acctagaaaa   8280

acatggagca atcacaagta gcaatacagc agctaacaat gctgcttgtg cctggctaga   8340

agcacaagag gaggaagagg tgggttttcc agtcacacct caggtacctt taagaccaat   8400

gacttacaag gcagctgtag atcttagcca ctttttaaaa gaaaaggggg gactggaagg   8460

gctaattcac tcccaaagaa gacaagatat ccttgatctg tggatctacc acacacaagg   8520

ctacttccct gattggcaga actacacacc agggccaggg gtcagatatc cactgacctt   8580

tggatggtgc tacaagctag taccagttga gccagataag gtagaagagg ccaataaagg   8640

agagaacacc agcttgttac accctgtgag cctgcatgga atggatgacc ctgagagaga   8700

agtgttagag tggaggtttg acagccgcct agcatttcat cacgtggccc gagagctgca   8760

tccggagtac ttcaagaact gctgacatcg agcttgctac aagggacttt ccgctgggga   8820

ctttccaggg aggcgtggcc tgggcgggac tggggagtgg cgagccctca gatgctgcat   8880

ataagcagct gctttttgcc tgtactgggt ctctctggtt agaccagatc tgagcctggg   8940

agctctctgg ctaactaggg aacccactgc ttaagcctca ataaagcttg ccttgagggc   9000
```

```
<210> SEQ ID NO 72
<211> LENGTH: 500
<212> TYPE: PRT
<213> ORGANISM: Artificial Sequence
<220> FEATURE:
<223> OTHER INFORMATION: Synthetic human immunodeficiency/simian
      immunodeficiency virus chimeric p6

<400> SEQUENCE: 72

Met Gly Ala Arg Ala Ser Val Leu Ser Gly Gly Glu Leu Asp Lys Trp
 1               5                  10                  15

Glu Lys Ile Arg Leu Arg Pro Gly Gly Lys Lys Gln Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Ile Ala Val Leu Tyr Cys Val His Gln Arg Ile Asp Val Lys Asp
                85                  90                  95
```

-continued

```
Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Asn Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Pro Glu Asp Pro Ala Val
    450                 455                 460

Asp Leu Leu Lys Asn Tyr Met Gln Ser Gln Arg Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500
```

-continued

<210> SEQ ID NO 73
<211> LENGTH: 1003
<212> TYPE: PRT
<213> ORGANISM: Human immunodeficiency virus

<400> SEQUENCE: 73

```
Phe Phe Arg Glu Asp Leu Ala Phe Pro Gln Gly Lys Ala Arg Glu Phe
 1               5                  10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Gln Lys Lys Ser Val Thr Val Leu Asp Val Gly Asp Ala Tyr Phe Ser
            260                 265                 270

Val Pro Leu Asp Lys Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Cys Ser Met Thr
305                 310                 315                 320

Lys Ile Leu Glu Pro Phe Arg Lys Gln Asn Pro Asp Val Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Phe Thr Thr Pro Asp Lys Lys His Gln Lys Glu Pro Pro Phe Leu Trp
    370                 375                 380
```

```
Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Ala Gly Ile Lys Val Arg
            420                 425                 430

Gln Leu Cys Lys Leu Leu Arg Gly Thr Lys Ala Leu Thr Glu Val Val
        435                 440                 445

Pro Leu Thr Glu Glu Ala Glu Leu Glu Leu Ala Glu Asn Arg Glu Ile
    450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Arg Asn Leu Lys Thr Gly Lys Tyr Ala Arg Met
            500                 505                 510

Lys Gly Ala His Thr Asn Asp Val Lys Gln Leu Thr Glu Ala Val Gln
        515                 520                 525

Lys Ile Ala Thr Glu Ser Ile Val Ile Trp Gly Lys Thr Pro Lys Phe
    530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Ile Gly Ala
            580                 585                 590

Glu Thr Phe Tyr Val Asp Gly Ala Ala Asn Arg Glu Thr Lys Leu Gly
        595                 600                 605

Lys Ala Gly Tyr Val Thr Asp Arg Gly Arg Gln Lys Val Val Pro Leu
    610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
    690                 695                 700

Lys Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Asp Phe Asn Leu Pro Pro Val Val Ala Lys Glu Ile Val
            740                 745                 750

Ala Ser Cys Asp Lys Cys Gln Leu Lys Gly Glu Ala Met His Gly Gln
        755                 760                 765

Val Asp Cys Ser Pro Gly Ile Trp Gln Leu Asp Cys Thr His Leu Glu
    770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
```

```
                805                 810                 815

Leu Lys Leu Ala Gly Arg Trp Pro Val Lys Thr Val His Thr Asp Asn
            820                 825                 830

Gly Ser Asn Phe Thr Ser Thr Thr Val Lys Ala Ala Cys Trp Trp Ala
        835                 840                 845

Gly Ile Lys Gln Glu Phe Gly Ile Pro Tyr Asn Pro Gln Ser Gln Gly
    850                 855                 860

Val Ile Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
        915                 920                 925

Gln Lys Gln Ile Thr Lys Ile Gln Asn Phe Arg Val Tyr Tyr Arg Asp
    930                 935                 940

Ser Arg Asp Pro Val Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln Asp Glu Asp
        995                 1000


<210> SEQ ID NO 74
<211> LENGTH: 192
<212> TYPE: PRT
<213> ORGANISM: Human immunodeficiency virus

<400> SEQUENCE: 74

Met Glu Asn Arg Trp Gln Val Met Ile Val Trp Gln Val Asp Arg Met
 1               5                  10                  15

Arg Ile Asn Thr Trp Lys Arg Leu Val Lys His His Met Tyr Ile Ser
            20                  25                  30

Arg Lys Ala Lys Asp Trp Phe Tyr Arg His His Tyr Glu Ser Thr Asn
        35                  40                  45

Pro Lys Ile Ser Ser Glu Val His Ile Pro Leu Gly Asp Ala Lys Leu
    50                  55                  60

Val Ile Thr Thr Tyr Trp Gly Leu His Thr Gly Glu Arg Asp Trp His
65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
            100                 105                 110

Asp Cys Phe Ser Glu Ser Ala Ile Arg Asn Thr Ile Leu Gly Arg Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Lys Pro Lys Gln Ile Lys
145                 150                 155                 160

Pro Pro Leu Pro Ser Val Arg Lys Leu Thr Glu Asp Arg Trp Asn Lys
                165                 170                 175
```

```
Pro Gln Lys Thr Lys Gly His Arg Gly Ser His Thr Thr Asn Gly His
            180                 185                 190


<210> SEQ ID NO 75
<211> LENGTH: 96
<212> TYPE: PRT
<213> ORGANISM: Human immunodeficiency virus

<400> SEQUENCE: 75

Met Glu Gln Ala Pro Glu Asp Gln Gly Pro Gln Arg Glu Pro Tyr Asn
 1               5                  10                  15

Glu Trp Thr Leu Glu Leu Leu Glu Glu Leu Lys Ser Glu Ala Val Arg
            20                  25                  30

His Phe Pro Arg Ile Trp Leu His Asn Leu Gly Arg His Ile Tyr Glu
        35                  40                  45

Thr Tyr Gly Asp Thr Trp Ala Gly Val Glu Ala Ile Ile Arg Ile Leu
    50                  55                  60

Gln Gln Leu Pro Phe Ile His Phe Arg Ile Gly Cys Arg His Ser Arg
65                  70                  75                  80

Ile Gly Val Thr Arg Gln Arg Arg Ala Arg Asn Gly Ala Ser Arg Ser
                85                  90                  95


<210> SEQ ID NO 76
<211> LENGTH: 86
<212> TYPE: PRT
<213> ORGANISM: Human immunodeficiency virus

<400> SEQUENCE: 76

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Met Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Ser Arg Gly Asp
65                  70                  75                  80

Pro Thr Gly Pro Lys Glu
                85


<210> SEQ ID NO 77
<211> LENGTH: 116
<212> TYPE: PRT
<213> ORGANISM: Human immunodeficiency virus

<400> SEQUENCE: 77

Met Ala Gly Arg Ser Gly Asp Ser Asp Glu Glu Leu Ile Arg Thr Val
 1               5                  10                  15

Arg Leu Ile Lys Leu Leu Tyr Gln Ser Asn Pro Pro Pro Asn Pro Glu
            20                  25                  30

Gly Thr Arg Gln Ala Arg Arg Asn Arg Arg Arg Arg Trp Arg Glu Arg
        35                  40                  45

Gln Arg Gln Ile His Ser Ile Ser Glu Arg Ile Leu Ser Thr Tyr Leu
    50                  55                  60

Gly Arg Ser Ala Glu Pro Val Pro Leu Gln Leu Pro Pro Leu Glu Arg
65                  70                  75                  80

Leu Thr Leu Asp Cys Asn Glu Asp Cys Gly Thr Ser Gly Thr Gln Gly
```

```
                85                  90                  95

Val Gly Ser Pro Gln Ile Leu Val Glu Ser Pro Thr Val Leu Glu Ser
            100                 105                 110

Gly Thr Lys Glu
        115


<210> SEQ ID NO 78
<211> LENGTH: 81
<212> TYPE: PRT
<213> ORGANISM: Human immunodeficiency virus

<400> SEQUENCE: 78

Met Gln Pro Ile Ile Val Ala Ile Val Ala Leu Val Val Ala Ile Ile
 1               5                  10                  15

Ile Ala Ile Val Val Trp Ser Ile Val Ile Ile Glu Tyr Arg Lys Ile
            20                  25                  30

Leu Arg Gln Arg Lys Ile Asp Arg Leu Ile Asp Arg Leu Ile Glu Arg
        35                  40                  45

Ala Glu Asp Ser Gly Asn Glu Ser Glu Gly Glu Val Ser Ala Leu Val
    50                  55                  60

Glu Met Gly Val Glu Met Gly His His Ala Pro Trp Asp Ile Asp Asp
65                  70                  75                  80

Leu


<210> SEQ ID NO 79
<211> LENGTH: 854
<212> TYPE: PRT
<213> ORGANISM: Human immunodeficiency virus

<400> SEQUENCE: 79

Met Arg Val Lys Glu Lys Tyr Gln His Leu Trp Arg Trp Gly Trp Lys
 1               5                  10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asp Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Asp Lys Val Gln Lys Glu Tyr Ala Phe Phe
                165                 170                 175

Tyr Lys Leu Asp Ile Val Pro Ile Asp Asn Thr Ser Tyr Arg Leu Ile
            180                 185                 190

Ser Cys Asn Thr Ser Val Ile Thr Gln Ala Cys Pro Lys Val Ser Phe
        195                 200                 205
```

-continued

```
Glu Pro Ile Pro Ile His Tyr Cys Ala Pro Ala Gly Phe Ala Ile Leu
    210                 215                 220

Lys Cys Asn Asn Lys Thr Phe Asn Gly Thr Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Asp Val Val Ile Arg Ser
            260                 265                 270

Ala Asn Phe Thr Asp Asn Ala Lys Thr Ile Ile Val Gln Leu Asn Thr
        275                 280                 285

Ser Val Glu Ile Asn Cys Thr Arg Pro Asn Asn Asn Thr Arg Lys Ser
    290                 295                 300

Ile Arg Ile Gln Arg Gly Pro Gly Arg Ala Phe Val Thr Ile Gly Lys
305                 310                 315                 320

Ile Gly Asn Met Arg Gln Ala His Cys Asn Ile Ser Arg Ala Lys Trp
                325                 330                 335

Asn Ala Thr Leu Lys Gln Ile Ala Ser Lys Leu Arg Glu Gln Phe Gly
            340                 345                 350

Asn Asn Lys Thr Ile Ile Phe Lys Gln Ser Ser Gly Gly Asp Pro Glu
        355                 360                 365

Ile Val Thr His Ser Phe Asn Cys Gly Gly Glu Phe Phe Tyr Cys Asn
    370                 375                 380

Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys
                405                 410                 415

Arg Ile Lys Gln Phe Ile Asn Met Trp Gln Glu Val Gly Lys Ala Met
            420                 425                 430

Tyr Ala Pro Pro Ile Ser Gly Gln Ile Arg Cys Ser Ser Asn Ile Thr
        435                 440                 445

Gly Leu Leu Leu Thr Arg Asp Gly Gly Asn Asn Asn Asn Gly Ser Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Arg Ala Val Gly
            500                 505                 510

Ile Gly Ala Leu Phe Leu Gly Phe Leu Gly Ala Ala Gly Ser Thr Met
        515                 520                 525

Gly Ala Ala Ser Met Thr Leu Thr Val Gln Ala Arg Gln Leu Leu Ser
    530                 535                 540

Asp Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Ile Leu Ala Val Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ala Ser Trp Ser Asn Lys Ser Leu Glu Gln Ile Trp Asn Asn Met
    610                 615                 620
```

-continued

Thr Trp Met Glu Trp Asp Arg Glu Ile Asn Asn Tyr Thr Ser Leu Ile
625 630 635 640

His Ser Leu Ile Glu Glu Ser Gln Asn Gln Gln Glu Lys Asn Glu Gln
645 650 655

Glu Leu Leu Glu Leu Asp Lys Trp Ala Ser Leu Trp Asn Trp Phe Asn
660 665 670

Ile Thr Asn Trp Leu Trp Tyr Ile Lys Leu Phe Ile Met Ile Val Gly
675 680 685

Gly Leu Val Gly Leu Arg Ile Val Phe Ala Val Leu Ser Ile Val Asn
690 695 700

Arg Val Arg Gln Gly Tyr Ser Pro Leu Ser Phe Gln Thr His Leu Pro
705 710 715 720

Ile Pro Arg Gly Pro Asp Arg Pro Glu Gly Ile Glu Glu Glu Gly Gly
725 730 735

Glu Arg Gly Arg Asp Arg Ser Ile Arg Leu Val Asn Gly Ser Leu Ala
740 745 750

Leu Ile Trp Asp Asp Leu Arg Ser Leu Cys Leu Phe Ser Tyr His Arg
755 760 765

Leu Arg Asp Leu Leu Leu Ile Val Thr Arg Ile Val Glu Leu Leu Gly
770 775 780

Arg Arg Gly Trp Glu Ala Leu Lys Tyr Trp Trp Asn Leu Leu Gln Tyr
785 790 795 800

Trp Ser Gln Glu Leu Lys Asn Ser Ala Val Asn Leu Leu Asn Ala Thr
805 810 815

Ala Ile Ala Val Ala Glu Gly Thr Asp Arg Val Ile Glu Val Leu Gln
820 825 830

Ala Ala Tyr Arg Ala Ile Arg His Ile Pro Arg Arg Ile Arg Gln Gly
835 840 845

Leu Glu Arg Ile Leu Leu
850

<210> SEQ ID NO 80
<211> LENGTH: 206
<212> TYPE: PRT
<213> ORGANISM: Human immunodeficiency virus

<400> SEQUENCE: 80

Met Gly Gly Lys Trp Ser Lys Ser Ser Val Ile Gly Trp Pro Ala Val
1 5 10 15

Arg Glu Arg Met Arg Arg Ala Glu Pro Ala Ala Asp Gly Val Gly Ala
20 25 30

Val Ser Arg Asp Leu Glu Lys His Gly Ala Ile Thr Ser Ser Asn Thr
35 40 45

Ala Ala Asn Asn Ala Ala Cys Ala Trp Leu Glu Ala Gln Glu Glu Glu
50 55 60

Glu Val Gly Phe Pro Val Thr Pro Gln Val Pro Leu Arg Pro Met Thr
65 70 75 80

Tyr Lys Ala Ala Val Asp Leu Ser His Phe Leu Lys Glu Lys Gly Gly
85 90 95

Leu Glu Gly Leu Ile His Ser Gln Arg Arg Gln Asp Ile Leu Asp Leu
100 105 110

Trp Ile Tyr His Thr Gln Gly Tyr Phe Pro Asp Trp Gln Asn Tyr Thr
115 120 125

Pro Gly Pro Gly Val Arg Tyr Pro Leu Thr Phe Gly Trp Cys Tyr Lys
130 135 140

```
Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205


<210> SEQ ID NO 81
<211> LENGTH: 9000
<212> TYPE: DNA
<213> ORGANISM: Artificial Sequence
<220> FEATURE:
<223> OTHER INFORMATION: Synthetic human immunodeficiency/simian
      immunodeficiency virus with chimeric p6

<400> SEQUENCE: 81

gccctcaagg caagctttat tgaggcttaa gcagtgggtt ccctagttag ccagagagct     60

cccaggctca gatctggtct aaccagagag acccagtaca ggcaaaaagc agctgcttat    120

atgcagcatc tgagggctcg ccactcccca gtcccgccca ggccacgcct ccctggaaag    180

tccccagcgg aaagtccctt gtagcaagct cgatgtcagc agttcttgaa gtactccgga    240

tgcagctctc gggccacgtg atgaaatgct aggcggctgt caaacctcca ctctaacact    300

tctctctcag ggtcatccat tccatgcagg ctcacagggt gtaacaagct ggtgttctct    360

cctttattgg cctcttctac cttatctggc tcaactggta ctagcttgta gcaccatcca    420

aaggtcagtg gatatctgac ccctggccct ggtgtgtagt tctgccaatc agggaagtag    480

ccttgtgtgt ggtagatcca cagatcaagg atatcttgtc ttctttggga gtgaattagc    540

ccttccagtc ccccctttc ttttaaaaag tggctaagat ctacagctgc cttgtaagtc     600

attggtctta aaggtacctg aggtgtgact ggaaaaccca cctcttcctc ctcttgtgct    660

tctagccagg cacaagcagc attgttagct gctgtattgc tacttgtgat tgctccatgt    720

ttttctaggt ctcgagatac tgctcccacc ccatctgctg ctggctcagc tcgtctcatt    780

ctttccctta cagcaggcca tccaatcaca ctactttttg accacttgcc acccatctta    840

tagcaaaatc ctttccaagc cctgtcttat tcttctaggt atgtggcgaa tagctctata    900

agctgcttgt aatacttcta taaccctatc tgtcccctca gctactgcta tggctgtggc    960

attgagcaag ttaacagcac tattctttag ttcctgactc caatactgta ggagattcca   1020

ccaatatttg agggcttccc acccccctgcg tcccagaagt tccacaatcc tcgttacaat   1080

caagagtaag tctctcaagc ggtggtagct gaagaggcac aggctccgca gatcgtccca   1140

gataagtgct aaggatccgt tcactaatcg aatggatctg tctctgcctc tctctccacc   1200

ttcttcttct attccttcgg gcctgtcggg tcccctcggg attgggaggt gggtctgaaa   1260

cgataatggt gaatatccct gcctaactct attcactata gaaagtacag caaaaactat   1320

tcttaaacct accaagcctc ctactatcat tatgaataat tttatatacc acagccaatt   1380

tgttatgtta aaccaattcc acaaacttgc ccatttatct aattccaata attcttgttc   1440

attcttttct tgctggtttt gcgattcttc aattaaggag tgtattaagc ttgtgtaatt   1500

gttaatttct ctgtcccact ccatccaggt catgttattc caaatctgtt ccagagattt   1560

attactccaa ctagcattcc aaggcacagc agtggtgcaa atgagttttc cagagcaacc   1620

ccaaatcccc aggagctgtt gatcctttag gtatctttcc acagccagga ttcttgcctg   1680
```

-continued

```
gagctgtttg atgccccaga ctgtgagttg caacagatgc tgttgcgcct caatagccct   1740
cagcaaattg ttctgctgct gcactatatc agacaataat tgtctggcct gtaccgtcag   1800
cgtcattgac gctgcgccca tagtgcttcc tgctgctccc aagaacccaa ggaacaaagc   1860
tcctattccc actgctcttt tttctctctg caccactctt ctctttgcct tggtgggtgc   1920
tactcctaat ggttcaattt ttactacttt atatttatat aattcacttc tccaattgtc   1980
cctcatatcg cctcctccag gtctgaagat ctcggaccca ttgttgttat taccaccatc   2040
tcttgttaat agcagcccag taatatttga tgaacatcta atttgtccac tgatgggagg   2100
ggcatacatt gcttttccta cttcctgcca catgtttata aattgtttta ttctgcatgg   2160
gagtgtgatt gtgtcacttc cttcagtgtt atttgaccct tcagtactcc aagtactatt   2220
aaaccaagta ctattaaaca gttgtgttga attacagtag aaaaattccc ctccacaatt   2280
aaaactgtgc gttacaattt ctgggtcccc tcctgaggat tgcttaaaga ttattgtttt   2340
attatttcca aattgttctc ttaatttgct agctatctgt tttaaagtgg cattccattt   2400
tgctctacta atgttacaat gtgcttgtct catatttcct atttttccta ttgtaacaaa   2460
tgctctccct ggtcccctct ggatacggat actttttctt gtattgttgt tgggtcttgt   2520
acaattaatt tctacagatg tgttcagctg tactattatg gttttagcat tgtctgtgaa   2580
attggcagat ctaattacta catcttcttc tgctagactg ccatttaaca gcagttgagt   2640
tgatactact ggcctgattc catgtgtaca ttgtactgtg ctgacatttg tacatggtcc   2700
tgttccattg aacgtcttat tattacattt tagaatcgca aaaccagccg gggcacaata   2760
atgtatgggg attggctcaa aggatacctt tggacaggcc tgtgtaatga ctgaggtgtt   2820
acaacttatc aacctatagc tggtattatc tattggtact atatcaagtt tataaaagaa   2880
tgcatattct ttctgcacct tatctcttat gcttgtgctg atattgaaag agcagttttt   2940
tatctctcct ttctccatta tcattctccc gctactacta ttggtattag tatcattctt   3000
caaatcagtg cactttaaac taacacagag tggggttaat tttacacatg gctttaggct   3060
ttgatcccat aaactgatta tatcctcatg catctgttct accatgtcat ctttccacat   3120
gttaaaattt tctgtcacat ttaccaatac tacttcttgt gggttggggt ctgtgggtac   3180
acaggcatgt gtggcccaaa cattatgtac ctctgtatca tatgctttag catctgatgc   3240
acaaaataga gtggtggttg cttccttcca cacaggtacc ccataataga ctgtgaccca   3300
caatttttct gtagcactac agatcatcaa tatcccaagg agcatggtgc cccatttcca   3360
cccccatctc cacaagtgct gatacttctc cttcactctc attgccactg tcttctgctc   3420
tttctattag tctatcaatt aacctgtcta tttttctttg tcttaatatt ttcctatatt   3480
ctatgattac tatggaccac acaactattg ctattattat tgctactact aatgctacta   3540
ttgctactat tataggttgc attacatgta ctacttactg ctttgataga gaagcttgat   3600
gagtctgact gttctgatga gctcttcgtc gctgtctccg cttcttcctg ccataggaga   3660
tgcctaaggc ttttgtcatg aaacaaactt ggcaatgaaa gcaacacttt ttacaatagc   3720
aattggtaca agcagtttta ggctgacttc ctggatgctt ccagggctct agtctaggat   3780
ctactggctc catttcttgc tctcctctgt cgagtaacgc ctattctgct atgtcgacac   3840
ccaattctga aatggataaa cggcagttgt tgcagaattc ttattatggc ttccactcct   3900
gcccaagtat ccccgtaagt ttcatagata tgtcgtccta agttatggag ccatatccta   3960
ggaaaatgtc taacagcttc actcttaagt tcctctaaaa gctctagtgt ccattcgttg   4020
```

-continued

```
tatggctccc tctgtggccc ttggtcttct ggggcttgtt ccatctgtcc tctgtcagtt   4080
tcctaacact aggcaaaggt ggctttatct gttttggttt tattaatgct gctagtgcca   4140
agtactgtag agatcctacc ttgttatgtc ctgcttgata ttcacaccta ggactaacta   4200
tacgtcctaa tatggtattt cttatagcag attctgaaaa acaatcaaaa tagtgcagat   4260
gaattagttg gtctgctagg tcagggtcta cttgtgtgct atatctcttt ttcctccatt   4320
ctatggagac tccctgaccc aaatgccagt ctctttctcc tgtatgcaga ccccaatatg   4380
ttgttattac taatttagca tcccctagtg ggatgtgtac ttctgaactt atttttggat   4440
tagtactttc atagtgatgt ctataaaacc agtccttagc tttccttgaa atatacatat   4500
ggtgttttac taatcttttc catgtgttaa tcctcatcct gtctacttgc cacacaatca   4560
tcacctgcca tctgttttcc ataatccctg atgatctttg cttttcttct tggcactact   4620
tttatgtcac tattatcttg tattactact gccccttcac ctttccagag gagctttgct   4680
ggtcctttcc aaactggatc tctgctgtcc ctgtaataaa cccgaaaatt ttgaattttt   4740
gtaatttgtt tttgtaattc tttagtttgt atgtctgttg ctattatgtc tactattctt   4800
tcccctgcac tgtacccccc aatcccccct tttcttttaa aattgtggat gaatactgcc   4860
atttgtactg ctgtcttaag atgttcagcc tgatctctta cctgtcctat aatttttcttt   4920
aattctttat tcatagattc tattactcct tgactttggg gattgtaggg aatgccaaat   4980
tcctgcttga ttcccgccca ccaacaggcg gccttaactg tagtactggt gaaattgctg   5040
ccattgtctg tatgtactgt ttttactggc catcttcctg ctaattttaa gaggaagtat   5100
gctgtttctt gccctgtctc tgctggaatt acttctgctt ctatatatcc actggctaca   5160
tgaactgcca ccaagataac ttttccttct aaatgtgtac aatctagctg ccatattcct   5220
gggctacagt ctacttgtcc atgcatggct tccccttttta gctgacattt atcacagctg   5280
gctactattt cttttgctac tacaggtggt aggttaaaat cactagccat tgctctccaa   5340
ttactgtgat atttctcatg ttcttcttgg gccttatcta ttccatctaa aaatagtact   5400
ttcctgattc cagcactgac caatttatct acttgttcat ttcctccaat tcctttgtgt   5460
gctggtaccc atgccaggta gactttttcc ttttttatta actgctctat tatttgactg   5520
actaactctg attcactctt atctggttgt gcttgaatga ttcccaatgc atattgtgag   5580
tctgtcacta tgtttacttc taatcccgaa tcctgcaaag ctagatgaat tgcttgtaac   5640
tcagtcttct gatttgttgt gtccgttagg gggacaactt tttgtcttcc tctgtcagtt   5700
acatatcctg cttttcctaa tttagtttcc ctattggctg ccccatctac atagaaagtt   5760
tctgctccta ttatgggttc tttctctaac tggtaccata acttcactaa gggaggggta   5820
ttgacaaact cccactcagg aatccaggtg gcttgccaat actctgtcca ccatgcttcc   5880
catgtttcct tttgtatggg taatttaaat ttaggagtct ttccccatat tactatgctt   5940
tctgtggcta ttttttgtac tgcctctgtt aattgtttca catcattagt gtgggcaccc   6000
ttcattcttg catactttcc tgttttcaga tttctaaatg gctcttgata aatttgatat   6060
gtccattggc cttgcccctg cttctgtatt tctgctatta agtcttttga tgggtcataa   6120
tacactccat gtaccggttc ttttagaatc tccctgtttt ctgccagttc tagctctgct   6180
tcttctgtta gtggtactac ttctgttagt gctttggttc ccctaagaag tttacataat   6240
tgccttactt taatccctgc ataaatctga cttgcccaat tcaattttcc cactaatttc   6300
tgtatgtcat tgacagtcca gctgtccttt tctggcagca ctataggctg tactgtccat   6360
ttatcaggat ggagttcata acccatccaa aggaatggag gttctttctg atgtttttttg   6420
```

-continued tctggtgtgg taaatcccca cctcaacaga tgttgtctca gttcctctat ttttgttcta 6480
tgctgcccta tttctaagtc agatcctaca tacaaatcat ccatgtattg atagatgact 6540
acgtctggat tttgttttct aaaaggctct aagatttttg tcatgctaca ctggaatatt 6600
gctggtgatc ctttccatcc ctgtggaagc acattgtact gatatctaat ccctggtgtc 6660
tcattgttta tactaggtat ggtaaatgca gtatacttcc tgaagtcttt atctaaggga 6720
actgaaaaat atgcatcgcc cacatccagt actgttactg atttttctg ttttaaccct 6780
gcaggatgtg gtattcctaa ttgaacttcc cagaaatctt gagttctctt attaagttct 6840
ctgaaatcta ctaattttct ccatttagta ctgtcttttt tctttatggc aaatactgga 6900
gtattgtatg gattttcagg cccaattttt gaaattttc cttccttttc catttctgta 6960
caaatttcta ctaatgcttt tattttttct tctgtcaatg gccattgttt aacttttggg 7020
ccatccattc ctggctttaa ttttactggt acagtctcaa taggactaat gggaaaattt 7080
aaagtgcagc caatctgagt caacagattt cttccaatta tgttgacagg tgtaggtcct 7140
actaatactg tacctatagc tttatgtccg cagatttcta tgagtatctg atcatactgt 7200
cttactttga taaaacctcc aattccccct atcattttg gtttccatct tcctggcaaa 7260
ttcatttctt ctaatactgt atcatctgct cctgtatcta atagagcttc ctttaattgc 7320
ccccctatct ttattgtgac gaggggtcgc tgccaaagag tgatctgagg gaagctaaag 7380
gatacagttc cttgtctatc ggctcctgcc tctgagaggg agtgtagttc tttagcagat 7440
ccacagctgg gtcttctggt ggggctgttg gctctggtct gctctgaaga aaattccctg 7500
gccttccctt gtgggaaggc cagatcttcc ctaaaaaatt agcctgtctc tcagtacaat 7560
ctttcatttg gtgtccttcc tttccacatt tccaacagcc ctttttccta ggggccctgc 7620
aatttttggc tatgtgccct tctttgccac aattgaaaca cttaacagtc tttctttggt 7680
tcctaaaatt gcctttctgt atcattatgg tagctggatt tgttacttgg ctcattgctt 7740
cagccaaaac tcttgcttta tggccgggtc cccccactcc ctgacatgct gtcatcattt 7800
cttctagtgt cgctcctggt cccagtgctt ttaaaatagt cttacaatct gggttcgcat 7860
tttggaccaa caaggtttct gtcatccaat tttttacctc ttgtgaagct tgctcggctc 7920
ttagagtttt atagaatcgg tctacatagt ctctaaaggg ttcctttggt ccttgtctta 7980
tgtccagaat gctggtaggg ctatacattc ttactatttt atttaatccc aggattatcc 8040
atcttttata gatttctcct actgggatag gtggattatg tgtcatccat cctatttgtt 8100
cctgaagggt actagtagtt cctgctatgt cacttcccct tggttctctc atctggcctg 8160
gtgcaatagg ccctgcatgc actggatgca atctatccca ttctgcagct tcctcattga 8220
tggtctcttt taacatttgc atggctgctt gatgtccccc cactgtgttt agcatggtat 8280
ttaaatcttg tggggtggct ccttctgata atgctgaaaa catgggtatt acttctgggc 8340
tgaaagcctt ctcttctact acttttaccc atgcatttaa agttctaggt gatatggcct 8400
gatgtaccat ttgcccctgg aggttctgca ctatagggta attttggctg acctggctgt 8460
tgtttcctgt gtcagctgct gcttgctgtg cctttttctt acttttgttt tgctcttcct 8520
ctatcttatc taaggcttcc ttggtgtctt ttacatctat cctttgatgc acacaataga 8580
ggactgctat tgtattatat aatgatctaa gttcttctga tcctgtctga agggatggtt 8640
gtagctgtcc cagtatttgt ctacagcctt ctgatgtctc taaaaggcca ggattaactg 8700
cgaatcgttc tagctccctg cttgcccata ctatatgttt tagtttatat tgtttctttc 8760
cccctggcct taaccgaatt ttttcccatt tatctaattc tcccccgctt aataccgacg 8820
ctctcgcacc catctctctc cttctagcct ccgctagtca aaatttttgg cgtactcacc 8880
agtcgccgcc cctcgcctct tgccgtgcgc gcttcagcaa gccgagtcct gcgtcgagag 8940
atctcctctg gctttacttt cgctttcaag tccctgttcg ggcgccactg ctagagattt 9000

<210> SEQ ID NO 82
<211> LENGTH: 9000
<212> TYPE: DNA
<213> ORGANISM: Human immunodeficiency virus

<400> SEQUENCE: 82
aaatctctag cagtggcgcc cgaacaggga cttgaaagcg aaagtaaagc cagaggagat 60
ctctcgacgc aggactcggc ttgctgaagc gcgcacggca agaggcgagg ggcggcgact 120
ggtgagtacg ccaaaaattt tgactagcgg aggctagaag gagagagatg ggtgcgagag 180
cgtcggtatt aagcggggga gaattagata aatgggaaaa aattcggtta aggccagggg 240
gaaagaaaca atataaacta aaacatatag tatgggcaag cagggagcta gaacgattcg 300
cagttaatcc tggcctttta gagacatcag aaggctgtag acaaatactg ggacagctac 360
aaccatccct tcagacagga tcagaagaac ttagatcatt atataataca atagcagtcc 420
tctattgtgt gcatcaaagg atagatgtaa aagacaccaa ggaagcctta gataagatag 480
aggaagagca aaacaaaagt aagaaaaagg cacagcaagc agcagctgac acaggaaaca 540
acagccaggt cagccaaaat taccctatag tgcagaacct ccaggggcaa atggtacatc 600
aggccatatc acctagaact ttaaatgcat gggtaaaagt agtagaagag aaggctttca 660
gcccagaagt aatacccatg ttttcagcat tatcagaagg agccacccca caagatttaa 720
ataccatgct aaacacagtg gggggacatc aagcagccat gcaaatgtta aaagagacca 780
tcaatgagga agctgcagaa tgggatagat tgcatccagt gcatgcaggg cctattgcac 840
caggccagat gagagaacca aggggaagtg acatagcagg aactactagt acccttcagg 900
aacaaatagg atggatgaca cataatccac ctatcccagt aggagaaatc tataaaagat 960
ggataatcct gggattaaat aaaatagtaa gaatgtatag ccctaccagc attctggaca 1020
taagacaagg accaaaggaa ccctttagag actatgtaga ccgattctat aaaactctaa 1080
gagccgagca agcttcacaa gaggtaaaaa attggatgac agaaaccttg ttggtccaaa 1140
atgcgaaccc agattgtaag actattttaa aagcactggg accaggagcg acactagaag 1200
aaatgatgac agcatgtcag ggagtggggg gacccggcca taaagcaaga gttttggctg 1260
aagcaatgag ccaagtaaca aatccagcta ccataatgat acagaaaggc aattttagga 1320
accaaagaaa gactgttaag tgtttcaatt gtggcaaaga agggcacata gccaaaaatt 1380
gcagggcccc taggaaaaag ggctgttgga aatgtggaaa ggaaggacac caaatgaaag 1440
attgtactga gagacaggct aatttttag ggaagatctg gccttcccac aagggaaggc 1500
cagggaattt tcttcagagc agaccagagc caacagcccc accagaagag agcttcaggt 1560
ttggggaaga gacaacaact ccctctcaga ggcaggagcc gatagacaag gaactgtatc 1620
ctttagcttc cctcagatca ctctttggca gcgacccctc gtcacaataa agataggggg 1680
gcaattaaag gaagctctat tagatacagg agcagatgat acagtattag aagaaatgaa 1740
tttgccagga agatggaaac caaaaatgat agggggaatt ggaggtttta tcaaagtaag 1800
acagtatgat cagatactca tagaaatctg cggacataaa gctataggta cagtattagt 1860
aggacctaca cctgtcaaca taattggaag aaatctgttg actcagattg gctgcacttt 1920
aaattttccc attagtccta ttgagactgt accagtaaaa ttaaagccag gaatggatgg 1980
cccaaaagtt aaacaatggc cattgacaga agaaaaaata aaagcattag tagaaatttg 2040
tacagaaatg gaaaaggaag gaaaaatttc aaaaattggg cctgaaaatc catacaatac 2100
tccagtattt gccataaaga aaaaagacag tactaaatgg agaaaattag tagatttcag 2160
agaacttaat aagagaactc aagatttctg ggaagttcaa ttaggaatac cacatcctgc 2220
agggttaaaa cagaaaaaat cagtaacagt actggatgtg ggcgatgcat atttttcagt 2280
tcccttagat aaagacttca ggaagtatac tgcatttacc atacctagta taaacaatga 2340
gacaccaggg attagatatc agtacaatgt gcttccacag ggatggaaag gatcaccagc 2400
aatattccag tgtagcatga caaaaatctt agagcctttt agaaaacaaa atccagacgt 2460
agtcatctat caatacatgg atgatttgta tgtaggatct gacttagaaa tagggcagca 2520
tagaacaaaa atagaggaac tgagacaaca tctgttgagg tggggattta ccacaccaga 2580
caaaaaacat cagaaagaac ctccattcct ttggatgggt tatgaactcc atcctgataa 2640
atggacagta cagcctatag tgctgccaga aaaggacagc tggactgtca atgacataca 2700
gaaattagtg ggaaaattga attgggcaag tcagatttat gcagggatta aagtaaggca 2760
attatgtaaa cttcttaggg gaaccaaagc actaacagaa gtagtaccac taacagaaga 2820
agcagagcta gaactggcag aaaacaggga gattctaaaa gaaccggtac atggagtgta 2880
ttatgaccca tcaaaagact taatagcaga aatacagaag caggggcaag gccaatggac 2940
atatcaaatt tatcaagagc catttagaaa tctgaaaaca ggaaagtatg caagaatgaa 3000
gggtgcccac actaatgatg tgaaacaatt aacagaggca gtacaaaaaa tagccacaga 3060
aagcatagta atatggggaa agactcctaa atttaaatta cccatacaaa aggaaacatg 3120
ggaagcatgg tggacagagt attggcaagc cacctggatt cctgagtggg agtttgtcaa 3180
tacccctccc ttagtgaagt tatggtacca gttagagaaa gaacccataa taggagcaga 3240
aactttctat gtagatgggg cagccaatag ggaaactaaa ttaggaaaag caggatatgt 3300
aactgacaga ggaagacaaa aagttgtccc cctaacggac acaacaaatc agaagactga 3360
gttacaagca attcatctag ctttgcagga ttcgggatta gaagtaaaca tagtgacaga 3420
ctcacaatat gcattgggaa tcattcaagc acaaccagat aagagtgaat cagagttagt 3480
cagtcaaata atagagcagt taataaaaaa ggaaaaagtc tacctggcat gggtaccagc 3540
acacaaagga attggaggaa atgaacaagt agataaattg gtcagtgctg gaatcaggaa 3600
agtactattt ttagatggaa tagataaggc ccaagaagaa catgagaaat atcacagtaa 3660
ttggagagca atggctagtg attttaacct accacctgta gtagcaaaag aaatagtagc 3720
cagctgtgat aaatgtcagc taaaagggga agccatgcat ggacaagtag actgtagccc 3780
aggaatatgg cagctagatt gtacacattt agaaggaaaa gttatcttgg tggcagttca 3840
tgtagccagt ggatatatag aagcagaagt aattccagca gagacagggc aagaaacagc 3900
atacttcctc ttaaaattag caggaagatg gccagtaaaa acagtacata cagacaatgg 3960
cagcaatttc accagtacta cagttaaggc cgcctgttgg tgggcgggaa tcaagcagga 4020
atttggcatt ccctacaatc cccaaagtca aggagtaata gaatctatga ataaagaatt 4080
aaagaaaatt ataggacagg taagagatca ggctgaacat cttaagacag cagtacaaat 4140
ggcagtattc atccacaatt ttaaaagaaa aggggggatt ggggggtaca gtgcagggga 4200
aagaatagta gacataatag caacagacat acaaactaaa gaattacaaa aacaaattac 4260

-continued

```
aaaaattcaa aattttcggg tttattacag ggacagcaga gatccagttt ggaaaggacc   4320
agcaaagctc ctctggaaag gtgaaggggc agtagtaata caagataata gtgacataaa   4380
agtagtgcca agaagaaaag caaagatcat cagggattat ggaaaacaga tggcaggtga   4440
tgattgtgtg gcaagtagac aggatgagga ttaacacatg gaaaagatta gtaaaacacc   4500
atatgtatat ttcaaggaaa gctaaggact ggttttatag acatcactat gaaagtacta   4560
atccaaaaat aagttcagaa gtacacatcc cactagggga tgctaaatta gtaataacaa   4620
catattgggg tctgcataca ggagaaagag actggcattt gggtcaggga gtctccatag   4680
aatggaggaa aaagagatat agcacacaag tagaccctga cctagcagac caactaattc   4740
atctgcacta ttttgattgt ttttcagaat ctgctataag aaataccata ttaggacgta   4800
tagttagtcc taggtgtgaa tatcaagcag gacataacaa ggtaggatct ctacagtact   4860
tggcactagc agcattaata aaaccaaaac agataaagcc acctttgcct agtgttagga   4920
aactgacaga ggacagatgg aacaagcccc agaagaccaa gggccacaga gggagccata   4980
caacgaatgg acactagagc ttttagagga acttaagagt gaagctgtta gacattttcc   5040
taggatatgg ctccataact taggacgaca tatctatgaa acttacgggg atacttgggc   5100
aggagtggaa gccataataa gaattctgca acaactgccg tttatccatt tcagaattgg   5160
gtgtcgacat agcagaatag gcgttactcg acagaggaga gcaagaaatg gagccagtag   5220
atcctagact agagccctgg aagcatccag gaagtcagcc taaaactgct tgtaccaatt   5280
gctattgtaa aaagtgttgc tttcattgcc aagtttgttt catgacaaaa gccttaggca   5340
tctcctatgg caggaagaag cggagacagc gacgaagagc tcatcagaac agtcagactc   5400
atcaagcttc tctatcaaag cagtaagtag tacatgtaat gcaacctata atagtagcaa   5460
tagtagcatt agtagtagca ataataatag caatagttgt gtggtccata gtaatcatag   5520
aatataggaa aatattaaga caaagaaaaa tagacaggtt aattgataga ctaatagaaa   5580
gagcagaaga cagtggcaat gagagtgaag gagaagtatc agcacttgtg gagatggggg   5640
tggaaatggg gcaccatgct ccttgggata ttgatgatct gtagtgctac agaaaaattg   5700
tgggtcacag tctattatgg ggtacctgtg tggaaggaag caaccaccac tctattttgt   5760
gcatcagatg ctaaagcata tgatacagag gtacataatg tttgggccac acatgcctgt   5820
gtacccacag accccaaccc acaagaagta gtattggtaa atgtgacaga aaattttaac   5880
atgtggaaag atgacatggt agaacagatg catgaggata taatcagttt atgggatcaa   5940
agcctaaagc catgtgtaaa attaacccca ctctgtgtta gtttaaagtg cactgatttg   6000
aagaatgata ctaataccaa tagtagtagc gggagaatga taatggagaa aggagagata   6060
aaaaactgct ctttcaatat cagcacaagc ataagagata aggtgcagaa agaatatgca   6120
ttcttttata aacttgatat agtaccaata gataatacca gctataggtt gataagttgt   6180
aacacctcag tcattacaca ggcctgtcca aaggtatcct ttgagccaat ccccatacat   6240
tattgtgccc cggctggttt tgcgattcta aaatgtaata ataagacgtt caatggaaca   6300
ggaccatgta caaatgtcag cacagtacaa tgtacacatg gaatcaggcc agtagtatca   6360
actcaactgc tgttaaatgg cagtctagca gaagaagatg tagtaattag atctgccaat   6420
ttcacagaca atgctaaaac cataatagta cagctgaaca catctgtaga aattaattgt   6480
acaagaccca acaacaatac aagaaaaagt atccgtatcc agaggggacc agggagagca   6540
tttgttacaa taggaaaaat aggaaatatg agacaagcac attgtaacat tagtagagca   6600
aaatggaatg ccactttaaa acagatagct agcaaattaa gagaacaatt tggaaataat   6660
```

```
aaaacaataa tctttaagca atcctcagga ggggacccag aaattgtaac gcacagtttt   6720
aattgtggag gggaattttt ctactgtaat tcaacacaac tgtttaatag tacttggttt   6780
aatagtactt ggagtactga agggtcaaat aacactgaag gaagtgacac aatcacactc   6840
ccatgcagaa taaaacaatt tataaacatg tggcaggaag taggaaaagc aatgtatgcc   6900
cctcccatca gtggacaaat tagatgttca tcaaatatta ctgggctgct attaacaaga   6960
gatggtggta ataacaacaa tgggtccgag atcttcagac ctggaggagg cgatatgagg   7020
gacaattgga gaagtgaatt atataaatat aaagtagtaa aaattgaacc attaggagta   7080
gcacccacca aggcaaagag aagagtggtg cagagagaaa aaagagcagt gggaatagga   7140
gctttgttcc ttgggttctt gggagcagca ggaagcacta tgggcgcagc gtcaatgacg   7200
ctgacggtac aggccagaca attattgtct gatatagtgc agcagcagaa caatttgctg   7260
agggctattg aggcgcaaca gcatctgttg caactcacag tctggggcat caaacagctc   7320
caggcaagaa tcctggctgt ggaaagatac ctaaaggatc aacagctcct ggggatttgg   7380
ggttgctctg gaaaactcat ttgcaccact gctgtgcctt ggaatgctag ttggagtaat   7440
aaatctctgg aacagatttg gaataacatg acctggatgg agtgggacag agaaattaac   7500
aattacacaa gcttaataca ctccttaatt gaagaatcgc aaaaccagca agaaaagaat   7560
gaacaagaat tattggaatt agataaatgg gcaagtttgt ggaattggtt taacataaca   7620
aattggctgt ggtatataaa attattcata atgatagtag gaggcttggt aggtttaaga   7680
atagtttttg ctgtactttc tatagtgaat agagttaggc agggatattc accattatcg   7740
tttcagaccc acctcccaat cccgagggga cccgacaggc ccgaaggaat agaagaagaa   7800
ggtggagaga gaggcagaga cagatccatt cgattagtga acggatcctt agcacttatc   7860
tgggacgatc tgcggagcct gtgcctcttc agctaccacc gcttgagaga cttactcttg   7920
attgtaacga ggattgtgga acttctggga cgcagggggt gggaagccct caaatattgg   7980
tggaatctcc tacagtattg gagtcaggaa ctaaagaata gtgctgttaa cttgctcaat   8040
gccacagcca tagcagtagc tgaggggaca gatagggtta tagaagtatt acaagcagct   8100
tatagagcta ttcgccacat acctagaaga ataagacagg gcttggaaag gattttgcta   8160
taagatgggt ggcaagtggt caaaaagtag tgtgattgga tggcctgctg taagggaaag   8220
aatgagacga gctgagccag cagcagatgg ggtgggagca gtatctcgag acctagaaaa   8280
acatggagca atcacaagta gcaatacagc agctaacaat gctgcttgtg cctggctaga   8340
agcacaagag gaggaagagg tgggttttcc agtcacacct caggtacctt taagaccaat   8400
gacttacaag gcagctgtag atcttagcca ctttttaaaa gaaaaggggg gactggaagg   8460
gctaattcac tcccaaagaa gacaagatat ccttgatctg tggatctacc acacacaagg   8520
ctacttccct gattggcaga actacacacc agggccaggg gtcagatatc cactgacctt   8580
tggatggtgc tacaagctag taccagttga gccagataag gtagaagagg ccaataaagg   8640
agagaacacc agcttgttac accctgtgag cctgcatgga atggatgacc ctgagagaga   8700
agtgttagag tggaggtttg acagccgcct agcatttcat cacgtggccc gagagctgca   8760
tccggagtac ttcaagaact gctgacatcg agcttgctac aagggacttt ccgctgggga   8820
ctttccaggg aggcgtggcc tgggcgggac tggggagtgg cgagccctca gatgctgcat   8880
ataagcagct gctttttgcc tgtactgggt ctctctggtt agaccagatc tgagcctggg   8940
agctctctgg ctaactaggg aacccactgc ttaagcctca ataaagcttg ccttgagggc   9000
```

<210> SEQ ID NO 83
<211> LENGTH: 500
<212> TYPE: PRT
<213> ORGANISM: Human immunodeficiency virus

<400> SEQUENCE: 83

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Gln Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Ile Ala Val Leu Tyr Cys Val His Gln Arg Ile Asp Val Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Asn Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
    370                 375                 380

```
Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Phe Gly Glu Glu Thr Thr Thr Pro Ser Gln Arg Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500


<210> SEQ ID NO 84
<211> LENGTH: 9000
<212> TYPE: DNA
<213> ORGANISM: Human immunodeficiency virus

<400> SEQUENCE: 84

gccctcaagg caagctttat tgaggcttaa gcagtgggtt ccctagttag ccagagagct      60

cccaggctca gatctggtct aaccagagag acccagtaca ggcaaaaagc agctgcttat     120

atgcagcatc tgagggctcg ccactcccca gtcccgccca ggccacgcct ccctggaaag     180

tccccagcgg aaagtccctt gtagcaagct cgatgtcagc agttcttgaa gtactccgga     240

tgcagctctc gggccacgtg atgaaatgct aggcggctgt caaacctcca ctctaacact     300

tctctctcag ggtcatccat tccatgcagg ctcacagggt gtaacaagct ggtgttctct     360

cctttattgg cctcttctac cttatctggc tcaactggta ctagcttgta gcaccatcca     420

aaggtcagtg gatatctgac ccctggccct ggtgtgtagt tctgccaatc agggaagtag     480

ccttgtgtgt ggtagatcca cagatcaagg atatcttgtc ttctttggga gtgaattagc     540

ccttccagtc ccccctttc ttttaaaaag tggctaagat ctacagctgc cttgtaagtc     600

attggtctta aaggtacctg aggtgtgact ggaaaaccca cctcttcctc ctcttgtgct     660

tctagccagg cacaagcagc attgttagct gctgtattgc tacttgtgat tgctccatgt     720

ttttctaggt ctcgagatac tgctcccacc ccatctgctg ctggctcagc tcgtctcatt     780

ctttccctta cagcaggcca tccaatcaca ctactttttg accacttgcc acccatctta     840

tagcaaaatc ctttccaagc cctgtcttat tcttctaggt atgtggcgaa tagctctata     900

agctgcttgt aatacttcta taaccctatc tgtcccctca gctactgcta tggctgtggc     960

attgagcaag ttaacagcac tattctttag ttcctgactc caatactgta ggagattcca    1020

ccaatatttg agggcttccc accccctgcg tcccagaagt tccacaatcc tcgttacaat    1080

caagagtaag tctctcaagc ggtggtagct gaagaggcac aggctccgca gatcgtccca    1140

gataagtgct aaggatccgt tcactaatcg aatggatctg tctctgcctc tctctccacc    1200

ttcttcttct attccttcgg gcctgtcggg tcccctcggg attgggaggt gggtctgaaa    1260

cgataatggt gaatatccct gcctaactct attcactata gaaagtacag caaaaactat    1320

tcttaaacct accaagcctc ctactatcat tatgaataat tttatatacc acagccaatt    1380
```

-continued

```
tgttatgtta aaccaattcc acaaacttgc ccatttatct aattccaata attcttgttc   1440
attcttttct tgctggtttt gcgattcttc aattaaggag tgtattaagc ttgtgtaatt   1500
gttaatttct ctgtcccact ccatccaggt catgttattc caaatctgtt ccagagattt   1560
attactccaa ctagcattcc aaggcacagc agtggtgcaa atgagttttc cagagcaacc   1620
ccaaatcccc aggagctgtt gatcctttag gtatctttcc acagccagga ttcttgcctg   1680
gagctgtttg atgccccaga ctgtgagttg caacagatgc tgttgcgcct caatagccct   1740
cagcaaattg ttctgctgct gcactatatc agacaataat tgtctggcct gtaccgtcag   1800
cgtcattgac gctgcgccca tagtgcttcc tgctgctccc aagaacccaa ggaacaaagc   1860
tcctattccc actgctcttt tttctctctg caccactctt ctctttgcct tggtgggtgc   1920
tactcctaat ggttcaattt ttactacttt atatttatat aattcacttc tccaattgtc   1980
cctcatatcg cctcctccag gtctgaagat ctcggaccca ttgttgttat taccaccatc   2040
tcttgttaat agcagcccag taatatttga tgaacatcta atttgtccac tgatgggagg   2100
ggcatacatt gcttttccta cttcctgcca catgtttata aattgtttta ttctgcatgg   2160
gagtgtgatt gtgtcacttc cttcagtgtt atttgaccct tcagtactcc aagtactatt   2220
aaaccaagta ctattaaaca gttgtgttga attacagtag aaaaattccc ctccacaatt   2280
aaaactgtgc gttacaattt ctgggtcccc tcctgaggat tgcttaaaga ttattgtttt   2340
attatttcca aattgttctc ttaatttgct agctatctgt tttaaagtgg cattccattt   2400
tgctctacta atgttacaat gtgcttgtct catatttcct atttttccta ttgtaacaaa   2460
tgctctccct ggtcccctct ggatacggat actttttctt gtattgttgt tgggtcttgt   2520
acaattaatt tctacagatg tgttcagctg tactattatg gttttagcat tgtctgtgaa   2580
attggcagat ctaattacta catcttcttc tgctagactg ccatttaaca gcagttgagt   2640
tgatactact ggcctgattc catgtgtaca ttgtactgtg ctgacatttg tacatggtcc   2700
tgttccattg aacgtcttat tattacattt tagaatcgca aaaccagccg gggcacaata   2760
atgtatgggg attggctcaa aggatacctt tggacaggcc tgtgtaatga ctgaggtgtt   2820
acaacttatc aacctatagc tggtattatc tattggtact atatcaagtt tataaaagaa   2880
tgcatattct ttctgcacct tatctcttat gcttgtgctg atattgaaag agcagttttt   2940
tatctctcct ttctccatta tcattctccc gctactacta ttggtattag tatcattctt   3000
caaatcagtg cactttaaac taacacagag tggggttaat tttacacatg gctttaggct   3060
ttgatcccat aaactgatta tatcctcatg catctgttct accatgtcat ctttccacat   3120
gttaaaattt tctgtcacat ttaccaatac tacttcttgt gggttggggt ctgtgggtac   3180
acaggcatgt gtggcccaaa cattatgtac ctctgtatca tatgctttag catctgatgc   3240
acaaaataga gtggtggttg cttccttcca cacaggtacc ccataataga ctgtgaccca   3300
caatttttct gtagcactac agatcatcaa tatcccaagg agcatggtgc cccatttcca   3360
cccccatctc cacaagtgct gatacttctc cttcactctc attgccactg tcttctgctc   3420
tttctattag tctatcaatt aacctgtcta tttttctttg tcttaatatt ttcctatatt   3480
ctatgattac tatggaccac acaactattg ctattattat tgctactact aatgctacta   3540
ttgctactat tataggttgc attacatgta ctacttactg ctttgataga gaagcttgat   3600
gagtctgact gttctgatga gctcttcgtc gctgtctccg cttcttcctg ccataggaga   3660
tgcctaaggc ttttgtcatg aaacaaactt ggcaatgaaa gcaacacttt ttacaatagc   3720
aattggtaca agcagtttta ggctgacttc ctggatgctt ccagggctct agtctaggat   3780
```

-continued

```
ctactggctc catttcttgc tctcctctgt cgagtaacgc ctattctgct atgtcgacac   3840

ccaattctga aatggataaa cggcagttgt tgcagaattc ttattatggc ttccactcct   3900

gcccaagtat ccccgtaagt ttcatagata tgtcgtccta agttatggag ccatatccta   3960

ggaaaatgtc taacagcttc actcttaagt tcctctaaaa gctctagtgt ccattcgttg   4020

tatggctccc tctgtggccc ttggtcttct ggggcttgtt ccatctgtcc tctgtcagtt   4080

tcctaacact aggcaaaggt ggctttatct gttttggttt tattaatgct gctagtgcca   4140

agtactgtag agatcctacc ttgttatgtc ctgcttgata ttcacaccta ggactaacta   4200

tacgtcctaa tatggtattt cttatagcag attctgaaaa acaatcaaaa tagtgcagat   4260

gaattagttg gtctgctagg tcagggtcta cttgtgtgct atatctcttt ttcctccatt   4320

ctatggagac tccctgaccc aaatgccagt ctctttctcc tgtatgcaga ccccaatatg   4380

ttgttattac taatttagca tcccctagtg ggatgtgtac ttctgaactt atttttggat   4440

tagtactttc atagtgatgt ctataaaacc agtccttagc tttccttgaa atatacatat   4500

ggtgttttac taatcttttc catgtgttaa tcctcatcct gtctacttgc cacacaatca   4560

tcacctgcca tctgttttcc ataatccctg atgatctttg cttttcttct tggcactact   4620

tttatgtcac tattatcttg tattactact gccccttcac ctttccagag gagctttgct   4680

ggtcctttcc aaactggatc tctgctgtcc ctgtaataaa cccgaaaatt ttgaattttt   4740

gtaatttgtt tttgtaattc tttagtttgt atgtctgttg ctattatgtc tactattctt   4800

tcccctgcac tgtacccccc aatcccccct tttcttttaa aattgtggat gaatactgcc   4860

atttgtactg ctgtcttaag atgttcagcc tgatctctta cctgtcctat aattttcttt   4920

aattctttat tcatagattc tattactcct tgactttggg gattgtaggg aatgccaaat   4980

tcctgcttga ttcccgccca ccaacaggcg gccttaactg tagtactggt gaaattgctg   5040

ccattgtctg tatgtactgt ttttactggc catcttcctg ctaattttaa gaggaagtat   5100

gctgtttctt gccctgtctc tgctggaatt acttctgctt ctatatatcc actggctaca   5160

tgaactgcca ccaagataac ttttccttct aaatgtgtac aatctagctg ccatattcct   5220

gggctacagt ctacttgtcc atgcatggct tccccttta gctgacattt atcacagctg   5280

gctactattt cttttgctac tacaggtggt aggttaaaat cactagccat tgctctccaa   5340

ttactgtgat atttctcatg ttcttcttgg gccttatcta ttccatctaa aaatagtact   5400

ttcctgattc cagcactgac caatttatct acttgttcat ttcctccaat tcctttgtgt   5460

gctggtaccc atgccaggta gactttttcc tttttttatta actgctctat tatttgactg   5520

actaactctg attcactctt atctggttgt gcttgaatga ttcccaatgc atattgtgag   5580

tctgtcacta tgtttacttc taatcccgaa tcctgcaaag ctagatgaat tgcttgtaac   5640

tcagtcttct gatttgttgt gtccgttagg gggacaactt tttgtcttcc tctgtcagtt   5700

acatatcctg cttttcctaa tttagtttcc ctattggctg ccccatctac atagaaagtt   5760

tctgctccta ttatgggttc tttctctaac tggtaccata acttcactaa gggaggggta   5820

ttgacaaact cccactcagg aatccaggtg gcttgccaat actctgtcca ccatgcttcc   5880

catgtttcct tttgtatggg taatttaaat ttaggagtct ttccccatat tactatgctt   5940

tctgtggcta ttttttgtac tgcctctgtt aattgtttca catcattagt gtgggcaccc   6000

ttcattcttg catactttcc tgttttcaga tttctaaatg gctcttgata aatttgatat   6060

gtccattggc cttgcccctg cttctgtatt tctgctatta agtcttttga tgggtcataa   6120
```

-continued

```
tacactccat gtaccggttc ttttagaatc tccctgtttt ctgccagttc tagctctgct   6180
tcttctgtta gtggtactac ttctgttagt gctttggttc ccctaagaag tttacataat   6240
tgccttactt taatccctgc ataaatctga cttgcccaat tcaattttcc cactaatttc   6300
tgtatgtcat tgacagtcca gctgtccttt tctggcagca ctataggctg tactgtccat   6360
ttatcaggat ggagttcata acccatccaa aggaatggag gttctttctg atgtttttg    6420
tctggtgtgg taaatcccca cctcaacaga tgttgtctca gttcctctat ttttgttcta   6480
tgctgcccta tttctaagtc agatcctaca tacaaatcat ccatgtattg atagatgact   6540
acgtctggat tttgttttct aaaaggctct aagatttttg tcatgctaca ctggaatatt   6600
gctggtgatc ctttccatcc ctgtggaagc acattgtact gatatctaat ccctggtgtc   6660
tcattgttta tactaggtat ggtaaatgca gtatacttcc tgaagtcttt atctaaggga   6720
actgaaaaat atgcatcgcc cacatccagt actgttactg atttttttctg ttttaaccct  6780
gcaggatgtg gtattcctaa ttgaacttcc cagaaatctt gagttctctt attaagttct   6840
ctgaaatcta ctaatttttct ccatttagta ctgtcttttt tctttatggc aaatactgga  6900
gtattgtatg gattttcagg cccaattttt gaaattttc cttccttttc catttctgta    6960
caaatttcta ctaatgcttt tatttttttct tctgtcaatg gccattgttt aactttttggg 7020
ccatccattc ctggctttaa ttttactggt acagtctcaa taggactaat gggaaaattt   7080
aaagtgcagc caatctgagt caacagattt cttccaatta tgttgacagg tgtaggtcct   7140
actaatactg tacctatagc tttatgtccg cagatttcta tgagtatctg atcatactgt   7200
cttactttga taaaacctcc aattccccct atcatttttg gtttccatct tcctggcaaa   7260
ttcatttctt ctaatactgt atcatctgct cctgtatcta atagagcttc ctttaattgc   7320
ccccctatct ttattgtgac gaggggtcgc tgccaaagag tgatctgagg gaagctaaag   7380
gatacagttc cttgtctatc ggctcctgcc tctgagaggg agttgttgtc tcttccccaa   7440
acctgaagct ctcttctggt ggggctgttg gctctggtct gctctgaaga aaattccctg   7500
gccttccctt gtgggaaggc cagatcttcc ctaaaaaatt agcctgtctc tcagtacaat   7560
ctttcatttg gtgtccttcc tttccacatt tccaacagcc ctttttccta ggggccctgc   7620
aatttttggc tatgtgccct tctttgccac aattgaaaca cttaacagtc tttctttggt   7680
tcctaaaatt gcctttctgt atcattatgg tagctggatt tgttacttgg ctcattgctt   7740
cagccaaaac tcttgcttta tggccgggtc ccccccactcc ctgacatgct gtcatcattt  7800
cttctagtgt cgctcctggt cccagtgctt ttaaaatagt cttacaatct gggttcgcat   7860
tttggaccaa caaggtttct gtcatccaat tttttacctc ttgtgaagct tgctcggctc   7920
ttagagtttt atagaatcgg tctacatagt ctctaaaggg ttcctttggt ccttgtctta   7980
tgtccagaat gctggtaggg ctatacattc ttactatttt atttaatccc aggattatcc   8040
atcttttata gatttctcct actgggatag gtggattatg tgtcatccat cctatttgtt   8100
cctgaagggt actagtagtt cctgctatgt cacttcccct tggttctctc atctggcctg   8160
gtgcaatagg ccctgcatgc actggatgca atctatccca ttctgcagct tcctcattga   8220
tggtctcttt taacatttgc atggctgctt gatgtccccc cactgtgttt agcatggtat   8280
ttaaatcttg tggggtggct ccttctgata atgctgaaaa catgggtatt acttctgggc   8340
tgaaagcctt ctcttctact acttttaccc atgcatttaa agttctaggt gatatggcct   8400
gatgtaccat ttgcccctgg aggttctgca ctatagggta attttggctg acctggctgt   8460
tgtttcctgt gtcagctgct gcttgctgtg cctttttctt acttttgttt tgctcttcct   8520
```

```
ctatcttatc taaggcttcc ttggtgtctt ttacatctat cctttgatgc acacaataga   8580

ggactgctat tgtattatat aatgatctaa gttcttctga tcctgtctga agggatggtt   8640

gtagctgtcc cagtatttgt ctacagcctt ctgatgtctc taaaaggcca ggattaactg   8700

cgaatcgttc tagctccctg cttgcccata ctatatgttt tagtttatat tgtttctttc   8760

cccctggcct taaccgaatt ttttcccatt tatctaattc tcccccgctt aataccgacg   8820

ctctcgcacc catctctctc cttctagcct ccgctagtca aaatttttgg cgtactcacc   8880

agtcgccgcc cctcgcctct tgccgtgcgc gcttcagcaa gccgagtcct gcgtcgagag   8940

atctcctctg gctttacttt cgctttcaag tccctgttcg ggcgccactg ctagagattt   9000


<210> SEQ ID NO 85
<211> LENGTH: 112
<212> TYPE: PRT
<213> ORGANISM: Simian immunodeficiency virus

<400> SEQUENCE: 85

Met Ser Asp Pro Arg Glu Arg Ile Pro Pro Gly Asn Ser Gly Glu Glu
 1               5                  10                  15

Thr Ile Gly Glu Ala Phe Glu Trp Leu Asn Arg Thr Val Glu Glu Ile
            20                  25                  30

Asn Arg Glu Ala Val Asn His Leu Pro Arg Glu Leu Ile Phe Gln Val
        35                  40                  45

Trp Gln Arg Ser Trp Glu Tyr Trp His Asp Glu Gln Gly Met Ser Pro
    50                  55                  60

Ser Tyr Val Lys Tyr Arg Tyr Leu Cys Leu Ile Gln Lys Ala Leu Phe
65                  70                  75                  80

Met His Cys Lys Lys Gly Cys Arg Cys Leu Gly Glu Gly His Gly Ala
                85                  90                  95

Gly Gly Trp Arg Pro Gly Pro Pro Pro Pro Pro Pro Pro Gly Leu Ala
            100                 105                 110


<210> SEQ ID NO 86
<211> LENGTH: 339
<212> TYPE: DNA
<213> ORGANISM: Simian immunodeficiency virus

<400> SEQUENCE: 86

atgtcagatc ccagggagag aatcccacct ggaaacagtg gagaagagac aataggagag     60

gccttcgaat ggctaaacag aacagtagag gagataaaca gagaggcggt aaaccaccta    120

ccaagggagc taattttcca ggtttggcaa aggtcttggg aatactggca tgatgaacaa    180

gggatgtcac caagctatgt aaaatacaga tacttgtgtt taatacaaaa ggctttattt    240

atgcattgca agaaaggctg tagatgtcta ggggaaggac atggggcagg gggatggaga    300

ccaggacctc ctcctcctcc ccctccagga ctagcataa                           339


<210> SEQ ID NO 87
<211> LENGTH: 339
<212> TYPE: DNA
<213> ORGANISM: Artificial Sequence
<220> FEATURE:
<223> OTHER INFORMATION: Synthetic codon optimized variant

<400> SEQUENCE: 87

atgagcgacc ccagagagag aatccccccc ggcaacagcg gcgaggagac catcggcgag     60

gccttcgagt ggctgaacag aaccgtggag gagatcaaca gagaggccgt gaaccacctg    120
```

-continued

```
cccagagagc tgatcttcca ggtgtggcag agaagctggg agtactggca cgacgagcag    180

ggcatgagcc ccagctacgt gaagtacaga tacctgtgcc tgatccagaa ggccctgttc    240

atgcactgca agaagggctg cagatgcctg ggcgagggcc acggcgccgg cggctggaga    300

cccggccccc cccccccccc cccccccggc ctggcctga                           339
```

CHIMERIC HUMAN IMMUNODEFICIENCY VIRUS TYPE 1 (HIV-1) WITH ENHANCED DENDRITIC CELL AND MACROPHAGE TROPISM COMPRISING THE SIMIAN IMMUNODEFICIENCY VIRUS (SIV) MINIMAL VPX PACKAGING DOMAIN

CROSS REFERENCE TO RELATED APPLICATIONS

This application claims priority under 35 USC §119(e) from U.S. Provisional Application Ser. No. 61/587,392, filed Jan. 17, 2012, which application is herein specifically incorporated by reference in its entirety.

GOVERNMENTAL SUPPORT

The research leading to the present invention was supported, at least in part, by National Institutes of Health (NIH) grant 5R01 A1067059 and NIH training grant 5T32 A1007180. Accordingly, the Government has certain rights in the invention.

FIELD OF INVENTION

The compositions and methods described herein relate to lentiviral vectors that can be used to generate virions that exhibit enhanced infectivity with respect to monocyte-derived macrophages (MDM) and dendritic cells (MDDC). More particularly, compositions and methods described herein relate to production of virions that can be used as components of vaccines that effectively stimulate innate immune responses. In a particular embodiment, compositions and methods described herein relate to production of virions that can be used as components of human immunodeficiency-1 (HIV-1) vaccines that effectively stimulate innate immune responses.

BACKGROUND OF INVENTION

Unlike simple retroviruses, lentiviruses encode a set of accessory proteins (Nef, Vif, Vpr, Vpu, and Vpx), each of which play a specific role in virus replication and pathogenesis, much of which are directed at evasion of the host adaptive or innate immune response (28, 33, 35, 36, 41, 46). Specifically, Nef downregulates cell surface CD4 molecules and disrupts antigen presentation, and Vif and Vpu serve to counteract the host restriction factors, APOBEC3G and BST-2/tetherin, respectively. Although the roles of Vpx and Vpr are less well understood, they are thought to aid in evasion of a yet uncharacterized restriction to virus replication in macrophages and dendritic cells (3, 7, 10, 18, 20, 22, 24, 27, 51). Sharing significant sequence and structural homology, the two proteins appear to have arisen from the duplication of a common ancestral precursor gene (44). Both are produced late in the viral life cycle and localize to the nucleus (5, 12, 31). A Vpr gene is present in the genome of all known lentiviruses, while Vpx is restricted to HIV-2 and the SIV of sooty mangabey (SIVsm) and macaque (SIVmac). Interestingly, SIV of the African green monkey encodes only Vpr, but this protein has some characteristics of Vpx, sharing the same virion packaging determinant and effect on virus replication in macrophages (1, 9).

A distinguishing feature of Vpr and Vpx is that they are packaged into virions at significant levels (2, 23, 50). Packaging of Vpr and Vpx occurs as the virion assembles and is mediated by amino acid motifs in the carboxy-terminal Gag protein p6, such that deletion of p6 prevents incorporation of both Vpr and Vpx (31, 38, 47). The packaging of Vpr and Vpx is also virus-specific (25). HIV-1 will not package SIVmac Vpr or Vpx, nor will SIVmac package HIV-1 Vpr. By analyzing viruses with mutated or truncated p6, various groups have identified amino acid motifs in p6 that mediate Vpr and Vpx incorporation. The motif $^{41}$LXXLF$^{44}$ (SEQ ID NO: 58) near the p6 carboxy-terminus was reported by Kondo et al. as the major determinant required for the packaging of Vpr (30). Subsequently, Zhu et al. (53) reported that mutation of that motif did not prevent Vpr packaging. Instead, in a virus deleted for amino acids 35-52, the $^{15}$FRFG$^{18}$ motif near the amino-terminus of p6 was required. This discrepancy has not yet been resolved. In SIVmac, the Vpx packaging motif has also been mapped to the N terminal region of p6, specifically to a conserved $^{17}$DXAXXLL$^{23}$ (SEQ ID NO: 60) motif (1). Packaging of SIVagm Vpr was also dependent on this motif, drawing a resemblance with Vpx.

Vpr and Vpx are important for virus replication and pathogenicity in vivo, as demonstrated in the rhesus macaque model, where Vpx-deleted $SIVmac_{239}$ is attenuated and Vpx/Vpr-deleted virus is further impaired (17). In vitro, neither Vpr nor Vpx is required for SIVmac replication in activated CD4 T cells (3, 18, 19). However, in monocyte-derived macrophages (MDM) and dendritic cells (MDDC), both proteins enhance SIVmac infection, although Vpr has a more modest effect. The presence of Vpx and Vpr in the virion suggests that they play a role early in virus replication. Vpr and Vpx were initially proposed to aid in nuclear import of the preintegration complex in infection of nondividing cells, a mechanism consistent with their karyophilic properties and their presence in the virion (5, 13). However, this view was challenged by the finding that HIV-1 deleted for Vpr maintained its ability to infect nondividing cells (48). Recently, a role for Vpx and Vpr in counteracting a restriction factor was suggested by the finding that both associated with an E3 ubiquitin ligase composed of damaged DNA binding protein 1 (DDB1), DDB1 cullen associated factor 1 (DCAF1), and Cullin 4A (Cul4A) (6, 21, 26, 39, 40, 42). By analogy with Vif, this finding suggested that Vpx and Vpr might act as substrate receptors that induce the ubiquitination of a host restriction factor (41, 43, 49). Evidence that Vpx plays a role in counteracting an MDM-specific host restriction was provided by somatic cell fusion experiments in which heterokaryons formed between MDM and COS were found to be nonpermissive for Vpx-deleted SIVmac (40). Furthermore, domain mapping of Vpx localized an activation domain at the amino-terminus that might serve as a binding site for the putative host restriction factor (21).

In studies investigating the mechanism by which Vpx promotes the infection of MDDC, Goujon et al. found that Vpx could facilitate infection when introduced into the target cell in trans (18, 20). For this, MDDC were exposed to virus-like particles (VLP) that contained Vpx and then were infected with Vpx-deleted SIVmac. The VLP dramatically enhanced the infectability of the cells. Additionally, Gramberg et al. found that VLP generated with a codon-optimized Vpx expression vector could boost the infection of MDM as much as 100-fold, while Vpr had little effect (21). In these cells, Vpx was found to relieve a block to infection at early reverse transcription or at uncoating. Interestingly, Vpx also dramatically enhanced HIV-1 infection of MDM and MDDC, even though the virus does not itself encode this accessory protein. Recently, Manel et al. used this property to achieve high levels of HIV-1 infected MDDC (32). The infected MDDC strongly induced innate immune defenses, resulting in the production of type-I IFN and upregulation of CD86. Surprisingly, the trigger that induced this response was not the incoming virus but, rather, the newly produced Gag protein.

The citation of references herein shall not be construed as an admission that such is prior art to the present invention.

SUMMARY OF THE INVENTION

To date, Vpx has been used to enhance HIV-1 infection of MDM and MDDC by pretreating cells with VLP. In this study, the present inventors sought to investigate the role of Vpx by generating an HIV-1 vector that would package the protein. Such a vector would obviate the need for Vpx-containing VLP. Virions/viruses generated using the resulting vector would have an enhanced ability to infect MDDC and MDM and be expected to induce an innate immune response in the cells. The present inventors constructed a vector having the desired properties by introducing a fragment of $SIVmac_{239}$ p6 into HIV-1 p6. In a further embodiment, the vector comprising the introduced fragment of $SIVmac_{239}$ p6 into HIV-1 p6 was further modified by placing vpx in the Nef position. More particularly, vpx was inserted into the first codon of Nef This arrangement prevents Nef expression, because protein synthesis is terminated by the vpx stop codon. Virions generated using the resulting vectors efficiently infected MDM and MDDC and induced high levels of type I IFN. In a MDDC/T cell transfer assay, the engineered virions so produced replicated much more efficiently than those generated using wild-type vector. These findings suggest that an important role of Vpx is to enhance the ability of virus to be transmitted from MDM and MDDC to CD4 T cells. Furthermore, such virions are useful for the production of an HIV vaccine that stimulates innate immune responses and for the generation of lentiviral virions that more efficiently infect these cell types.

In accordance with the present findings, a chimeric vector comprising HIV-1 nucleic acid sequences and $SIVmac_{239}$ nucleic acid sequences is presented herein, wherein the $SIVmac_{239}$ nucleic acid sequences encode an $SIVmac_{239}$ amino acid sequence consisting of a minimal Vpx packaging motif that confers Vpx packaging activity to the chimeric vector. In an embodiment thereof, the chimeric vector does not comprise any SIVmac nucleic acid sequences except for or in addition to the minimal Vpx packaging motif.

In a further embodiment, the chimeric vector further comprises vpx inserted in nef of the HIV-1 nucleic acid sequences. In a particular embodiment thereof, the vpx is $SIVmac_{239}$ vpx. In a more particular embodiment, the vpx is a codon-optimized $SIVmac_{239}$ vpx. In a still further embodiment, the chimeric vector that further comprises vpx, does not comprise any $SIVmac_{239}$ nucleic acid sequences except for or in addition to the minimal Vpx packaging motif and the vpx.

In a further aspect, the minimal Vpx packaging motif consists of at least 10 contiguous amino acids of $SIVmac_{239}$ comprising of $^{17}$DPAVDLLKNY$^{26}$ (SEQ ID NO: 1), wherein the 5' terminus of the minimal Vpx packaging motif is the aspartic acid (D) at amino acid position 17 of the $SIVmac_{239}$ amino acid sequence. More particularly, the minimal Vpx packaging motif consists of $^{17}$DPAVDLLKNY$^{26}$, (SEQ ID NO: 1)

$^{17}$DPAVDLLKNYM$^{27}$, (SEQ ID NO: 2)

$^{17}$DPAVDLLKNYMG$^{28}$, (SEQ ID NO: 3)

-continued $^{17}$DPAVDLLKNYMQL$^{29}$, (SEQ ID NO: 4)

$^{17}$DPAVDLLKNYMQLG$^{30}$, (SEQ ID NO: 5)

$^{17}$DPAVDLLKNYMQLGK$^{31}$, (SEQ ID NO: 6)

$^{17}$DPAVDLLKNYMQLGKQ$^{32}$, (SEQ ID NO: 7)

$^{17}$DPAVDLLKNYMQLGKQQ$^{33}$, (SEQ ID NO: 8)

$^{17}$DPAVDLLKNYMQLGKQQRE$^{34}$, (SEQ ID NO: 9)

$^{17}$DPAVDLLKNYMQLGKQQREK$^{35}$, (SEQ ID NO: 10)

$^{17}$DPAVDLLKNYMQLGKQQREKQ$^{36}$, (SEQ ID NO: 11)

$^{17}$DPAVDLLKNYMQLGKQQREKQ$^{37}$, (SEQ ID NO: 12)

$^{17}$DPAVDLLKNYMQLGKQQREKQR$^{38}$, (SEQ ID NO: 13)

$^{17}$DPAVDLLKNYMQLGKQQREKQRE$^{39}$, (SEQ ID NO: 14)

$^{17}$DPAVDLLKNYMQLGKQQREKQRES$^{40}$, (SEQ ID NO: 15)

$^{17}$DPAVDLLKNYMQLGKQQREKQRESR$^{41}$, (SEQ ID NO: 16)

$^{17}$DPAVDLLKNYMQLGKQQREKQRESRE$^{42}$, (SEQ ID NO: 17)

$^{17}$DPAVDLLKNYMQLGKQQREKQRESREK$^{43}$, (SEQ ID NO: 18)

$^{17}$DPAVDLLKNYMQLGKQQREKQRESREKP$^{44}$, (SEQ ID NO: 19)

$^{17}$DPAVDLLKNYMQLGKQQREKQRESREKPY$^{45}$, (SEQ ID NO: 20)

$^{17}$DPAVDLLKNYMQLGKQQREKQRESREKPYK$^{46}$, (SEQ ID NO: 21)

$^{17}$DPAVDLLKNYMQLGKQQREKQRESREKPYKE$^{47}$, (SEQ ID NO: 22)
or $^{17}$DPAVDLLKNYMQLGKQQREKQRESREKPYKEV$^{48}$. (SEQ ID NO: 23)

In a still further aspect, the minimal Vpx packaging motif consists of $^{17}$DPAVDLLKNY$^{26}$ (SEQ ID NO: 1).

Chimeric vectors described herein may comprise $SIVmac_{239}$ nucleic acid sequences encoding the minimal Vpx packaging motif, wherein $SIVmac_{239}$ nucleic acid sequences comprise at least one codon optimized nucleic acid sequence.

In a particular embodiment, the $SIVmac_{239}$ nucleic acid sequences encoding the minimal Vpx packaging motif are inserted into the HIV-1 nucleic acid sequences encoding p6 of HIV-1 Gag polyprotein.

In a more particular embodiment, the $SIVmac_{239}$ nucleic acid sequences encoding the minimal Vpx packaging motif are inserted into the HIV-1 nucleic acid sequences encoding p6 of HIV-1 Gag polyprotein to generate a hybrid HIV-1/$SIVmac_{239}$ nucleic acid sequence that encodes a hybrid HIV-1/$SIVmac_{239}$ p6 wherein amino acids 1-14 of HIV-1 p6 are linked directly to the minimal Vpx packaging motif consisting of at least 10 contiguous amino acids of $SIVmac_{239}$ p6 comprising of $^{17}$DPAVDLLKNY$^{26}$ (SEQ ID NO: 1), wherein the 5' terminus of the minimal Vpx packaging motif is the aspartic acid (D) at amino acid position 17 of the $SIVmac_{239}$ p6 amino acid sequence. See, for example, FIG. 1.

In another aspect, the chimeric vector comprises HIV-1 nucleic acid sequences that encode Gag and Pol.

In yet another aspect, the chimeric vector comprising HIV-1 nucleic acid sequences, wherein the HIV-1 nucleic acid sequences comprise HIV-1 p6 or pNL.Ba.L.

In a further aspect, a method of making a plurality of virions/viruses having enhanced infectivity for monocyte-derived macrophages (MDM) and dendritic cells (MDDC) is presented, the method comprising transfecting a population of cells with a lentiviral vector comprising 5' and 3' long terminal repeats (LTRs) and a nucleic acid sequence encoding at least one immunogen of a peptide or protein, a vector encoding vesicular stomatitis virus (VSV) envelope glycoprotein, a vector encoding Vpx, and a chimeric vector comprising HIV-1 nucleic acid sequences and $SIVmac_{239}$ nucleic acid sequences (as described herein), wherein the $SIVmac_{239}$ nucleic acid sequences encode an $SIVmac_{239}$ amino acid sequence consisting of a minimal Vpx packaging motif that confers Vpx packaging activity to the chimeric vector, to generate a transfected population of cells, wherein the transfected population of cells produces the plurality of virions having enhanced infectivity for MDM and dendritic cells MDDC.

In an embodiment thereof, the vector comprising 5' and 3' LTRs further comprises a nucleic acid sequence encoding at least one dendritic cell activator protein and/or at least one cytokine. An exemplary dendritic cell activator protein useful for such purposes is CD40 ligand (CD40L). Cytokines and cell surface proteins that would activate DC or could be expressed in DCs to activate T cells include: IL-2 (GenBank No. S82692), IL-12 (GenBank No. NM_000882), TNF-alpha (GenBank No. XO2910.1), and CD28 (GenBank No. NM_006139.3).

In a particular aspect, the above method may further comprise the step of administering the plurality of virions having enhanced infectivity for MDM and dendritic cells MDDC or a composition thereof to a subject in a therapeutically effective amount sufficient to enhance innate immune responses to the peptide or protein in the subject. In a particular embodiment thereof, the plurality of virions/viruses comprises at least one immunogen of an HIV-1 encoded peptide or protein, and the plurality of virions/viruses or the composition thereof is administered to a subject in a therapeutically effective amount sufficient to enhance innate immune responses to HIV-1 in the subject. In a particular embodiment thereof, the subject is infected with HIV-1 or suspected to be infected with HIV-1. In a more particular embodiment, the subject is a mammal. In an even more particular embodiment, the mammal is a primate or a human.

Also encompassed herein is a plurality of virions/viruses having enhanced infectivity for MDM and MDDC, which are suitable for use in humans. As described herein, the plurality of virions/viruses having enhanced infectivity for MDM and MDDC is produced by a method comprising transfecting a population of cells with a lentiviral vector comprising 5' and 3' long terminal repeats (LTRs) and a nucleic acid sequence encoding at least one immunogen of a peptide or protein, a vector encoding vesicular stomatitis virus (VSV) envelope glycoprotein, a vector encoding Vpx, and a chimeric vector comprising HIV-1 nucleic acid sequences and $SIVmac_{239}$ nucleic acid sequences (as described herein), wherein the $SIVmac_{239}$ nucleic acid sequences encode an $SIVmac_{239}$ amino acid sequence consisting of a minimal Vpx packaging motif that confers Vpx packaging activity to the chimeric vector, to generate a transfected population of cells, wherein the transfected population of cells produces the plurality of virions having enhanced infectivity for MDM and dendritic cells MDDC. Compositions comprising the plurality of virions/viruses having enhanced infectivity for MDM and MDDC and pharmaceutically acceptable carriers are also envisioned. The plurality of virions/viruses made in accordance with the present method is suitable for use in humans at least in part because it is produced using the chimeric vector comprising HIV-1 nucleic acid sequences and $SIVmac_{239}$ nucleic acid sequences described herein.

In a further aspect, a method of enhancing innate immune responses to a peptide or protein in a subject is presented, the method comprising: administering the plurality of virions/viruses having enhanced infectivity for MDM and MDDC or a composition thereof to the subject, wherein the plurality of virions/viruses comprises the at least one immunogen of the peptide or protein, and wherein the plurality of virions/viruses or a composition thereof is administered to the subject in a therapeutically effective amount sufficient to enhance innate immune responses to the peptide or protein in the subject. In a particular embodiment, the subject is a mammal. In an even more particular embodiment, the mammal is a primate or a human.

In a still further aspect, a method of enhancing innate immune responses to human immunodeficiency virus 1 (HIV-1) in a subject is presented, the method comprising: administering the plurality of virions/viruses having enhanced infectivity for MDM and MDDC or a composition thereof to the subject, wherein the plurality of virions/viruses comprises the at least one immunogen of the peptide or protein and the peptide or protein is an HIV-1 encoded peptide or protein, and wherein the plurality of virions/viruses or the composition thereof is administered to the subject in a therapeutically effective amount sufficient to enhance innate immune responses to HIV-1 in the subject. In a particular embodiment thereof, the subject is infected with HIV-1 or suspected to be infected with HIV-1. In a more particular embodiment, the subject is a mammal. In an even more particular embodiment, the mammal is a primate or a human.

Other objects and advantages will become apparent to those skilled in the art from a review of the following description which proceeds with reference to the following illustrative drawings.

Two days later, cell lysate and virions were pelleted by ultracentrifugation and analyzed on an immunoblot. The immunoblot was probed with antibody to myc-tagged Vpx, HIV-1 p24 CA, or tubulin. A pcVpx-myc alone transfection was included to rule-out nonspecific release of Vpx. C. HIV-1 p6 chimeras that map amino acids required for Vpx packaging. Virions were prepared by transfection and analyzed on an immunoblot as in (B). D. Effects of p6 mutations on packaging of HIV-1 Vpr. 293T were cotransfected with wild-type or chimeric p6 pNL4-3 and pcVpr.myc or empty vector. Cell lysate and virions were analyzed on an immunoblot as in (B).

Figure 2:
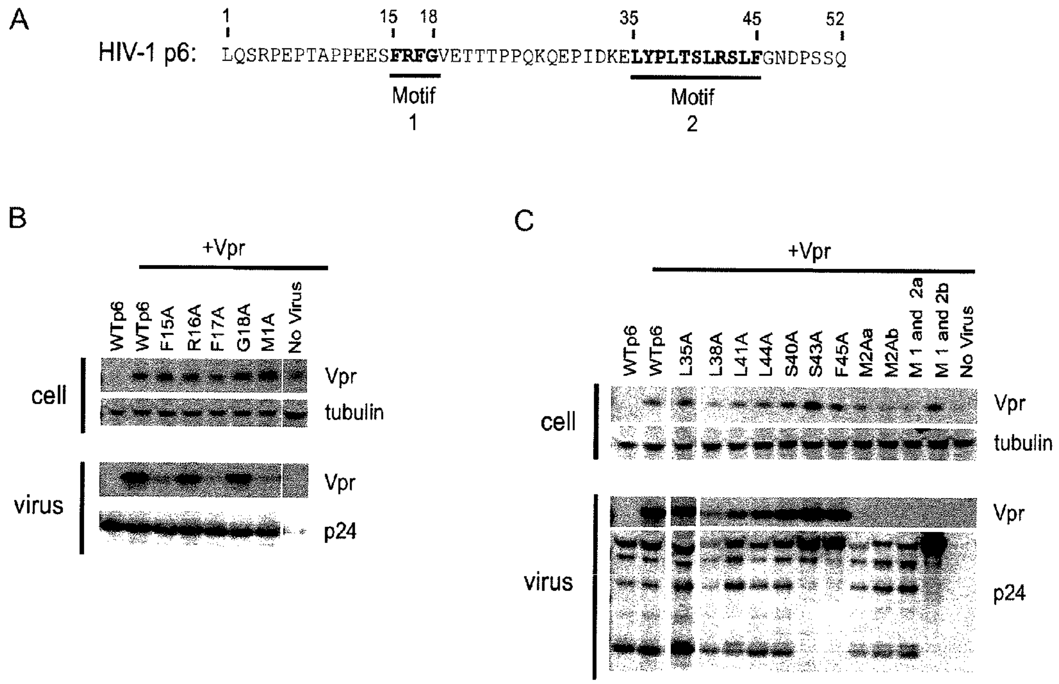

FIGS. 2A-C. Relative contribution of the two proposed Vpr packaging motifs of HIV-1. A. Sequence of the two reported Vpr packaging motifs of HIV-1 p6. The two motifs are underlined in bold. The amino acid sequence of HIV-1 p6 is designated SEQ ID NO: 65. B. Immunoblot analysis of Vpr packaged by motif 1 mutant virions. Virions were generated by transfection of 293T cells with pNL4-3 containing a wild-type or mutant p6 and a pcVpr.myc expression vector or empty vector. The virions were pelleted from the culture supernatants by ultracentrifugation and analyzed on an immunoblot probed with antibody to myc-tagged Vpr, HIV-1 CA p24, or tubulin. C. Immunoblot analysis of Vpr packaged by motif 2. Mutant virions prepared as in (B). M1A is F15, R16, F17, and G18 in motif 1 mutated to alanine. M2Aa is L35,L38, L41, and L44 in motif 2 mutated to alanine. M2Ab is M2Aa with the addition of S40, S43, and F45 mutated to alanine. M1 and 2a is the combination of M1A and M2Aa. M1 and 2b is the combination of M1A and M2Ab.

Figure 3:
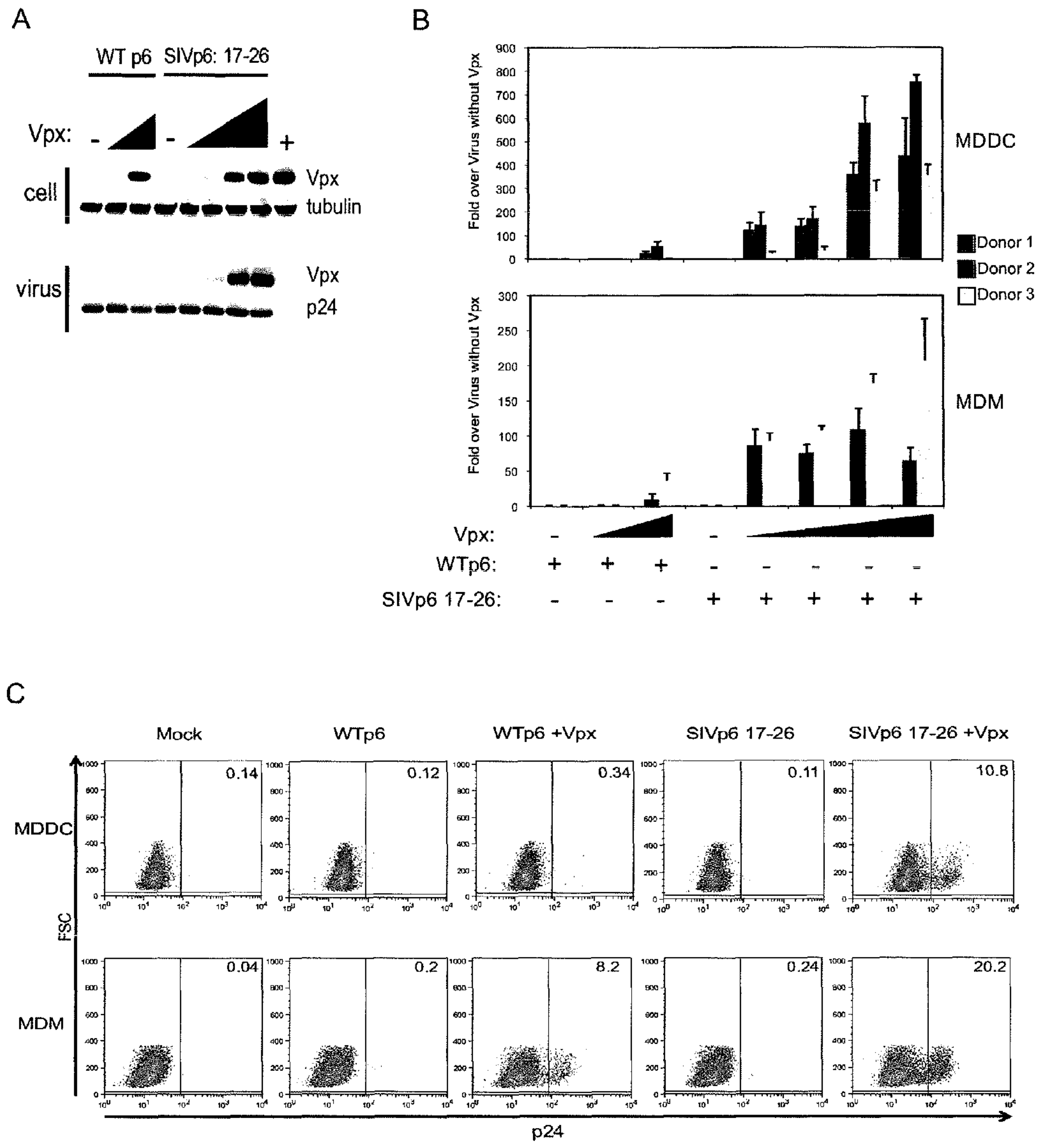

FIGS. 3A-C. Chimeric HIV-1 containing the Vpx packaging motif has an enhanced ability to infect MDDC and MDM. A. Expression and packaging of Vpx provided in trans. Luciferase reporter viruses were generated by cotransfection of 293T cells with wild-type or the 17-26 chimeric proviral reporter virus plasmid (18 μs) and increasing amounts of pcVpx.myc (0.3 μg, 0.6 μg, 3.0 μg, 6.0 μs) with the total mass of DNA held constant by the addition of pcDNA plasmid. The resulting virions were analyzed on an immunoblot probed with antibody to myc-tagged Vpx, HIV-1 CA p24, or tubulin. B. The effect of Vpx on MDDC and MDM infection. MDDC (upper panel) and MDM (lower panel) were infected with VSV-G pseudotyped luciferase reporter viruses normalized for infectivity on 293T cells. After 4 days, the cultures were harvested and the luciferase activity was determined. The data are displayed as the fold-enhancement of the virus containing Vpx divided by virus lacking Vpx. Error bars indicate the standard deviation of triplicate measurements. Results from three MDDC and two MDM donors are shown. C. P24 analysis of MDDC and MDM infection by HIV-1 containing Vpx. MDDC (upper panels) and MDM (lower panels) were infected with luciferase reporter virus. Three days later, the cells were collected and intracellular p24-FITC was determined by flow cytometry.

FIGS. 4A-B. Comparison of SIVmac Vpx, SIVagm Vpr, and HIV-$2_{rod}$ Vpx. Luciferase reporter viruses were generated by cotransfection of 293T cells with wild-type or p6 chimeric HIV-1 and expression vectors for SIV$mac_{239}$ Vpx, HIV-$2_{rod}$ Vpx, or SIVagm Vpr. A. Expression and packaging of codon-optimized SIV$mac_{239}$ Vpx, HIV-$2_{rod}$ Vpx, and SIVagm Vpr. Cell lysates and pelleted virions were analyzed on an immunoblot probed with antibody to myc-tagged Vpx , myc-tagged Vpr, HIV-1 p24 CA, or tubulin. B. Effect of HIV-1 packaging SIV$mac_{239}$ Vpx, HIV-$2_{rod}$ Vpx, or SIVagm Vpr on MDDC and MDM infection. MDDC and MDM were infected with the indicated virus, normalized by luciferase activity on 293T, and, 4 days postinfection, luciferase activity was determined. Error bars indicate the standard deviation of triplicates. Three MDDC and MDM donors are shown.

Figure 5:
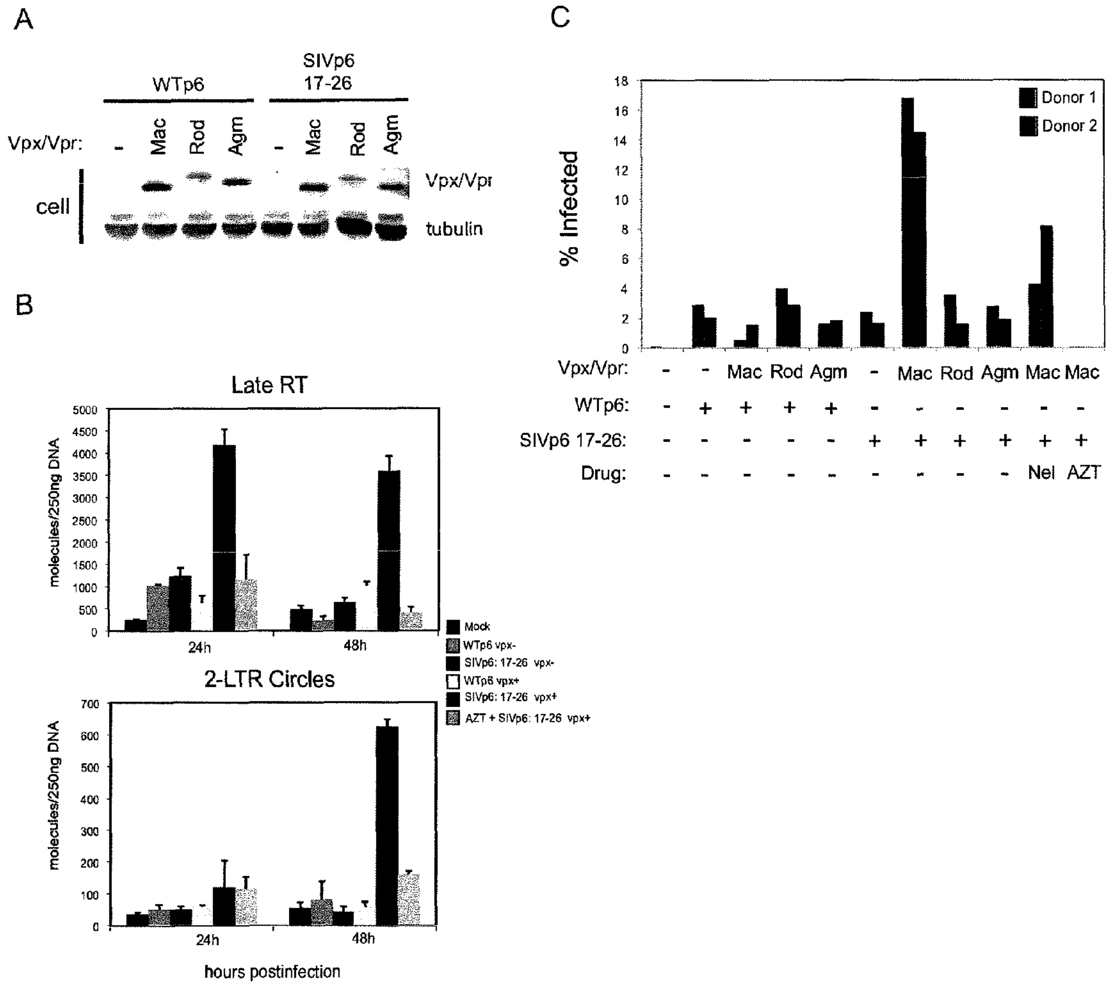

FIGS. 5A-C. CCR5-using chimeric virus with Vpx in cis replicates more efficiently in MDDC and MDM. Wild-type and chimeric p6 NL.Ba.L viruses that express Vpx in cis were generated by transfection of 293T cells. A. Immunoblot of SIV$mac_{239}$ Vpx, HIV-$2_{rod}$ Vpx and SIVagm Vpr expressed in cis in the cell lysates of cells treated for 5 h with 20 μM MG132. The cell lysates were analyzed on an immunoblot probed for myc-tagged Vpx, myc-tagged Vpr, or tubulin. B. The effect of p6 chimeric virus with vpx in cis on MDM infection. MDM were infected with wild-type or p6 chimeric vpx in cis virus. After 24 and 48 h, total DNA was prepared and the reverse transcripts were quantified by qRT-PCR using primers specific for the late products and 2-LTR circles. Early products were not quantified as these were found to be present in the virions prior to infection as a result of endogenous reverse transcription. AZT (25 μM) was added to the sample infected with the p6 chimeric virus encoding Vpx and served to control for plasmid contamination and intra-virion reverse transcripts. C. MDDC infection by p6 chimeric virus with vpx or vpr in cis. MDDC were infected with virus normalized for p24. After 3 days, the cells were collected, stained for intracellular p24 with anti-p24-FITC, and analyzed by flow cytometry. AZT (25 μM) was used to control for contamination with input virus. Nelfinavir (3 μM) was used to limit replication to a single cycle. Results from two donors are shown.

Figure 6:
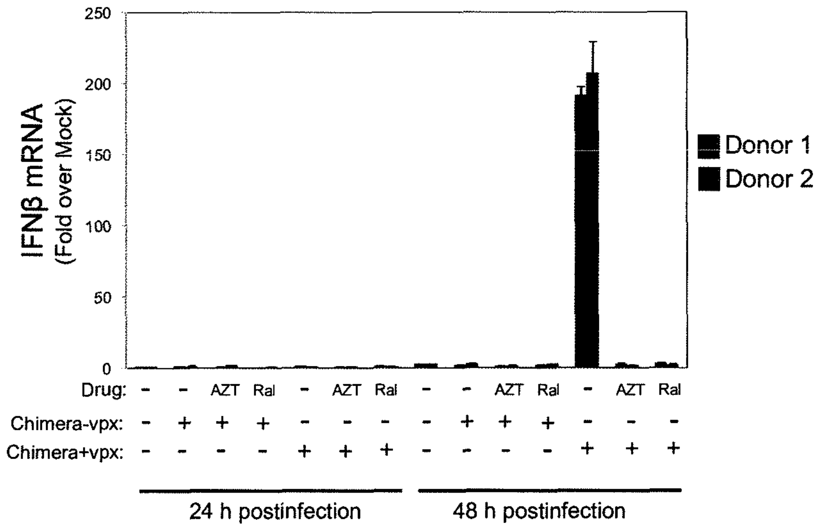

FIG. 6. Infection of MDDC with Vpx-containing virus stimulates an innate immune response. MDDC from two healthy donors were infected with the p6 chimeric virus complemented in trans with Vpx. AZT (25 μM) or Raltegravir (10 μM) was added to the indicated samples. The cultures were harvested 24 and 48 h postinfection and IFN-β mRNA was quantified by qRT-PCR. The data are presented relative to G6PDH mRNA amplified in parallel.

Figure 7:
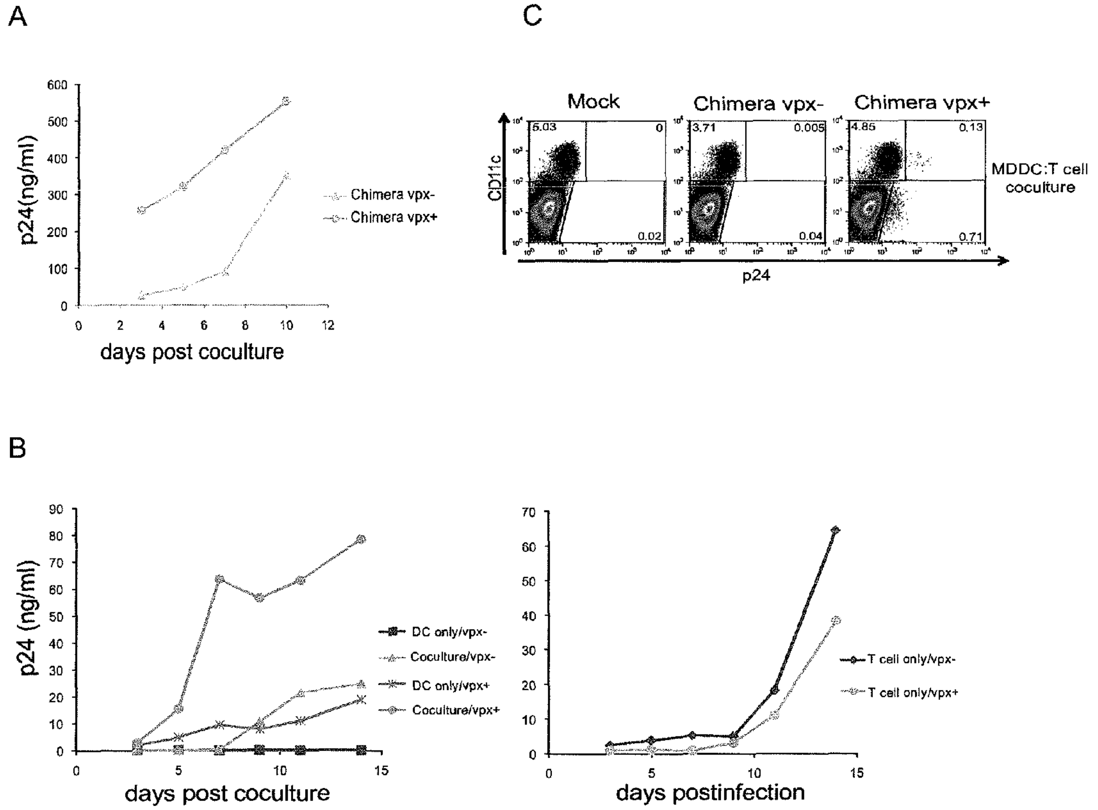

FIGS. 7A-C. Exposure of MDDC to Vpx-containing virus allows for efficient transfer of virus to T cells. A. MDDC were infected with NL.Ba.1 wild-type or p6 chimeric virus containing vpx in cis and with or without additional Vpx complementation in trans. After 6 h, free virus was removed, and after 48 h, CD3/CD28-activated autologous CD4 T cells were added. Supernatant p24 was measured over 10 days. Results are representative of MDDC and CD4 T cells from two donors. B. MDDC were infected as in (A). After 6 h, free virus was removed. After 48 h, media or CD3/CD28-activated autologous T cells were added. In parallel, T cells alone were infected as in (A) and after 6 h, free virus was removed. Supernatant p24 was measured over 14 days. The results shown are representative of MDDC and CD4+ T cells from two donors. C. MDDC and T cells were infected as in (A) and cells were collected at day 3 post coculture. The cells were incubated with anti-CD11c-APC and anti-p24-FITC and analyzed by flow cytometry. The cell populations were gated on CD11c and then evaluated for intracellular p24 using FACS. Result shown is representative of three donors tested.

FIG. 8. Nucleotide sequences of codon-optimized SIVmac239 Vpx, HIV-2rod Vpx, and SIVagm Vpr open reading frames. Total length is indicated following the final base. Nucleotide sequences presented with regard to codon-optimized SIVmac239 Vpx, HIV-2rod Vpx, and SIVagm Vpr open reading frames are designated herein as SEQ ID NOs: 68, 69, and 70 respectively.

Figure 9:
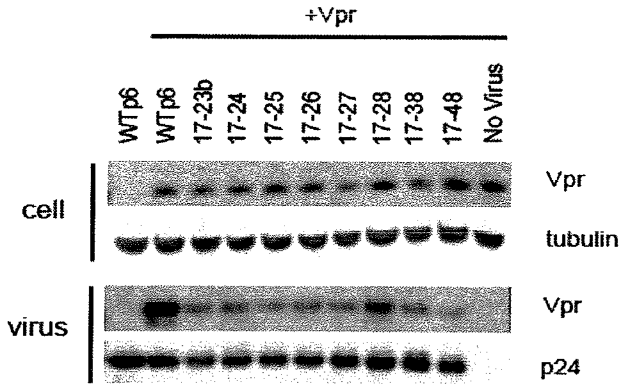

FIG. 9. P6 chimeric mutants package reduced amounts of HIV-1 Vpr. 293T were cotransfected with wild-type or chimeric p6 pNL4-3 and pcVpr.myc or empty vector. Cell lysate and virions were analyzed on an immunoblot probed with antibody against myc-tagged Vpr, HIV-1 p24 CA, or tubulin.

Figure 10A:
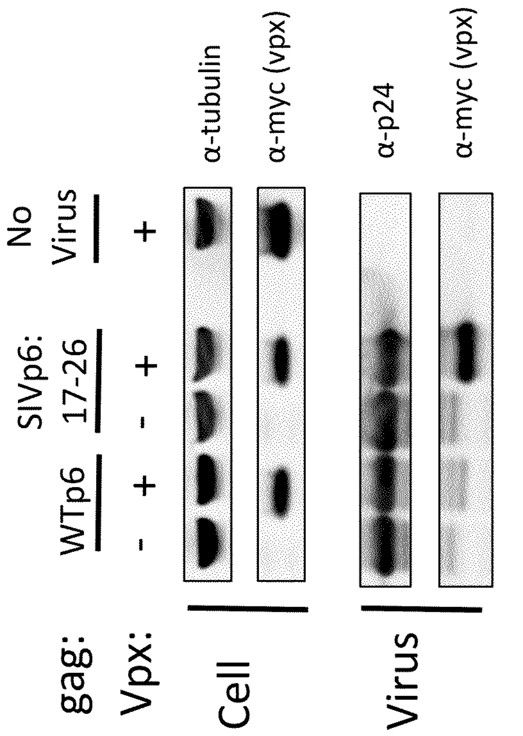
Figure 10B:
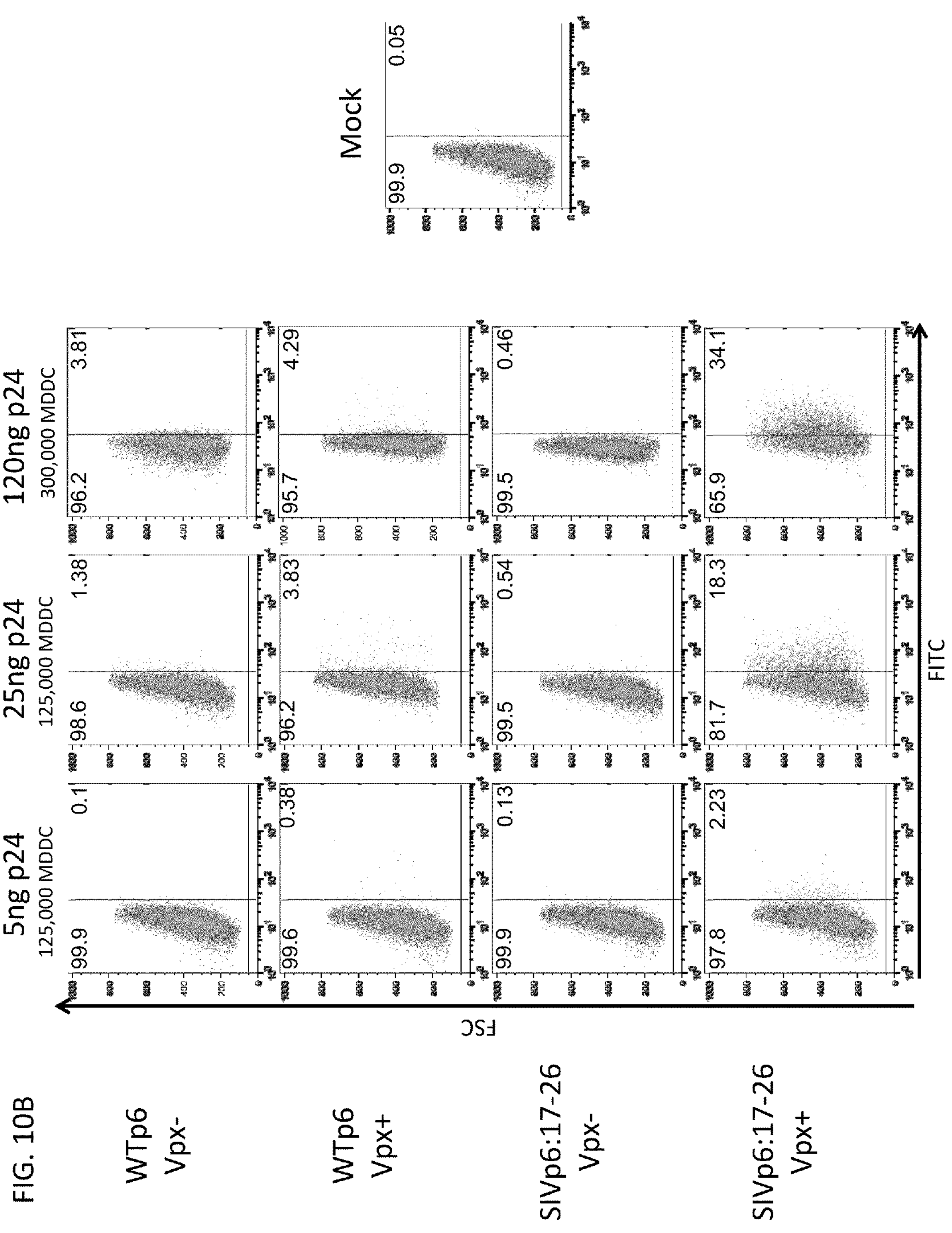
Figure 10C:
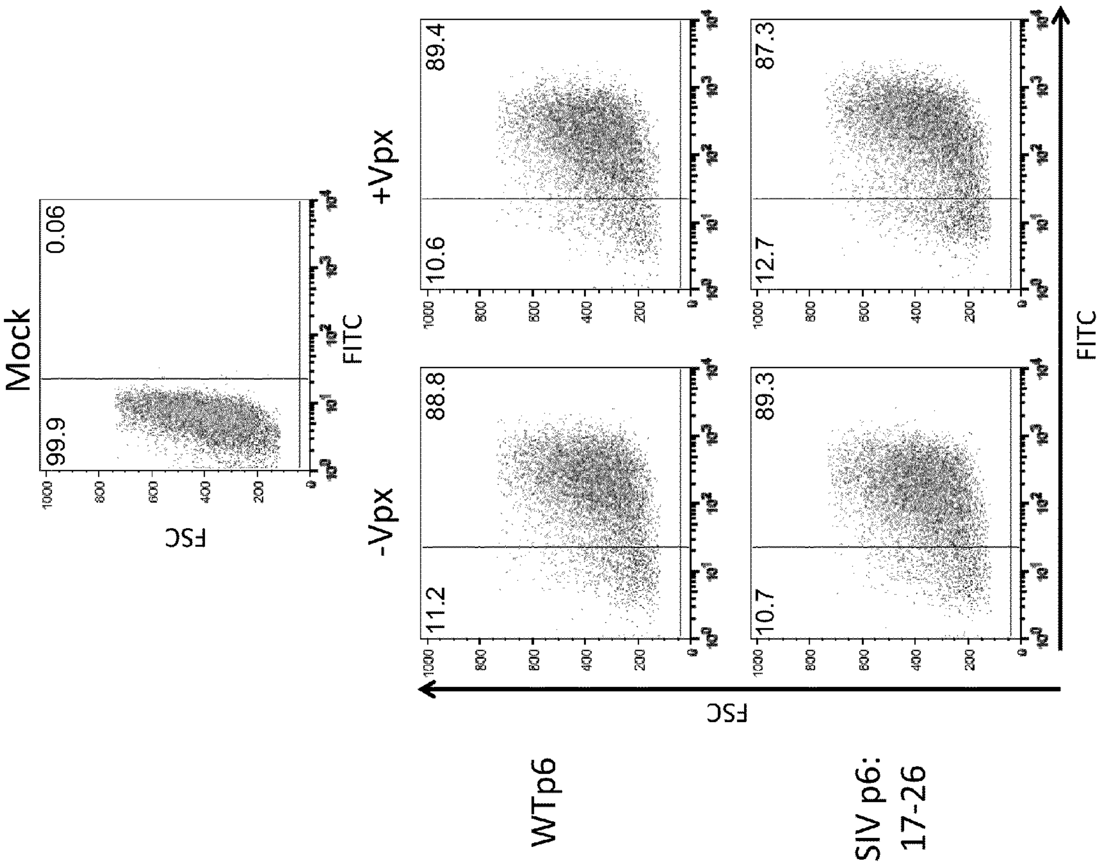

FIGS. 10A-C. Alteration of gag-pol to contain SIVp6 17-26 allows for packaging of Vpx and enhanced infection of MDDC. pGK-NGFR-IRES GFP lentivirus was generated by cotransfecting 293T with the proviral plasmid pGK-NGFR-IRES-GFP, the wild-type or p6 chimeric gag/pol packaging plasmid (pMDLg/pRRE or pMDLg-SIVp6_17-26, respectively), pcRSV-REV, pcVSV-G, and pcDNA6 or pcVpx.my-chis. A. Immunoblot analysis of Vpx packaging by lentivirus with wild-type or p6 chimeric gag. Cell lysates and pelleted virions were analyzed on an immunoblot probed with antibody to myc-tagged Vpx, HIV-2 p24 CA, or tubulin. B. Effect of Vpx packaging on MDDC infection by pGK-NGFR-IRES-GFP. MDDC ($1.25\times10^5$) were infected with pGK-NGFR-IRES-GFP at 5 or 25 ng p24, and MDDC ($3.0\times10^5$) were infected with 120 ng p24. Three days after infection, cells were collected and examined for GFP expression by FACS. C. Effect of Vpx packing on 293T infection by pGK-NGFR-IRES-GFP. 293T ($2.5\times10^5$) were infected with pGK-NGFR-IRES-GFP at 120 ng p24. Three days after infection, cells were collected and examined for GFP expression by FACS.

FIG. 11 shows nucleic and amino acid sequences of NL4.3 Sequence-Full Length with Chimeric p6, 17-26. The NL4.3 nucleic acid sequence (sense strand) is designated herein SEQ ID NO: 71 and the reverse strand is designated herein SEQ ID NO: 81. The amino acid sequences for GAG polyprotein precursor, POL polyprotein precursor, VIF protein, VPR protein, TAT protein, REV protein, VPU protein, and ENV polyprotein precursor are designated herein SEQ ID NOs: 72-80, respectively.

FIG. 12 shows nucleic and amino acid sequences of NL4.3 Sequence-Full Length, Wild Type. The wild type NL4.3 nucleic acid sequence (sense strand) is designated herein SEQ ID NO: 82 and the reverse strand is designated herein SEQ ID NO: 84. The amino acid sequence for wild type GAG polvprotein precursor is designated herein SEQ ID NO: 83 and the amino acid sequences for POL polyprotein precursor, VIF protein, VPR protein, TAT protein, REV protein, VPU protein, and ENV polyprotein precursor are designated herein SEQ ID NOs: 73-80, respectively.

FIG. 13 shows SIVmac239 Vpx wild-type and codon-optimized sequences. The amino acid sequence of SIVmac239 Vpx is designated herein SEQ ID NO: 85; the wild-type nucleic acid sequence encoding SIVmac239 Vpx is designated herein SEQ ID NO: 86; and the codon-optimized nucleic acid sequence encoding SIVmac239 Vpx is designated herein SEQ ID NO: 87.

Figure 14:
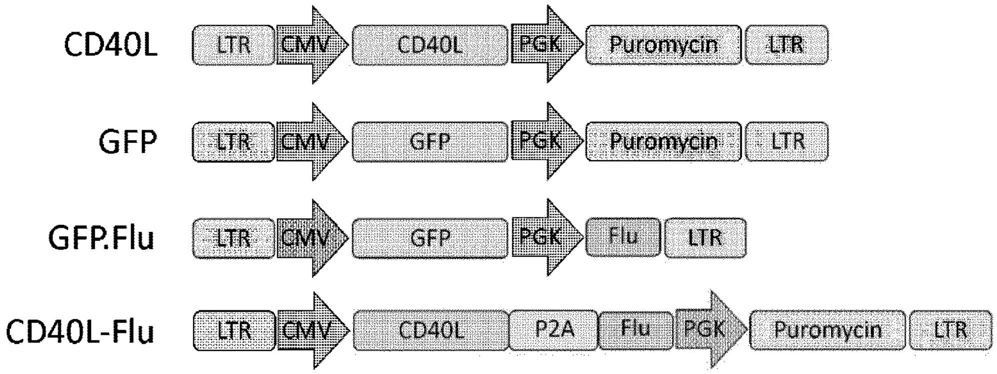

FIG. 14. The structure of LV vectors used to transduce DCs. The vectors express a CMV promoter-driven CD40L, GFP or CD40-P2A-Flu fusion protein (CD40L-Flu) and a PGK-driven puromycin resistance gene or ER-retention signal linked to Flu matrix amino acids 58-66, GILGFVFTL (Chang et al. Methods in Molecular Biology 614:161-171, 2010), (Flu). The vectors were produced as viruses that contained or lacked Vpx by transfection of 293T cells with the LV vector plasmid, the Gag/Pol packaging vector, HIV-1 Rev, and SIVmac Vpx expression vector pcVpx and pseudotyped with VSV-G.

Figure 15:
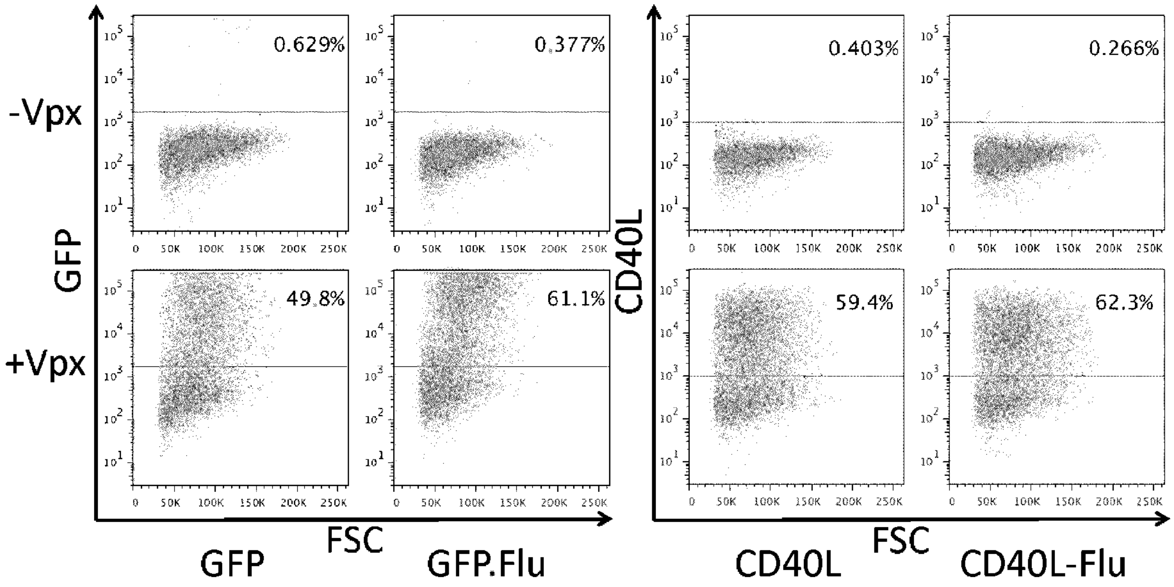

FIG. 15. Packaged Vpx allows for efficient DC transduction. DCs were transduced with LV vector indicated below each panel. Transduction efficiency was determined by analysis of GFP and CD40L expression. (Vpx+ constructs on top).

Figure 16A:
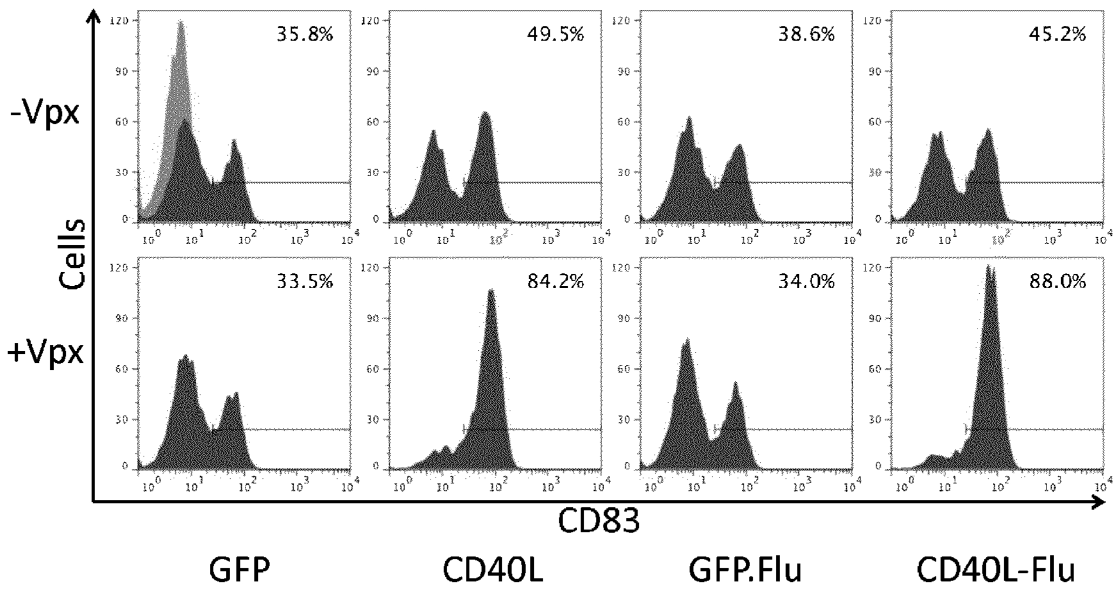
Figure 16B:
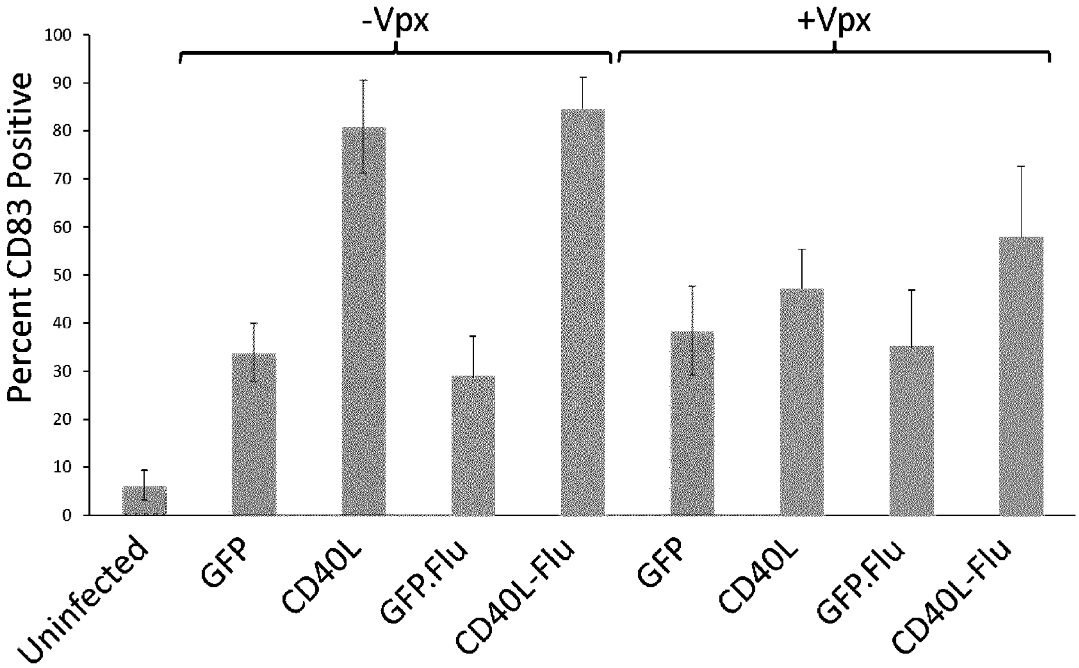
Figure 17A:
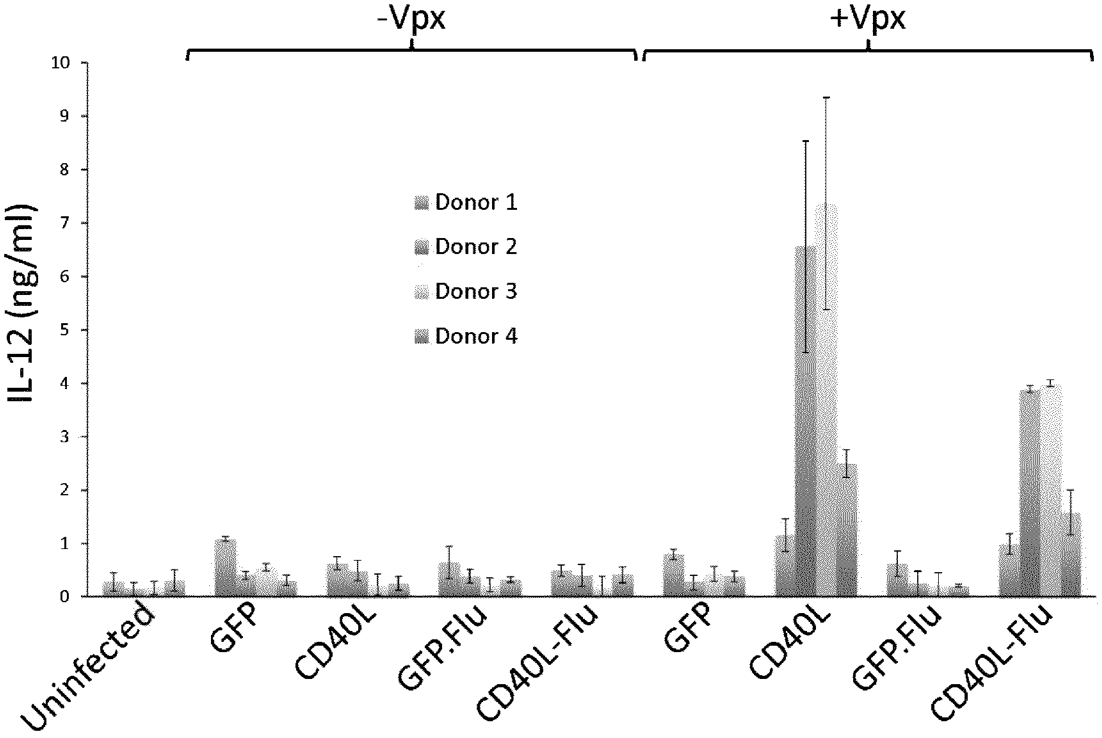
Figure 17B:
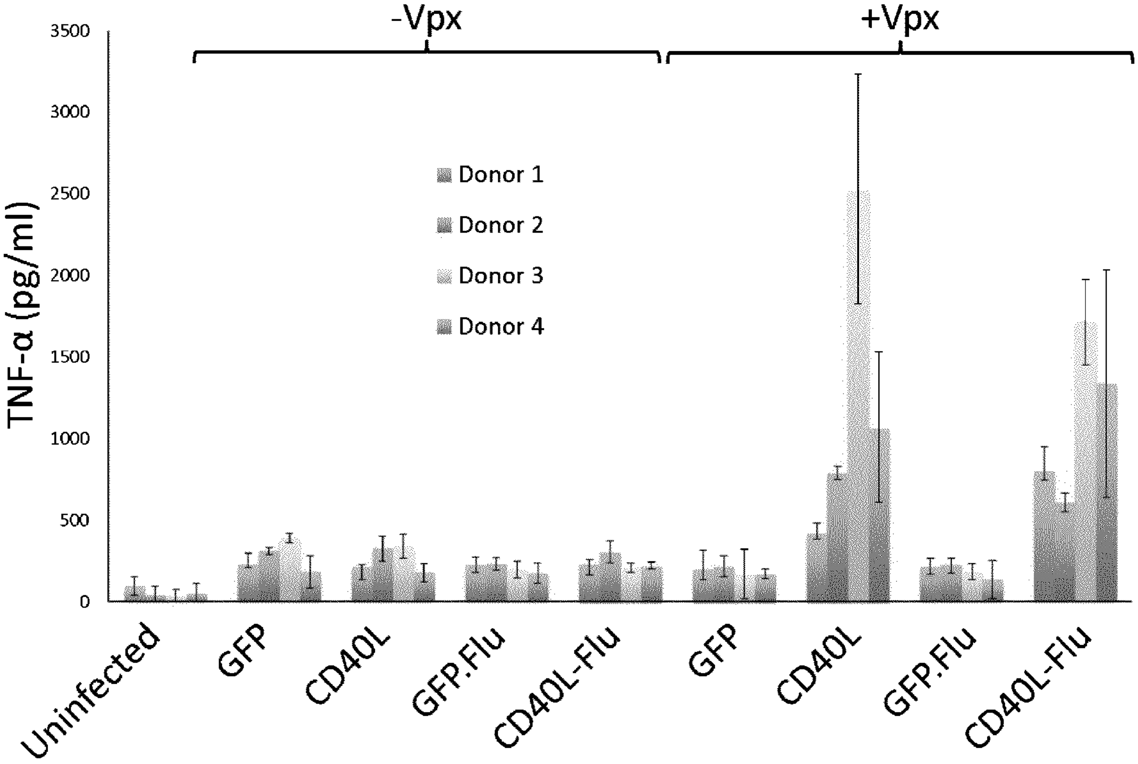

FIGS. 16A-B. Transduction of DCs with Vpx-containing vectors expressing CD40L induces DC maturation. DCs were transduced with the LV vectors that contained or lacked Vpx. After 48 and 72 h, the number of cells that expressed CD83 and CD86 were determined by flow cytometry. A. CD83 expression at 72 h post-transduction (Vpx+ constructs on top). CD83 expression for each infected DC population (blue) is contrasted against uninfected DCs (red). B. CD83 expression on the DC of four donors FIGS. 17A-B. Transduction of DCs with Vpx-containing LV vectors expressing CD40L induces a high level of IL-12. Cytokine bead array analysis on culture supernatants shows the IL-12 levels secreted by DCs from four different donors at 72 h post transduction with different LV constructs as compared to IL-12 levels secreted from uninfected DCs.

Figure 18:
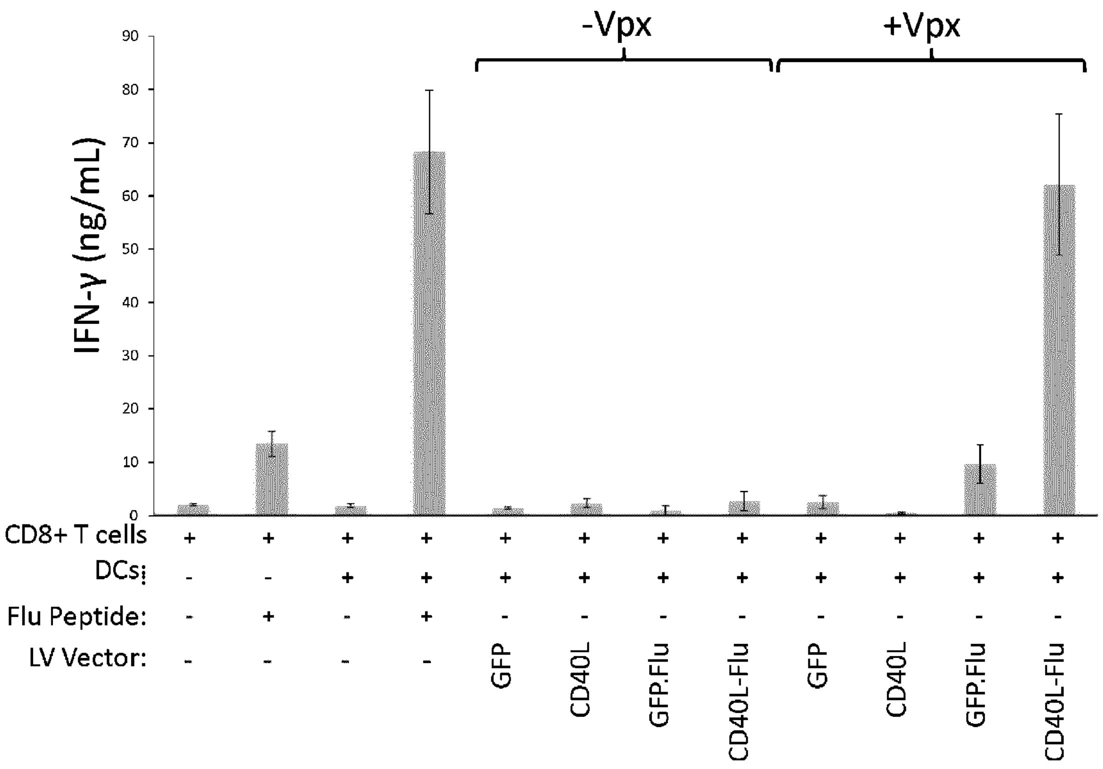

FIG. 18. DCs transduced with peptide and CD40L expressing lentiviral vectors activate a CTL response. Transduced DCs were cultured with CTL clone. After 24 h, the supernatant IFN-γ was quantified by CBA. As a control, the cells were pulsed with synthetic flu peptide, T cells alone, T cell clones co-cultured with uninfected DCs, and T cell clones co-cultured with uninfected DCs and then pulsed with synthetic flu peptide.

Figure 19:
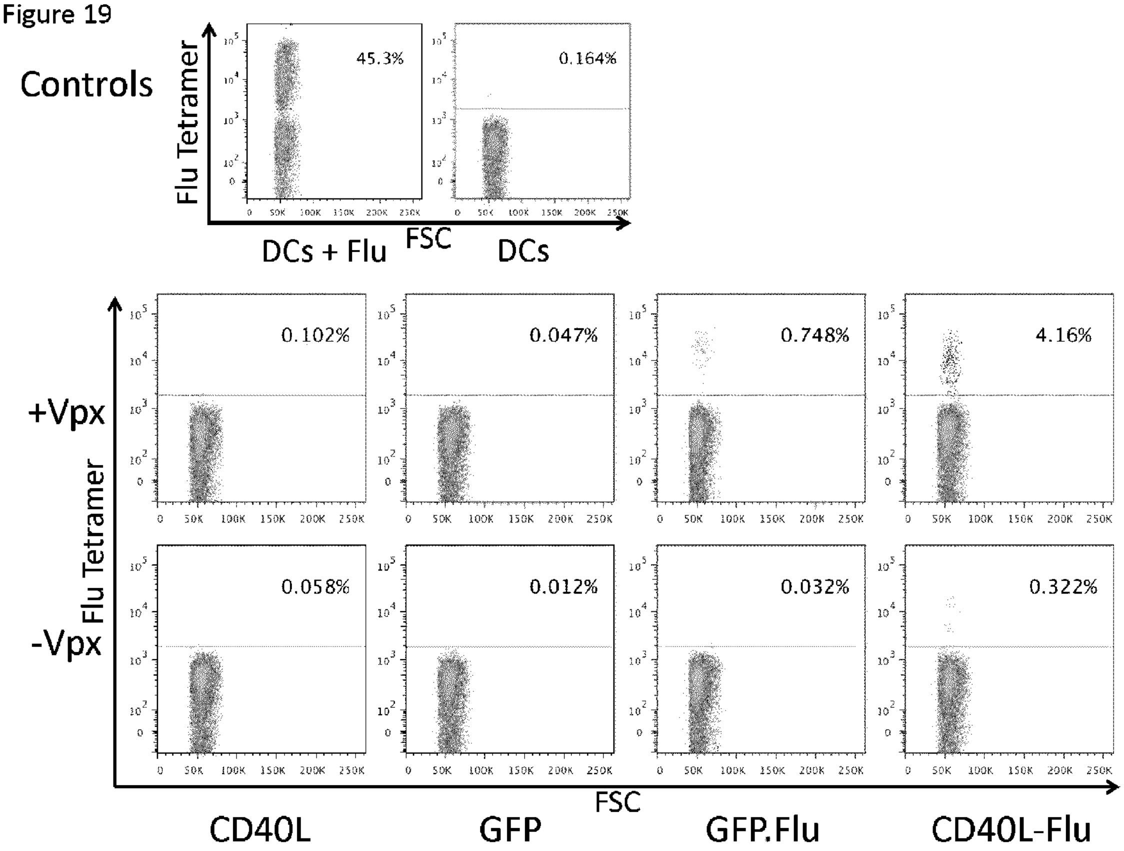

FIG. 19. DCs transduced with Vpx-containing LV vectors encoding CD40L and a peptide epitope from influenza enhance antigen-specific CD8+ memory T cell responses. To assess for a Flu-specific memory response, flu-specific tetramer staining was performed on autologous CD8+CD3+ T cells two weeks after being co-cultured with DCs transduced by different LV vector constructs (Vpx+ constructs on top). Analysis on T cells co-cultured with uninfected DC and uninfected DC pulsed with synthetic flu peptide were performed as controls.

Figure 20:
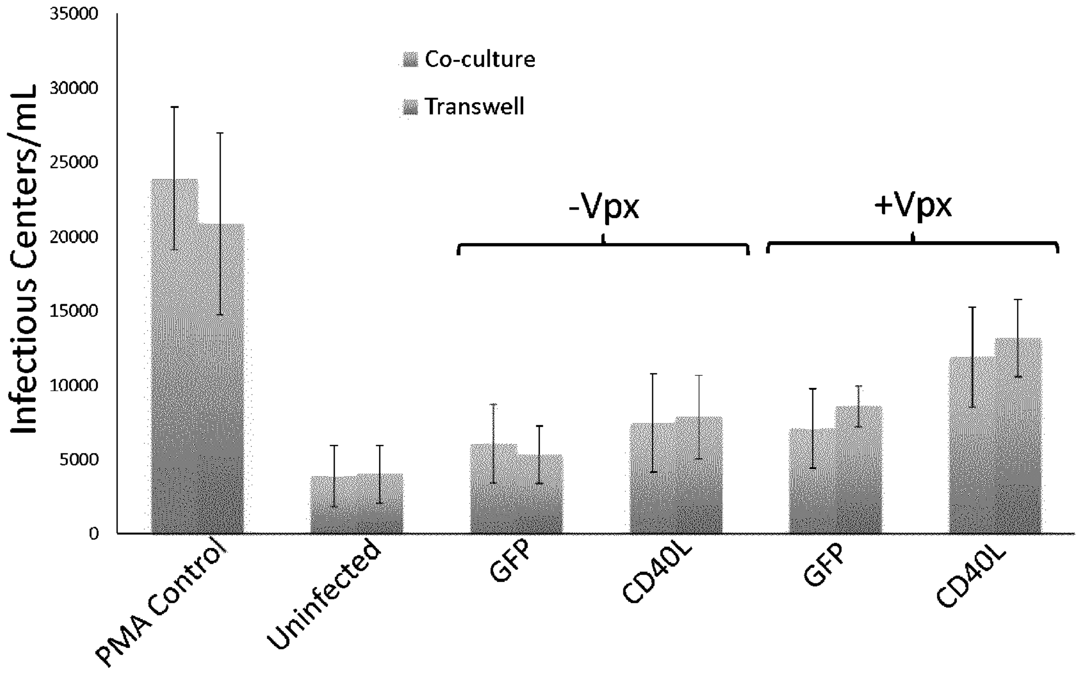

FIG. 20. DCs transduced with CD40L expressing lentiviral vectors packaged with Vpx induce reactivation of latent HIV from ACH-2 cells. DCs were transduced with indicated LV vector and then co-cultured with ACH-2 cells. Infectious virus in the supernatant was quantified by TZM-bl assay to assess reactivation of HIV-1 proviruses.

DETAILED DESCRIPTION OF THE INVENTION

The lentiviral Vpx accessory protein is thought to facilitate the infection of macrophages and dendritic cells by counteracting a yet unidentified host restriction. Although HIV-1 does not encode Vpx, it can be provided to monocyte-derived macrophages (MDM) and monocyte-derived dendritic cells (MDDC) through virus-like particles to dramatically enhance their susceptibility to HIV-1. Vpx and the related accessory protein Vpr are packaged into virions through a virus-specific interaction with the p6 carboxy-terminal domain of Gag. Here, the present inventors determined the minimal Vpx packaging motif of $SIVmac_{239}$ p6 and introduced this ten amino acid sequence into the p6 region of an infectious HIV-1 molecular clone. The chimeric virus efficiently packaged Vpx provided in trans and was substantially more infectious on MDDC and MDM. The present inventors further engineered the virus to express Vpx in cis by introducing the coding sequence in place of nef. The resulting virus produced less Vpx but was significantly enhanced in its infectivity on MDDC and MDM. Infection of the cells with Vpx-containing HIV-1 induced a potent type I interferon response. In a co-culture system, Vpx-containing HIV-1 was enhanced in its ability to be transmitted from MDDC to T cells. These findings suggest that Vpx could facilitate dendritic cell to T cell virus transmission in vivo. See, for example, Examples 1-2 herein below. The chimeric viruses described herein are envisioned as useful for the design of dendritic cell vaccines that induce an innate immune response in MDDC. Additionally, this approach can be useful for designing and generating engineered lentiviral vectors to produce virions that can be used to transduce these relatively resistant cells.

Further to the above, dendritic cells (DCs) are central to the induction of innate and adaptive immune responses yet are difficult to manipulate for therapeutic purposes due to their resistance to the introduction of transfection or transduction. Lentiviral vectors offer the ability to express genes stably in cells but are restricted in DCs by SAMHD1, a host factor that blocks retroviruses at reverse transcription. Examples 1 and 2 illustrate that the present inventors have developed lentiviral vectors and have used same to produce lentiviral vector virions that escape the restriction in DCs by virtue of packaging the SIV accessory protein Vpx. Such lentiviral vector virions comprise the lentiviral vector used to produce the virions. As a proof of principal, the present inventors have constructed lentiviral vectors that express an HLA A2-restricted influenza (Flu) peptide and immunostimulatory CD40L. As described in Example 3, the Flu peptide was expressed as a fusion protein with CD40L separated by the P2A self-cleaving peptide. Because CD40L is a type II transmembrane protein, this configuration places the carboxy-terminal Flu peptide in the endoplasmic reticulum (ER) where it can be shunted into the antigen presentation pathway during biosynthesis. The Vpx-containing vectors infected DCs 60-fold better than control Vpx-negative viruses. Vpx-containing vectors induced the DCs to mature as judged by CD83 and CD86 upregulation and induced Th1-skewing inflammatory cytokines. The transduced DCs, moreover, stimulated a Flu-peptide-specific CD8+ CTL clone and antigen-specific CD8+ cells in PBMC from healthy human donors, as assessed by IFNγ and tetramer staining. This system, therefore, provides the basis for the development of an effective DC-targeted anti-HIV-1 vaccine.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" is any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF), and particularly, the TNF bispecific modality demonstrated in U.S. Ser. No. 60/355,838 filed Feb. 13, 2002 incorporated herein in its entirety) or a toxin (e.g., ricin) or anti-mitotic or apoptotic agent or factor.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "adjuvant" refers to a compound or mixture that enhances the immune response, particularly to an antigen. An adjuvant can serve as a tissue depot that slowly releases the antigen and also as a lymphoid system activator that non-specifically enhances the immune response (Hood et al., *Immunology, Second Ed*, 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

As used herein, the term "immunomodulator" refers to an agent which is able to modulate an immune response. An example of such modulation is an enhancement of cell activation or of antibody production.

The term "effective amount" of an immunomodulator refers to an amount of an immunomodulator sufficient to enhance a vaccine-induced immune response, be it cell-mediated, humoral or antibody-mediated. An effective amount of an immunomodulator, if injected, can be in the range of about 0.1-1,000 μg, preferably 1-900 μg, more preferably 5-500 μg, for a human subject, or in the range of about 0.01-10.0 μg/Kg body weight of the subject animal. This amount may vary to some degree depending on the mode of administration, but will be in the same general range. If more than one immunomodulator is used, each one may be present in these amounts or the total amount may fall within this range. An effective amount of an antigen may be an amount capable of eliciting a demonstrable immune response in the absence of an immunomodulator. For many antigens, this is in the range of about 5-100 μg for a human subject. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The term "immunogen" refers to a substance that provokes an immune response.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N— or C— terminal of the peptide may however be contemplated, such as the chemical modification of the terminal to add a protecting group or the like, e.g. the amidation of the C— terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

As used herein, "pg" means picogram, "ng" means nanogram, "ug" or "μg" mean microgram, "mg" means milligram, "ul" or "μl" mean microliter, "ml" means milliliter, "l" means liter.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.,* 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |

-continued

TABLE OF CORRESPONDENCE

| SYMBOL | | |
|---|---|---|
| 1-Letter | 3-Letter | AMINO ACID |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background.

Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding protein or peptide sequences as provided herein, or comprising sequences which are degenerate thereto. DNA sequences having the nucleic acid sequence encoding the peptides of the invention are contemplated, including degenerate sequences thereof encoding the same, or a conserved or substantially similar, amino acid sequence. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in the sequences encoding the protein or peptide sequences of the invention, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Further, variants and subtypes of HIV are known and recognized and any such variants or subtype corresponding protein or peptide sequences of the invention (e.g., Vpx) are encompassed and contemplated herein.

Codon-optimized forms of vpx, for example, are used to advantage in the chimeric viruses and lentiviral vectors described herein.

The following is one example of various groupings of amino acids:

Amino acids with nonpolar R groups

Alanine, Valine, Leucine, Isoleucine, Proline, Phenylalanine, Tryptophan, Methionine Amino acids with uncharged polar R groups Glycine, Serine, Threonine, Cysteine, Tyrosine, Asparagine, Glutamine Amino acids with charged polar R groups (negatively charged at Ph 6.0)

Aspartic acid, Glutamic acid

Basic amino acids (positively charged at pH 6.0)

Lysine, Arginine, Histidine (at pH 6.0)

Another grouping may be those amino acids with phenyl groups:

Phenylalanine, Tryptophan, Tyrosine

Another grouping may be according to molecular weight (i.e., size of R groups):

| | | | |
|---|---|---|---|
| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:

Lys for Arg and vice versa such that a positive charge may be maintained;

Glu for Asp and vice versa such that a negative charge may be maintained;

Ser for Thr such that a free -OH can be maintained; and

Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense or stimulates a response that would be elicited on binding of a natural binder to a binding site.

The term 'assay' means any process used to measure a specific property of a compound or agent. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, or pharmaceutical agent that will elicit the biological or medical response of a subject that is being sought by a medical doctor or other clinician. As an example, with regard to immune response, the term "effective amount" is intended to include an effective amount of a compound or agent that will bring about a biologically meaningful increase in the amount of or extent of immune response, activation indicator and/or a biologically meaningful increase in the amount or extent of dendritic cell, T cell and/or B cell effects. The phrase "therapeutically effective amount" is used herein to mean an amount sufficient to promote, and preferably increase by at least about 30 percent, more preferably by at least 50 percent, most preferably by at least 90 percent, a clinically significant change in the immune response or immune cell indicator or response, or in a patient's response to an antigen, vaccine, or other immune agent, or in a patient's clearance of an infectious agent, or other feature of pathology such as for example, elevated activated T or B cells, activated DC cell count, fever or white cell count.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, the term "replication defective HIV vector" refers to a vector that encodes HIV peptides/proteins, but does not encode live virus.

HIV-1 comprises several major genes that encode structural proteins that are common to all lentiviruses and several nonstructural genes. The gag (group specific antigen) gene encodes the Gag polyprotein, which is processed during maturation to matrix protein (MA, p17), capsid protein (CA, p24), spacer peptide 1 (SP1, p2), nucleocapsid protein (NC, p7), spacer peptide 2 (SP2, p 1) and p6. These proteins provide for the physical infrastructure of the virus. The pol gene encodes viral enzymes for reverse transcriptase (RT), integrase (IN), and HIV protease (PR).

B. Detailed Disclosure

Lentiviral vectors are currently used to stably express proteins and small RNAs in a variety of cell types, including primary cells. However, myeloid cells, such as macrophages and dendritic cells, are relatively resistant to viral transduction by current lentiviral systems. Macrophages and dendritic cells are initiators of adaptive immune responses that confer immunity during vaccination and also mediate innate immune responses to pathogens. A lentiviral vector that efficiently transduces this cell type would facilitate improved expression of therapeutic proteins and RNAs in macrophages and dendritic cells. Methods using such lentiviral vectors would, moreover, be useful in the design of vaccines against HIV and/or other pathogens to induce a stronger immune response to the immunogen.

Vpx is a lentiviral accessory protein encoded by a subset of lentiviruses, including SIVmac of the rhesus macaque, but is absent from HIV-1. Consequently, the Vpx protein is packaged in SIV virions, but not in those of HIV-1 or lentiviral vectors based on HIV-1. In SIVmac, Vpx greatly enhances the ability of the virus to infect MDM and MDDC.

The invention described herein allows Vpx to be delivered and packaged into HIV-1 and HIV-1 derived lentiviral vector virions. To allow for Vpx packaging, the present inventors altered the p6 region of HIV-1 to encode a ten amino acid sequence in p6 of $SIVmac_{239}$. As defined herein, the ten amino acid sequence ($^{17}$DPAVDLLKNY$^{26}$) is the minimal sequence required for Vpx packaging. To generate the modified virions, 293 cells were transfected with lentiviral vector DNA, VSV-G expression plasmid and p6-chimeric HIV-1 Gag/pol expression vector. After 3 days, virus-containing culture supernatant is collected and frozen for later use. Details pertaining to making these constructs and virions and their composition are presented in, for example, the Drawings and Examples.

The constructs, vectors, and virions described herein can be used to improve the efficiency of transduction of myeloid cells by lentiviral vectors. The virions contain high copy numbers of functional Vpx, increasing their infectivity 100-fold in MDM and MDDC.

The present constructs, vectors, and virions differ in many respects when compared to those generated by other investigators. The introduction of the minimal Vpx packaging motif into HIV-1 based lentiviral vectors generates a new genus of lentiviral vector having unique structural features (e.g., nucleic acid sequences) that confer new and surprising functional properties, predominant among these properties is the enhanced ability of HIV-1 virions generated therefrom to infect MDM and MDDC. More particularly, the presence of the minimal Vpx packaging motif in the new genus of HIV-1 based lentiviral vectors makes it possible to package Vpx supplied in trans into virus like particles generated therefrom that can promote HIV-1 infection of MDM and MDDC. In a further embodiment, the present inventors have modified the new genus of HIV-1 based lentiviral vectors comprising the minimal Vpx packaging motif to include SIV vpx. Accordingly, in a second generation of HIV-1 based lentiviral vectors, Vpx is supplied in cis, thus eliminating the need for additional constructs/vectors/VLPs encoding Vpx. Methods described herein thus produce lentiviral vector particles which comprise packaged Vpx protein.

The methods described herein can be used to generate lentiviral vectors that express a protein or RNA of interest that have an improved ability to infect MDM and MDDC. This is useful for basic research into signal transduction pathways in these specific cells types. The approach may also be used advantageously in the clinic for gene therapy to achieve stable expression of protein or RNA in vivo for the treatment of genetic deficiencies.

The method may also find application for vaccination approaches that rely on transduction of MDM and MDDC. The chimeric vectors, constructs, and VLPs described herein will enhance the delivery and subsequent expression of antigens in such cells and thus, lead to more effective vaccine responses. Indeed, current efforts to generate dendritic cell-based cancer vaccines would be significantly enhanced by incorporating the chimeric vectors and constructs described herein.

Both HIV-1 p6 and pNL.Ba.L are identical to the HIV-1 reference strain NL4-3, as present in Genbank and presented herein. The essential genes of HIV-1 p6 and pNL.Ba.L with respect to the present chimeric vectors and constructs include the following:

GAG Polyprotein Precursor: 168-1670
Nucleotide Sequence (SEQ ID NO: 24)

```
atg ggtgcgagag cgtcggtatt aagcggggga gaattagata aatgggaaaa aattcggtta aggccagggg
gaaagaaaca atataaacta aaacatatag tatgggcaag cagggagcta gaacgattcg cagttaatcc tggcctttta
gagacatcag aaggctgtag acaaatactg ggacagctac aaccatccct tcagacagga tcagaagaac ttagatcatt
atataataca atagcagtcc tctattgtgt gcatcaaagg atagatgtaa aagacaccaa ggaagcctta gataagatag
aggaagagca aaacaaaagt aagaaaaagg cacagcaagc agcagctgac acaggaaaca acagccaggt cagccaaaat
taccctatag tgcagaacct ccaggggcaa atggtacatc aggccatatc acctagaact ttaaatgcat gggtaaaagt
agtagaagag aaggctttca gcccagaagt aatacccatg ttttcagcat tatcagaagg agccacccca caagatttaa
ataccatgct aaacacagtg gggggacatc aagcagccat gcaaatgtta aaagagacca tcaatgagga agctgcagaa
tgggatagat tgcatccagt gcatgcaggg cctattgcac caggccagat gagagaacca aggggaagtg acatagcagg
aactactagt acccttcagg aacaaatagg atggatgaca cataatccac ctatcccagt aggagaaatc tataaaagat
ggataatcct gggattaaat aaaatagtaa gaatgtatag ccctaccagc attctggaca taagacaagg accaaaggaa
ccctttagag actatgtaga ccgattctat aaaactctaa gagccgagca agcttcacaa gaggtaaaaa attggatgac
agaaaccttg ttggtccaaa atgcgaaccc agattgtaag actattttaa aagcactggg accaggagcg acactagaag
aaatgatgac agcatgtcag ggagtggggg gacccggcca taaagcaaga gttttggctg aagcaatgag ccaagtaaca
aatccagcta ccataatgat acagaaaggc aattttagga accaaagaaa gactgttaag tgtttcaatt gtggcaaaga
agggcacata gccaaaaatt gcagggcccc taggaaaaag ggctgttgga aatgtggaaa ggaaggacac caaatgaaag
attgtactga gagacaggct aattttttag ggaagatctg gccttcccac aagggaaggc cagggaattt tcttcagagc
agaccagagc caacagcccc accagaagag agcttcaggt ttggggaaga gacaacaact ccctctcaga ggcaggagcc
gatagacaag gaactgtatc ctttagcttc cctcagatca ctctttggca gcgacccctc gtcacaataa agataggggg
```

Translation (SEQ ID NO: 25)

```
MGARASVLSGGELDKWEKIRLRPGGKKQYKLKHIVWASRELERFAVNPGLLETSEGCRQILGQLQPSLQTGSEELRSLYNTIAVLYCVH
QRIDVKDTKEALDKIEEEQNKSKKKAQQAAADTGNNSQVSQNYPIVQNLQGQMVHQAISPRTLNAWVKVVEEKAFSPEVIPMFSALSEG
ATPQDLNTMLNTVGGHQAAMQMLKETINEEAAEWDRLHPVHAGPIAPGQMREPRGSDIAGTTSTLQEQIGWMTHNPPIPVGEIYKRWII
LGLNKIVRMYSPTSILDIRQGPKEPFRDYVDRFYKTLRAEQASQEVKNWMTETLLVQNANPDCKTILKALGPGATLEEMMTACQGVGGP
GHKARVLAEAMSQVTNPATIMIQKGNFRNQRKTVKCFNCGKEGHIAKNCRAPRKKGCWKCGKEGHQMKDCTERQANFLGKIWPSHKGRP
GNFLQSRPEPTAPPEESFRFGEETTTPSQRQEPIDKELYPLASLRSLFGSDPSSQ
```

POL Polyprotein Precursor: 1463-4474
Nucleotide Sequence (SEQ ID NO: 26)

```
ttttttag ggaagatctg gccttcccac aagggaaggc cagggaattt tcttcagagc agaccagagc caacagcccc
accagaagag agcttcaggt ttggggaaga gacaacaact ccctctcaga ggcaggagcc gatagacaag gaactgtatc
ctttagcttc cctcagatca ctctttggca gcgacccctc gtcacaataa agataggggg gcaattaaag gaagctctat
tagatacagg agcagatgat acagtattag aagaaatgaa tttgccagga agatggaaac caaaaatgat agggggaatt
ggaggtttta tcaaagtaag acagtatgat cagatactca tagaaatctg cggacataaa gctataggta cagtattagt
aggacctaca cctgtcaaca taattggaag aaatctgttg actcagattg gctgcacttt aaattttccc attagtccta
ttgagactgt accagtaaaa ttaaagccag gaatggatgg cccaaaagtt aaacaatggc cattgacaga agaaaaaata
aaagcattag tagaaatttg tacagaaatg gaaaaggaag gaaaaatttc aaaaattggg cctgaaaatc catacaatac
tccagtattt gccataaaga aaaaagacag tactaaatgg agaaaattag tagatttcag agaacttaat aagagaactc
aagatttctg ggaagttcaa ttaggaatac cacatcctgc agggttaaaa cagaaaaaat cagtaacagt actggatgtg
ggcgatgcat atttttcagt tcccttagat aaagacttca ggaagtatac tgcatttacc atacctagta taaacaatga
gacaccaggg attagatatc agtacaatgt gcttccacag ggatggaaag gatcaccagc aatattccag tgtagcatga
caaaaatctt agagcctttt agaaaacaaa atccagacgt agtcatctat caatacatgg atgatttgta tgtaggatct
gacttagaaa tagggcagca tagaacaaaa atagaggaac tgagacaaca tctgttgagg tggggattta ccacaccaga
caaaaaacat cagaaagaac ctccattcct ttggatgggt tatgaactcc atcctgataa atggacagta cagcctatag
tgctgccaga aaaggacagc tggactgtca atgacataca gaaattagtg ggaaaattga attgggcaag tcagatttat
gcagggatta aagtaaggca attatgtaaa cttcttaggg gaaccaaagc actaacagaa gtagtaccac taacagaaga
agcagagcta gaactggcag aaaacaggga gattctaaaa gaaccggtac atggagtgta ttatgaccca tcaaaagact
taatagcaga aatacagaag caggggcaag gccaatggac atatcaaatt tatcaagagc catttagaaa tctgaaaaca
ggaaagtatg caagaatgaa gggtgcccac actaatgatg tgaaacaatt aacagaggca gtacaaaaaa tagccacaga
aagcatagta atatggggaa agactcctaa atttaaatta cccatacaaa aggaaacatg ggaagcatgg tggacagagt
attggcaagc cacctggatt cctgagtggg agtttgtcaa tacccctccc ttagtgaagt tatggtacca gttagagaaa
gaacccataa taggagcaga aactttctat gtagatgggg cagccaatag ggaaactaaa ttaggaaaag caggatatgt
aactgacaga ggaagacaaa aagttgtccc cctaacggac acaacaaatc agaagactga gttacaagca attcatctag
ctttgcagga ttcgggatta gaagtaaaca tagtgacaga ctcacaatat gcattgggaa tcattcaagc acaaccagat
aagagtgaat cagagttagt cagtcaaata atagagcagt taataaaaaa ggaaaaagtc tacctggcat gggtaccagc
acacaaagga attggaggaa atgaacaagt agataaattg gtcagtgctg gaatcaggaa agtactattt ttagatggaa
tagataaggc ccaagaagaa catgagaaat atcacagtaa ttggagagca atggctagtg attttaacct accacctgta
```

-continued gtagcaaaag aaatagtagc cagctgtgat aaatgtcagc taaaagggga agccatgcat ggacaagtag actgtagccc
aggaatatgg cagctagatt gtacacattt agaaggaaaa gttatcttgg tggcagttca tgtagccagt ggatatatag
aagcagaagt aattccagca gagacagggc aagaaacagc atacttcctc ttaaaattag caggaagatg gccagtaaaa
acagtacata cagacaatgg cagcaatttc accagtacta cagttaaggc cgcctgttgg tgggcgggaa tcaagcagga
atttggcatt ccctacaatc cccaaagtca aggagtaata gaatctatga ataaagaatt aaagaaaatt ataggacagg
taagagatca ggctgaacat cttaagacag cagtacaaat ggcagtattc atccacaatt ttaaaagaaa aggggggatt
ggggggtaca gtgcagggga aagaatagta gacataatag caacagacat acaaactaaa gaattacaaa aacaaattac
aaaaattcaa aattttcggg tttattacag ggacagcaga gatccagttt ggaaaggacc agcaaagctc ctctggaaag
gtgaaggggc agtagtaata caagataata gtgacataaa agtagtgcca agaagaaaag caaagatcat cagggattat
ggaaaacaga tggcaggtga tgattgtgtg gcaagtagac aggatgagga ttaa Translation (SEQ ID NO: 27)

FFREDLAFPQGKAREFSSEQTRANSPTRRELQVWGRDNNSLSEAGADRQGTVSFSFPQITLWQRPLVTIKIGGQLKEALLDTGADDTVL
EEMNLPGRWKPKMIGGIGGFIKVRQYDQILIEICGHKAIGTVLVGPTPVNIIGRNLLTQIGCTLNFPISPIETVPVKLKPGMDGPKVKQ
WPLTEEKIKALVEICTEMEKEGKISKIGPENPYNTPVFAIKKKDSTKWRKLVDFRELNKRTQDFWEVQLGIPHPAGLKQKKSVTVLDVG
DAYFSVPLDKDFRKYTAFTIPSINNETPGIRYQYNVLPQGWKGSPAIFQCSMTKILEPFRKQNPDVVIYQYMDDLYVGSDLEIGQHRTK
IEELRQHLLRWGFTTPDKKHQKEPPFLWMGYELHPDKWTVQPIVLPEKDSWTVNDIQKINGKLNWASQIYAGIKVRQLCKLLRGTKALT
EVVPLTEEAELELAENREILKEPVHGVYYDPSKDLIAEIQKQGQGQWTYQIYQEPFRNLKTGKYARMKGAHTNDVKQLTEAVQKIATES
IVIWGKTPKFKLPIQKETWEAWWTEYWQATWIPEWEFVNTPPLVKLWYQLEKEPIIGAETFYVDGAANRETKLGKAGYVTDRGRQKVVP
LTDTTNQKTELQAIHLALQDSGLEVNIVTDSQYALGIIQAQPDKSESELVSQIIEQLIKKEKVYLAWVPAHKGIGGNEQVDKLVSAGIR
KVLFLDGIDKAQEEHEKYHSNWRAMASDFNLPPVVAKEIVASCDKCQLKGEAMHGQVDCSPGIWQLDCTHLEGKVILVAVHVASGYIEA
EVIPAETGQETAYFLLKLAGRWPVKTVHTDNGSNFTSTTVKAACWWAGIKQEFGIPYNPQSQGVIESMNKELKKIIGQVRDQAEHLKTA
VQMAVFIHNFKRKGGIGGYSAGERIVDIIATDIQTKELQKQITKIQNFRVYYRDSRDPVWKGPAKLLWKGEGAVVIQDNSDIKVVPRRK
AKIIRDYGKQMAGDDCVASRQDED

VIF Protein: 4419-4997
Nucleotide Sequence (SEQ ID NO: 28)

at ggaaaacaga tggcaggtga tgattgtgtg gcaagtagac aggatgagga ttaacacatg gaaaagatta
gtaaaacacc atatgtatat ttcaaggaaa gctaaggact ggttttatag acatcactat gaaagtacta atccaaaaat
aagttcagaa gtacacatcc cactagggga tgctaaatta gtaataacaa catattgggg tctgcataca ggagaaagag
actggcattt gggtcaggga gtctccatag aatggaggaa aaagagatat agcacacaag tagaccctga cctagcagac
caactaattc atctgcacta ttttgattgt ttttcagaat ctgctataag aaataccata ttaggacgta tagttagtcc
taggtgtgaa tatcaagcag gacataacaa ggtaggatct ctacagtact tggcactagc agcattaata aaaccaaaac
agataaagcc acctttgcct agtgttagga aactgacaga ggacagatgg aacaagcccc agaagaccaa gggccacaga
gggagccata caacgaatgg acactag Translation (SEQ ID NO: 29)

MENRWQVMIVWQVDRMRINTWKRLVKHHMYISRKAKDWFYRHHYESTNPKISSEVHIPLGDAKLVITTYWGLHTGERDWHLGQGVSIEW
RKKRYSTQVDPDLADQLIHLHYFDCFSESAIRNTILGRIVSPRCEYQAGHNKVGSLQYLALAALIKPKQIKPPLPSVRKLTEDRWNKPQ
KTKGHRGSHTTNGH

VPR Protein: 4937-5227
Nucleotide Sequence (SEQ ID NO: 30)

atgg aacaagcccc agaagaccaa gggccacaga gggagccata caacgaatgg acactagagc ttttagagga
acttaagagt gaagctgtta gacattttcc taggatatgg ctccataact taggacgaca tatctatgaa acttacgggg
atacttgggc aggagtggaa gccataataa gaattctgca acaactgccg tttatccatt tcagaattgg gtgtcgacat
agcagaatag gcgttactcg acagaggaga gcaagaaatg gagccagtag atcctag Translation (SEQ ID NO: 31)

MEPVDPRLEPWKHPGSQPKTACTNCYCKKCCFHCQVCFMTKALGISYGRKKRRQRRRAHQNSQTHQASLSKQPTSQSRGDPTGPKE

TAT Protein: 5208-7792 (translate 5208-5422, 7747-7792)
Nucleotide Sequence (SEQ ID NO: 32)

atg gagccagtag atcctagact agagccctgg aagcatccag gaagtcagcc taaaactgct tgtaccaatt
gctattgtaa aaagtgttgc tttcattgcc aagtttgttt catgacaaaa gccttaggca tctcctatgg caggaagaag
cggagacagc gacgaagagc tcatcagaac agtcagactc atcaagcttc tctatcaaag cagtaagtag tacatgtaat
gcaacctata atagtagcaa tagtagcatt agtagtagca ataataatag caatagttgt gtggtccata gtaatcatag
aatataggaa aatattaaga caaagaaaaa tagacaggtt aattgataga ctaatagaaa gagcagaaga cagtggcaat
gagagtgaag gagaagtatc agcacttgtg gagatggggg tggaaatggg gcaccatgct ccttgggata ttgatgatct
gtagtgctac agaaaaattg tgggtcacag tctattatgg ggtacctgtg tggaaggaag caaccaccac tctattttgt
gcatcagatg ctaaagcata tgatacagag gtacataatg tttgggccac acatgcctgt gtacccacag accccaaccc
acaagaagta gtattggtaa atgtgacaga aaattttaac atgtggaaag atgacatggt agaacagatg catgaggata
taatcagttt atgggatcaa agcctaaagc catgtgtaaa attaacccca ctctgtgtta gtttaaagtg cactgatttg
aagaatgata ctaataccaa tagtagtagc gggagaatga taatggagaa aggagagata aaaaactgct ctttcaatat
cagcacaagc ataagagata aggtgcagaa agaatatgca ttcttttata aacttgatat agtaccaata gataatacca
gctataggtt gataagttgt aacacctcag tcattacaca ggcctgtcca aaggtatcct ttgagccaat tcccatacat
tattgtgccc cggctggttt tgcgattcta aaatgtaata ataagacgtt caatggaaca ggaccatgta caaatgtcag
cacagtacaa tgtacacatg gaatcaggcc agtagtatca actcaactgc tgttaaatgg cagtctagca gaagaagatg
tagtaattag atctgccaat ttcacagaca atgctaaaac cataatagta cagctgaaca catctgtaga aattaattgt
acaagaccca acaacaatac aagaaaaagt atccgtatcc agaggggacc agggagagca tttgttacaa taggaaaaat
aggaaatatg agacaagcac attgtaacat tagtagagca aaatggaatg ccactttaaa acagatagct agcaaattaa
gagaacaatt tggaaataat aaaacaataa tctttaagca atcctcagga ggggacccag aaattgtaac gcacagtttt
aattgtggag gggaattttt ctactgtaat tcaacacaac tgtttaatag tacttggttt aatagtactt ggagtactga
agggtcaaat aacactgaag gaagtgacac aatcacactc ccatgcagaa taaaacaatt tataaacatg tggcaggaag
taggaaaagc aatgtatgcc cctcccatca gtggacaaat tagatgttca tcaaatatta ctgggctgct attaacaaga -continued gatggtggta ataacaacaa tgggtccgag atcttcagac ctggaggagg cgatatgagg gacaattgga gaagtgaatt
atataaatat aaagtagtaa aaattgaacc attaggagta gcacccacca aggcaaagag aagagtggtg cagagagaaa
aaagagcagt gggaatagga gctttgttcc ttgggttctt gggagcagca ggaagcacta tgggcgcagc gtcaatgacg
ctgacggtac aggccagaca attattgtct gatatagtgc agcagcagaa caatttgctg agggctattg aggcgcaaca
gcatctgttg caactcacag tctggggcat caaacagctc caggcaagaa tcctggctgt ggaaagatac ctaaaggatc
aacagctcct ggggatttgg ggttgctctg gaaaactcat ttgcaccact gctgtgcctt ggaatgctag ttggagtaat
aaatctctgg aacagatttg gaataacatg acctggatgg agtgggacag agaaattaac aattacacaa gcttaataca
ctccttaatt gaagaatcgc aaaaccagca agaaaagaat gaacaagaat tattggaatt agataaatgg gcaagtttgt
ggaattggtt taacataaca aattggctgt ggtatataaa attattcata atgatagtag gaggcttggt aggtttaaga
atagtttttg ctgtactttc tatagtgaat agagttaggc agggatattc accattatcg tttcagaccc acctcccaat
cccgagggga cccgacaggc ccgaaggaat ag Translation (SEQ ID NO: 33)

MEPVDPRLEPWKHPGSQPKTACTNCYCKKCCFHCQVCFMTKALGISYGRKKRRQRRRAHQNSQTHQASLSKQPTSQSRGDPTGPKE

REV Protein: 5347-8021 (translate 5347-5422, 7747-8021)
Nucleotide Sequence (SEQ ID NO: 34)

atgg caggaagaag cggagacagc gacgaagagc tcatcagaac agtcagactc atcaagcttc tctatcaaag
cagtaagtag tacatgtaat gcaacctata atagtagcaa tagtagcatt agtagtagca ataataatag caatagttgt
gtggtccata gtaatcatag aatataggaa aatattaaga caaagaaaaa tagacaggtt aattgataga ctaatagaaa
gagcagaaga cagtggcaat gagagtgaag gagaagtatc agcacttgtg gagatggggg tggaaatggg gcaccatgct
ccttgggata ttgatgatct gtagtgctac agaaaaattg tgggtcacag tctattatgg ggtacctgtg tggaaggaag
caaccaccac tctattttgt gcatcagatg ctaaagcata tgatacagag gtacataatg tttgggccac acatgcctgt
gtacccacag accccaaccc acaagaagta gtattggtaa atgtgacaga aaattttaac atgtggaaag atgacatggt
agaacagatg catgaggata taatcagttt atgggatcaa agcctaaagc catgtgtaaa attaacccca ctctgtgtta
gtttaaagtg cactgatttg aagaatgata ctaataccaa tagtagtagc gggagaatga taatggagaa aggagagata
aaaaactgct ctttcaatat cagcacaagc ataagagata aggtgcagaa agaatatgca ttcttttata aacttgatat
agtaccaata gataatacca gctataggtt gataagttgt aacacctcag tcattacaca ggcctgtcca aaggtatcct
ttgagccaat tcccatacat tattgtgccc cggctggttt tgcgattcta aaatgtaata ataagacgtt caatggaaca
ggaccatgta caaatgtcag cacagtacaa tgtacacatg gaatcaggcc agtagtatca actcaactgc tgttaaatgg
cagtctagca gaagaagatg tagtaattag atctgccaat ttcacagaca atgctaaaac cataatagta cagctgaaca
catctgtaga aattaattgt acaagaccca acaacaatac aagaaaaagt atccgtatcc agaggggacc agggagagca
tttgttacaa taggaaaaat aggaaatatg agacaagcac attgtaacat tagtagagca aaatggaatg ccactttaaa
acagatagct agcaaattaa gagaacaatt tggaaataat aaaacaataa tctttaagca atcctcagga ggggacccag
aaattgtaac gcacagtttt aattgtggag gggaattttt ctactgtaat tcaacacaac tgtttaatag tacttggttt
aatagtactt ggagtactga agggtcaaat aacactgaag gaagtgacac aatcacactc ccatgcagaa taaaacaatt
tataaacatg tggcaggaag taggaaaagc aatgtatgcc cctcccatca gtggacaaat tagatgttca tcaaatatta
ctgggctgct attaacaaga gatggtggta ataacaacaa tgggtccgag atcttcagac ctggaggagg cgatatgagg
gacaattgga gaagtgaatt atataaatat aaagtagtaa aaattgaacc attaggagta gcacccacca aggcaaagag
aagagtggtg cagagagaaa aaagagcagt gggaatagga gctttgttcc ttgggttctt gggagcagca ggaagcacta
tgggcgcagc gtcaatgacg ctgacggtac aggccagaca attattgtct gatatagtgc agcagcagaa caatttgctg
agggctattg aggcgcaaca gcatctgttg caactcacag tctggggcat caaacagctc caggcaagaa tcctggctgt
ggaaagatac ctaaaggatc aacagctcct ggggatttgg ggttgctctg gaaaactcat ttgcaccact gctgtgcctt
ggaatgctag ttggagtaat aaatctctgg aacagatttg gaataacatg acctggatgg agtgggacag agaaattaac
aattacacaa gcttaataca ctccttaatt gaagaatcgc aaaaccagca agaaaagaat gaacaagaat tattggaatt
agataaatgg gcaagtttgt ggaattggtt taacataaca aattggctgt ggtatataaa attattcata atgatagtag
gaggcttggt aggtttaaga atagtttttg ctgtactttc tatagtgaat agagttaggc agggatattc accattatcg
tttcagaccc acctcccaat cccgagggga cccgacaggc ccgaaggaat agaagaagaa ggtggagaga gaggcagaga
cagatccatt cgattagtga acggatcctt agcacttatc tgggacgatc tgcggagcct gtgcctcttc agctaccacc
gcttgagaga cttactcttg attgtaacga ggattgtgga acttctggga cgcagggggt gggaagccct caaatattgg
tggaatctcc tacagtattg gagtcaggaa ctaaagaata g Translation (SEQ ID NO: 35)

MAGRSGDSDEELIRTVRLIKLLYQSNPPPNPEGTRQARRNRRRRWRERQRQIHSISERILSTYLGRSAEPVPLQLPPLERLTLDCNEDC
GTSGTQGVGSPQILVESPTVLESGTKE

VPU Protein: 5439-5684
Nucleotide Sequence (SEQ ID NO: 36)

at gcaacctata atagtagcaa tagtagcatt agtagtagca ataataatag caatagttgt gtggtccata
gtaatcatag aatataggaa aatattaaga caaagaaaaa tagacaggtt aattgataga ctaatagaaa gagcagaaga
cagtggcaat gagagtgaag gagaagtatc agcacttgtg gagatggggg tggaaatggg gcaccatgct ccttgggata
ttgatgatct gtag Translation (SEQ ID NO: 37)

MQPIIVAIVALVVAIIIAIVVWSIVIIEYRKILRQRKIDRLIDRLIERAEDSGNESEGEVSALVEMGVEMGHHAPWDIDDL

ENV Polyprotein Precursor: 5599-8163
Nucleotide Sequence (SEQ ID NO: 38)

at gagagtgaag gagaagtatc agcacttgtg gagatggggg tggaaatggg gcaccatgct ccttgggata
ttgatgatct gtagtgctac agaaaaattg tgggtcacag tctattatgg ggtacctgtg tggaaggaag caaccaccac
tctattttgt gcatcagatg ctaaagcata tgatacagag gtacataatg tttgggccac acatgcctgt gtacccacag
accccaaccc acaagaagta gtattggtaa atgtgacaga aaattttaac atgtggaaag atgacatggt agaacagatg
catgaggata taatcagttt atgggatcaa agcctaaagc catgtgtaaa attaacccca ctctgtgtta gtttaaagtg
cactgatttg aagaatgata ctaataccaa tagtagtagc gggagaatga taatggagaa aggagagata aaaaactgct
ctttcaatat cagcacaagc ataagagata aggtgcagaa agaatatgca ttcttttata aacttgatat agtaccaata -continued gataatacca gctataggtt gataagttgt aacacctcag tcattacaca ggcctgtcca aaggtatcct ttgagccaat
ccccatacat tattgtgccc cggctggttt tgcgattcta aaatgtaata ataagacgtt caatggaaca ggaccatgta
caaatgtcag cacagtacaa tgtacacatg gaatcaggcc agtagtatca actcaactgc tgttaaatgg cagtctagca
gaagaagatg tagtaattag atctgccaat ttcacagaca atgctaaaac cataatagta cagctgaaca catctgtaga
aattaattgt acaagaccca acaacaatac aagaaaaagt atccgtatcc agaggggacc agggagagca tttgttacaa
taggaaaaat aggaaatatg agacaagcac attgtaacat tagtagagca aaatggaatg ccactttaaa acagatagct
agcaaattaa gagaacaatt tggaaataat aaaacaataa tctttaagca atcctcagga ggggacccag aaattgtaac
gcacagtttt aattgtggag gggaattttt ctactgtaat tcaacacaac tgtttaatag tacttggttt aatagtactt
ggagtactga agggtcaaat aacactgaag gaagtgacac aatcacactc ccatgcagaa taaaacaatt tataaacatg
tggcaggaag taggaaaagc aatgtatgcc cctcccatca gtggacaaat tagatgttca tcaaatatta ctgggctgct
attaacaaga gatggtggta ataacaacaa tgggtccgag atcttcagac ctggaggagg cgatatgagg gacaattgga
gaagtgaatt atataaatat aaagtagtaa aaattgaacc attaggagta gcacccacca aggcaaagag aagagtggtg
cagagagaaa aaagagcagt gggaatagga gctttgttcc ttgggttctt gggagcagca ggaagcacta tgggcgcagc
gtcaatgacg ctgacggtac aggccagaca attattgtct gatatagtgc agcagcagaa caatttgctg agggctattg
aggcgcaaca gcatctgttg caactcacag tctggggcat caaacagctc caggcaagaa tcctggctgt ggaaagatac
ctaaaggatc aacagctcct ggggatttgg ggttgctctg gaaaactcat ttgcaccact gctgtgcctt ggaatgctag
ttggagtaat aaatctctgg aacagatttg gaataacatg acctggatgg agtgggacag agaaattaac aattacacaa
gcttaataca ctccttaatt gaagaatcgc aaaaccagca agaaaagaat gaacaagaat tattggaatt agataaatgg
gcaagtttgt ggaattggtt taacataaca aattggctgt ggtatataaa attattcata atgatagtag gaggcttggt
aggtttaaga atagtttttg ctgtactttc tatagtgaat agagttaggc agggatattc accattatcg tttcagaccc
acctcccaat cccgagggga cccgacaggc ccgaaggaat agaagaagaa ggtggagaga gaggcagaga cagatccatt
cgattagtga acggatcctt agcacttatc tgggacgatc tgcggagcct gtgcctcttc agctaccacc gcttgagaga
cttactcttg attgtaacga ggattgtgga acttctggga cgcagggggt gggaagccct caaatattgg tggaatctcc
tacagtattg gagtcaggaa ctaaagaata gtgctgttaa cttgctcaat gccacagcca tagcagtagc tgaggggaca
gatagggtta tagaagtatt acaagcagct tatagagcta ttcgccacat acctagaaga ataagacagg gcttggaaag
gattttgcta taa Translation (SEQ ID NO: 39)

MRVKEKYQHLWRWGWKWGTMLLGILMICSATEKLWVTVYYGVPVWKEATTTLFCASDAKAYDTEVHNVWATHACVPTDPNPQEVVLVNV
TENFNMWKDDMVEQMHEDIISLWDQSLKPCVKLTPLCVSLKCTDLKNDTNTNSSSGRMIMEKGEIKNCSFNISTSIRDKVQKEYAFFYK
LDIVPIDNTSYRLISCNTSVITQACPKVSFEPIPIHYCAPAGFAILKCNNKTFNGTGPCTNVSTVQCTHGIRPVVSTQLLLNGSLAEED
VVIRSANFTDNAKTIIVQLNTSVEINCTRPNNNTRKSIRIQRGPGRAFVTIGKIGNMRQAHCNISRAKWNATLKQIASKLREQFGNNET
IIFKQSSGGDPEIVTHSFNCGGEFFYCNSTQLFNSTWFNSTWSTEGSNNTEGSDTITLPCRIKQFINMWQEVGKAMYAPPISGQIRCSS
NITGLLLTRDGGNNNNGSEIFRPGGGDMRDNWRSELYKYKVVKIEPLGVAPTKAKRRVVQREKRAVGIGALFLGFLGAAGSTMGAASMT
LTVQARQLLSDIVQQQNNLLRAIEAQQHLLQLTVWGIKQLQARILAVERYLKDQQLLGIWGCSGKLICTTAVPWNASWSNKSLEQIWNN
MTWMEWDREINNYTSLIHSLIEESQNQQEKNEQELLELDKWASLWNWFNITNWLWYIKLFIMIVGGLVGLRIVFAVLSIVNRVRQGYSP
LSFQTHLPIPRGPDRPEGIEEEGGERGRDRSIRLVNGSLALIWDDLRSLCLFSYHRLRDLLLIVTRIVELLGRRGWEALKYWWNLLQYW
SQELKNSAVNLLNATAIAVAEGTDRVIEVLQAAYRAIRHIPRRIRQGLERILL

NEF Protein: 8165-8785
Nucleotide Sequence (SEQ ID NO: 40)

atgggt ggcaagtggt caaaaagtag tgtgattgga tggcctgctg taagggaaag aatgagacga gctgagccag
cagcagatgg ggtgggagca gtatctcgag acctagaaaa acatggagca atcacaagta gcaatacagc agctaacaat
gctgcttgtg cctggctaga agcacaagag gaggaagagg tgggttttcc agtcacacct caggtacctt taagaccaat
gacttacaag gcagctgtag atcttagcca ctttttaaaa gaaaaggggg gactggaagg gctaattcac tcccaaagaa
gacaagatat ccttgatctg tggatctacc acacacaagg ctacttccct gattggcaga actacacacc agggccaggg
gtcagatatc cactgacctt tggatggtgc tacaagctag taccagttga gccagataag gtagaagagg ccaataaagg
agagaacacc agcttgttac accctgtgag cctgcatgga atggatgacc ctgagagaga agtgttagag tggaggtttg
acagccgcct agcatttcat cacgtggccc gagagctgca tccggagtac ttcaagaact gctga Translation (SEQ ID NO: 41)

MGGKWSKSSVIGWPAVRERMRRAEPAADGVGAVSRDLEKHGAITSSNTAANNAACAWLEAQEEEEVGFPVTPQVPLRPMTYKAAVDLSH
FLKEKGGLEGLIHSQRRQDILDLWIYHTQGYFPDWQNYTPGPGVRYPLTFGWCYKLVPVEPDKVEEANKGENTSLLHPVSLHGMDDPER
EVLEWRFDSRLAFHHVARELHPEYFKNC

HIV-1 p6*: sequence of this virus is presented in the Drawings attached hereto.
pNL.Ba.L. The DNA sequence of the Ba.L Env sequence is shown below (SEQ ID NO: 42). This sequence was used to replace the Env sequence of NL4.3 in constructs with the Ba.L envelope.
Unannotated (sense strand only; this sequence replaces the NL4.3 envelope sequence in the constructs with the Ba.L envelope):
CCAACATAGCAGAATAGGTATTATTCAACAGAGGAGAGCAAGAAATGGAGCCAGTAGATCCTAAACTAGAGCCCTGGAAGCATCCAGGA
AGTCAGCCTAAGACTGCTTGTACCACTTGCTATTGTAAAAAGTGTTGCTTTCATTGCCAAGTTTGCTTCATAACAAAAGGCTTAGGCAT
CTCCTATGGCAGGAGGAAGCGGAGACAGCGACGAAGAGCTCCTCAAGACAGTCAGACTCATCAAGTTTCTCTATCAAAGCAGTAAGTAG
TACATGTAATGCAAGCTTTACAAATATCAGCAATAGTAGCATTAGTAGTAGCAGCAATAATAGCAATAGTTGTGTGGACCATAGTATTC
ATAGAATATAGGAAAATATTAAGGCAAAGAAAAATAGACAGGTTAATTGATAGAATAACAGAAAGAGCAGAAGACAGTGGCAATGAGAG
TGATGGAGATCAGGAGGAATTATCAGCACTGGTGGAGATGGGGCATCATGCTCCTTGGGATGTTAATGATCTGTAATGCTGAAGAAAAA
TTGTGGGTCACAGTCTATTATGGGGTACCTGTGTGGAAAGAAGCAACCACCACTCTATTTTGTGCATCAGATGCTAAAGCATATGATAC
AGAGGTACATAATGTTTGGGCCACACATGCCTGTGTACCCACAGACCCCGACCCACAAGAAGTAAAATTGGAAAATGTGACAGAAAATT
TTAACATGTGGAAAAATAAAATGGTAGAACAGATGCATGAGGATATAATCAGTTTATGGGATCAAAGCCTAAAGCCATGTGTAAAATTA
ACTCCACTCTGTGTTACTTTAAATTGCACTGTAAGCGGGGGAATGATGGGGGGAGGAGAAATGAAAAATTGCTCTTTCAATATCACCAC
AAACATAAGAGGTAAGGTGCAGAAAGAATATGCACTTTTTTATGAACTTGATATAGTACCAATAGATAATAAAAATGATAGCTATAGGT
TGATAAGTTGTAACACCTCAGTCATTACACAGGCCTGTCCAAAGGTATCCTTTGAGCCAATTCCCATACATTATTGTGCCCCGGCTGGT
TTTGCGATTCTAAAGTGTAAAGATAATAAGTTCAATGGAAAAGGACCATGTACAAATGTCAGCACAGTACAATGTACACATGGAATTAG
GCCAGTAGTATCAACTCAACTGCTGTTAAATGGCAGTCTAGCAGAAGAAGAGGTAGTAATTAGATCCGAAAATTTCACGAACAATGCTA
AAACCATAATAGTACAGCTGAATGAATCTGTAGTAATTAATTGTACAAGACCCAACAACAATACAAGAAAAAGTATAAATATAGGACCA
GGCAGAGCATTTTATACAACAGGAGAAATAATAGGAGATATAAGACAAGCACATTGTAACCTTAGTAGAGCAAAATGGAATGACACTTT
AAATAAGATAGTTATAAAATTAAGAGAACAATTTGGGAATAAAACAATAGTCTTTAAGCACTCCTCAGGAGGAGACCCAGAAATTGTGA -continued CGCACAGTTTTAATTGTGGAGGGGAATTTTTCTACTGTAATTCAACACAACTGTTTAATAGTACTTGGAATGTTACTGAAGAGTCAAAT
AACACTGTAGAAAATAACACAATCACACTCCCATGCAGAATAAAACAAATTATAAACATGTGGCAGGAAGTAGGAAGAGCAATGTATGC
CCCTCCCATCAGAGGACAAATTAGATGTTCATCAAATATTACAGGGCTGCTATTAACAAGAGATGGTGGTCCTGAGGACAACAAGACCG
AGGTCTTCAGACCTGGAGGAGGAGATATGAGGGATAATTGGAGAAGTGAATTATATAAATATAAAGTAGTAAAAATTGAACCATTAGGA
GTAGCACCCACCAAGGCAAAGAGAAGAGTGGTGCAGAGAGAAAAAAGAGCAGTGGGAATAGGAGCTGTGTTCCTTGGGTTCTTGGGAGC
AGCAGGAAGCACTATGGGCGCAGCGTCAATGACGCTGACGGTACAGGCCAGACTATTATTGTCTGGTATAGTGCAACAGCAGAACAATC
TGCTGAGAGCTATTGAGGCGCAACAGCATCTGTTGCAACTCACAGTCTGGGGCATCAAGCAGCTCCAGGCAAGAGTCCTGGCTGTGGAA
AGATACCTAAGGGATCAACAGCTCCTGGGGATTTGGGGTTGCTCTGGAAAACTCATCTGCACCACTGCTGTGCCTTGGAATGCTAGTTG
GAGTAATAAATCTCTGAATAAGATTTGGGATAACATGACCTGGATGGAGTGGGACAGAGAAATTAACAATTACACAAGCATAATATACA
GCTTAATTGAAGAATCGCAGAACCAACAAGAAAAGAATGAACAAGAATTATTAGAATTAGATAAATGGGCAAGTTTGTGGAATTGGTTT
GACATAACAAAATGGCTGTGGTATATAAAAATATTCATAATGATAGTAGGAGGCTTGATAGGTTTAAGAATAGTTTTTCTGTACTTTC
TATAGTGAATAGAGTTAGGCAGGGATACTCACCATTATCGTTTCAGACCCACCTCCCAGCCTCGAGGGGACCCGACAGGCCCGGAGGAA
TCGAAGAAGAAGGTGGAGAGAGAGACAGAGACAGATCCGGTTCATTAGTGAACG CD40 Ligand: Accession: CAA48077.1 GI: 38412

CD40 Ligand Nucleic Acid Sequence (786 base pairs; SEQ ID NO: 43):

ATGATCGAAACATACAACCAAACTTCTCCCCGATCTGCGGCCACTGGACTGCCCATCAGCATGAAAATTTTTATGTATTTACTTACTGT
TTTTCTTATCACCCAGATGATTGGGTCAGCACTTTTTGCTGTGTATCTTCATAGAAGGTTGGACAAGATAGAAGATGAAAGGAATCTTC
ATGAAGATTTTGTATTCATGAAAACGATACAGAGATGCAACACAGGAGAAAGATCCTTATCCTTACTGAACTGTGAGGAGATTAAAAGC
CAGTTTGAAGGCTTTGTGAAGGATATAATGTTAAACAAAGAGGAGACGAAGAAAGAAAACAGCTTTGAAATGCAAAAAGGTGATCAGAA
TCCTCAAATTGCGGCACATGTCATAAGTGAGGCCAGCAGTAAAACAACATCTGTGTTACAGTGGGCTGAAAAAGGATACTACACCATGA
GCAACAACTTGGTAACCCTGGAAAATGGGAAACAGCTGACCGTTAAAAGACAAGGACTCTATTATATCTATGCCCAAGTCACCTTCTGT
TCCAATCGGGAAGCTTCGAGTCAAGCTCCATTTATAGCCAGCCTCTGCCTAAAGTCCCCCGGTAGATTCGAGAGAATCTTACTCAGAGC
TGCAAATACCCACAGTTCCGCCAAACCTTGCGGGCAACAATCCATTCACTTGGGAGGAGTATTTGAATTGCAACCAGGTGCTTCGGTGT
TTGTCAATGTGACTGATCCAAGCCAAGTGAGCCATGGCACTGGCTTCACGTCCTTTGGCTTACTCAAACTCTGA

Translation of CD40 Ligand (261 amino acids, SEQ ID NO: 44):

MIETYNQTSPRSAATGLPISMKIFMYLLTVFLITQMIGSALFAVYLHRRLDKIEDERNLHEDFVFMKTIQRCNTGERSLSLLNCEEIKS
QFEGFVKDIMLNKEETKKENSFEMQKGDQNPQIAAHVISEASSKTTSVLQWAEKGYYTMSNNLVTLENGKQLTVKRQGLYYIYAQVTFC
SNREASSQAPFIASLCLKSPGRFERILLRAANTHSSAKPCGQQSIHLGGVFELQPGASVFVNVTDPSQVSHGTGFTSFGLLKL

HIV Peptides:

| Peptides | Protein of origin[a] | Sequence |
|---|---|---|
| A9M | Pol (188-196) | ALVEICTEM (SEQ ID NO: 45) |
| I9V | Pol (464-472) | YLKEPVHGV (SEQ ID NO: 46) |
| K9L | Env gp120 (120-128) | YLTPLCVSL (SEQ ID NO: 47) |
| T9V | Gag p24 (19-27) | YLNAWVKVV (SEQ ID NO: 48) |
| V9L | Pol (334-342) | YIYQYMDDL (SEQ ID NO: 49) |
| P10L | Nef (134-143) | YLTFGWCFKL (SEQ ID NO: 50) |
| V11V | Pol (263-273) | VLDVGDAYFSV (SEQ ID NO: 51) |
| P9L | Pol (576-584) | YLVKLWYQL (SEQ ID NO: 52) |
| S9L | Gag p17 (77-85) | SLYNTVATL (SEQ ID NO: 53) |
| E9V | Gag p24 (212-221) | YMMTACQGV (SEQ ID NO: 54) |
| L10V | Pol (79-88) | LLDTGADDTV (SEQ ID NO: 55) |
| L9V | Pol (956-964) | LLWKGEGAV (SEQ ID NO: 56) |
| K9L (T) | Env gp120 (120-128) | YLTPLCVTL (SEQ ID NO: 57) |

See Iglesias et al. Mol Ther 15, 1203-1210, doi:10.1038/sj.mt.6300135 (2007), the entire content of which is incorporated herein by reference, with respect to the HIV-1 peptides indicated above.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Methods

Cells and cell culture. 293T cells were cultured in Dulbecco's modified Eagle's Medium (DMEM)-10% fetal bovine serum (FBS). MDM, MDDC, and T cells were cultured in RPMI 1640-5% Human AB. Peripheral blood mononuclear cells (PBMC) were purified from normal human donor blood by Ficoll density gradient. Monocytes were purified from healthy donor PBMC by adherence to plastic or by positive selection on anti-CD14-coated magnetic beads (Miltenyi Biotec Inc.). Bead purified monocytes were typically >98% $CD14^+$. The monocytes were differentiated to MDM by culturing for 4-6 days in medium containing 50 ng/ml GM-CSF (Invitrogen Inc.). MDDC were generated by culturing the monocytes for 5-6 days in medium containing 50 ng/ml GM-CSF and 100 ng/ml IL-4 (R&D Systems). Autologous T cells were obtained from the CD 14-negative fraction by positive selection on anti-CD4-conjugated magnetic beads (Miltenyi Biotec Inc.). The T cells were then activated using anti-CD3/CD28 beads (Invitrogen) and cultured in medium containing 10 ng/ml IL-2 (R&D Systems).

Plasmids. Codon-optimized, epitope-tagged $SIVmac_{239}$ and HIV-$2_{rod}$ Vpx and SIVagm Vpr expression vectors were generated by overlapping PCR and cloned into pcDNA6 (Invitrogen Inc.) at the EcoR-I and Xho-I sites (FIG. 8). HIV-1 p6 chimeras and point mutants were generated in the pNL4-3-based luciferase reporter virus, pNL.Luc3. An Apa-I to EcoR-I subclone containing the p6 region was subcloned into pBluescript-KS+ (Fermentas Life Sciences) that had been modified to remove the multi-cloning site Pst-I site. Mutations were introduced by overlapping PCR and the mutated fragment was cloned back into the subcloned fragment in pBS-KS+ at the Apa-I and Pst-I sites. The mutant fragment was then cloned into NL4-3 at the Apa-I and EcoR-I sites. Vpr and vpx were cloned into the nef position of NL.Luc3 by removing the luciferase gene with Not-I and Xho-I and replacing it with codon optimized vpr and vpx amplicons that had been amplified with primers that introduced Not-I and Sal-I sites.

Codon optimization of vpx was undertaken where non-optimal codons were present in the original vpx sequence. Non-optimal codons were altered to be the most commonly used mammalian codon which encodes the indicated amino acid. An alignment of the wildtype and codon-optimized Vpx sequences is shown in FIG. 8.

Virus preparation and infections. HIV-1 and $SIVmac_{239}$ luciferase reporter viruses were generated as described previously (10, 34). Briefly, to produce trans complemented reporter viruses, 293T cells were cotransfected using lipofectamine 2000 with pNL-luc3-$E^-R^-$, pcVSV-G, and pcVpr, pcVpx, or pcDNA at a mass ratio of 2:1:1. Supernatants were harvested 48 h posttransfection, passed through 0.45 μm pore-size filters, aliquoted, and frozen at −80° C. Luciferase reporter virus infectivity was normalized for luciferase activity on 293T cells by infecting $2.0\times10^4$ cells with 50 μl of virus. Three days later, luciferase activity was measured using SteadyLite HTS reagents (PerkinElmer), typically yielding $1.0\text{-}3.0\times10^6$ counts per second (cps) per 50 μl. P24 content of virus-containing supernatants was quantified by ELISA using commercially available capture and sandwich antibodies (Aalto Bioreagents, LTD)

MDM ($1.0\times10^5$) and MDDC ($1.25\times10^5$) were seeded in a 96-well plate and then infected with reporter virus corresponding to $3.0\times10^5$ cps. MDM were spin-infected with reporter virus for 2 h at 500×g. The data are presented as the average cps of triplicate infections with error bars indicating the standard deviation. For intracellular p24 detection, MDM ($3.0\times10^5$) or MDDC ($3.0\times10^5$) were infected with 20 ng p24. For infections in which Vpx was produced in cis, MDM ($5.0\times10^5$) were infected with 200 ng p24 and MDDC ($1.25\times10^5$) were infected with 50 ng of p24. To control for input virus, one sample was treated with 25 μM AZT (AIDS Research and Reference Reagent Program, NIH) prior to infection. To limit replication to one round, 3 μM Nelfinavir (AIDS Research and Reference Reagent Program, NIH) was added to the samples 6 hours post infection. The cells were fixed, permeabilized, and stained as described below. For MDDC:T cell trans infection assays, either $2.5\times10^5$ or $1.0\times10^5$ MDDC were seeded in a 96 well culture plate. The next day, the cells were treated with 50 or 25 ng p24, respectively, and, after 6 h, washed three times with medium. After 48 h, autologous CD3/CD28-activated T cells ($1.0\times10^6$ or $4.0\times10^5$) were added to wells designated for co-culture, resulting in a final ratio of MDDC to T cell of 1:4. To test T cell infection in the absence of MDDC, CD3/CD28-activated T cells ($4.0\times10^5$) were infected with 25 ng virus, and, after 6 h, media was changed. Supernatant was collected either at 3, 5, 7, and 10 days or 3, 5, 7, 9, and 14 days post coculture, and p24 was then quantified. To detect intracellular p24, cells were collected at 3 days post coculture, fixed, permeabilized, and stained as described below.

Quantitative Real-time PCR (qRT-PCR). To quantify HIV-1 reverse transcripts in newly infected cells, $3\times10^5$ MDM were infected with 5 ng p24 of virus treated for 1 h with 50 U/ml of Benzonase (Invitrogen, Inc.). To the sample infected with the p6 chimeric virus encoding Vpx, 25 μM AZT was added prior to infection to control for residual plasmid DNA. After 24 h and 48 h, DNA was isolated (Qiagen). Late reverse transcripts and 2-LTR circles were quantitated by qRT-PCR using 250 ng DNA template as described previously (8, 21). Amplicons were detected with SYBR Green (Applied Biosystems) using an ABI Prism 7300 (Applied Biosystems). Absolute copy numbers were determined by normalization to standard curves generated from serially diluted proviral plasmid and two-LTR plasmid.

Induction of interferon-$\beta_1$ (IFN-$\beta_1$) in response to HIV-1 in MDDC was measured by qRT-PCR. MDDC were infected with 50 ng p24. To two samples, 25 μM AZT or 10 μM of Raltegravir (Merck) was added prior to infection. After 24 h and 48 h, RNA was isolated using Triazol (Invitrogen Inc.), and cDNA was generated using Transcriptor reverse transcriptase (Roche) primed with oligo-(dT). IFN-$\beta_1$ and glucose-6-phosphate dehydrogenase (G6PDH) were then amplified with primers previously described by Di Domizio et al. (11) Relative threshold Cycle (Ct) value for IFN-$\beta_1$ was normalized to G6PDH.

Immunoblot analysis. Virions were harvested from culture supernatants two days posttransfection, filtered, pelleted through 20% sucrose at 100,000×g for 20 min. at 4° C., and then lysed in buffer containing 0.5% NP40. Cell and virus proteins were analyzed on immunoblots as previously described (21). The filters were probed with anti-myc MAb 9E10 (Covance), anti-p24 MAb #183-H12-SC (AIDS Research and Reference Reagent Program, NIH), and anti-α-tubulin (Sigma). The filters were then hybridized with biotinylated goat anti-mouse immunoglobulin and Streptavidin DyeLight 680 or 800 conjugate (Pierce) and imaged on an Odyssey Infrared Imaging System (LiCOR) at 700 or 800 nm, respectively.

Intracellular p24 Staining. The cells were removed from culture dishes in phosphate-buffered saline (PBS) containing 5.0 mM EDTA, fixed and permeabilized with BD Cytofix/Cytoperm (BD-Pharmingen), and washed with BD Perm/Wash (BD-Pharmingen) according to the manufacturer's instructions. The cells were then stained with a 1:200 dilution of either PE- or FITC-conjugated anti-p24 MAb KC57 (Beckman Coulter) and analyzed by flow cytometry using Flojo software. The cells were gated for forward and side scatter and analyzed for PE or FITC fluorescence with mock infected cells as a negative control.

For analysis of the cells in the MDDC:T cell trans infection assays, the cells in the mixed cultures were removed from the culture dishes and stained with a 1:25 dilution of APC-conjugated CD11c (BD Pharmingen). They were then fixed and permeabilized and stained with for p24. T cells and MDDC were gated on CD11c and intracellular p24 was detected by FITC fluorescence. Mock-infected cells were used as a negative control.

Results

Figure 1:
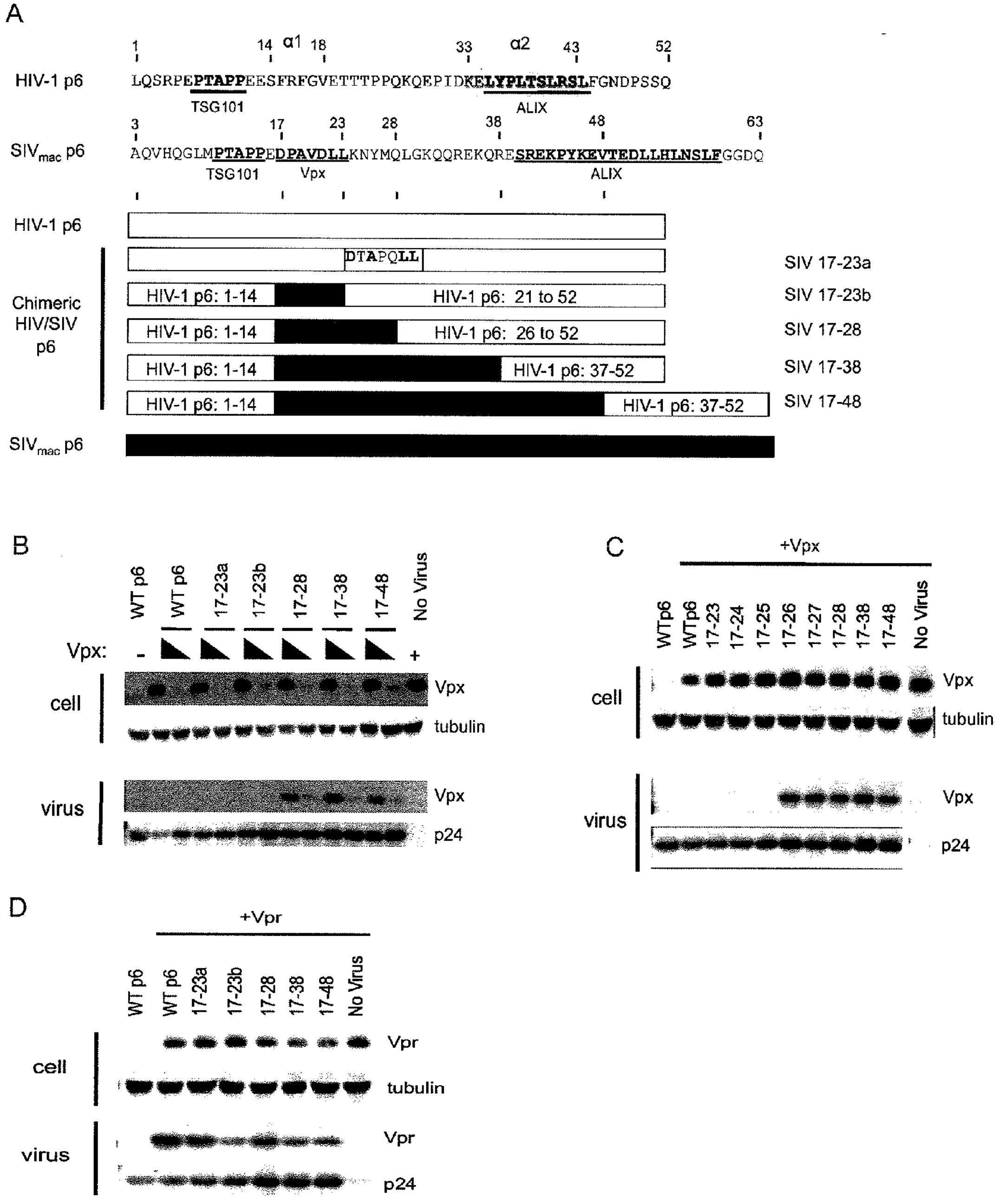
FIGS. 1A-D. Identification of the minimal Vpx packaging motif in SIVmac p6 by transfer into HIV-1 p6. A. Alignment of NL4-3 and $SIVmac_{239}$ p6 amino acid sequence. The two proposed alpha helices ($\alpha$1 and $\alpha$2) are shaded and the PTAPP late domain and TSG101 binding site are in bold underline. Binding sites for ALIX and Vpx are in bold underline. Below are diagrams of the HIV-1/SIVmac p6 chimeras with white for HIV-1 and black for SIV sequence. The SIV sequence is inserted at position 14 of HIV-1 p6, except in chimera 17-23(a), where the Vpx binding motif is displaced to position 21 to not alter the $^{14}$FRFG$^{18}$ Vpr packaging motif. The amino acid sequences of HIV-1 p6 and $SIVmac_{239\,p}6$ are designated SEQ ID NOs: 65 ands 66, respectively. The indicated amino acid sequence of SIV 17-23*a* is designated SEQ ID NO: 67. B. Immunoblot analysis shows packaging of $SIVmac_{239}$ Vpx in chimeras containing the Vpx packaging motif 293T cells were cotransfected with pNL4-3 containing a wild-type or chimeric p6 and pcVpx.myc or empty vector.

Mapping of the Vpx packaging determinant in Gag. Packaging of Vpx into virions is mediated by its interaction with the C-terminal domain of the Gag polyprotein precursor, p6 (1, 47). The interaction is virus-specific, such that Vpx is packaged by SIVmac but not by HIV-1(25). P6 is structured as two alpha helices with the PTAPP late domain motif that binds TSG101 adjacent to helix 1 and the ALIX binding motif overlapping helix 2 (14, 52) (FIG. 1A). Accola et al. mapped the Vpx packaging site in p6 to the amino acid sequence $^{17}$DPAVDLL$^{23}$, just C-terminal to the PTAPP late domain motif (1). As a first step in engineering an HIV-1 that would package SIVmac Vpx, we determined the minimal SIVmac p6 amino acid sequence that needed to be introduced into HIV-1 to allow Vpx packaging. To do this, we generated chimeric HIV-1 genomes 17-23(a), 17-23(b), 17-28, 17-38, and 17-48, where the indicated region of SIVmac p6 was transferred to HIV-1 p6 (FIG. 1A). In chimera 17-23(a), the SIV sequence was displaced by six codons to preserve amino acids 14-18 that contain the $^{14}$FRFG$^{18}$ motif previously reported to play a role in Vpr packaging (53). We determined the ability of the chimeric viruses to package Vpx by cotransfecting 293T cells with the chimeric proviral DNA and two different amounts of the myc-tagged SIVmac Vpx expression vector, pcVpx.myc. After two days, the culture supernatant was harvested and the virions were pelleted by ultracentrifugation and analyzed on an immunoblot (FIG. 1B). The results showed that chimeras 17-23(a) and 17-23(b) failed to package Vpx, but the addition of five more amino acids from SIVmac p6 in chimera 17-28 allowed for packaging of Vpx. Extension of the chimeric region in chimeras 17-38 and 17-48 did not further increase Vpx packaging at either of the two amounts of cotransfected pcVpx.myc. The failure of chimera 17-23 to package Vpx was unexpected as this chimera contained the previously described $^{17}$DPAVDLL$^{23}$ motif, suggesting that the packaging motif extends further C-terminal. To more precisely define the Vpx packaging motif, we generated chimeras 17-24, 17-25, 17-26, 17-27, and 17-28, where single amino acids from positions 24 to 28 were added (FIG. 1C). Immunoblot analysis of virions derived from these chimeric genomes showed that addition of SIVmac p6 amino acids 24 and 25 did not allow for Vpx packaging. When the chimeric region was extended to position 26, packaging was restored. We conclude that the minimal Vpx packaging motif required to allow efficient packaging of SIVmac Vpx into HIV-1 virions is $^{17}$ DPAVDLLKNY$^{26}$ (SEQ ID NO: 1).

Mapping the Vpr packaging determinant in p6. Since p6 also contains the packaging determinant for Vpr, it was possible that alteration of this region would affect Vpr packaging. Previous reports have mapped the Vpr packaging motif in p6 to two separate locations. Kondo et al. mapped the determinant in HIV-1 and SIVmac to a $^{41}$LXXLF$^{45}$ (SEQ ID NO: 58) motif near the C-terminus of p6 that overlaps with the ALIX binding motif (here termed “motif 2”; FIG. 2A) (30). Subsequently, Zhu et al. reported that p6 deleted for motif 2 retained the ability to package Vpr (53). Instead, they found that the $^{15}$FRFG$^{18}$ (SEQ ID NO: 59) motif (motif 1) near the N-terminus of p6 was required for Vpr packaging. In that study, motif 1 was tested only in the context of a truncated p6 that lacked motif 2. To evaluate the roles of the two motifs in Vpr packaging, we generated p6 point mutants in both motifs and tested the resulting virions for Vpr packaging. For motif 1, mutants F15A and F17A decreased packaging by about 80%, while mutants R16A and G18A were similar to wild-type (FIG. 2B). Mutation of the entire $^{15}$FRFG$^{18}$ (SEQ ID NO: 59) motif to alanine (M1A) did not further reduce the amount of Vpr packaged below that of the point mutants. In the case of motif 2, single mutations to alanine had little effect (FIG. 2C). L38 mutated virions appeared to contain a reduced amount of Vpr; however, production of the virions was also reduced, suggesting that the Vpr content per virion had been unaltered. Mutation of amino acids S43 and S45 did not decrease the amount of Vpr packaged. In fact, both appeared to package more Vpr than wild-type virus. These two mutant viruses generated virions that were defective for Gag processing, probably because those amino acids are close to the proteolytic processing site and interfere with recognition by the viral protease. Unprocessed virions are highly stable and as a result may be more effective at packaging Vpr. Although single amino acid mutations in motif 2 had little effect, mutation of the four conserved leucines together (M2Aa) blocked Vpr packaging, confirming the importance of motif 2 in Vpr packaging. Combination of the motif 1 and motif 2 mutations (M1 and 2a and M1 and 2b) also prevented Vpr packaging. We conclude that both motifs play a role in Vpr packaging.

Having identified both motifs as important, we next measured Vpr packaging by the p6 chimeras. To do this, we produced the chimeric virions in cells cotransfected with a Vpr expression vector and then analyzed the resulting virions on an immunoblot. We found that chimera 17-23a, in which the $^{15}$FRFG$^{18}$ (SEQ ID NO: 59) motif is intact, maintained its ability to package Vpx, while the other chimeras, in which the $^{15}$FRFG$^{18}$ (SEQ ID NO: 59) motif has been altered, packaged about one third as much Vpr (FIGS. 2D and 9). For reasons that are not clear, chimera 17-28 reproducibly packaged Vpr somewhat better (70% of wild-type) despite lacking the $^{15}$FRFG$^{18}$ motif, perhaps due to a conformational effect on motif 2.

HIV-1 p6 chimera containing SIVmac Vpx efficiently infects MDDC and MDM. The introduction of Vpx into MDM and MDDC using VLP increases the infectivity of HIV-1 (18, 21). These findings predict that HIV-1 virions packaging Vpx should have an increased ability to infect MDM and MDDC. To determine whether this is the case, we used the 17-26 p6 chimeric virus that contains the minimum $SIVmac_{239}$ Vpx packaging sequence. Chimeric p6 and wild-type luciferase reporter viruses were produced as VSV-G pseudotypes in 293T cells cotransfected with increasing amounts of pcVpx.myc. The viruses were normalized for infectivity on 293T cells and were then used to infect MDDC and MDM from three donors. Immunoblot analysis of the virions showed that wild-type virions contained only small amounts of Vpx over the Vpx expression vector titration curve, while the p6 chimeric virions packaged Vpx proportional to the amount of transfected Vpx expression vector (FIG. 3A). On MDDC, the wild-type virus that lacked Vpx was poorly infectious. Complementation with the highest amount of Vpx significantly enhanced its infectivity, suggesting that the small amount of Vpx packaged was sufficient to provide an effect on the target cell (FIG. 3B). The p6 chimeric virus complemented with increasing amounts of Vpx became even more infectious. The smallest amount of Vpx, which was barely detectable in the virion by immunoblot analysis, enhanced the infectivity of the virus an average of 100-fold. Increasing amounts of Vpx further enhanced the infectivity to 600-800-fold, depending on the donor. Similar results were obtained using cell preparations from 7 additional donors. Vpx was also active in the infection of MDM, although the fold-enhancement was not as dramatic (about 3-fold lower). The titration curve on the MDM suggests that they are more sensitive to a low level of packaged Vpx, with infectivity reaching nearly half-maximal with the lowest amount of cotransfected Vpx expression vector.

The luciferase reporter virus does not distinguish between effects on the number of cells infected and the provirus transcriptional activity per infected cell. To determine whether packaged Vpx increases the number of infected cells, we quantified intracellular p24 in the infected MDM and MDDC by flow cytometry (FIG. 3C). We found that the wild-type and p6 chimeric viruses lacking Vpx were poorly infectious on MDDC, as was the wild-type virus complemented with Vpx.

In contrast, complementation of the p6 chimeric virus with Vpx increased the number of infected cells 98-fold. On MDM, complementation of the chimeric virus increased its infectivity by 84-fold. On these cells, the Vpx-complemented wild-type virus was also considerably enhanced, resulting in nearly 40% as many infected cells as the complemented p6 chimeric virus. This result suggests that MDM are less restrictive to virus lacking Vpx and are therefore sensitive to low levels of packaged Vpx. The mean fluorescence intensity of the p24-positive cells was not affected, indicating that Vpx did not affect transcription of the provirus or translation of the viral proteins.

Comparison of the activities of lentiviral Vpx. Besides SIVmac, HIV-2 encodes a Vpx. In addition, SIVagm encodes a protein that has been termed Vpr but is more similar to Vpx, sharing its ability to enhance infection of MDM and inability to induce $G_2$ arrest (9, 45). To determine whether these proteins enhance HIV-1 infection, we complemented wild-type or p6 chimeric viruses with expression vectors for $SIVmac_{239}$ Vpx, $HIV\text{-}2_{rod}$Vpx, or SIVagm Vpr. Immunoblot analysis showed that each of the accessory proteins could be packaged into the p6 chimeric virus but not into the wild-type virus (FIG. 4A). SIVagm Vpr and $HIV\text{-}2_{rod}$ Vpx were packaged in smaller amounts due to their relatively low level expression in the cell. On MDDC, the three accessory proteins had no effect on the infectivity of the wild-type virus. $SIVmac_{239}$ Vpx and $HIV\text{-}2_{rod}$ Vpx both enhanced the infectivity of the p6 chimeric virus (FIG. 4B, top panel). $HIV\text{-}2_{rod}$ Vpx was only about 8% as active as $SIVmac_{239}$ Vpx, but this may be the result of its relatively low expression level. $SIVmac_{239}$ Vpx and $HIV2_{rod}$ Vpx also enhanced the infectivity of the p6 chimeric virus on MDM (FIG. 4B, bottom panel). As in the earlier experiments, the MDM were overall less restrictive than MDDC. SIVagm Vpr had no detectable effect on infection of MDDC and the less restrictive MDM. The lack of enhancement may indicate a species-restriction to the AGM protein. Intracellular p24 staining of infected MDDC further supported these findings (not shown).

A p6 chimeric virus that encodes Vpx. In the experiments described above, the Vpx containing virions were produced by trans complementation in cells cotransfected with a replication-defective reporter virus and a Vpx expression vector. Expression of Vpx in cis would allow for Vpx expression through multiple rounds of virus replication and would obviate the need to complement by cotransfection. To generate a Vpx-containing virus that expressed Vpx in cis, we placed a codon-optimized vpx open reading frame in place of nef, a position that has been found to allow for expression of an inserted reporter gene without affecting virus replication (10, 29, 34). We considered placing the vpx in the vpr position; however, this would disrupt the overlapping reading frames and splice signals in this region of the viral genome. The cis virus is based on pNL.Ba.L, an NL4-3 that contains the CCR5-specific envelope glycoprotein of Ba.L. The provirus was further modified by introduction of the Vpx packaging residues 17-26 of $SIVmac_{239}$ p6 and a codon-optimized $SIVmac_{239}$ vpx, $HIV\text{-}2_{rod}$vpx, or SIVagm vpr in nef. Immunoblot analysis of virions produced by 293T cells transfected with each proviral DNA showed that they expressed low levels of the accessory proteins (FIG. 5A). These could be detected in cell lysates treated with MG132 to stabilize the relatively short-lived proteins. Due to the low levels of Vpx production, we measured the infectivity of the cis viruses in newly infected cells by the sensitive method of qRT-PCR quantification. For this, we infected MDM with cis virus encoding $SIVmac_{239}$ Vpx and, after 24 and 48 h, measured the early reverse transcription products and 2-LTR circles. The analysis showed that at both time points the p6 chimeric virus encoding Vpx generated about 4-fold more late cDNA molecules than virus with wild-type p6 or virus that lacked Vpx. After 48 h, the p6 chimeric virus with vpx in cis generated six-fold more 2-LTR circles (FIG. 5B). To determine the relative numbers of infected cells, we infected MDDC with the cis viruses and analyzed them for intracellular p24 by flow cytometry. The analysis showed that the p6 chimeric virus encoding $SIVmac_{239}$ Vpx infected 8-fold more MDDC compared to viruses lacking Vpx (FIG. 5C). The $HIV2_{rod}$ and SIVagm viruses were not significantly enhanced compared to the controls. Addition of the protease inhibitor, Nelfinavir, to the $SIVmac_{239}$ Vpx-encoding p6 chimeric virus decreased the number of infected cells by an average of 58%, suggesting that the virus had replicated beyond the first cycle. We conclude that the cis virus containing $SIVmac_{239}$ Vpx replicated in the cells with enhanced efficiency despite having small amounts of Vpx.

HIV-1 containing Vpx induces Type I IFN in MDDC. Using pretreatment with Vpx-containing VLP, Manel et al. recently showed that HIV-1 infection of MDDC activates an innate immune response, resulting in the induction of CD86 and type I IFN (32). Induction of the response appeared to be triggered by newly synthesized viral Gag protein that had activated an as yet unidentified sensor. These findings predict that Vpx-containing HIV-1 will induce an innate immune response in MDDC. To determine whether this is the case, we infected MDDC with p6 chimeric virus containing or lacking Vpx and, after 24 and 48 h, quantified IFN-Iβ mRNA. The results showed a robust Vpx-dependent induction of IFN-β 48 h postinfection (FIG. 6). The IFN-β induction was blocked by AZT and Raltegravir, inhibitors that block reverse transcription and integration, respectively. This result suggests that the response was triggered post-integration and not induced by the in-coming virion. Furthermore, the lack of induction at 24 h is also consistent with a late event in virus replication, supporting the findings of Manel et al. (32). These results suggest that the p6 chimeric virus induced an innate immune response in the MDDC.

Vpx facilitates the transfer of HIV-1 from MDDC to T cells. In vitro, MDDC can be shown to transmit HIV-1 to CD4 T cells by trans-infection, a process in which the virus binds to cell surface lectin-like proteins on MDDC, such as DC-SIGN, and is then directly transferred to the T cell (16). In trans-infection, the MDDC does not become infected but binds the virus at the plasma membrane. Since Vpx enhances infection of MDDC, we hypothesized that, in addition to transmission through trans-infection, HIV-1 virions containing Vpx could be efficiently transmitted from MDDC to CD4 T cells through a direct infection mechanism analogous to cell-cell transmission by T cells (37). To test whether Vpx would allow for enhanced transmission of HIV-1 from MDDC to CD4 T cells, we infected MDDC with the NL.Ba.L p6 chimeric virus containing Vpx (Vpx+) or lacking Vpx (Vpx−) in cis. The free virus was removed and two days later, autologous activated CD4 T cells were added. We harvested the culture supernatant over 10 days for p24 quantification. The results showed that the Vpx-containing chimeric virus replicated with more rapid kinetics, producing greater than 8-fold more p24 at earlier timepoints than virus lacking Vpx (FIG. 7A).

The increased p24 production in this experiment could have been due simply to production from the MDDC. Alternatively, it could have been due to an effect of Vpx on HIV-1 replication in the activated CD4 T cells. To better determine the relative contribution of the two cell-types to virus replication, we established three cultures: MDDC alone, activated CD4 T cells alone, and a coculture of activated CD4 T cells and MDDC. All three cultures were infected with the NL.Ba.L chimeric p6 virus either containing Vpx (Vpx+) or lacking Vpx (Vpx−) in cis. In the case of the coculture, the MDDC were infected and, after 6 h, the virus was removed. Two days later, activated CD4 T cells were then added. We collected supernatants over the next 14 days for p24 quantification. In the MDDC alone culture, the Vpx− virus produced undetectable p24, while the Vpx+ virus produced moderate p24 after 10 days (FIG. 7B). In the coculture, the Vpx− virus replicated to a similar moderate level, while the Vpx+ virus replicated faster and to a higher p24 amount. This result could be explained either by more efficient transfer of the Vpx+ virus from MDDC to CD4 T cell or, alternatively, by better replication of the Vpx+ virus in the T cells independent of the MDDC. In the CD4 T cell alone culture, the Vpx+ and Vpx− viruses replicated with similar kinetics. This result suggests that Vpx does not enhance virus replication directly in CD4 T cells, consistent with earlier findings. Thus, in the cocultures the increased replication was due to transfer of the virus from infected MDDC to activated CD4 T cell.

To determine the number of infected CD4 T cells and MDDC in the cocultures, we stained the cells for intracellular p24 and gated on the CD11c+ (MDDC) and CD11c− (T cell) populations. The analysis showed that both the CD11c+ and CD11c− cells were infected more efficiently by the Vpx+ as compared to the Vpx− virus (FIG. 7C). As Vpx does not have a significant effect on HIV-1 replication in T cells, the result further suggests a role for Vpx in transmission of virus from MDDC to CD4 T cell.

Discussion

We report here on the development of an HIV-1 with a p6 that has been modified to allow packaging of Vpx. With the addition of a ten amino acid Vpx packaging motif from SIVmac$_{239}$, the engineered virus efficiently packaged SIVmac$_{239}$ Vpx, HIV-2$_{rod}$ Vpx, or SIVagm Vpr expressed in trans in the producer cell. The virus containing SIVmac$_{239}$ Vpx was dramatically enhanced in its ability to infect MDDC and MDM, induced a strong innate immune response, and replicated more efficiently in MDDC:CD4 T cell co-cultures than wild-type virus. Replication-competent, R5-tropic p6 chimeric virus that expressed Vpx in cis produced a relatively small amount of the accessory protein, but, in the case of SIVmac$_{239}$ Vpx, this was sufficient to provide a significant replicative advantage in MDDC. MDDC were more restrictive than MDM, an effect that was apparent in infections with viruses that had packaged only a limited amount of Vpx. In addition, there was variability in the stringency of the restriction in the cells of different donors. Vpx had no detectable effect on replication of the virus in activated CD4 T cells. As Vpx has been proposed to counteract a yet unidentified host restriction factor, our results imply that MDDC express more of the hypothetical restriction factor than MDM and that donors differ in how much of the factor their cells express.

Because Vpx packaging is virus-specific, engineering the virus required the introduction of the amino acid motif of SIVmac$_{239}$ that mediates Vpx packaging into HIV-1 p6 (25). To construct the virus, we first showed that the SIVmac$_{239}$ p6 sequence $^{17}$DPAVDLLKNY$^{26}$ (SEQ ID NO: 1) was the minimal motif needed to confer Vpx packaging on HIV-1. This sequence includes the $^{17}$DxAxxLL$^{23}$ (SEQ ID NO: 60) identified as the Vpx packaging motif by Accola et al., with the addition of three carboxy-terminal amino acids (1). Introduction of the motif adjacent to the PTAPP (SEQ ID NO: 61) late domain resulted in a chimeric virus that efficiently packaged SIVmac$_{239}$ Vpx, HIV-2$_{rod}$ Vpx, and SIVagm Vpr. When SIVmac$_{239}$ Vpx was provided in trans, the resulting virus was 10-100-fold more infectious on MDM and MDDC. Due to low level expression, HIV-2$_{rod}$ Vpx only slightly enhanced MDM and MDDC infection. SIVagm Vpr, which shares properties with Vpx, did not enhance the infection in human MDM or MDDC, suggesting that its function may be species-specific. When expressed in cis, only SIVmac$_{239}$ Vpx enhanced the infection of the MDM and MDDC.

The packaging of Vpr is mediated by a separate amino acid motif in p6. Two groups have reported on p6 residues required for Vpr packaging but with different results. Kondo et al. showed that p6 could be transferred to MuLV to allow virion packaging of Vpr and that the critical region required for packaging was the leucine motif, termed here motif 2 (30). In contrast, Zhu et al. found that virus containing a truncation of p6 at amino acid 35 that deletes motif 2 maintained Vpr packaging (53). In the truncated virus, the motif required for Vpr packaging mapped to $^{15}$FRFG$^{18}$, here termed motif 1. In this study, we show that in the context of full-length Gag both motifs play a role in Vpr packaging, although our results differ somewhat from both groups. Kondo et al. found that single amino acid mutations in motif 2 at positions 41, 44, or 45 prevented Vpr packaging. In contrast, we found that the individual mutations had no effect, but mutation of all four hydrophobic residues prevented Vpr packaging. This difference is probably because Kondo et al. tested the p6 mutants in the context of MuLV Gag, whereas we analyzed them in the context of HIV-1 Gag. Our results differed from those of Zhu et al. in that single amino acid mutations in the motif 1 $^{15}$FRFG$^{18}$ (SEQ ID NO: 59) sequence partially reduced but did not prevent Vpr packaging. The difference is probably because they analyzed the mutations in the context of truncated Gag, whereas we tested them in full-length Gag. A likely explanation for the role of the two motifs in Vpr packaging is that one serves as a binding site and the other affects p6 conformation. It is difficult to distinguish between these roles because both motifs lie in predicted alpha helices (14). However, it is likely that the hydrophobic alpha helical leucines of motif 2 face inward in the protein and thus are more likely to play a conformational role than serve as a binding site. Based on the importance of both motifs, the chimeric 17-26 p6 virus was able to maintain a low level of Vpr packaging despite the alteration of the overlapping $^{15}$FRFG$^{18}$ (SEQ ID NO: 59) motif.

Despite the use of a codon optimized open reading frame, expression of Vpx in cis resulted in a low level of intracellular expression and suboptimal packaging. The reduced level of Vpx packaging was probably caused by two factors. First, Vpx is rapidly degraded in the cell through a proteasomal pathway (data not shown). When expressed in trans by a high copy expression vector, the protein overwhelms the capacity of the proteasomal pathway, thereby increasing the half-life of Vpx. Second, expression in the nef position may not be optimal due to the temporal regulation of this position. Nef is expressed early from a fully-spliced mRNA (15). In contrast, virion assembly and Vpx packaging occurs later when there is a bias towards the Rev-induced production of unspliced mRNAs that encode the structural proteins. Due to its short half-life, Vpx produced early is likely to be degraded before it can be packaged.

In vivo, MDDC activate T cells by costimulation of the TCR and CD28 through a cell contact-dependent mechanism (4). This cell:cell interaction could provide an effective means by which the virus spreads throughout the body. Our findings with the replication of the chimeric virus in MDDC:T cell cocultures supports such a mechanism. In the previously described trans-infection mechanism, virus binds to the MDDC surface through DC-SIGN and other type C lectins. The virus does not infect the cell but is transferred to the CD4 T cell through an infectious synapse. We propose that Vpx can provide a second mechanism of transmission in which virus produced in the infected MDDC is transmitted to a CD4 T cell. It is unlikely that Vpx would act through trans-infection as it is thought to act in the target cell and not in the virion attached to the cell surface. Whether the transmission is through a virological synapse or cell-free virus could not be distinguished in the coculture system. It is remarkable that HIV-1 is susceptible to the hypothetical host restriction factor yet lacks the gene for Vpx to counteract it (19, 21). This role does not appear to have been subsumed by Vpr, which in culture does not have the potency of Vpx in increasing MDDC infection. It is conceivable that MDDC to T cell spread of virus is more important for a virus such as SIVmac than for HIV-1, where the infection may be driven more by T cell to T cell spread, especially once the virus has developed the ability to use CXCR4.

The infected MDDC were induced to produce IFNβ by infection with the Vpx-complemented HIV-1, a property that might interfere with transmission of the virus to T cells. Manel et al. suggested that IFNβ production by infected MDDC may inhibit virus spread to T cells (32). In our experiments this effect did not appear to interfere with replication of the Vpx-containing virus in T cells, perhaps due to our use of lower virus doses in the infections. It is possible that there is a balance between the enhancing and inhibitory activities of infected MDDC and it is difficult to know which condition exists in vivo.

The chimeric virus developed here will provide a tool for studying the role of Vpx in infection and may also provide a tool for vaccine and lentiviral vector design. Because of the role of MDDC in presenting antigens to T cells, the chimeric p6 virus could be a vehicle to enhance immune responses to lentiviral vector encoded immunogens. Additionally, lentiviral vectors that are engineered to package Vpx could provide a means to increase the transduction of MDDC and MDM.

EXAMPLE 2

Generation of an Exemplary Gag/pol Packaging Vector that Produces HIV-1 Based Lentiviral Vectors with Enhanced Dendritic Cell and Macrophage Tropism Methods:

Cells and cell culture. 293T cells were cultured in Dulbecco's modified Eagle's Medium (DMEM)-10% fetal bovine serum (FBS). MDDC were cultured in RPMI 1640-5% Human AB Serum. Peripheral blood mononuclear cells (PBMC) were purified from normal human donor blood by Ficoll density gradient. Monocytes were purified from healthy donor PBMC by adherence to plastic. Monocyte-derived dendritic cells (MDDC) were generated by culturing the monocytes for 5-6 days in medium containing 50 ng/ml GM-CSF and 100 ng/ml IL-4 (R&D Systems).

Plasmids. Codon-optimized, epitope-tagged $SIVmac_{239}$ Vpx expression vector was generated by overlapping PCR and cloned into pcDNA6 (Invitrogen Inc.) at the EcoR-I and Xho-I sites. pMDLg-SIVp6__17-26/pRRE was generated by cloning in the chimeric p6 region of pNL-luc3-E$^-$R/SIVp6__17-26 into the corresponding gag region in pMDLg/pRRE using the Age-I and Mfe-I sites.

Virus preparation and infections. To produce lentivirus using the lentiviral vector pGK-NGFR-IRES-GFP, 293T cells were cotransfected using lipofectamine 2000 with pGK-NGFR-IRES-GFP (14 μg), pcVSV-G (3.5 μg), pRSV-Rev (2.5 μg), pMDLg/pRRE or pMDLg-SIVp6__17-26/pRRE (5 μg), and pcVpx.mychis or pcDNA6 (4.7 μg). Supernatants were harvested 48 h post-transfection, passed through 0.45 μm pore-size filters, aliquoted, and frozen at −80° C. P24 content of virus-containing supernatants was quantified by ELISA using commercially available capture and sandwich antibodies (Aalto Bioreagents, LTD).

MDDC ($1.25\times10^5$) were seeded in a 96-well plate and then infected with lentivirus at either 5 or 25 ng p24. MDDC ($3\times10^5$) and 293T ($2.5\times10^5$) were seeded in a 24-well and 12-well plate, respectively, and then were infected with lentivirus at 120 ng p24. Three days post-infection, the cells were fixed and analyzed by flow cytometry using Flojo software (BD Biosciences). The cells were gated for forward and side scatter and analyzed for FITC fluorescence with mock infected cells as a negative control.

Background: Lentiviral vectors have found great utility for the expression of proteins in cell culture. They are also starting to be used in human gene therapy trials. Although the vectors are generally produced as VSV-G pseudotypes and thus can infect all cell-types, they have poor infectivity with respect to macrophages and dendritic cells. Such cells are important in the immune system due to their ability to present peptide antigens to T cells. They are also important because of they contribute to activation of innate immune pathways. In one approach, dendritic cell based vaccines are being developed as cancer vaccines. The present inventors have discovered and developed reagents and devised a method using same that can be used to generate lentiviral vectors that exhibit a greatly enhanced ability to infect macrophages and dendritic cells relative to lentiviral vectors generated via other means, including those generated as VSV-G pseudotypes. Such vectors are useful for vaccine development and/or for expression of exogenous proteins in gene therapy.

The lentiviral accessory protein Vpx has been shown to facilitate HIV-1 infection of myeloid cells, such as macrophages and dendritic cells, although this virus does not encode it. In order to take advantage of this property, Vpx is added separately or independently from HIV-1 by pre-treating the target cells with SIVmac viral-like particles (VLP). VLPs lack a viral genome but contain the proteins normally delivered to the target cell, such as Vpx. To the best of the inventors' knowledge, Vpx has never been added to HIV-1 via any other means. The system described herein circumvents the use of VLPs. By placing a ten amino acid SIVmac Vpx packaging sequence into the p6 of HIV-1, the present inventors constructed an HIV-1 that is able to directly package Vpx. The resulting virions are also dramatically enhanced in their ability to infect MDDC, in some donors up to 100-fold (based on intracellular p24). By not having to add Vpx separately from the actual virus, the present system prevents the chance of artifacts or immune responses arising due to the presence of large amounts of VLPs. This may become especially important in vaccine design.

Results:

Lentivirus constructed with p6 chimeric gag-pol packages Vpx and infects MDDC. As shown in Example 1 above, the present inventors showed that when placed into HIV-1 p6 the residues $^{17}$DPAVDLLKNY$^{26}$ (SEQ ID NO: 1) of $SIVmac_{239}$ p6 are sufficient to allow for Vpx packaging. Furthermore, the resulting virus was significantly enhanced in its ability to infect MDDC by an average of 100-fold. Current HIV-1 gag-pol expression plasmids used in generating lentivirus are unable to allow for efficient packaging of Vpx. These results predict that the addition of these $SIVmac_{239}$ p6 residues to a gag-pol plasmid used with third generation lentiviral vector systems would boost the ability of the resulting virus to transduce dendritic cells, a cell type that is relatively resistant to infection.

To test this hypothesis, the present inventors constructed a p6 chimeric gag-pol plasmid by modifying the pMDLg/pRRE plasmid to contain the $SIVmac_{239}$ p6 residues $^{17}$DPAVDLLKNY$^{26}$ (SEQ ID NO: 1) in gag. The pGK-NGFR-IRES-GFP lentivirus was generated by cotransfecting 293T with this proviral plasmid, the wild-type or chimeric packaging plasmid (pMDLg/pRRE or pMDLg-SIVp6_17-26/pRRE), pcRSV-Rev, and pcDNA6 or pcVpx.mychis. After two days, the supernatant was harvested. To examine whether the chimeric gag allowed for packaging of Vpx, the virions were pelleted through ultracentrifugation and subsequently analyzed on an immunoblot (FIG. 10A). Lentivirus made with wild-type gag failed to efficiently package Vpx. In contrast, lentivirus produced in the presence of a p6 chimeric gag incorporated significant amounts of Vpx.

To test infection, the present inventors normalized the virus for CA p24 and infected monocyte-derived dendritic cells (MDDC) and 293T. The number of cells infected after three days was measured by examining GFP expression by FACS. The present inventors found that viruses that lacked Vpx infected few MDDC (FIG. 10B). In contrast, virus that packaged Vpx infected significantly more cells at all amounts, with the increase substantially greater for the p6 chimeric lentivirus. The viruses all infected 293T to a similar extent (FIG. 10C). These findings demonstrate that the Vpx and/or the alteration of Gag were not deleterious to the virus and that the Vpx effect is cell-type specific.

Various references are cited throughout this Specification, each of which is incorporated herein by reference in its entirety.

REFERENCES

1. Accola, M. A., A. A. Bukovsky, M. S. Jones, and H. G. Göttlinger. 1999. A conserved dileucine-containing motif in p6(gag) governs the particle association of Vpx and Vpr of simian immunodeficiency viruses SIV(mac) and SIV (agm). J Virol 73:9992-9.
2. Arthur, L. O., J. W. Bess, R. C. Sowder, R. E. Benveniste, D. L. Mann, J. C. Chermann, and L. E. Henderson. 1992. Cellular proteins bound to immunodeficiency viruses: implications for pathogenesis and vaccines. Science 258: 1935-8.
3. Balliet, J. W., D. L. Kolson, G. Eiger, F. M. Kim, K. A. McGann, A. Srinivasan, and R. Collman. 1994. Distinct effects in primary macrophages and lymphocytes of the human immunodeficiency virus type 1 accessory genes vpr, vpu, and nef: mutational analysis of a primary HIV-1 isolate. Virology 200:623-31.
4. Banchereau, J., and R. M. Steinman. 1998. Dendritic cells and the control of immunity. Nature 392:245-52.
5. Belshan, M., L. A. Mahnke, and L. Ratner. 2006. Conserved amino acids of the human immunodeficiency virus type 2 Vpx nuclear localization signal are critical for nuclear targeting of the viral preintegration complex in non-dividing cells. Virology 346:118-26.
6. Bergamaschi, A., D. Ayinde, A. David, E. Le Rouzic, M. Morel, G. Collin, D. Descamps, F. Damond, F. Brun-Vezinet, S. Nisole, F. Margottin-Goguet, G. Pancino, and C. Transy. 2009. The human immunodeficiency virus type 2 Vpx protein usurps the CUL4A-DDB1 DCAF1 ubiquitin ligase to overcome a postentry block in macrophage infection. J Virol 83:4854-60.
7. Berger, G., C. Goujon, J.-L. Darlix, and A. Cimarelli. 2009. SIVMAC Vpx improves the transduction of dendritic cells with nonintegrative HIV-1-derived vectors. Gene Ther 16:159-63.
8. Butler, S. L., E. P. Johnson, and F. D. Bushman. 2002. Human immunodeficiency virus cDNA metabolism: notable stability of two-long terminal repeat circles. J Virol 76:3739-47.
9. Campbell, B. J., and V. M. Hirsch. 1997. Vpr of simian immunodeficiency virus of African green monkeys is required for replication in macaque macrophages and lymphocytes. J Virol 71:5593-602.
10. Connor, R. I., B. K. Chen, S. Choe, and N. R. Landau. 1995. Vpr is required for efficient replication of human immunodeficiency virus type-1 in mononuclear phagocytes. Virology 206:935-44.
11. Di Domizio, J., A. Blum, M. Gallagher-Gambarelli, J.-P. Molens, L. Chaperot, and J. Plumas. 2009. TLR7 stimulation in human plasmacytoid dendritic cells leads to the induction of early IFN-inducible genes in the absence of type I IFN. Blood 114:1794-802.
12. Di Marzio, P., S. Choe, M. Ebright, R. Knoblauch, and N. R. Landau. 1995. Mutational analysis of cell cycle arrest, nuclear localization and virion packaging of human immunodeficiency virus type 1 Vpr. J Virol 69:7909-16.
13. Fletcher, T. M., B. Brichacek, N. Sharova, M. A. Newman, G. Stivahtis, P. M. Sharp, M. Emerman, B. H. Hahn, and M. Stevenson. 1996. Nuclear import and cell cycle arrest functions of the HIV-1 Vpr protein are encoded by two separate genes in HIV-2/SIV(SM). EMBO J 15:6155-65.
14. Fossen, T., V. Wray, K. Bruns, J. Rachmat, P. Henklein, U. Tessmer, A. Maczurek, P. Klinger, and U. Schubert. 2005. Solution structure of the human immunodeficiency virus type 1 p6 protein. J Biol Chem 280:42515-27.
15. Freed, E. O. 2001. HIV-1 replication. Somat Cell Mol Genet 26:13-33.
16. Geijtenbeek, T. B., D. S. Kwon, R. Torensma, S. J. van Vliet, G. C. van Duijnhoven, J. Middel, I. L. Cornelissen, H. S. Nottet, V. N. KewalRamani, D. R. Littman, C. G. Figdor, and Y. van Kooyk. 2000. DC-SIGN, a dendritic cell-specific HIV-1-binding protein that enhances trans-infection of T cells. Cell 100:587-97.
17. Gibbs, J. S., A. A. Lackner, S. M. Lang, M. A. Simon, P. K. Sehgal, M. D. Daniel, and R. C. Desrosiers. 1995. Progression to AIDS in the absence of a gene for vpr or vpx. J Virol 69:2378-83.
18. Goujon, C., V. Arfi, T. Pertel, J. Luban, J. Lienard, D. Rigal, J.-L. Darlix, and A. Cimarelli. 2008. Characterization of simian immunodeficiency virus SIVSM/human immunodeficiency virus type 2 Vpx function in human myeloid cells. J Virol 82:12335-45.
19. Goujon, C., L. Jarrosson-Wuilleme, J. Bernaud, D. Rigal, J.-L. Darlix, and A. Cimarelli. 2006. With a little help from a friend: increasing HIV transduction of monocyte-derived dendritic cells with virion-like particles of SIV(MAC). Gene Ther 13:991-4.
20. Goujon, C., L. Riviere, L. Jarrosson-Wuilleme, J. Bernaud, D. Rigal, J.-L. Darlix, and A. Cimarelli. 2007. SIVSM/HIV-2 Vpx proteins promote retroviral escape from a proteasome-dependent restriction pathway present in human dendritic cells. Retrovirology 4:2.
21. Gramberg, T., N. Sunseri, and N. R. Landau. 2010. Evidence for an activation domain at the amino terminus of simian immunodeficiency virus Vpx. J Virol 84:1387-96.
22. Hattori, N., F. Michaels, K. Fargnoli, L. Marcon, R. C. Gallo, and G. Franchini. 1990. The human immunodeficiency virus type 2 vpr gene is essential for productive infection of human macrophages. Proc Natl Acad Sci USA 87:8080-4.

23. Henderson, L. E., R. C. Sowder, T. D. Copeland, R. E. Benveniste, and S. Oroszlan. 1988. Isolation and characterization of a novel protein (X-ORF product) from SIV and HIV-2. Science 241:199-201.
24. Hirsch, V. M., M. E. Sharkey, C. R. Brown, B. Brichacek, S. Goldstein, J. Wakefield, R. Byrum, W. R. Elkins, B. H. Hahn, J. D. Lifson, and M. Stevenson. 1998. Vpx is required for dissemination and pathogenesis of SIV(SM) PBj: evidence of macrophage-dependent viral amplification. Nat Med 4:1401-8.
25. Horton, R., P. Spearman, and L. Ratner. 1994. HIV-2 viral protein X association with the GAG p27 capsid protein. Virology 199:453-7.
26. Hrecka, K., M. Gierszewska, S. Srivastava, L. Kozaczkiewicz, S. K. Swanson, L. Florens, M. P. Washburn, and J. Skowronski. 2007. Lentiviral Vpr usurps Cul4-DDB1 [VprBP] E3 ubiquitin ligase to modulate cell cycle. Proc Natl Acad Sci USA 104:11778-83.
27. Kappes, J. C., J. A. Conway, S. W. Lee, G. M. Shaw, and B. H. Hahn. 1991. Human immunodeficiency virus type 2 vpx protein augments viral infectivity. Virology 184:197-209.
28. Kasper, M. R., J. F. Roeth, M. Williams, T. M. Filzen, R. I. Fleis, and K. L. Collins. 2005. HIV-1 Nef disrupts antigen presentation early in the secretory pathway. J Biol Chem 280:12840-8.
29. Kestler, H. W., D. J. Ringler, K. Mori, D. L. Panicali, P. K. Sehgal, M. D. Daniel, and R. C. Desrosiers. 1991. Importance of the nef gene for maintenance of high virus loads and for development of AIDS. Cell 65:651-62.
30. Kondo, E., and H. G. Gottlinger. 1996. A conserved LXXLF sequence is the major determinant in p6gag required for the incorporation of human immunodeficiency virus type 1 Vpr. J Virol 70:159-64.
31. Lu, Y. L., P. Spearman, and L. Ratner. 1993. Human immunodeficiency virus type 1 viral protein R localization in infected cells and virions. J Virol 67:6542-50.
32. Manel, N., B. Hogstad, Y. Wang, D. E. Levy, D. Unutmaz, and D. R. Littman. 2010. A cryptic sensor for HIV-1 activates antiviral innate immunity in dendritic cells. Nature 467:214-7.
33. Marin, M., K. M. Rose, S. L. Kozak, and D. Kabat. 2003. HIV-1 Vif protein binds the editing enzyme APOBEC3G and induces its degradation. Nat Med 9:1398-403.
34. Münk, C., S. M. Brandt, G. Lucero, and N. R. Landau. 2002. A dominant block to HIV-1 replication at reverse transcription in simian cells. Proc Natl Acad Sci USA 99:13843-8.
35. Ndolo, T., M. George, H. Nguyen, and S. Dandekar. 2006. Expression of simian immunodeficiency virus Nef protein in CD4+ T cells leads to a molecular profile of viral persistence and immune evasion. Virology 353:374-87.
36. Neil, S. J. D., T. Zang, and P. D. Bieniasz. 2008. Tetherin inhibits retrovirus release and is antagonized by HIV-1 Vpu. Nature 451:425-30.
37. Nobile, C., C. Petit, A. Moris, K. Skrabal, J.-P. Abastado, F. Mammano, and O. Schwartz. 2005. Covert human immunodeficiency virus replication in dendritic cells and in DC-SIGN-expressing cells promotes long-term transmission to lymphocytes. J Virol 79:5386-99.
38. Paxton, W., R. I. Connor, and N. R. Landau. 1993. Incorporation of Vpr into human immunodeficiency virus type 1 virions: requirement for the p6 region of gag and mutational analysis. J Virol 67:7229-37.
39. Schröfelbauer, B., Y. Hakata, and N. R. Landau. 2007. HIV-1 Vpr function is mediated by interaction with the damage-specific DNA-binding protein DDB1. Proc Natl Acad Sci USA 104:4130-5.
40. Sharova, N., Y. Wu, X. Zhu, R. Stranska, R. Kaushik, M. Sharkey, and M. Stevenson. 2008. Primate lentiviral Vpx commandeers DDB 1 to counteract a macrophage restriction. PLoS Pathog 4:e1000057.
41. Sheehy, A. M., N. C. Gaddis, and M. H. Malim. 2003. The antiretroviral enzyme APOBEC3G is degraded by the proteasome in response to HIV-1 Vif. Nat Med 9:1404-7.
42. Srivastava, S., S. K. Swanson, N. Manel, L. Florens, M. P. Washburn, and J. Skowronski. 2008. Lentiviral Vpx accessory factor targets VprBP/DCAF1 substrate adaptor for cullin 4 E3 ubiquitin ligase to enable macrophage infection. PLoS Pathog 4:e1000059.
43. Stopak, K., C. de Noronha, W. Yonemoto, and W. C. Greene. 2003. HIV-1 Vif blocks the antiviral activity of APOBEC3G by impairing both its translation and intracellular stability. Mol Cell 12:591-601.
44. Tristem, M., C. Marshall, A. Karpas, and F. Hill. 1992. Evolution of the primate lentiviruses: evidence from vpx and vpr. EMBO J 11:3405-12.
45. Tristem, M., C. Marshall, A. Karpas, J. Petrik, and F. Hill. 1990. Origin of vpx in lentiviruses. Nature 347:341-2.
46. Van Damme, N., D. Goff, C. Katsura, R. L. Jorgenson, R. Mitchell, M. C. Johnson, E. B. Stephens, and J. Guatelli. 2008. The interferon-induced protein BST-2 restricts HIV-1 release and is downregulated from the cell surface by the viral Vpu protein. Cell Host Microbe 3:245-52.
47. Wu, X., J. A. Conway, J. Kim, and J. C. Kappes. 1994. Localization of the Vpx packaging signal within the C terminus of the human immunodeficiency virus type 2 Gag precursor protein. J Virol 68:6161-9.
48. Yamashita, M., and M. Emerman. 2005. The cell cycle independence of HIV infections is not determined by known karyophilic viral elements. PLoS Pathog 1:e18.
49. Yu, X., Y. Yu, B. Liu, K. Luo, W. Kong, P. Mao, and X.-F. Yu. 2003. Induction of APOBEC3G ubiquitination and degradation by an HIV-1 Vif-Cul5-SCF complex. Science 302:1056-60.
50. Yu, X. F., M. Matsuda, M. Essex, and T. H. Lee. 1990. Open reading frame vpr of simian immunodeficiency virus encodes a virion-associated protein. J Virol 64:5688-93.
51. Yu, X. F., Q. C. Yu, M. Essex, and T. H. Lee. 1991. The vpx gene of simian immunodeficiency virus facilitates efficient viral replication in fresh lymphocytes and macrophage. J Virol 65:5088-91.
52. Zhai, Q., M. B. Landesman, H. Robinson, W. I. Sundquist, and C. P. Hill. 2011. Identification and structural characterization of the ALIX-binding late domains of simian immunodeficiency virus SIVmac239 and SIVagmTan-1. J Virol 85:632-7.
53. Zhu, H., H. Jian, and L.-J. Zhao. 2004. Identification of the 15FRFG domain in HIV-1 Gag p6 essential for Vpr packaging into the virion. Retrovirology 1:26.

Additional references are cited in Example 3 below, each of which is incorporated herein by reference in its entirety.

EXAMPLE 3

Vpx-Containing Lentiviral Vector Targets Dendritic Cells to Induce Antigen-specific CD8+ T Cell Responses Methods:

Plasmid construction. To construct the pLenti.CD40L.Puro LV vector, a DNA fragment containing the CD40L coding sequence and 5' and 3' BamHI and Sal-I ends was generated by RT-PCR from human lymphocyte RNA using specific primers. The fragment was cleaved with BamHI and SalI and ligated to similarly cleaved pLenti CMV GFP Puro (658-5 Addgene™), replacing the GFP sequence. To construct pLenti.GFP.Flu, an amplicon was generated that encoded the influenza virus matrix protein epitope GILGFVFTL[20] (SEQ ID NO: 62) fused to the ER retention signal MRYMILGLLALAAVCSAA.[22](SEQ ID NO: 63) The DNA fragment was cloned into the Pst-I and Xho-I sites of pLenti CMV GFP Puro, replacing the puro$^r$ sequence. To construct pLenti.CD40LP2AF1u.Puro, an amplicon was constructed in which the CD40L coding sequence was fused to the self-cleaving picornavirus 2A (P2A) sequence GSGATNFSLLKQAGDVEENPGP[21] (SEQ ID NO: 64) and influenza peptide using specific primers and overlapping PCR. The amplicon was cloned into pLenti.GFP.Puro at the BamHI and Sal-I sites, replacing GFP.

Cell culture. 293T cells were cultured in Dulbecco's Modified Eagles Medium (DMEM) supplemented with 10% fetal bovine serum (FBS) and penicillin/streptomycin. Monocyte-derived dendritic cells (MDDC) were cultured in RPMI supplemented with 1 mM HEPES, gentamicin, and 5% heat inactivated pooled human serum (PHS). T cells were cultured in Iscove's Modified Dulbecco's Medium supplemented with 1.0 mM HEPES, 2 mM L-glutamine, penicillin/streptomycin, MEM nonessential amino acids, and 5% heat-inactivated PHS. Peripheral blood mononuclear cells (PBMCs) and cord blood of anonymous healthy donors were obtained from the New York Blood Center. Buffy coats were prepared from the cells by Ficoll density gradient centrifugation and the cells were typed for MHC Class I HLA-A2 by flow cytometry with an anti-A2 monoclonal antibody (mAb). The monocytes were purified by plastic adherence and then cultured for 4 days in medium supplemented with 100 U/mL granulocyte-macrophage colony stimulating factor (GM-CSF; Invitrogen Inc.) and 300 U/mL interleukin-4 (IL-4; R&D systems) to generate MDDC. The cells were fed every other day with medium containing fresh cytokines. To isolate autologous CD8+ T cells, the non-adherent fraction was sorted with anti-CD8-conjugated magnetic beads (Miltenyi Biotec). The cells were frozen in PHS/10% dimethyl sulfoxide prior to use.

Virus preparation and infections. To prepare LV vector stocks, 293T cells were cotransfected using calcium phosphate coprecipitation with LV plasmid, the P6-modified HIV-1 Gag/Pol expression vector pMDL-X, pcRev, pcVSV-G and pcVpx or pcDNA at a mass ratio of 28:10:7:5:2. After 48 h, virus-containing supernatant was harvested, passed through a 0.45-μm filter, concentrated 10-fold through a 100K MWCO centrifugal filter (Millipore) and frozen at −80° C. in aliquots. GFP and CD40L expressing viruses were titered on 293 cells by flow cytometry to determine the number of GFP+ or CD40L+ cells per ml of virus.

Lentiviral vector-induced DC maturation and activation. DCs ($2\times10^5$) were plated in a 96 well dish and then infected with titered LV vector stock at a multiplicity of infection (MOI) of 2. The number of GFP+ and CD40L+ cells was determined at 48 and 72 h post-infection by flow cytometry. The differentiation status of DCs was determined 48 and 72 h post-infection by CD83 and CD86 staining and measurement of supernatant IL-12p70, TNF-α, IL-6, and IL-1β using the Human Inflammatory Cytokine Cytometric Bead Array (BD Pharmingen).

Naive and memory responses to LV-transduced DC. DCs ($2\times10^5$) were plated in a 96 well plate and infected with LV vectors at an MOI of 2. After 48 h, $5.0\times10^4$ transduced DCs were co-cultured with $5\times10^4$ Flu MP (58-66) A0201-restricted CD8+ T cell clones in a 96 well plate at an effector to target ratio of 1:1. As a control for maximal stimulation, 1 μg/mL Flu peptide (58-66) was added. After 24 h, supernatant IFN-γ was measured by Cytokine Cytometric Bead Array (BD Pharmingen).

To determine the ability of transduced DC to present peptide antigens and to activate memory CD8+ T cells, transduced DC ($2.5\times10^4$) were co-cultured with thawed autologous CD8+ T cells ($2\times10^5$) in a 96 well dish in medium supplemented with 25 U/ml interleukin 2 (IL-2) and 5 ng/ml interleukin 7 (IL-7) and replenished every 2 to 3 days. After 14 days, half of the cells were harvested for Flu T cell receptor (TCR) quantification by staining with allophycocyanin (APC)-conjugated Flu-specific tetramer and analysis by flow cytometry. The remaining autologous cells were stimulated with 5.0 μg/ml Flu peptide. Brefeldin A (10 μg/ml) was added one hour later and after another five hours, the cells were stained with antibodies against CD3 and CD8 and then fixed in 1% paraformaldehyde. The cells were permeabilized with PBS containing 0.1% bovine serum albumin and 0.1% saponin and the intracellular IFN-γ and TNF-α was stained and analyzed by flow cytometry. Naive T cell responses were measured as for the memory response with the exception that cord blood T cells were used instead of adult CD8 T cells.

Measuring ACH-2 cells provirus reactivation response to LV-transduced DC. DC were transduced with LV vector and after 24 h were cultured with $2.0\times10^5$ ACH-2 cells [23] in a 96 well plate. After 48 h the supernatant was harvested and applied to $2.0\times10^4$ TZM-bl cells in a 96 well plate in serial 3-fold dilutions with 2.0 μg/mL polybrene (Millipore). After 48 h, the cells were fixed in PBS containing 2% gluaraldehyde (Sigma) and 2% formaldehyde (Sigma). The cells were then stained with X-gal for 2 h at 37° C., fixed in 100% methanol for 5 min, and dried. Infectious centers were counted using an Elispot reader.

Background:

Dendritic Cells (DCs) are professional antigen presenting cells that activate antigen-specific CD4+ and CD8+ T cells to initiate an immune response. Immature DCs efficiently take-up and process antigens on class I and class II major histocompatibility complexes (WIC), and upon maturation, induce the expression of cytokines and cell surface proteins that stimulate antigen-specific CD4+ and CD8+ T cells. DC-based vaccine strategies currently under development involve isolation of DCs from the individual, ex vivo pulsing with antigenic peptide, and subsequent reinfusion to stimulate T cell response;[1-5] a strategy that results in short-term antigen presentation. Alternatively, DCs can be transduced with lentiviral (LV) vectors to express peptide antigens. LV vectors are advantageous because they infect non-dividing cells and result in transgene expression over the lifetime of the cell and in daughter cells.[6-8] The vectors have the disadvantage that they are blocked in DCs by a post-entry restriction mediated by endogenous SAMHD1. SAMHD1 is a host nucleotide phosphohydrolyase that dephosphorylates intracellular dNTPs, thereby diminishing the pool of nucleotide precursors used by the virus in the synthesis of its genome.[9] In HIV-2 and some SIVs, SAMHD1 is counteracted by the viral Vpx accessory protein that targets SAMHD1 for degradation and counteracts the restriction.[10,11] HIV-1 does not encode such a protein, yet engineering HIV-1 to package Vpx protein results in virus with significantly improved ability to infect DC. The present inventors recently reported on viral vectors that allow for the production of Vpx-containing HIV-1 based LV vectors and showed that they efficiently infected primary human DC in culture.[12]

DC maturation results following antigen and cytokine exposure and is essential for optimizing T cell responses. CD40 ligand (CD40L), also known as CD 154, is a transmembrane protein expressed on activated T-helper cells that promotes activation, maturation, and enhanced survival of DCs upon engagement with the CD40 receptor.[13-15] It has also been shown to help induce memory T cells and activate humoral immunity by promoting the proliferation of B cells, their differentiation to antibody-secreting plasma cells and memory B cells, and immunoglobulin class-switching.[14,16]

CD40-CD40L interactions play a significant role in the production of several Th1-skewing and pro-inflammatory cytokines, such as IL-12, TNF-$\alpha$ and IL-6 that may lead to enhanced cell mediated immunity.[13,14,17] Endogenous expression of CD40L by LV vector transduction of DCs induces autonomous maturation as evidenced by enhanced expression of immunologically relevant markers (CD83, CD80) and secretion of IL-12.[17] With respect to HIV, immunization with chimeric CD40L/SHIV virus-like particles was found to induce DC activation and enhance humoral and cellular responses to the SIV Gag and HIV Env proteins in mouse models, lending credence to the possibility that incorporating CD40L may be helpful in developing effective HIV vaccines.[18] Moreover, the use CD40L appears to be safe in humans.[19]

Long-term highly active antiretroviral therapy (HAART) reduces viral loads in many patients to low levels and may even completely suppress virus replication yet does not result in eradication of the virus. As a result, patients must remain on life-long therapy. The ability of the virus to integrate into the host chromosomal DNA allows it to remain in quiescent T cells. Strategies to reactivate latently infected cells in patients are under development and have met with some success, yet are not thought to result in purging of the reservoir, as virus production in itself is not sufficient to induce cellular apoptosis and the immune response under long-term HAART is not adequate to lyse infected cells. If such a strategy is to work it will require both reactivation of the proviruses in latently infected cells coupled with a mechanism by which the cells are targeted. To devise such an approach, the present inventors have taken advantage of a LV vector system described herein that allows for highly efficient transduction of myeloid cells. The vectors also facilitate stable expression of antigenic peptides and immunostimulatory proteins. The former feature stimulates antigen-specific CD4+ and CD8+ effector cells and the latter enhances the immune response and induces viral production from latently infected cells.

Accordingly, the present inventors tested the ability of Vpx-containing LV vectors to induce antigen-specific CD8+ T cell responses. As shown herein, these vectors have a markedly improved ability to transduce DCs and cells transduced thereby are very effective at activating antigen-specific CD8+ T cells. The vectors expressed the HLA-A2.1 restricted influenza peptide[20] fused to CD40L via a self-cleaving picornavirus 2A peptide.[21] As CD40L is a type II transmembrane protein, fusion of the peptide to CD40L proved an effective method of antigen presentation since CD40L is targeted to the ER lumen with its C-terminal domain, thereby enabling the peptide to be cleaved directly into the ER lumen for efficient processing. Furthermore, by capitalizing on the immunostimulatory effect of CD40L, the ability to augment the antigen-specific Th1 response and induce quiescent HIV proviruses from latently infected cells is demonstrated, thereby establishing a DC-targeted LV vector system that serves as the basis for developing an HIV immunotherapeutic or antigen-specific vaccine.

Results:

Vpx-containing LV vectors that encode a CD40L-Flu peptide epitope. Lentiviral vectors in which the virions contain packaged SIV Vpx escape SAMHD1-mediated restriction and thus infect cells such as DC with significantly improved efficiency. The present inventors used this principle to generate lentiviral vectors encoding a CMV promoter-driven nominal peptide antigen and an immunostimulatory gene. As nomimal antgen, an influenza matrix protein peptide that forms an immunodominant epitope to which the CD8 T cells of most HLA-A2.1 donors respond was used. In the vector, pLenti.CD40L.Flu, the peptide is expressed as a carboxy-terminal fusion to CD40L with an intervening picornavirus-2A (P2A) self-cleaving peptide (FIG. 14). Because CD40L is a type II transmembrane protein, it is synthesized with its carboxy-terminus facing the ER lumen such that cleavage of the peptide during biosynthesis releases it into the ER lumen where it has direct access to the antigen presentation pathway. The CD40L, a T cell expressed protein that binds to CD40L on DC, serves to induce maturation and augment antigen presentation pathways of the transduced DC. As controls, vectors were constructed that encode (i) CMV promoter-driven CD40L, (ii) GFP, and (iii) CMV-driven GFP with PGK promoter-driven Flu peptide. Virus stocks in which the virions contained or lacked packaged Vpx were produced by cotransfecting 293 cells with vector plasmid and pMDL-X, an HIV-1 Gag/Pol expression vector in which the Vpx packaging motif has been placed in P6, and with or without Vpx expression vector. The viruses were normalized for infectious titer on 293 cells.

To test the efficiency with which the vectors transduced DC, HLA-A2+ donor DC were infected at an MOI=1 equivalent as measured by infectivity on 293 cells. After 48 and 72 h the number of GFP+ and CD40L+ DCs was quantified by flow cytometry. Viruses that lacked Vpx, failed to transduce the DC with detectable efficiency. In contrast, viruses that contained Vpx transduced 36% to 65% of the cells (FIG. 15). In some cases the GFP vectors appeared to be more infectious than the CD40L-expressing vectors; however this was likely the result of less sensitive detection of CD40L as compared to GFP. The results demonstrated that the packaged Vpx had allowed for much more efficient transduction of the DC.

CD40L-peptide fusion protein induces DC maturation. As DC mature they secrete stimulatory cytokines and upregulate CD83 and CD86. To test whether transduction of the DC with the CD40L-peptide peptide expressing lentiviral vectors would cause the DC to mature, DCs were transduced with the panel of LV and 48 and 72 h later their CD83 and CD86 expression levels were quantified. The results showed that viruses produced without Vpx induced a moderate amount of maturation, with between 36% to 50% of the cells becoming CD83+ and only a small effect of CD40L. In contrast, for Vpx-containing viruses that expressed CD40L or CD40L-Flu, induced nearly all of the DCs to mature, resulting in 84% and 88% CD83+ cells, respectively (FIG. 16). Vpx-containing vectors that lacked CD40L (GFP or GFP.Flu vectors) induced no maturation over base-line. The cause of the maturation by Vpx-lacking virions is not clear but is most likely the result of an innate immune response to the virions themseleves and not the result of direct infection, as these viruses are largely uninfectious with respect to DCs. The results demonstrated that the Vpx-containing lentviral vectors that expressed CD40L potently stimulated the DC to mature.

To determine whether the vectors induced Th1/Th2 skewing cytokines in the DC, the DC of four donors were transduced with the panel of LV containing or lacking Vpx and after 48 h and 72 h IL-12 and TNF-α were measured in the culture supernaants. Vectors that lacked Vpx induced little IL-12 over base-line, uninfected cells. In contrast, when the viruses contained Vpx, the vectors that expressed CD40L and CD40L-Flu induced IL-12 production (FIG. 17). IL-12 reached levels up to 7,000 times greater than controls. The results show that the Vpx-containing vectors that expressed CD40L efficiently induced the maturation of the DC and induced these cells to produce cytokines that enhance the Th1 response.

DC transduced with Vpx-containing LV vectors present antigens to CTL. The ability of the Vpx-containing vectors to induce DC to present antigen and stimulate antigen-specific T cells was then assessed. To this end, DCs were transduced with various vectors described herein and after 48 h, co-cultured with an A2-restricted CTL clone specific for the influenza peptide epitope. After 24 h, IFN-γ in the culture medium was quantified as a measure of the T cell response. The present inventors found that the Vpx-containing vectors that encoded the Flu peptide were more potent than the control vectors and that CD40L enhanced the response of the CTL clone. The vectors encoding the peptide epitope induced a 10,000-fold increase in IFN-γ production and the vector that expressed the peptide epitope and CD40L induced a 70,000 fold increase as compared to the controls (FIG. 18). The response was comparable and in some cases higher than that induced by pulsing the DC with synthetic peptide. To see the response at the single cell level, the present inventors also analyzed the IFN-γ response by intracellular staining. The results showed that the Vpx-containing vectors encoding Flu peptide activated a similar number of the CTL clone regardless of whether or not they encoded CD40L, however, the addition of CD40L increased the intensity of the IFN-γ response, suggesting that CD40L amplified the amount of IFN-γ activation of the responding cells and not the number of cells that respond. To determine the potency of the transduced DCs, the effect of reducing the DC:CTL ratio was evaluated. The titration showed that as the DC:CTL ratio was decreased from 1:1 to 1:40, the Vpx-containing vectors that expressed CD40L and peptide epitope induced much greater levels of IFN-γ compared to controls.

Transduced DCs elicit antigen-specific memory and naive CD8 responses. To assess whether the transduced DCs would expand a CD8 memory response from primary donor T cells, the DC were transduced with various vectors described herein and after 48 h, autologous CD8 T cells were added. The cells were allowed to expand for two weeks after which the peptide-specific T cells were quantified by tetramer staining (FIG. 19). Results showed that DC transduced with Vpx-containing LV vectors encoding Flu peptide induced a significant antigen-specific memory response compared to LV vectors that lacked Vpx. Additional ICS analysis performed revealed that IFN-γ and TNF-α secretion by the autologous cytotoxic T cells following reticulation with synthetic influenza peptide mirrored the tetramer results.

Transduced DCs activate quiescent HIV-1 provirus expression from latently infected cells. To determine if the transduced DCs could reactivate latent HIV, transduced DCs were cocultured with ACH-2 cells, a cell line that harbors a quiescent provirus.[23] After 48 h, supernatants were assessed for HIV reactivation using TZM-bl cell infection as a function of Tat-induced luciferase reporter gene expression after a single round of HIV infection. TZM-bl cells contain the reporter gene for *E. coli* β-galactosidase under the control of an HIV-1 LTR. Expression of β-galactosidase is induced by viral Tat protein, and when X-gal is added to the cells it is cleaved by the enzyme to form a blue product. The number of blue spots (infected cells) observed is directly proportional to the number of infectious virions present in the analyte and can be counted using an Elispot reader. Results showed that DC transduced with the Vpx-containing LV vector encoding CD40L induced 5-fold more infectious virions than vectors lacking CD40L or Vpx. These levels were on par or greater than those induced by control PMA suggesting the Vpx-containing LV vectors encoding CD40L may stimulate HIV reactivation from the latent viral reservoir.

Discussion

DCs have been targeted for vaccine development due to their role as antigen-presenting cells and their capacity to stimulate adaptive immunity by inducing durable antigen-specific memory T cell responses. LV vectors have been explored as a method of gene delivery given their ability to transduce non-dividing cells and maintain long-term transgene expression via integration into the host genome. While genome integration poses theoretical safety concerns, particularly given the cases of lymphoid leukemia and myelodysplasia seen in trials using murine leukemia virus (MLV)-based γ-retroviral vectors,[24-26] LV vectors based on HIV have shown low oncogenic potential in animal models.[27] Moreover, several trials utilizing LV vectors are being pursued that will hopefully help to further delineate this potential risk.

With respect to DCs, however, LV vector infectivity is limited due to a post-entry restriction to infection mediated by SAMHD1. SAMHD1 hydrolyzes intracellular deoxynucleotide triphosphates (dNTPs) thereby lowering the concentration of dNTPs below that required for synthesis of viral DNA by reverse transcriptase and thus limiting infection. SIV Vpx bypasses this restriction by degrading SAMHD1 to allow for productive infection. Given that, the present inventors used the LV vector system described herein that packages SIV Vpx to improve DC transduction and enhance antigen presentation. Results presented herein clearly show that DC transduction efficiency is markedly improved with LV vectors that package Vpx. Indeed, the absolute degree of DC infectivity derived from Vpx-containing LV vectors varies from donor to donor, possibly owing to varying levels of donor DC SAMHD1 expression, however, LV vectors lacking Vpx consistently show negligible infectivity via flow cytometry analysis.

By modifying the Vpx-packaged LV vectors to encode the immunostimulatory protein, CD40L, the present inventors demonstrated that these vectors can be used to enhance DC maturation, as evident by upregulation of DC surface markers CD83 and CD86. This is significant, since DC maturation is directly related to effective antigen presentation. However, maturation alone does not dictate the type of immune response induced by DCs. Mature DCs are capable of inducing various T cell responses, including $T_H1$, $T_H2$, and $T_H17$ responses, and it is the cytokines produced by DCs that influence direction in which T cell differentiation is skewed. Examination of the supernatants of transduced DCs revealed that the Vpx-containing LV vectors encoding CD40L described herein stimulated increased secretion of pro-$T_H1$ cytokines, namely IL-12 and TNF-α, thereby favoring priming of an adaptive immune response.

In turn, to assess antigen presentation efficiency, the WIC class I conserved major epitope of influenza was encoded into our LV vectors and then co-cultured DCs transduced with such vectors with an influenza-specific cytotoxic T cell clone and measured T cell IFN-γ production. Results presented herein showed that not only is Vpx packaging necessary for efficient antigen presentation, but that the combination of CD40L and Vpx markedly increased the intensity of IFN-γ production, reaching levels over 70,000 times greater (pg/mL) than control vectors. These findings confirm the validity of the present inventors' hypothesis that enhancing DC maturation and $T_H1$ skewing cytokine production can lead to amplification of antigen-specific cytotoxic T cell immune responses. Further intracellular staining analysis for IFN-γ on the T Cell clone co-cultured with transduced DC supported this finding as demonstrated by the observation that while Vpx-containing vectors encoding influenza stimulated similar proportions of the cytotoxic T cell clones, vectors that encoded CD40L significantly intensified IFN-γ secretion. The present inventors also showed that the amount of synthetic influenza peptide needed to stimulate detectable clone IFN-γ release was significantly less when the clone was cocultured with DC transduced with Vpx-packaged LV vectors encoding CD40L than when transduced with vectors lacking CD40L. One pitfall of using an antigen-specific clone, however, is that the cells are already terminally differentiated, such that TCR upregulation cannot be assessed. In turn, the present inventors also co-cultured transduced DC with autologous CD8+ T cells to evaluate induction of an antigen-specific memory response and showed that not only do Vpx-containing LV vectors effectively expand a CD8 memory response, but that this too is bolstered by the addition of CD40L.

Results presented herein affirm the LV vector system described herein can be modified to encode specific antigens and thus, provide the basis for either a DC-targeted antigen specific vaccine or immunotherapeutic. With respect to HIV-1, infected persons can readily achieve virologic control with highly active antiretroviral therapy (HAART), however, a cure remains unattainable due to the persistence of a latently infected viral reservoir that reemerges upon cessation of therapy.[28] One theory to eradicate this reservoir is to provide a trigger that can awaken HIV proviruses from latently infected cells to allow for subsequent targeting of the infected cells as a result of viral cytopathic effects (CPEs) or host immune responses. However, Siliciano et al. (2012, Immunity 36(3):491-501) showed that while the histone deacetylase (HDAC) inhibitor, suberoylanilide hydroxamic acid (SAHA), induced virus reactivation from resting CD4+ T cells, reactivation did not result in death of infected cells and that the CTLs from patients on HAART failed to kill latently infected CD4+ T cells, thereby suggesting that reactivation of latent HIV-1 alone will not purge the viral latent reservoir unless there is stimulation of HIV-1 specific CTL responses prior to reactivation.[29] Given results presented herein showing that DC transduced with Vpx-packaged LV vectors encoding CD40L reactivate HIV-1 proviruses from ACH-2 cells 5-fold greater than control vectors, the present inventors envision that by encoding HIV-1 specific antigens into LV vectors described herein, such vectors will be able to supply both the "kick and kill" mechanisms necessary eradicate the latent reservoir.

In summary, the present inventors have established a DC targeted LV vector virion that matures and activates DC to facilitate an efficient antigen-specific CTL response and shows potential to be the basis of an HIV immunotherapeutic and/or vaccine that can be used to induce quiescent HIV proviruses from latently infected cells and target them for elimination.

References Relating to Example 3

1 Connolly, N. C. et al. Therapeutic immunization with human immunodeficiency virus type 1 (HIV-1) peptide-loaded dendritic cells is safe and induces immunogenicity in HIV-1-infected individuals. *Clin Vaccine Immunol* 15, 284-292, doi:10.1128/CVI.00221-07 (2008).

2 Gandhi, R. T. et al. A randomized therapeutic vaccine trial of canarypox-HIV-pulsed dendritic cells vs. canarypox-HIV alone in HIV-1-infected patients on antiretroviral therapy. *Vaccine* 27, 6088-6094, doi:10.1016/j.vaccine.2009.05.016 (2009).

3 Garcia, F. et al. Therapeutic immunization with dendritic cells loaded with heat-inactivated autologous HIV-1 in patients with chronic HIV-1 infection. *J Infect Dis* 191, 1680-1685, doi: 10.1086/429340 (2005).

4 Ide, F. et al. Peptide-loaded dendritic-cell vaccination followed by treatment interruption for chronic HIV-1 infection: a phase 1 trial. *J Med Virol* 78, 711-718, doi:10.1002/jmv.20612 (2006).

5 Lu, W., Arraes, L. C., Ferreira, W. T. & Andrieu, J. M. Therapeutic dendritic-cell vaccine for chronic HIV-1 infection. *Nature medicine* 10, 1359-1365, doi:10.1038/nm1147 (2004).

6 Chang, L. J. Lentiviral vector transduction of dendritic cells for novel vaccine strategies. *Methods in molecular biology* 614, 161-171, doi:10.1007/978-1-60761-533-0_11 (2010).

7 He, Y. K., Zhang, J. Y., Mi, Z. B., Robbins, P. & Falo, L. D. Immunization with lentiviral vector-transduced dendritic cells induces strong and long-lasting T cell responses and therapeutic immunity. *Journal of immunology* 174, 3808-3817 (2005).

8 Dyall, J., Latouche, J. B., Schnell, S. & Sadelain, M. Lentivirus-transduced human monocyte-derived dendritic cells efficiently stimulate antigen-specific cytotoxic T lymphocytes. *Blood* 97, 114-121 (2001).

9 Lahouassa, H. et al. SAMHD1 restricts the replication of human immunodeficiency virus type 1 by depleting the intracellular pool of deoxynucleoside triphosphates. *Nat Immunol* 13, 223-228, doi:10.1038/ni.2236 (2012).

10 Hrecka, K. et al. Vpx relieves inhibition of HIV-1 infection of macrophages mediated by the SAMHD1 protein. *Nature* 474, 658-661, doi:10.1038/nature10195 (2011).

11 Laguette, N. et al. SAMHD1 is the dendritic- and myeloid-cell-specific HIV-1 restriction factor counteracted by Vpx. *Nature* 474, 654-657, doi:10.1038/nature10117 (2011).

12 Sunseri, N., O'Brien, M., Bhardwaj, N. & Landau, N. R. Human immunodeficiency virus type 1 modified to package Simian immunodeficiency virus Vpx efficiently infects macrophages and dendritic cells. *Journal of virology* 85, 6263-6274, doi:10.1128/JVI.00346-11 (2011).

13 Shreedhar, V. et al. Dendritic cells require T cells for functional maturation in vivo. Immunity 11, 625-636 (1999).

14 van Kooten, C. & Banchereau, J. CD40-CD40 ligand. *Journal of leukocyte biology* 67, 2-17 (2000).

15 Caux, C. et al. Activation of human dendritic cells through CD40 cross-linking. *The Journal of experimental medicine* 180, 1263-1272 (1994).

16 Gray, D., Dullforce, P. & Jainandunsing, S. Memory B cell development but not germinal center formation is impaired by in vivo blockade of CD40-CD40 ligand interaction. *The Journal of experimental medicine* 180, 141-155 (1994).

17 Koya, R. C. et al. Potent maturation of monocyte-derived dendritic cells after CD40L lentiviral gene delivery. *Journal of immunotherapy* 26, 451-460 (2003).

18 Zhang, R., Zhang, S., Li, M., Chen, C. & Yao, Q. Incorporation of CD40 ligand into SHIV virus-like particles (VLP) enhances SHIV-VLP-induced dendritic cell activation and boosts immune responses against HIV. *Vaccine* 28, 5114-5127, doi:10.1016/j.vaccine.2010.03.079 (2010).

19 Vonderheide, R. H. et al. CD40 activation of carcinoma cells increases expression of adhesion and major histocompatibility molecules but fails to induce either CD80/CD86 expression or T cell alloreactivity. *International journal of oncology* 19, 791-798 (2001).

20 Bednarek, M. A. et al. The minimum peptide epitope from the influenza virus matrix protein. Extra and intracellular loading of HLA-A2. *Journal of immunology* 147, 4047-4053 (1991).

21 Szymczak, A. L. et al. Correction of multi-gene deficiency in vivo using a single 'self-cleaving' 2A peptide-based retroviral vector. *Nature biotechnology* 22, 589-594, doi: 10.1038/nbt957 (2004).

22 Anderson, K. et al. Endogenously synthesized peptide with an endoplasmic reticulum signal sequence sensitizes antigen processing mutant cells to class I-restricted cell-mediated lysis. *The Journal of experimental medicine* 174, 489-492 (1991).

23 Folks, T. M. et al. Tumor necrosis factor alpha induces expression of human immunodeficiency virus in a chronically infected T-cell clone. *Proc Natl Acad Sci U S A* 86, 2365-2368 (1989).

24 Hacein-Bey-Abina, S. et al. LMO2-associated clonal T cell proliferation in two patients after gene therapy for SCID-X1. *Science* 302, 415-419, doi:10.1126/science.1088547 (2003).

25 Howe, S. J. et al. Insertional mutagenesis combined with acquired somatic mutations causes leukemogenesis following gene therapy of SCID-X1 patients. *The Journal of clinical investigation* 118, 3143-3150, doi:10.1172/JCI35798 (2008).

26 Stein, S. et al. Genomic instability and myelodysplasia with monosomy 7 consequent to EVI1 activation after gene therapy for chronic granulomatous disease. *Nature medicine* 16, 198-204, doi:10.1038/nm.2088 (2010).

27 Montini, E. et al. Hematopoietic stem cell gene transfer in a tumor-prone mouse model uncovers low genotoxicity of lentiviral vector integration. *Nature biotechnology* 24, 687-696, doi:10.1038/nbt1216 (2006).

28 Chun, T. W., Davey, R. T., Jr., Engel, D., Lane, H. C. & Fauci, A. S. Re-emergence of HIV after stopping therapy. *Nature* 401, 874-875, doi:10.1038/44755 (1999).

29 Shan, L. et al. Stimulation of HIV-1-specific cytolytic T lymphocytes facilitates elimination of latent viral reservoir after virus reactivation. *Immunity* 36, 491-501, doi: 10.1016/j.immuni.2012.01.014 (2012).

30 Koguchi, Y., Thauland, T. J., Slifka, M. K. & Parker, D. C. Preformed CD40 ligand exists in secretory lysosomes in effector and memory CD4+ T cells and is quickly expressed on the cell surface in an antigen-specific manner. *Blood* 110, 2520-2527, doi:10.1182/blood-2007-03-081299 (2007).

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

---

What is claimed is:

1. A chimeric vector comprising HIV-1 nucleic acid sequences and $SIVmac_{239}$ nucleic acid sequences, wherein the $SIVmac_{239}$ nucleic acid sequences encode an $SIVmac_{239}$ amino acid sequence consisting of a minimal Vpx packaging motif that confers Vpx packaging activity to the chimeric vector and the nucleic acid sequences encoding the Vpx packaging motif are inserted after the nucleic acid codon that encodes amino acid 14 of the p6 protein of the chimeric vector and the chimeric vector does not comprise any SIVmac nucleic acid sequences except for the minimal Vpx packaging motif.

2. The chimeric vector of claim 1, wherein the minimal Vpx packaging motif consists of at least 10 contiguous amino acids of $SIVmac_{239}$ comprising of $^{17}$DPAVDLLKNY$^{26}$ (SEQ ID NO:1), wherein the 5' terminus of the minimal Vpx packaging motif is the aspartic acid (D) at amino acid position 17 of the $SIVmac_{239}$ amino acid sequence.

3. The chimeric vector of claim 2, wherein the minimal Vpx packaging motif consists of $^{17}$DPAVDLLKNY$^{26}$, (SEQ ID NO: 1)

$^{17}$DPAVDLLKNYM$^{27}$, (SEQ ID NO: 2)

$^{17}$DPAVDLLKNYMG$^{28}$, (SEQ ID NO: 3)

$^{17}$DPAVDLLKNYMQL$^{29}$, (SEQ ID NO: 4)

$^{17}$DPAVDLLKNYMQLG$^{30}$, (SEQ ID NO: 5)

$^{17}$DPAVDLLKNYMQLGK$^{31}$, (SEQ ID NO: 6)

$^{17}$DPAVDLLKNYMQLGKQ$^{32}$, (SEQ ID NO: 7)

$^{17}$DPAVDLLKNYMQLGKQQ$^{33}$, (SEQ ID NO: 8)

$^{17}$DPAVDLLKNYMQLGKQQRE$^{34}$, (SEQ ID NO: 9)

$^{17}$DPAVDLLKNYMQLGKQQREK$^{35}$, (SEQ ID NO: 10)

$^{17}$DPAVDLLKNYMQLGKQQREKQ$^{36}$, (SEQ ID NO: 11)

$^{17}$DPAVDLLKNYMQLGKQQREKQ$^{37}$, (SEQ ID NO: 12)

$^{17}$DPAVDLLKNYMQLGKQQREKQR$^{38}$, (SEQ ID NO: 13)

$^{17}$DPAVDLLKNYMQLGKQQREKQRE$^{39}$, (SEQ ID NO: 14)

-continued $^{17}$DPAVDLLKNYMQLGKQQREKQRES$^{40}$, (SEQ ID NO: 15)

$^{17}$DPAVDLLKNYMQLGKQQREKQRESR$^{41}$, (SEQ ID NO: 16)

$^{17}$DPAVDLLKNYMQLGKQQREKQRESRE$^{42}$, (SEQ ID NO: 17)

$^{17}$DPAVDLLKNYMQLGKQQREKQRESREK$^{43}$, (SEQ ID NO: 18)

$^{17}$DPAVDLLKNYMQLGKQQREKQRESREKP$^{44}$, (SEQ ID NO: 19)

$^{17}$DPAVDLLKNYMQLGKQQREKQRESREKPY$^{45}$, (SEQ ID NO: 20)

$^{17}$DPAVDLLKNYMQLGKQQREKQRESREKPYK$^{46}$, (SEQ ID NO: 21)

$^{17}$DPAVDLLKNYMQLGKQQREKQRESREKPYKE$^{47}$, (SEQ ID NO: 22)

or $^{17}$DPAVDLLKNYMQLGKQQREKQRESREKPYKEV$^{48}$. (SEQ ID NO: 23)

4. The chimeric vector of claim 1, wherein the minimal Vpx packaging motif consists of $^{17}$DPAVDLLKNY$^{26}$ (SEQ ID NO:1).

5. The chimeric vector of claim 1, wherein the $SIVmac_{239}$ nucleic acid sequences encoding the minimal Vpx packaging motif comprise at least one codon optimized nucleic acid sequence.

6. The chimeric vector of claim 1, wherein the $SIVmac_{239}$ nucleic acid sequences encoding the minimal Vpx packaging motif are inserted into the HIV-1 nucleic acid sequences encoding p6 of HIV-1 Gag polyprotein to generate a hybrid HIV-1/$SIVmac_{239}$ nucleic acid sequence that encodes a hybrid HIV-1/$SIVmac_{239}$ p6 wherein amino acids 1-14 of HIV-1 p6 are linked directly to the minimal Vpx packaging motif consisting of at least 10 contiguous amino acids of $SIVmac_{239}$ p6 comprising of $^{17}$DPAVDLLKNY$^{26}$ (SEQ ID NO:1), wherein the 5' terminus of the minimal Vpx packaging motif is the aspartic acid (D) at amino acid position 17 of the $SIVmac_{239}$ p6 amino acid sequence.

7. The chimeric vector of claim 1, wherein the HIV-1 nucleic acid sequences encode Gag and Pol.

8. A method of making a plurality of virions having enhanced infectivity for monocyte-derived macrophages (MDM) and dendritic cells (MDDC), the method comprising transfecting a population of cells with a lentiviral vector comprising 5' and 3' long terminal repeats (LTRs) and a nucleic acid sequence encoding at least one immunogen of a peptide or protein, a vector encoding vesicular stomatitis virus (VSV) envelope glycoprotein, a vector encoding Vpx, and the chimeric vector of claim 1 to generate a transfected population of cells, wherein the transfected population of cells produces the plurality of virions having enhanced infectivity for MDM and dendritic cells MDDC.

9. The method of claim 8, wherein the vector comprising 5' and 3' LTRs further comprises a nucleic acid sequence encoding at least one dendritic cell activator protein and/or at least one cytokine.

10. A plurality of virions, wherein the plurality of virions is produced by the method of claim 8.

11. A composition comprising the plurality of virions of claim 10 and a pharmaceutically acceptable carrier.

12. A method of enhancing innate immune responses to a peptide or protein in a subject, the method comprising: administering the plurality of virions of claim 10 or a composition thereof to the subject, wherein the plurality of virions comprises the at least one immunogen of the peptide or protein, and wherein the plurality of virions or a composition thereof is administered to the subject in a therapeutically effective amount sufficient to enhance innate immune responses to the peptide or protein in the subject.

13. A method of enhancing innate immune responses to human immunodeficiency virus 1 (HIV-1) in a subject, the method comprising: administering the plurality of virions of claim 10 or a composition thereof to the subject, wherein the plurality of virions comprises the at least one immunogen of the peptide or protein and the peptide or protein is an HIV-1 encoded peptide or protein, and wherein the plurality of virions or the composition thereof is administered to the subject in a therapeutically effective amount sufficient to enhance innate immune responses to HIV-1 in the subject.

14. The method of claim 13, wherein the subject is infected with HIV-1 or suspected to be infected with HIV-1.

15. The method of claim 12, wherein the subject is a human.

* * * * *